(12) United States Patent
Vitek et al.

(10) Patent No.: US 8,288,335 B2
(45) Date of Patent: Oct. 16, 2012

(54) APOE ANALOGS AND METHODS FOR THEIR USE

(75) Inventors: Michael P. Vitek, Cary, NC (US); Suzanne E. McKenna, Raleigh, NC (US)

(73) Assignee: Cognosei, Inc., Research Triangle Park, NC (US)

( * ) Notice: Subject to any disclaimer, the term of this patent is extended or adjusted under 35 U.S.C. 154(b) by 0 days.

(21) Appl. No.: 13/096,423

(22) Filed: Apr. 28, 2011

(65) Prior Publication Data

US 2011/0306550 A1 Dec. 15, 2011

Related U.S. Application Data

(63) Continuation of application No. 11/661,777, filed as application No. PCT/US2005/031431 on Sep. 2, 2005, now Pat. No. 7,947,645.

(60) Provisional application No. 60/606,506, filed on Sep. 2, 2004, provisional application No. 60/608,148, filed on Sep. 9, 2004, provisional application No. 60/606,507, filed on Sep. 2, 2004.

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. .......... 514/1.1; 530/324; 530/325; 530/326

(58) Field of Classification Search .................. None
See application file for complete search history.

(56) References Cited

U.S. PATENT DOCUMENTS

| | | | |
|---|---|---|---|
| 4,902,505 | A | 2/1990 | Pardridge et al. |
| 5,182,364 | A | 1/1993 | Dyer et al. |
| 5,204,327 | A | 4/1993 | Kiyota et al. |
| 5,473,039 | A | 12/1995 | Dyer et al. |
| 5,604,198 | A | 2/1997 | Poduslo et al. |
| 5,686,416 | A | 11/1997 | Kozarich et al. |
| 6,245,751 | B1 | 6/2001 | Crutcher et al. |
| 6,274,603 | B1 * | 8/2001 | Poirier ............ 514/330 |
| 6,472,507 | B1 | 10/2002 | Fischer et al. |
| 6,605,588 | B1 | 8/2003 | Lee et al. |
| 7,205,280 | B2 | 4/2007 | Laskowitz et al. |
| 7,399,747 | B1 * | 7/2008 | Clair et al. ......... 514/1.2 |
| 7,947,645 | B2 * | 5/2011 | Vitek et al. ......... 514/1.1 |
| 2002/0164789 | A1 | 11/2002 | Laskowitz et al. |
| 2003/0077641 | A1 * | 4/2003 | Laskowitz et al. ....... 435/6 |
| 2004/0014652 | A1 | 1/2004 | Trouet et al. |
| 2009/0131315 | A1 | 5/2009 | Vitek et al. |
| 2009/0169614 | A1 * | 7/2009 | Laskowitz et al. ...... 424/450 |
| 2011/0021413 | A1 * | 1/2011 | Laskowitz et al. ...... 514/1.9 |

FOREIGN PATENT DOCUMENTS

| | | |
|---|---|---|
| WO | WO 92/10512 | 6/1992 |
| WO | WO 95/06456 | 3/1995 |
| WO | WO 97/14437 | 4/1997 |
| WO | WO 98/01101 | 1/1998 |
| WO | WO 99/08701 A1 | 2/1999 |
| WO | WO 99/45950 | 9/1999 |
| WO | WO 00/32236 * | 6/2000 |
| WO | WO 03/026479 A2 | 4/2003 |
| WO | WO 03/026479 A3 | 4/2003 |

OTHER PUBLICATIONS

Drin et al. Studies on the Internalization Mechanism of Cationic Cell-penetrating Peptides. The Journal of Biological Chemistry. Jun. 3, 2003, vol. 278, Nol. 33, pp. 31192-31201.*

Aono, et al., "Protective Effects of Peptides Corresponding to the Receptor Binding Region of Apolipoprotein E on NMDA Excitotoxicity in Primary Neuronal-Glial Cultures", Trip Report: 31$^{st}$ Annual Meeting of the Society for Neuroscience, San Diego, California (Nov. 2001).

Barger, et al., "Microglial Activation by Alzheimer Amyloid Precursor Protein and Modulation by Apolipoprotein E", Nature 388: 878-881 (Aug. 1997).

Benazzouz, et al., "Riluzole Prevents MPTP-induced Parkinsonism in the Rhesus Monkey: A Pilot Study," *Eur. J. Pharmacol.* 284:299-307 (1995).

Bowie, et al., "Deciphering the message in protein sequences tolerance to amino acid substitutions", Science, 247: 1306-1310 (1990).

Cardin, et al., "Inhibition of Lymphocyte Proliferation b Synthetic Peptides Homologous to Human Plasma Apolipoproteins B and E", Biochemical and Biophysical Research Communications, 154: 741-745 (Jul. 1998).

Champe, et al., "IV. Tertiary Structure of Globular Proteins," "V. Quaternary Structure of Proteins," "VI Denaturation of Proteins," and "VII. Protein Misfolding," pp. 18-21 in *Lippincott's Illustrated Reviews: Biochemistry, 3rd Ed* Lippincott Williams & Wilkins, Philadelphia, Pennsylvania, USA (2005).

Chen, et al., "Motor and Cognitive Deficits in Apolipoprotein E Deficient Mice After Closed Head Injury," *Neuroscience* 80:1255-1262 (1997).

Christie, et al., "Expression of the Very Low-Density Lipoprotein Receptor (VLDL-r), an Apolipoprotein-E Receptor, in the Central Nervous System and in Alzheimer's Disease", Journal of Neuropathology and Experimental Neurology, 55(4): 491-498 (1996).

Clay, et al., "Localization of a Domain in Apolipoprotein E with Both Cytostatic and Cytotoxic Activity", Biochemistry, 34: 11142-11151 (1995).

Crutcher, et al., "Neurite degeneration elicited by apolipoprotein E peptides", Experimental Neurology 130(1):120-126 (1994).

Dong, et al., "Enhanced binding activity of an apolipoprotein E mutant, APO E5, to LDL receptors on human fibroblasts", Biochemical & Biophysical Research Communications 168(2):409-414 (Apr. 1990).

(Continued)

*Primary Examiner* — Marcela M Cordero Garcia
(74) *Attorney, Agent, or Firm* — Cooley LLP

(57) ABSTRACT

Novel ApoE peptide derivatives and ApoE-protein transduction domain conjugates are disclosed which are useful for treating disorders including CNS inflammation, traumatic brain injury, inflammatory bowel disease (also known as Crohn's Disease or ulcerative colitis), cerebral ischemia, atherosclerosis, sepsis, multiple sclerosis and arthritic diseases, Alzheimer's Disease and other brain disorders. The invention encompasses methods for protecting subjects having undergone irradiation or radiotherapy by administration of ApoE or at least one ApoE mimetic peptide.

26 Claims, 46 Drawing Sheets

OTHER PUBLICATIONS

Dong, et al., "Site-directed mutagenesis of an apolipoprotein E mutant, apo E5(Glu3—Lys) and its binding to low density lipoprotein receptors", Biochemical & Biophysical Research Communications 187(2):1180-1186 (Sep. 1992).

Dyer, et al., "A Synthetic Peptide Mimetic of Plasma Apolipoprotein E that Binds the LDL Receptor", Journal of Biological Chemistry, 266: 22803-22806 (Dec. 1991).

Dyer, et al., "Only Multimers of a Synthetic Peptide of Human Apolipoprotein E Are Biologically Active", Journal of Biological Chemistry, 266: 15009-15015 (1991).

Gordon, et al., "Derangement in Stress Response of Apolipoprotein E-deficient Mice," *Neuroscience Letters* 206:212-214 (1996).

Holtzman, et al., "Low density lipoprotein receptor-related protein mediates apolipoprotein E-dependent neurite outgrowth in a central nervous system-derived neuronal cell line", Proc. Natl. Acad. Sci. USA, 92: 9480-9484 (1995).

Innerarity, et al., "Binding of arginine-rich (E) apoprotein after recombination with phospholipid vesicles to the low density lipoprotein receptors of fibroblasts", Journal of Biological Chemistry 254(10):4186-4190 (1979).

International Search Report for PCT/US99/05221 (mailed Nov. 3, 1999).

Jordan, et al., "Isoform-Specific Effect of Apolipoprotein E on Cell Survival and β-Amyloid-induced Toxicity in Rat Hippocampal Pyramidal Neuronal Cultures,"*J. Neurosci.* 18:195-204 (1998).

Lalazar, et al., "Site-specific Mutagenesis of Human Apolipoprotein E", Journal of Biological Chemistry, 263: 3542-3545 (1988).

Laskowitz, et al., "Endogenous apolipoprotein E suppresses LPS-stimulated microglial nitric oxide production", Neuroreport. 9(4):615-618 (1998).

Laskowitz, et al., "Apolipoprotein E and the CNS response to injury", Journal of Cerebral Blood Flow & Metabolism 18(5): 465-471 (1998).

Laskowitz, et al., "Apolipoprotein E suppresses glial cell secretion of TNF alpha", Journal of Neuroimmunology 76(1-2):70-74, (1997).

Laskowitz, et al., "Apolipoprotein E-deficient mice have increased susceptibility to focal cerebral ischemia", Journal of Cerebral Blood Flow & Metabolism 17(7):753-758 (1997).

Laskowitz, et al., "Downregulation of Microglial Activation by Apolipoprotein E and ApoE-Mimetic Peptide", Experimental Neurology, 167: 74-85 (2001).

Ludwig, "Supplementary European Search Report," 3 pages, from EP Appl. No. 02775888.7, European Patent Office, Munich, Germany (mailed Mar. 9, 2007).

Marzolo, et al., "Expression of α2-Macroglobulin Receptor/ Low Density Lipoprotein Receptor-Related Protein (LRP) in Rat Microglial Cells," *J. Neurosci. Res.* 60:401-411 (2000).

Mickle, et al., "Genotype-phenotype relationships in cystic fibrosis", Med. Clin. North Am., 84 (3): 597-607 (May 2000).

Misra, et al., "Apolipoprotein E and Mimetic Peptide Initiate a Calcium-Dependent Signaling Response in Macrophages", Journal Leukocyte Bio. 70: 677-683 (2001).

Mrak, et al., "Glial Cytokines in Alzheimer's Disease: Review and Pathogenic Implications", Hum. Pathol. 26: 816-823 (Aug. 1995).

Pardridge, "Chapter 12: Blood-brain barrier peptide transport and peptide delivery to the brain, Peptide-based drug design", Ed. Taylor et al., American Chemical Society, 265-296 (1995).

Tolar, et al., "Truncated Apolipoprotein E (ApoE) Causes Increased Intracellular Calcium and May Mediate ApoE Neurotoxicity," *J. Neuroscience* 19(16): 7100-7110 (1999).

Vitek, et al., "Modulation of nitric oxide production in human macrophages by apolipoprotein-E and amyloid-beta peptide", Biochemical & Biophysical Research Communications 240(2):391-394 (1997).

Voet, et al., Biochemistry, John Wiley & Sons, Inc., 126-128 and 228-234 (1990).

Weisgraber, et al., "The receptor-binding domain of human apolipoprotein E. Monoclonal antibody inhibition of binding", Journal of Biological Chemistry 258(20):12348-12354 (1983).

Yan, et al., "Two-amino acid molecular switch in an epithelial morphogen that regulates binding to two distinct receptors", Science, 290: 523-527 (2000).

Zielasek, et al., Advances in Neuroimmunology, 6 (2): 191-222 (1996).

Hruby, "Designing Peptide Receptor Agonists and Antagonists.," Nature Reviews. Drug Discovery, vol. 1: 847-858 (2002).

Drin et al., "Studies on the Internalization Mechanism of Cationic Cell-penetrating Peptides," J Biol Chem., vol. 278: 31192-31201 (2003).

Lynch et al., "APOE genotype and an ApoE-mimetic peptide modify the systemic and central nervous system inflammatory response," J. Biol. Chem., vol. 278:48529-48533 (2003).

\* cited by examiner

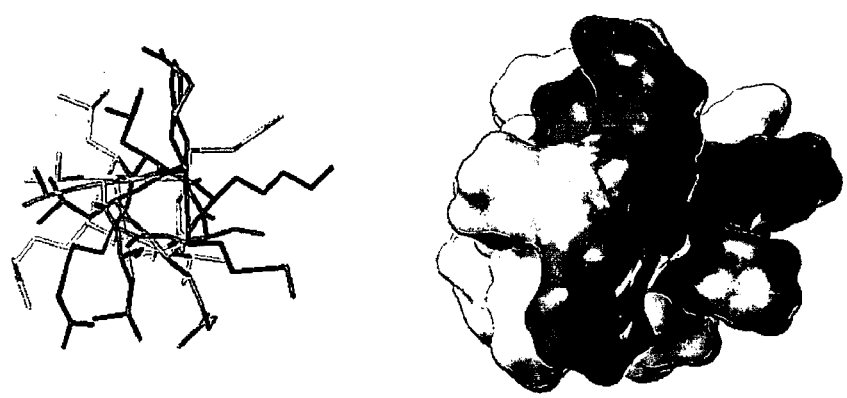
Figure 1. Helical wheel projection of COG133 peptide; looking down the helix axis with the carboxy terminus in the foreground.

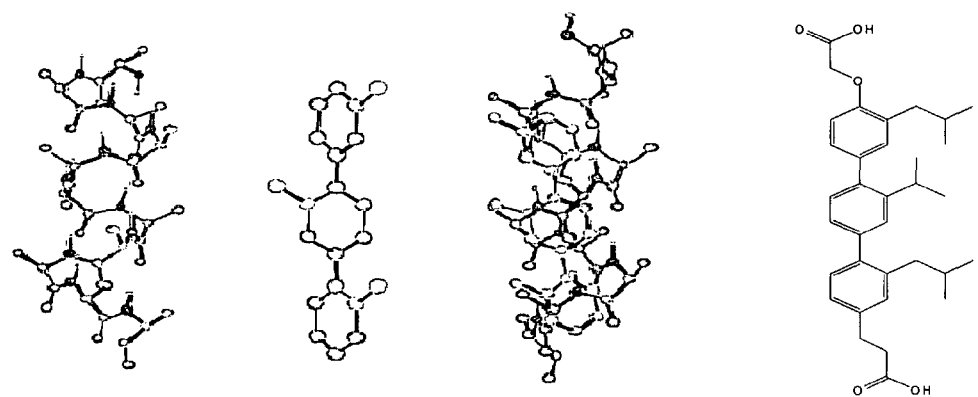
Figure 2. Exemplary mimetics such as tris functionalized terphenyls mimic surface functionality presented along one face of an alpha helix.

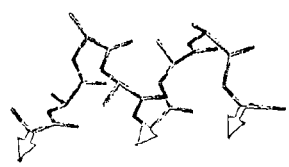 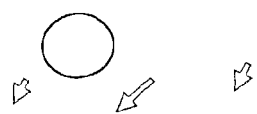
Helical Peptide    Presentation of pharmacophore
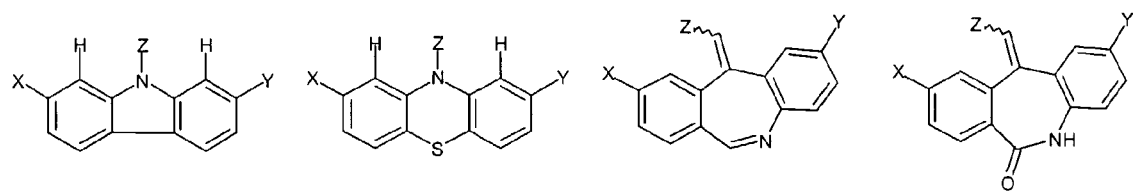
Figure 3. Tricyclic scaffolds as Helix mimetics Figure 5. Closed head injury was performed using a stereotactically guided pneumatic impact device.
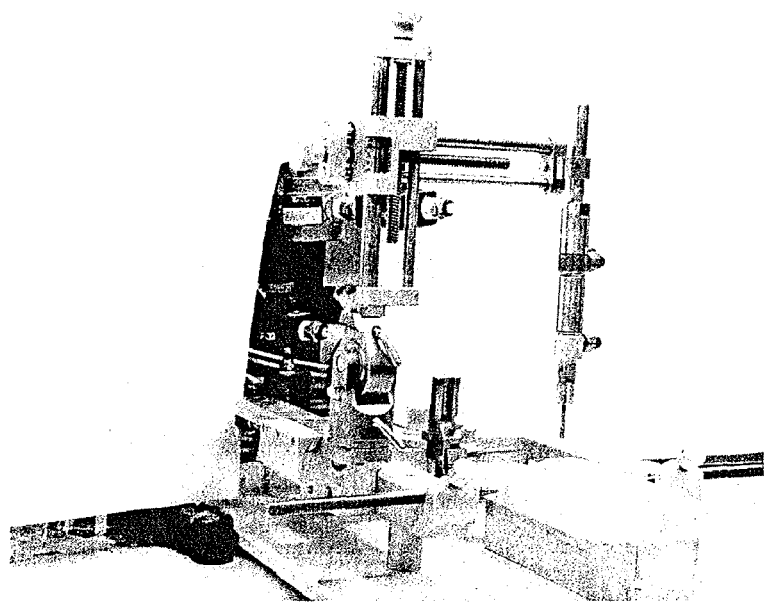

(A)
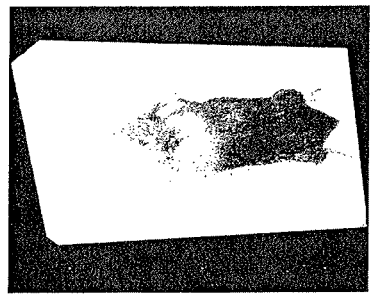
(B)
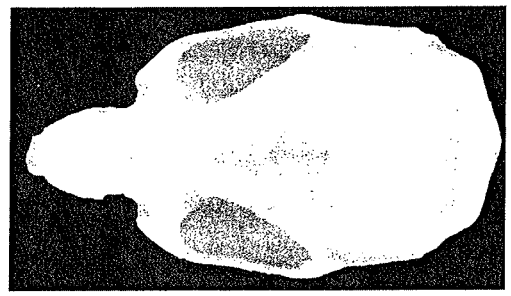
(C)
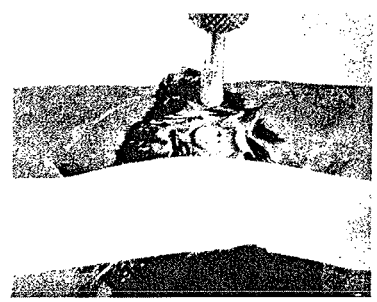
Figure 6. Mice are intubated and placed in an acrylic mold (A). The scalp is incised, and a 3 mm metal disc is placed just caudal to bregma (B) prior to pneumatic impact (C).

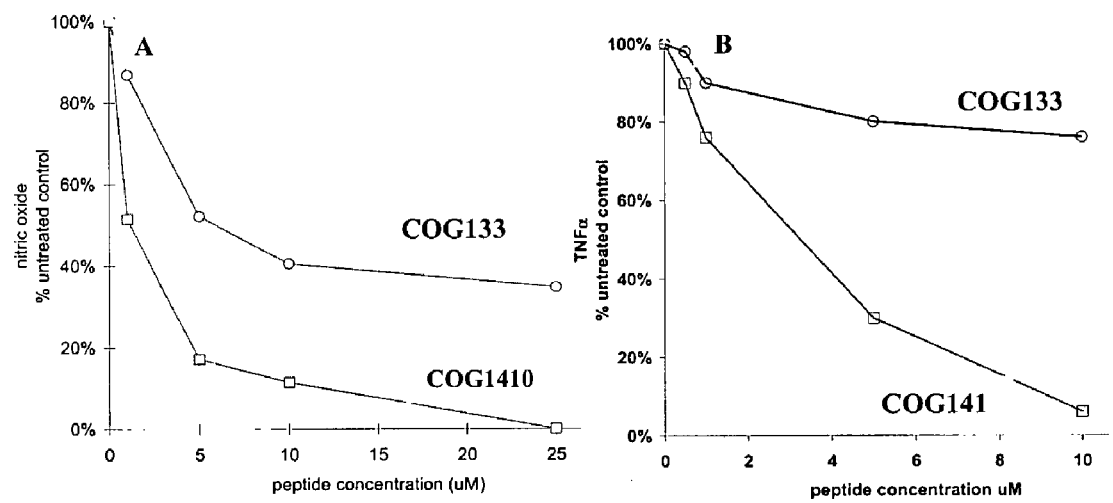
Figure 7. Suppression of release of nitric oxide (A) and TNFa (B) in LPS-treated BV2 microglia cells. COG1410 exhibits significantly greater potency compared to COG133.

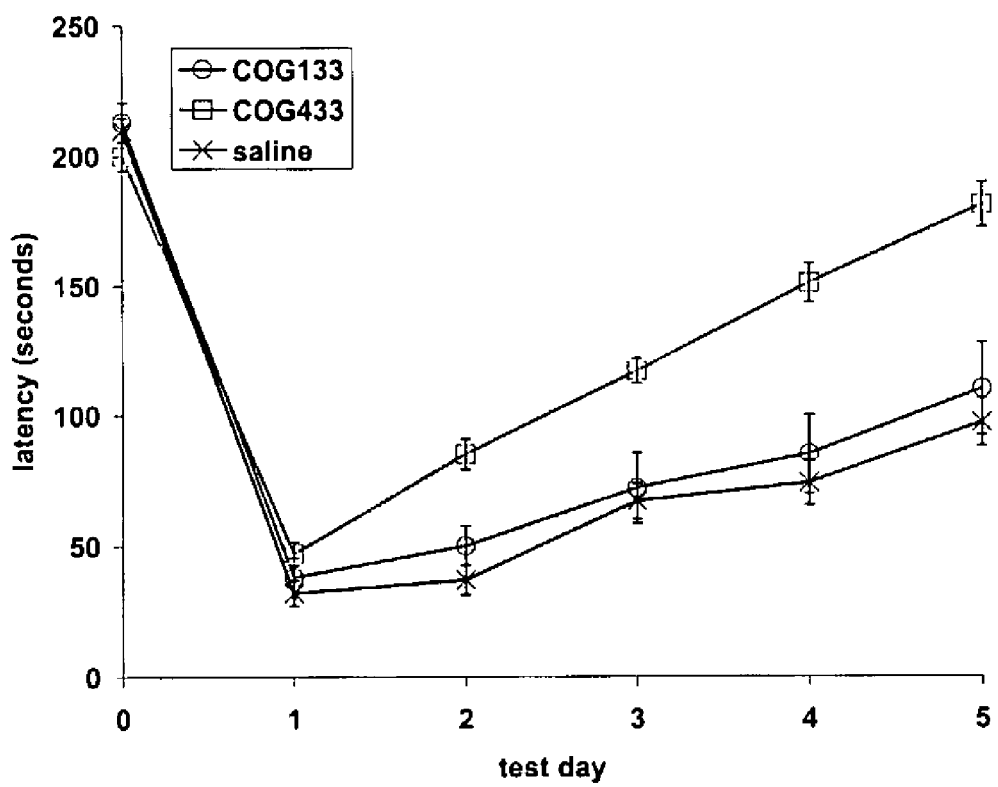
Figure 8. Rotorod shows COG1410 is neuroprotective when administered 120 minutes after TBI compared to saline, $p<0.05$; COG133 is not significantly different than saline, $p>0.05$.

A
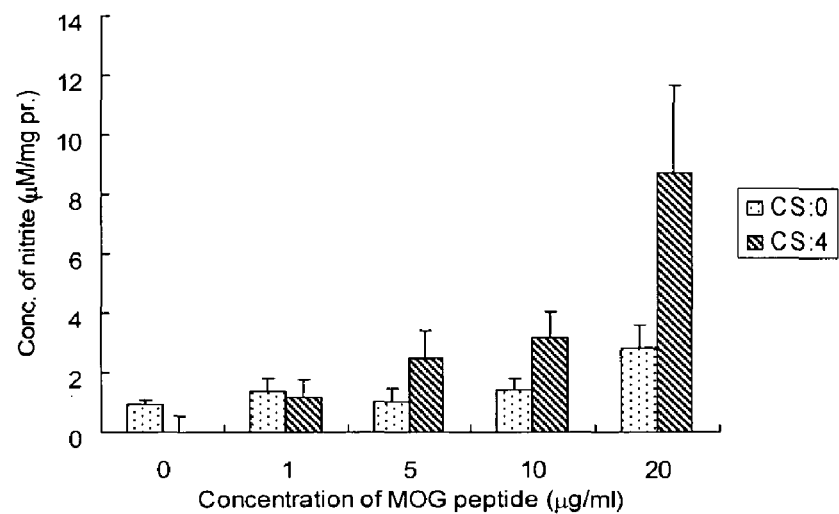
B
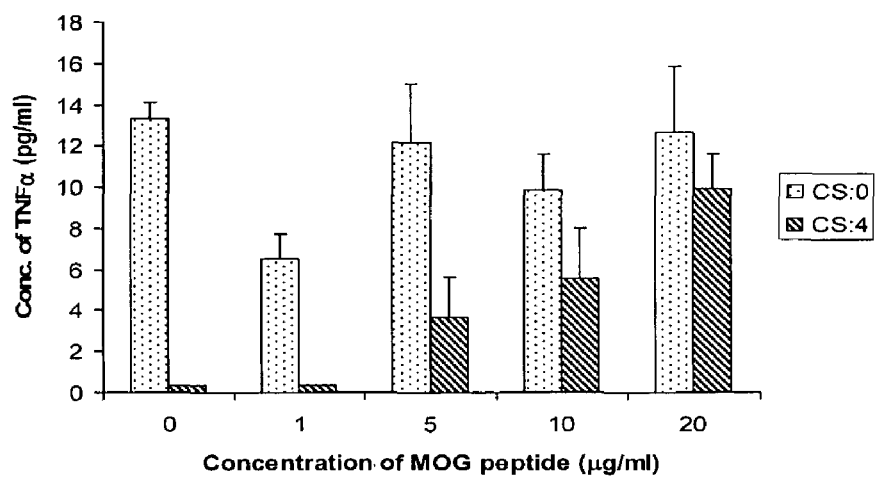
Figure 11

C
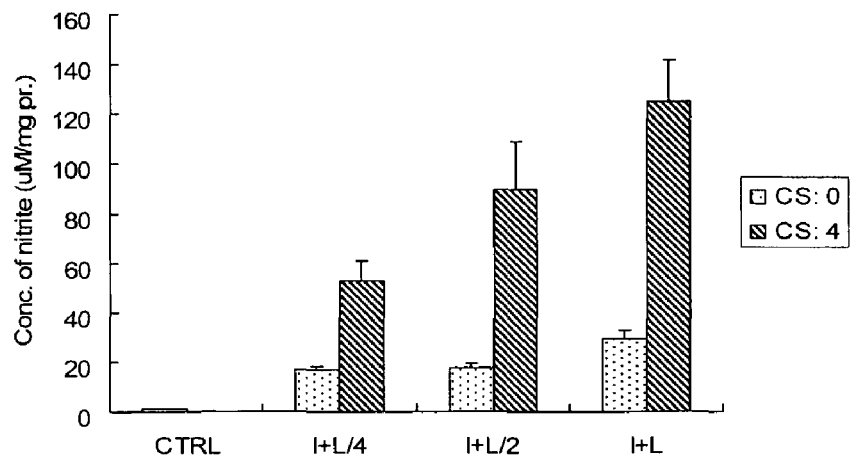
D
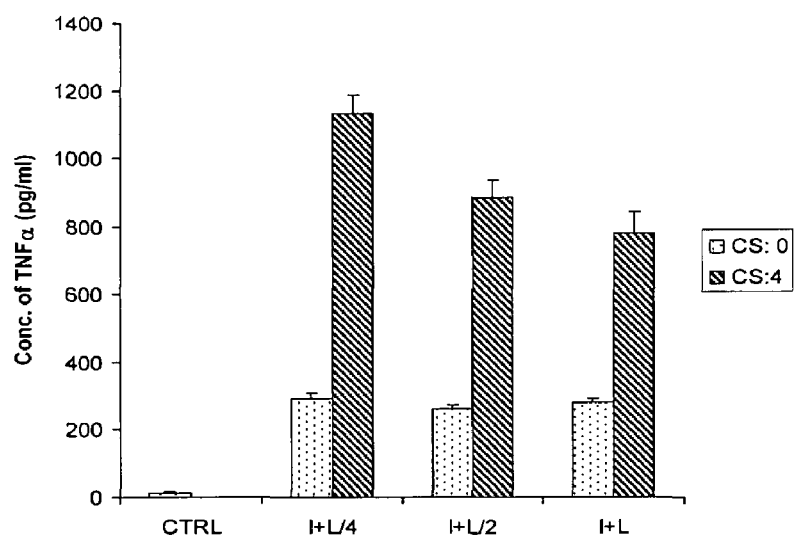
Figure 11 continued

A
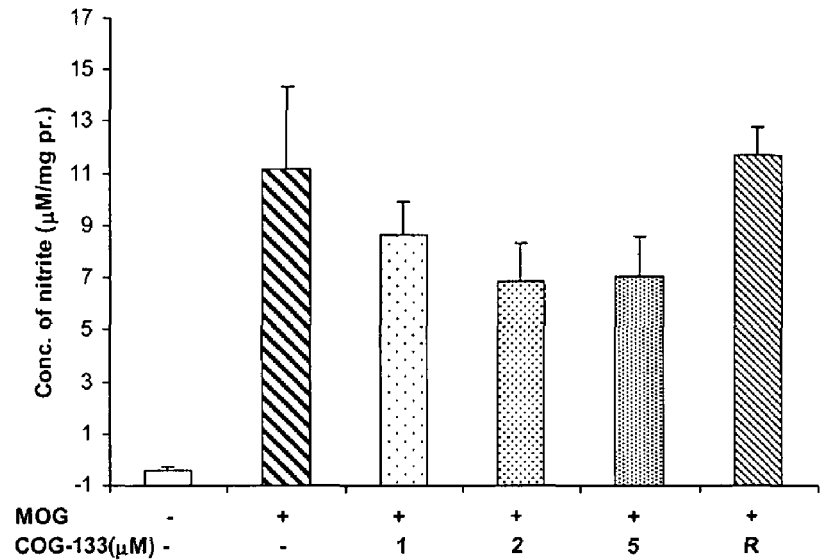
B
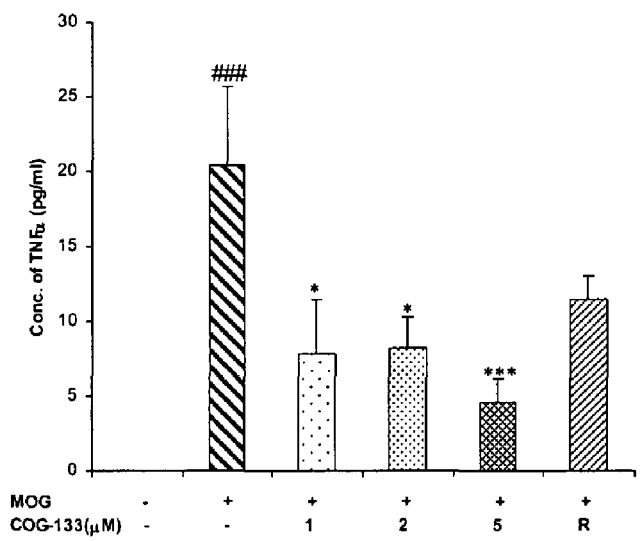
Figure 12

A
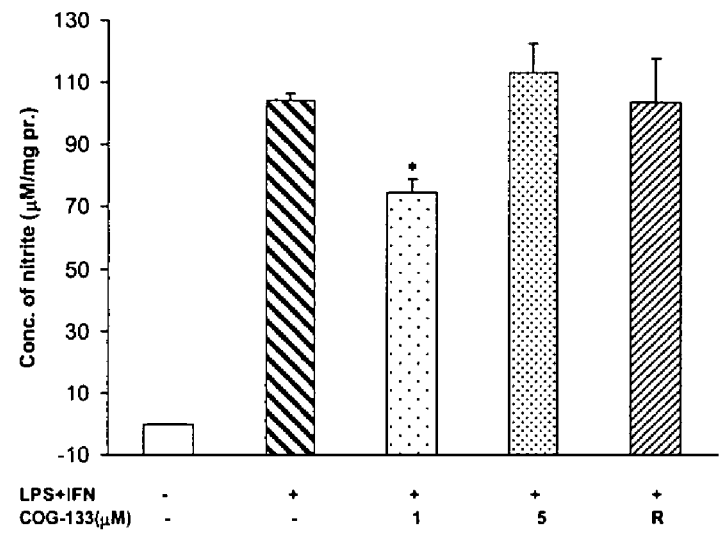
B
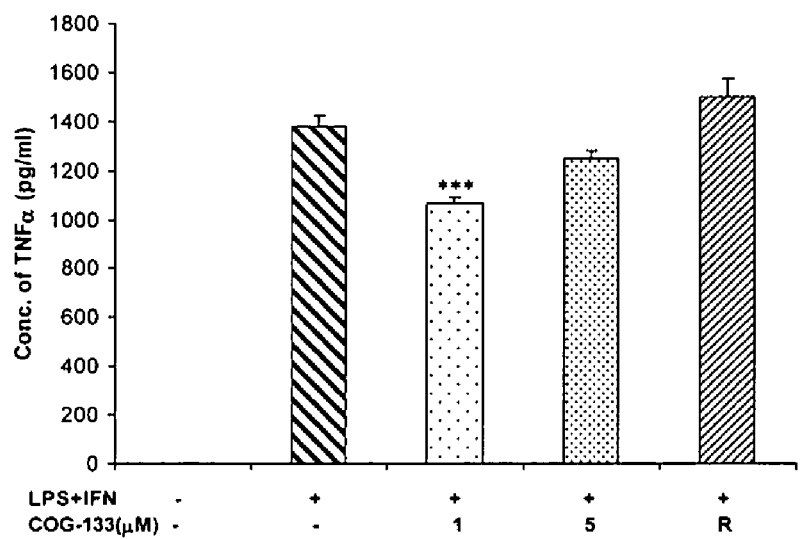
Figure 13

A
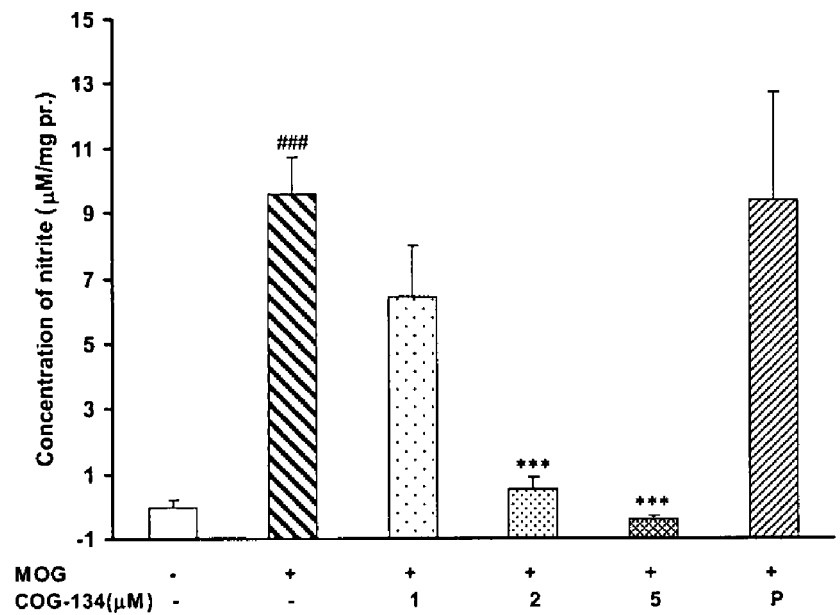
B
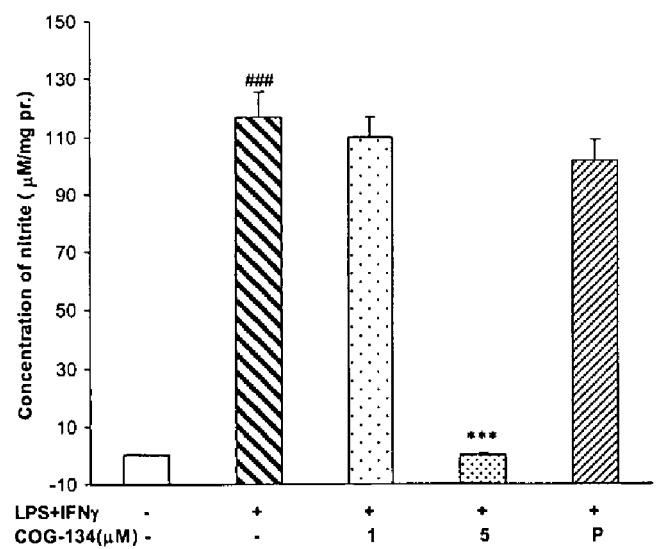
Figure 14

C
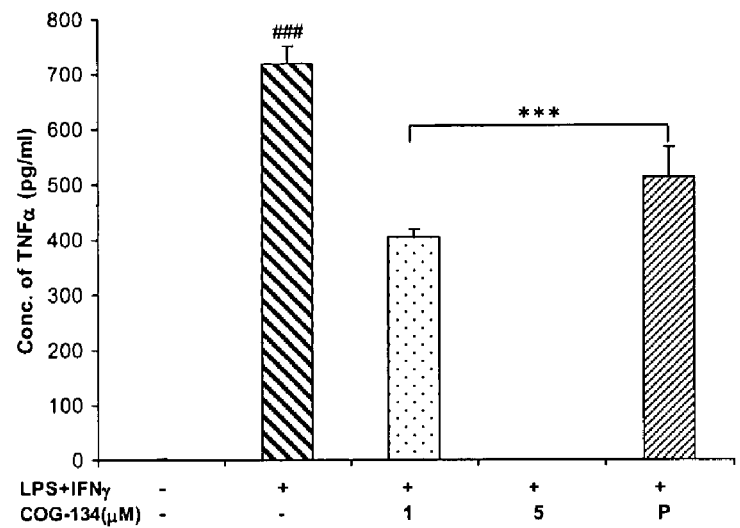
D
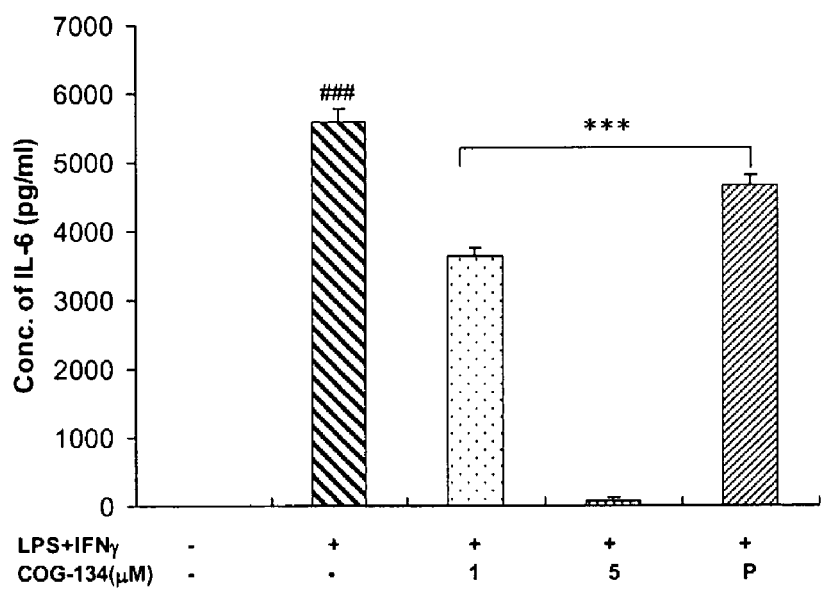
Figure 14 continued

Figure 16. COG133 suppressed nitrite release in LPS-stimulated BV2 microglial cells in a dose dependent manner. Fifty % suppression occurred at 3 μM.

Figure 17. TAT-COG133 did not suppress nitrite release in LPS-stimulated BV2 microglial cells at doses in the nM range. Higher doses were cytotoxic.

Figure 18. Penetratin-COG133 suppressed nitrite release in LPS-stimulated BV2 cells in a dose dependent manner. Fifty % suppression occurred at 30 nM.

Figure 19. PTDCOG133 conjugates inhibit LPS-mediated nitric oxide production.

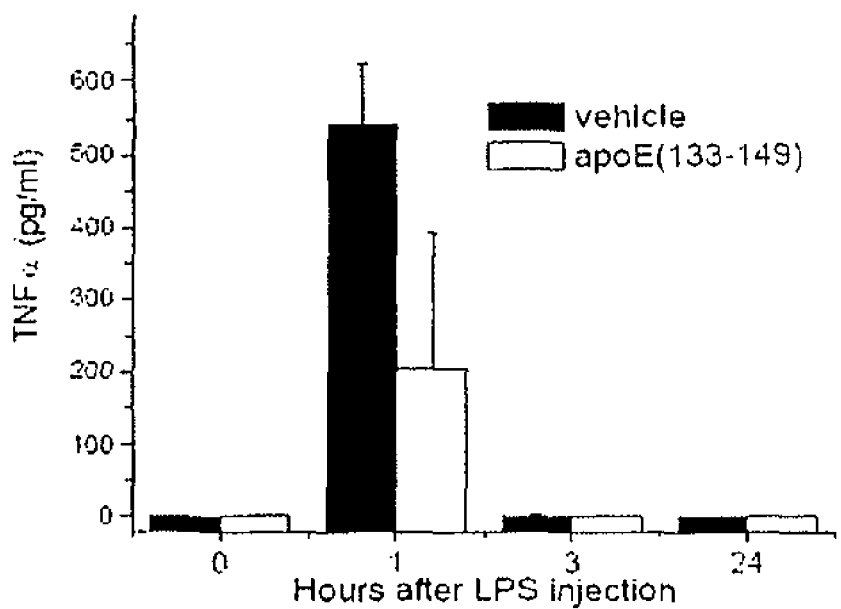
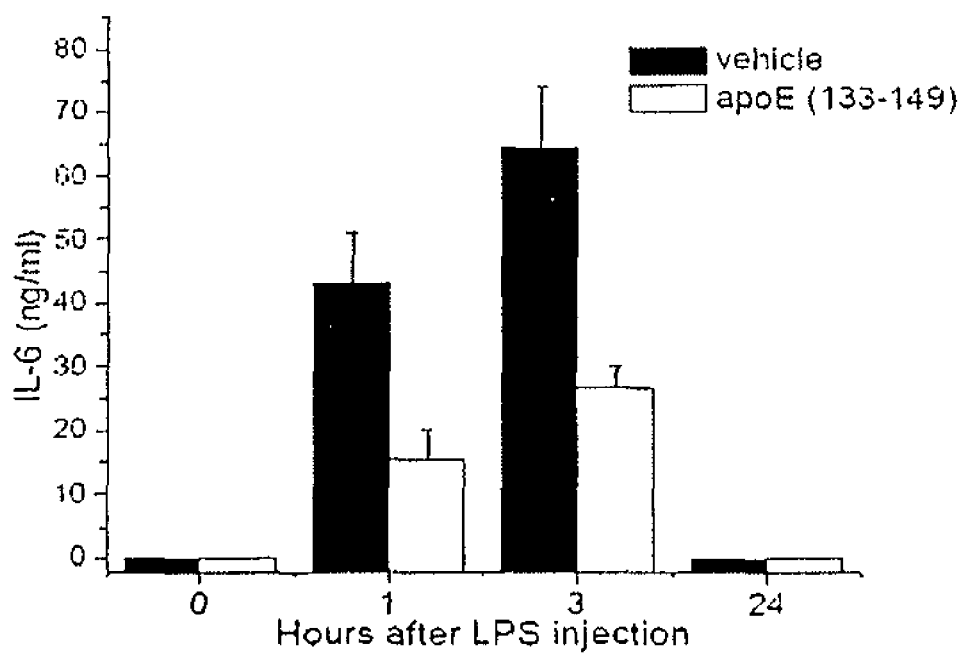
Figure 24

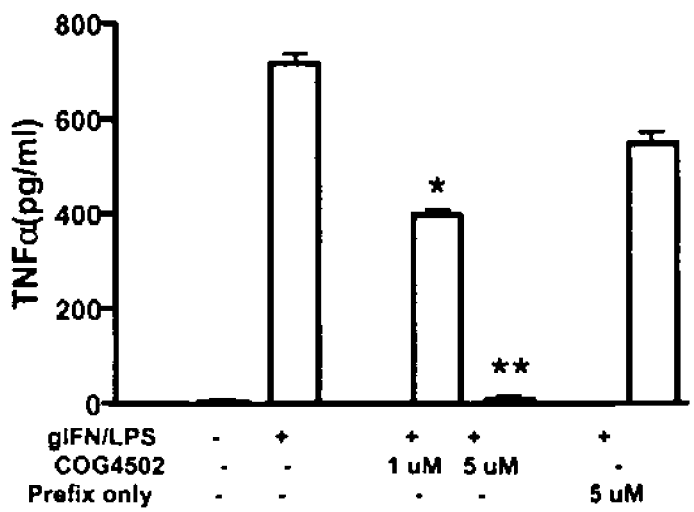
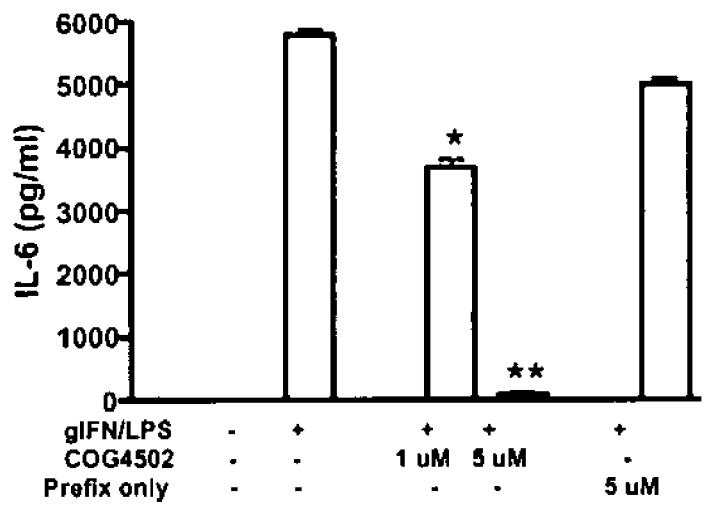
Figure 27

APOE ANALOGS AND METHODS FOR THEIR USE

1. CROSS-REFERENCE TO RELATED APPLICATIONS

This application is a continuation of U.S. application Ser. No. 11/661,777, filed Apr. 11, 2008, now U.S. Pat. No. 7,947,645, which is a national stage of International Application No. PCT/US2005/031431, filed Sep. 2, 2005, which claims priority to provisional applications 60/606,506, filed Sep. 2, 2004; 60/608,148, filed Sep. 9, 2004 and 60/606,507, filed Sep. 2, 2004, all of which are herein incorporated by reference in their entireties. This application is also related to application Ser. No. 09/260,430, filed Mar. 1, 1999; 09/957,909, filed Sep. 21, 2001; 10/252,120, filed Sep. 23, 2002 and 11/091,336, filed Mar. 29, 2005, which are herein incorporated by reference in their entireties.

DESCRIPTION OF THE TEXT FILE SUBMITTED ELECTRONICALLY

The contents of the text file submitted electronically herewith are incorporated herein by reference in their entirety: The computer readable format copy of the Sequence Listing (filename: COGO_010_02US SeqList.txt, date recorded: Jul. 15, 2011, file size 42 kilobytes).

2. FIELD OF THE INVENTION

The present invention provides compounds and methods for the treatment of traumatic brain injury, inflammatory bowel disease (IBD), Crohn's disease, ulcerative colitis, arthritis, multiple sclerosis, atherosclerosis and sepsis. The present invention also relates to methods of protecting subjects from the effects of radiation, including total body irradiation and localized radiotherapy, and is relevant to the fields of transplantation, cancer therapy and emergency medicine in the case of an accidental or deliberate exposure to ionizing radiation.

3. BACKGROUND

There are multiple convergent lines of evidence suggesting that apoE (apolipoprotein-E) plays an important role in modifying clinical outcome in acute and chronic neurological diseases. These clinical observations, based on apoE genotype of the patient, are consistent with murine models of stroke and traumatic brain injury (TBI) in which apoE exerts neuroprotective effects (Laskowitz et al. 1997, Sheng et al. 1998, 1999, Lynch et al., see below).

ApoE is a 299 amino acid protein with multiple biological properties. First identified for its role in the transport and metabolism of cholesterol and triglycerides, apoE serves as a ligand for the low density lipoprotein (LDL) receptor, the LDL-receptor related protein (LRP) and the very low density lipoprotein (VLDL) receptor (Weisgraber 1994). In addition to its role in cholesterol metabolism, recent compelling clinical data suggests that apoE also plays a significant role in the neurobiology of acute and chronic human disease. There are three common human isoforms, designated apoE2, apoE3, and apoE4 which differ by single amino acid interchanges at residues 112 and 158 (Weisgraber 1994). Presence of the APOE4 allele has been associated with increased susceptibility of developing late onset familial and sporadic Alzheimer's disease (AD). Recent clinical evidence also strongly implicates the presence of the APOE4 allele with poor outcome following acute brain injury (See, Laskowitz et al. 1998a, 1998b, Crawford et al. 2002).

It has been observed that apoE influences development of late onset and familial AD. This effect is robust and dose-dependent, such that homozygous individuals with an APOE4/4 genotype have an approximately 20-fold increased risk of developing AD, and heterozygous individuals with an APOE3/4 genotype have a 4-fold increased risk relative to patients who are homozygous for the most common APOE3/3 genotype (Strittmatter et al., 1993; Corder et al., 1993; reviewed by Laskowitz et al., 1998a). This observation has led to a resurgence of interest in the function of apoE in the mammalian central nervous system (CNS). Because of its association with AD, multiple laboratories have examined interactions between apoE and proteins believed to play a role specific to the pathogenesis of AD. Thus, several laboratories have described isoform-specific interactions between apoE and Abeta or apoE and tau (Strittmatter et al. 1994; Gallo et al. 1994; Fleming et al. 1996; reviewed by Laskowitz et al., 1998a). The role of apoE in the CNS, however, remains undefined and it is unclear which of these interactions are relevant in human neurodegenerative disease.

Traumatic brain injury (TBI) is a leading cause of injury-related death and disability among children, young adults and the elderly in the United States. Epidemiological data have demonstrated the serious socioeconomic impact of TBI to society estimating that the cost of hospital care alone exceeds $1 billion per year. The estimated incidence of TBI doubles between the ages of 5 and 14 years, and peaks for both males and females during early adulthood to approximately 250 per 100,000. Because the lives of most survivors of moderate to severe TBI involve chronic, life-long neurological disabilities with varying degrees of dependence, the cost in individual suffering, family burden, and financial burden to society may be greater for those who have more years to live. Thus, there is a need for improved treatments for TBI.

U.S. application Ser. No. 10/252,120, filed Sep. 23, 2002, discloses methods of using apoE analogs, including COG133, to treat or ameliorate the neurological effects of cerebral ischemia or cerebral inflammation. COG133 is a small truncated peptide, comprised of residues 133-149 of the entire apoE protein. While COG133 has proved useful in animal studies, it has a limited treatment window within which it must be administered. Thus, there is still a need for improved treatments for TBI.

In addition to TBI, toxicities associated with chemotherapy and radiotherapy can adversely affect short and long-term patient quality of life, can limit the dose and duration of treatment, can be life-threatening, and may contribute to both the medical and non-medical care costs. Adverse consequences of cancer treatment have led to the development of specific agents designed to ameliorate or eliminate certain chemotherapy- and radiotherapy toxicities. The ideal chemotherapy- and radiotherapy-protectant agent would prevent all toxicities, from non-life-threatening side effects (alopecia) to irreversible morbidities (hearing loss, neurotoxicity) to potentially fatal events (severe cardiomyopathy, severe thrombocytopenia), without adversely affecting the antitumor efficacy of the cancer therapy, and would be easy to administer and relatively nontoxic in its own right. However, most agents developed to date have a much narrower spectrum of toxicity protection (Hensley et al., 1999).

Xerostomia and mucositis are major toxicities that are associated with radiation therapy. The risk of these complications is related to the area undergoing radiation, the dose and schedule of radiation therapy, whether radiation therapy is combined with chemotherapy, and a number of host-disease-related factors that are only partially understood (Mossman, 1994). Although these toxicities are rarely associated with mortality, the morbidity can be quite significant for patients, with acute and long-term consequences. Xerostomia is the most common toxicity associated with standard fractionated radiation therapy to the head and neck region. Whereas acute xerostomia from radiation is due to an inflammatory reaction, late xerostomia, which includes xerostomia occurring 1 year after radiation, reflects fibrosis of the salivary gland and, as such, is usually permanent. Xerostomia results in symptoms of dry mouth; this affects the patient's ability to eat and speak. Additionally, patients with xerostomia are at an increased risk for dental caries, oral infections, and osteonecrosis.

Radiotherapy is the primary treatment for patients with brain cancers. Independent of the modality with which the radiation is delivered to the brain (medical therapy, attacks or nuclear accidents), the brain typically responds in a slow manner with severe clinical symptoms indicating brain cell death (Fike et al., 1988). While these problems are severe and may be fatal over a course of months, less severe acute symptoms are also debilitating in the days to weeks following radiotherapy (Mandell et al., 1990).

The reasons for the death and/or dysfunction of brain cells are not precisely known, but are thought to arise from a variety of responses following the application of radiation. Ionizing radiation causes damage to living tissues through a series of molecular events depending on the radiation energy. Acute radiation damage is due to the aqueous free radicals, generated by the action of radiation on water. The major free radicals resulting from aqueous radiolysis are OH., H., $HO_2$, $H_3O^+$, etc. (Scholes, 1983; Pradhan et al., 1973; Dragaric and Dragaric, 1971). These free radicals react with cellular macromolecules, such as DNA, RNA, proteins, and membranes and cause cell dysfunction that may ultimately lead to mortality. The radiation damage to a cell is potentiated or mitigated depending on several factors, such as the presence of oxygen, sulflaydryl compounds and other molecules in the cellular milieu (Pradhan et al., 1973; Bacq 1965). In the presence of oxygen, hydrated electrons and H atoms react with molecular oxygen to produce radicals, such as $HO_2$, $O_2^-$, apart from other aqueous free radicals (Baraboi et al., 1994; Biakov and Stepanov, 1997).

Beyond the direct effects of radiation to generate radical species, several reports document the release of cytokines in the brain following radiation treatment (e.g., Girinsky et al., 1994; Hong et al., 1995; Chiang et al., 1997). In particular, Hong et al. (1995) report that mRNA for tumor necrosis factor alpha (TNFa), interleukin 1 alpha and beta (IL1a and IL1b) significantly increased in the brains of mice receiving a single 25 Gray (Gy) dose of brain irradiation, a dose that translates to less that 10% mortality. To a lesser extent, interleukin 6 (IL6) is also induced in a dose dependent fashion with increasing radiation dose. Total body irradiation generated a similar pattern of cytokine induction, but the levels of induction were much less than those seen with brain-specific irradiation. These observed changes in cytokine levels following irradiation are consistent with the astrocytosis and microgliosis associated with the typical innate immune response that the brain mounts in response to disease and/or invasion of pathogens. As reported in our recent publication (Lynch et al. 2003), peripheral treatment with lipopolysaccharide (LPS) can also induce a brain inflammatory response which includes astrocytosis, microgliosis and cytokine release similar to that seen by these authors with radiation treatments.

Three agents are currently approved by the United States Food and Drug Administration (FDA) for chemotherapy and/or radiotherapy protection: dexrazoxane, mesna, and amifostine. However, each of these approved agents has significant issues that limit their efficacy. Dexrazoxane and mesna each have relatively limited spectra of toxicity protection, cardiac and urothelial, respectively, whereas amifostine has a broader potential cytoprotection spectrum. The good news is that these agents (with the probable exception of mesna) act systemically, are not clearly targeted to one specific cell type, and probably function to protect most cell types. Unlike myelosuppression or acute nausea/vomiting, measurement of the toxicities associated with these agents are more difficult or labor-intensive to reproducibly assess in clinical trials because of outcome subjectivity (neurotoxicity), latent onset (cardiomyopathy), or unclear clinical relevance (asymptomatic increases in serum creatinine, microscopic hematuria, or asymptomatic decreases in cardiac ejection fraction) (Hensley et al., 1999).

Amifostine, formerly known as WR-2721 and whose active metabolite is an aminothiol, can protect cells from damage by scavenging oxygen-derived free radicals. This drug arose from a classified nuclear warfare project sponsored by the United States Army and was ultimately selected from a group of more than 4,400 chemicals screened because of its superior radioprotective properties and safety profile (Schucter and Glick, 1993). Subsequently, amifostine was evaluated for its potential role in reducing the toxicity of radiation therapy and of chemo therapeutic agents that alter the structure and function of DNA, such as alkylating agents and platinum agents. Unlike dexrazoxane and mesna, for which the protective effects are directed against specific organs, amifostine has been evaluated as a broad-spectrum cytoprotective agent. A profile emerged from preclinical studies that demonstrated the ability of amifostine to selectively protect almost all normal tissues, except the central nervous system (CNS) and neoplastic tissues, from the cytotoxic effects of radiation therapy (Schucter and Glick, 1993; Coleman et al., 1988). Accordingly, there remains a significant need for effective treatments to reduce the effects of radiation and radiotherapy, particularly in the brain and CNS.

Inflammatory bowel disease (IBD), also known as Crohn's Disease or ulcerative colitis, affects approximately 1 million Americans with inflammation of the intestines, abdominal pain, cramping, and diarrhea. These symptoms vary in severity, but are often debilitating for patients to the extent that they greatly alter their quality of life. There are a wide array of therapies available, with nearly all patients requiring a combination of treatment modalities depending on the severity of disease. These treatments, however, are often very expensive as is the case with infliximab (anti-TNF monoclonal antibody), and typically display major unwanted side-effects such as seen with corticosteroids and immunosuppressants that include risk of infections or malignancies, diabetes, pancreatitis, and severe bone loss. In addition to these problems, the extensive morbidity faced by IBD patients is a clear driving factor for continued efforts to develop new and effective therapies. Although apoE appears to have beneficial effects in innate immunity, as evidenced by loss of innate immunity to systemic infection and exacerbation of sepsis and inflammation in apoE-deficient mice, the role of apoE in intestinal inflammation remains completely unexplored.

4. SUMMARY

The present invention provides analogs and derivatives of COG133, a truncated peptide comprised of residues 133-149 of apoE. This truncated apoE peptide, referred to as COG133 (LRVRLASHLRKLRKRLL (SEQ. ID. NO. 1)) proved useful in treating or reducing cerebral ischemia or cerebral inflammation. U.S. application Ser. No. 10/252,120, filed Sep. 23, 2002, incorporated herein by reference in its entirety. In an animal model however, COG133 is most effective when administered immediately following TBI. The compounds of the present invention provide a wider therapeutic window for the treatment and prevention of neurological effects of traumatic brain injury. Therapeutic window refers to the time period during which the compounds of the invention can be effectively administered following TBI. By increasing the therapeutic window, the compounds of the present invention can be administered at greater time intervals following TBI and effectively treat or prevent neurological effects of TBI, decrease cerebral inflammation or ischemia or improve cognitive function following TBI. In addition, the compounds of the present invention provide enhanced efficacy, a greater therapeutic index and a longer therapeutic window for the treatment and prevention of neurological effects of traumatic brain injury.

The present invention also provides methods for the use of the compounds described above. For instance, the compounds of the present invention can be used for the treatment of central nervous system (CNS) disorders and injuries, including traumatic brain injury, Alzheimer's, cerebral ischemia, cerebral edema or the reduction of glial or microglial activation. The present invention also provides methods for the amelioration of symptoms associated with CNS trauma, inflammation or cerebral ischemia. In one embodiment, the present invention provides methods for reducing neuronal cell death or suppressing macrophage activation.

In treating CNS disorders and injuries, the blood brain barrier (BBB) drastically limits the transport of polar molecules, such as peptides, into the brain. Preliminary data in vivo indicate that the efficacy of COG133 and other ApoE peptide mimetics can be significantly improved by conjugation to a protein transduction domain (PTD). PTDs are short basic peptides that promote the intracellular delivery of cargo that would otherwise fail to, or only minimally, traverse the cell membrane. However, the ability of a PTD to transport cargo intracellularly does not guarantee it is capable of transport through the BBB, which is significantly more complex of a process, and the number of PTDs tested for the transport of cargo across the BBB in vivo has been relatively few. Therefore, the appropriate PTD for BBB transport needs to be determined empirically, and/or created by modifications of known PTDs. The present invention provides compounds comprising PTD conjugations of apoE analogs and derivatives, including COG133 and derivatives and analogs thereof.

The present invention also provides methods of using the compounds described herein to treat, prevent or ameliorate central nervous system (CNS) injuries and disorders and the like in peripheral tissues such as arthritic joints, lungs and heart. In one embodiment, the present invention also provides methods for reducing neuronal cell death or suppressing macrophage activation. In another embodiment, the present invention provides methods for treating atherosclerosis or reducing atherosclerotic plaques. In yet another embodiment, the present invention provides methods for the treatment, prevention or amelioration of the symptoms of bacterial sepsis.

One aspect of the present invention provides methods for suppressing glial or microglial activation, either in vitro or in a mammalian subject, by administering at least one ApoE analog as described above. In one embodiment, the methods provide that the compound can be administered in an amount that reduces glial or microglial activation.

One aspect of the present invention provides methods of treating or ameliorating symptoms associated with CNS trauma, CNS inflammation, cerebral ischemia or cerebral edema by administering at least one compound as described above. The at least one compound can be administered in an amount that reduces CNS trauma, CNS inflammation, cerebral ischemia or cerebral edema as compared to that which would occur in the absence of the compound. In certain embodiments, the methods of the invention reduce CNS trauma, CNS inflammation, cerebral ischemia or cerebral edema following traumatic brain injury. In certain embodiments, the methods hasten recovery from traumatic brain injury. In certain embodiments, the methods improve functional recovery or cognitive function following traumatic brain injury.

In one embodiment, the present invention provides methods of reducing neuronal cell death associated with glutamate excitotoxicity or N-methyl-D-aspartate (NMDA) exposure in a mammalian subject by administering to said subject at least one compound of the present invention. The at least one compound can be administered in an amount that reduces neuronal cell death associated with glutamate toxicity as compared to reduction that would occur in the absence of the compound.

In another embodiment, the present invention provides methods of suppressing macrophage activation in a mammalian subject, by administering at least one compound described herein. The at least one compound can be administered in an amount that suppresses macrophage activation as compared to activation that would occur in the absence of the compound.

In one embodiment, the present invention provides methods of treating or ameliorating the symptoms of arthritis or rheumatic diseases. In certain embodiments, the methods provide for the treatment or amelioration of the symptoms of rheumatoid arthritis, psoriatic arthritis, ankylosing spondilitis and the like.

In one embodiment, the present invention provides methods of treating or ameliorating the symptoms of multiple sclerosis (MS). In certain embodiments, the methods provide for the treatment or amelioration of the symptoms of relapsing/remitting MS, secondary progressive MS, progressive relapsing MS or primary progressive MS comprising administering at least one compound described herein.

In one embodiment, the present invention provides methods of administering the compounds during or contemporaneously with coronary artery bypass graft (CABG) surgery.

In another embodiment, the present invention provides methods of treating atherosclerosis or of reducing the formation of atherosclerotic plaques, comprising administering at least one compound described herein. The at least one compound can be administered in an amount that reduces the formation of atherosclerotic plaques as compared to that which would occur in the absence of the compound. In certain embodiments, the methods provide for the prevention of atherosclerotic plaque development by administering at least one compound as described herein.

In yet another embodiment, the present invention provides methods for the treatment, prevention or amelioration of the symptoms of bacterial sepsis by the administration of at least one compound as described herein. The at least one compound can be administered in an amount that reduces sepsis-associated inflammation as compared to that which would occur in the absence of the compound.

In certain embodiments, the invention provides pharmaceutical compositions comprising at least one of the compounds described herein. In certain embodiments, the invention provides pharmaceutical compositions comprising at least one compound described herein with another drug for the treatment, prevention or amelioration of CNS or neurologic injury, rheumatic diseases, multiple sclerosis, CABG surgery, atherosclerosis or bacterial sepsis. The pharmaceutical compositions of the invention can be provided in such a way as to facilitate administration to a subject in need thereof, including, for example, by intravenous, intramuscular, subcutaneous or transdermal administration. See, Remingtons Pharmaceutical Sciences, 19th ed. Remington and Gennaro, eds. Mack Publishing Co., Easton, Pa., incorporated herein by reference. The methods of the present invention further provide for various dosing schedules, administration times, intervals and duration to treat, prevent or ameliorate the disorders described herein. Also included are functional variants of the disclosed compounds and variants identified using the assays disclosed in the present invention, wherein such compounds mediate the functional effects disclosed herein. Consistent therewith, the invention also includes use of the disclosed compounds and functional variants thereof in methods of making medicaments for treating the various diseases and disorders discussed herein.

The present invention further provides novel treatments for protection against one or more effects of radiation and radiotherapy, comprising administering to a subject in need thereof, ApoE protein or one or more ApoE mimetic peptides. The methods may be used for the treatment of subjects undergoing total body irradiation (TBI), for instance as part of a blood or bone marrow transplantation procedure. The methods may also be used to treat subjects undergoing radiation therapy, for instance for the treatment of cancer, or for the protection or treatment of individuals exposed to environmental radiation.

The present invention further provides novel treatments for inflammatory bowel disease (IBD), Crohn's Disease or ulcerative colitis, comprising administering to a subject in need thereof, ApoE protein or one or more ApoE mimetic peptides in an amount that reduces the symptoms of IBD, Crohn's Disease or ulcerative colitis as compared to that which would occur in the absence of the compound.

5. BRIEF DESCRIPTION OF THE FIGURES

FIG. 1 provides a helical wheel projection of COG133 peptide;

FIG. 2 provides exemplary mimetics;

FIG. 3 provides tricyclic scaffolds as helix mimetics;

FIG. 4. The improvement in rotorod performance over time for mice following traumatic brain injury (TBI) when treated with peptide 432 (AcASHLRKLAibKRLL (SEQ. ID. NO. 6)) at 4 mg/ml and 1 mg/ml and saline. The y-axis is the percentage performance on the rotorod. Baseline performance on the rotorod prior to TBI is 100%.

FIG. 5 provides a picture of a pneumatic impact device used for the murine closed head injury model; and FIGS. 6 (A), (B) and (C) provide pictures of mice treatment and handling prior to pneumatic impact.

FIG. 7 provides graphs showing suppression of release of nitric oxide (A) and TNFa (B) in LPS-treated BV2 microglia cells. COG1410 exhibits significantly greater potency compared to COG133.

FIG. 8 provides a graph of rotorod results showing COG1410 is neuroprotective when administered 120 minutes after TBI compared to saline, $p<0.05$; COG133 is not significantly different than saline, $p>0.05$.

FIG. 9 provides a graph showing plasma concentration of COG133 over time.

FIG. 10 provides a graph showing the mean clinical score of COG133 versus control peptides in a mouse model of murine experimental autoimmune encephalomyelitis.

FIG. 11 provides graphs showing that MOG peptide induces macrophage production of NO (A) and TNF alpha (B), while LPS/IFN gamma treatment induces macrophage production of NO(C), TNF alpha (D) and IL-6 (E).

FIG. 12 provides graphs showing that COG133 inhibited MOG-mediated production of NO (A) and TNF alpha (B) in a concentration dependent manner.

FIG. 13 provides graphs showing that COG133 inhibited LPS/IFN gamma-induced production of NO (A), TNF alpha (B) and IL-6 (C) in a concentration dependent manner.

FIG. 14 provides graphs showing that COG134, containing (Antennapedia-COG133 chimera) inhibited MOG-mediated production of NO (A), and LPS/IFN gamma-induced production of NO (B), TNF alpha (C) and IL-6 (D) in a concentration dependent manner, whereas the prefix peptide alone (P) showed no activity.

FIGS. 15A and 15B provide the results of rotorod and Morris Water Maze tests on mice treated following traumatic brain injury;

FIG. 16 provides a graph of nitrite release suppression by COG133;

FIG. 17 provides a graph of nitrite release suppression by TAT-COG133;

FIG. 18 provides a graph of nitrite release suppression by Penetratin-COG133.

FIG. 19 provides a graph showing PTDCOG133 conjugates inhibit LPS-mediated nitric oxide production.

FIG. 20 provides a graph of rotorod latency for mice treated with COG133 or penetratin-COG133, 90 minutes following TBI. Mice treated with COG133, 90 minutes following TBI were not different from saline treated mice. However, mice receiving penetratin-COG133 90 minutes following TBI exhibited significantly increased latencies compared to saline treated mice.

FIG. 21 provides a graph of rotorod latency for mice treated with synB3-COG133 2 hours following TBI. Mice treated with SynB3-COG133 at 2 hours following TBI performed significantly better than saline treated mice on the rotorod task, $p<0.01$. Treatment with COG133, 2 hours following TBI was not effective (data not shown).

FIG. 22 provides a graph comparing resistance to radiation induced death of ApoE-containing animals versus apoE knockout animals. A group of 10 wild type animals were exposed to 7 Gy of TBI and 100% survived to Day 30 post irradiation. A group of 10 apoE knockout animals were exposed to 7 Gy of TBI and 80% survived to Day 30 post irradiation. A group of 10 wild type animals were exposed to 8 Gy of TBI and 40% survived to Day 36 post irradiation. A group of 10 apoE knockout animals were exposed to 8 Gy of TBI and 0% survived to Day 13 post irradiation (Y axis=Percent Survival; X axis=days post total body irradiation).

FIG. 23 provides a graph showing the survival of apolipoprotein-e containing wild-type mice following 10 gray of total body irradiation in the presence or absence of cog133, a peptide mimetic of apolipoprotein-e. intraperitoneal administration of cog133 (4 mg/kg in 100 ul saline vehicle) at 1 minute post-tbi improved survival compared to saline vehicle controls. ip administration of 4 doses of cog133 (each dose at 4 mg/kg in 100 ul saline) at 1 hour, 1 day, 2 days, and 3 days post-tbi significantly improved survival compared to controls, p<0.01 by repeated measures anova.

FIG. 24A provides a graph showing COG133 treatment significantly reduces plasma levels of TNFα at 1 hour post-LPS injection compared to LPS-only controls (p<0.05). TNFα levels at 0, 3 and 24 hours were not different from background controls. From Lynch et al. 2003.

FIG. 24B provides a graph COG133 treatment significantly reduces plasma levels of IL-6 at 1 and 3 hours post-LPS injection compared to LPS-only controls (p<0.05). IL-6 levels at 0 and 24 hours were not different from background controls. From Lynch et al. 2003.

FIG. 25 is an image showing that COG133 inhibited demyelination in spinal cord of MOG-induced EAE mice. Animals were sacrificed on dpi 30, whole spinal cord was removed and 5-mm-thick sections were made from cervical (A, D), thoracic (B, E) and lumbar (C, F) segments. COG133-treated animals (D, E, F, H) and Normal Saline treated controls (A, B, C, G) were stained with Luxol fast blue (for myelin, stained in blue) and then counterstained with eosin (showing peripheral infiltrates, in red-purple). Picture G is the magnified inset of A and picture H is the magnified inset of D.

FIG. 26 presents a graph showing COG compounds produce dose-dependent inhibition of nitric oxide release from mouse BV2 microglial cells stimulated with LPS for 40 hours. From these data, the approximate IC50 of COG133 is 2 uM, IC50 of COG1410 is 2 uM, and IC50 of COG4502 is 10 nM. Each data point is the average of 3 replicates. Error bars are shown, but are smaller than the symbols used to graph the results.

FIG. 27 presents a graph showing COG4502 produces a dose-dependent inhibition of TNFa or IL6 release from mouse peritoneal macrophages stimulated in culture with gamma interferon and LPS for 24 hours. Significance is marked with one asterisk for the p<0.05 level and with two asterisks for the p<0.01 level vs. controls.

FIG. 28 presents a graph showing that colonic arginase and iNOS induction after $C.$ $rodentium$ infection for 14 days. A, arginase I, arginase II, and iNOS mRNA levels by RT-PCR. B, Western blotting for arginase I and II. In A and B, each lane is tissue from a different mouse.

FIG. 29 presents an image of immunohistochemical detection of arginase I (A-C, H) and iNOS (D-F, I). A, uninfected mouse (200×). B-C, $C.$ $rodentium$-infected mouse (B, 200×; C, 400×) stained for arginase I; D-F same tissues stained for iNOS. G, serial section of B and E, in which rabbit IgG replaced primary Ab, and shows no staining. H and I, different colitic mouse (200×), stained for arginase I, and iNOS, respectively.

FIG. 30 presents a graph showing Colonic arginase activity (A), serum NO concentration (B), and serum L-Arg concentration (C) in control (Ctrl) or $C.$ $rodentium$-infected ($C.$ $rod$) mice, n=3 for Ctrl and n=6 for $C.$ $rodentium$. *p<0.05, ***p<0.001.

FIG. 31 presents a graph showing changes in survival (A), body weight (B), and colon weight (C) in WT and iNOS$^{-/-}$ mice infected with $C.$ $rodentium$. Mice were given L-Arg starting day 1 post-infection or water alone, n=31 for WT infected with $C.$ $rodentium$ (v), 32 for L-Arg-treated WT infected mice (□), 23 for infected iNOS$^{-/-}$ mice (σ), and 20 for infected iNOS$^{-/-}$ mice given L-Arg (O). For A-C: *p<0.05, ***p<0.001 vs day 0; §p<0.05, §§p<0.01, §§§p<0.001 vs WT-water; #p<0.05 vs iNOS$^{-/-}$ without L-Arg.

FIG. 32 present a graph of histologic findings in H & E stained colon of $C.$ $rodentium$-infected mice. A, Uninfected WT, normal tissue. B, Infected WT with severe colitis. C, Histologic improvement in iNOS$^{-/-}$ mice. D, Further improvement in L-Arg-treated iNOS$^{-/-}$ mice. E, Histology scores (0-12 scale) in $C.$ $rodentium$ colitis, n=19 for WT, 17 for WT-L-Arg, 12 for iNOS$^{-/-}$, and 11 for iNOS$^{-/-}$-L-Arg. **p<0.01 vs WT, §p<0.05 vs iNOS$^{-/-}$. All were inoculated with the same amount of $C$ $rodentium$ (5×10$^8$ CFU/mouse) and sacrificed on days 12-14; mice that died earlier were excluded.

FIG. 33 presents a graph showing cytokine mRNA levels for IFN-γ (A), TNF-α (B), and IL-1 (C) in $C.$ $rodentium$-infected mice vs uninfected WT control. mRNA levels were determined by real-time PCR. n=3-5 per group. **p<0.01 vs WT uninfected control; §p<0.05, §§p<0.01 vs WT $C.$ $rodentium$.

FIG. 34 presents a graph showing colonic ODC activity (A) and polyamine concentrations (B) in $C.$ $rodentium$-infected WT mice, n=4 for control, n=7 for $C.$ $rodentium$, n=5 for $C.$ $rodentium$+L-Arg. *p<0.05, **p<0.01 vs control; §§p<0.01 vs $C.$ $rodentium$.

FIG. 35 present a graph showing that mice were given 4% DSS in the drinking water for 6 days, and tissues harvested on day 10. A, mRNA levels of arginase I and II, and iNOS, assessed by RT-PCR. B, protein levels, assessed by Western blotting.

FIG. 36 presents a graph showing the effect of DSS colitis on arginase I protein expression. Tissues were fixed in formalin at sacrifice and immunohistochemistry performed by the immunoperoxidase technique using a polyclonal antibody to arginase I (1:400 dilution; Research Diagnostics, Inc.). Note the staining of epithelial cells, especially in the crypts, and inflammatory cells in the ulcerated areas.

FIG. 37 presents a graph showing improvement in DSS colitis with L-Arg (1%), or iNOS knockout. A, survival; B, body wt; C, colon wt. In A, *p<0.05 vs. time 0, §p<0.05 vs. WT; in B and C, *p<0.05, **p<0.01 vs. WT, #p<0.05, ##p<0.01 vs. iNOS$^{-/-}$. n=12-21.

FIG. 38 presents a graph showing histologic findings in H & E stained slides from mice with DSS colitis. A, WT mice with severe colitis; B, Improvement in WT mice with L-Arg, C, further improvement with iNOS$^{-/-}$+L-Arg. D, Histology scores (0-40 scale). *p<0.05, **p<0.01 vs. WT, n=10.

FIG. 39 presents a graph showing cytokine mRNA levels, determined by real-time PCR, for IFN-γ (A), TNF-α (B), and IL-1 (C) in DSS colitis tissues vs. WT control. n=3-6 per group. **p<0.01 vs. WT control; p<0.05, §§p<0.01 vs. WT DSS; #p<0.05 vs. iNOS$^{-/-}$.

Figure 42:
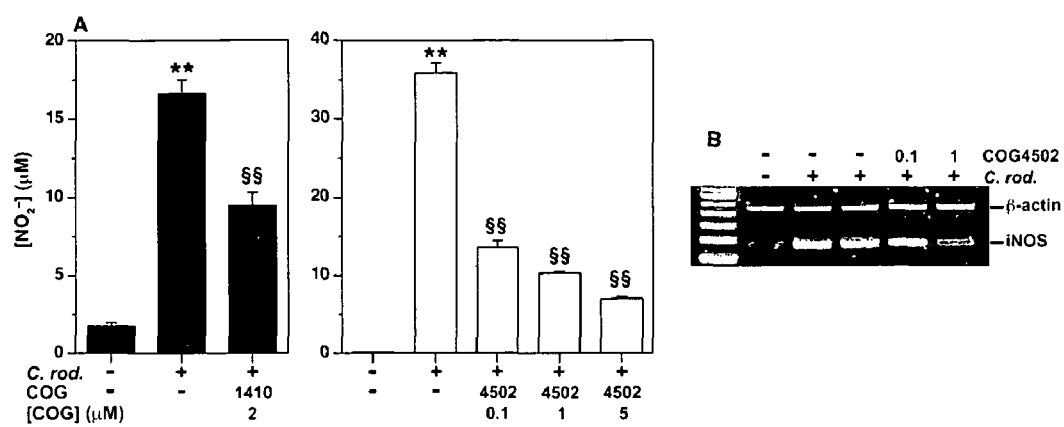

FIG. 42 is graph showing inhibition of $C.$ $rodentium$-induced iNOS by COG peptides in murine macrophages. RAW 264.7 cells were stimulated with French-pressed lysates of $C.$ $rodentium$ at a multiplicity of infection of 100. A, NO production was measured by determination of $NO_2^-$ levels. **p<0.01 vs. control, §§p<0.01 vs. $C.$ $rodentium$ alone. B, RT-PCR for iNOS.

6. DETAILED DESCRIPTION OF THE INVENTION

The present invention provides compounds, compositions and methods for the treatment of central nervous system (CNS) disorders, including cerebral edema, cerebral ischemia and Alzheimers as well as rheumatic disease, multiple sclerosis, CABG surgery, atherosclerosis, sepsis, colitis and radioprotection. The compounds, compositions and methods described herein ameliorate symptoms associated with CNS disorders and improve cognitive function.

Compounds

Without being bound to any theory, there is evidence to support at least two distinct mechanisms for apoE action in the injured brain: glial modulation and neuroprotection. The brain has a limited repertoire of responses to acute and chronic injury. Glial activation with subsequent release of reactive oxygen species (ROS), glutamate, proteases, and inflammatory cytokines is believed to contribute to neuronal injury in both neurodegenerative processes such as those observed in Alzheimer's Disease (AD) and in acute brain injury. Applicants have recently demonstrated that apoE downregulates glial activation, release of nitric oxide (NO) and release of inflammatory cytokines in mixed glial cultures and in purified microglial cultures following stimulation with lipopolysaccharide (LPS) (See, Laskowitz et al. 1997). These in vitro observations appear to be biologically relevant as the expression of inflammatory genes is significantly upregulated in the brains of apoE deficient mice injected with LPS or subjected to closed head injury when compared to matched controls expressing mouse apoE protein (Lynch et al. 2001). The association between apoE and modulation of glial activation and inflammatory cytokine release is particularly intriguing in light of a recent report suggesting that apoE induces a signaling response in macrophages which are closely related to the brain specific macrophages known as microglia (Misra et al. 2001). Further evidence of an apoE/glial-activation association is provided by clinical observations that progression of disability in multiple sclerosis appears to depend upon the particular apoE isoform that the patient expresses (Chapman et al. 1999).

Another mechanism by which apoE may play a role in neurological disease is by exerting direct neuroprotective effects. A growing body of evidence implicates an isoform-specific role for apoE in promoting neurite outgrowth (Nathan et al., 1994; Bellosta et al., 1995; Holtzman et al., 1995), protecting against oxidative stress (Hayek et al., 1994; Miyata and Smith, 1996; Matthews and Beal, 1996), and interacting with growth factors (Gutman et al., 1997) to promote neuronal survival. Applicants recently demonstrated that apoE exerts neuroprotective effects on primary neuronal cultures in bioassays of glutamate-induced excitotoxicity and oxidative stress which are consistent with the protective effects of apoE seen in murine models of focal and global ischemia (Sheng et al., 1998a & 1999b). Misra et al. 2001, along with others, have recently demonstrated that apoE initiates a calcium-dependent signaling cascade in neurons. Thus, one possibility is that these neuroprotective effects are related to the ability of apoE to induce a signaling cascade in neurons (Muller et al., 1998; Misra et al. 2001).

A large number of analogs of the apoE 130-150 peptide were previously created and their activity tested in a cell-based assay for suppression of release of inflammatory cytokines and free radicals and in receptor binding assays. Lynch et al., 2003, *J. Biol. Chem.* 278(4), 48529-33 and U.S. application Ser. Nos. 10/252,120 (filed Sep. 23, 2002), 09/957,909 (filed Sep. 21, 2001) and 09/260,430 (filed Mar. 1, 1999), now abandoned, which claims the benefit of U.S. Provisional Application No. 60/077,551 (filed Mar. 11, 1998), the contents of each of which are incorporated herein by reference in their entireties.

The present invention provides analogs and derivatives of COG133, a small peptide comprised of residues 133-149 of apoE. This apoE peptide, referred to as COG133 (LRVR-LASHLRKLRKRLL (SEQ. ID. NO. 1)) proved useful in treating or reducing cerebral ischemia or cerebral inflammation. U.S. application Ser. No. 10/252,120, filed Sep. 23, 2002, incorporated herein by reference in its entirety. In an animal model however, COG133 is most effective when administered within 30 minutes immediately following TBI. The present invention provides analogs and derivatives of COG133, including amino acid substitution derivatives, peptide mimetics and fusion protein conjugates, that provide a wider therapeutic window and wider therapeutic index for the treatment and prevention of neurological effects of traumatic brain injury.

Therapeutic window refers to the time period during which the compounds of the invention can be effectively administered following TBI. By increasing the therapeutic window, the compounds of the present invention can be administered at greater time intervals following TBI and effectively treat or prevent neurological effects of TBI, decrease cerebral inflammation or ischemia or improve cognitive function following TBI. The compounds of the present invention, their analogs and derivatives also provide a wider therapeutic index than COG133. Therapeutic index refers to the maximum tolerated dose at which no animal dies divided by the minimal effective dose at which performance after injury is significantly better than saline controls. The compounds of the present invention provide increased CNS penetration or increase the therapeutic window for the treatment and prevention of neurological effects of traumatic brain injury. CNS penetration refers to the ability of a compound, including a peptide, to cross the blood brain barrier and enter the Central Nervous System (CNS).

Without being bound to any theory, it is hypothesized that PTDs can enhance CNS penetration of compounds, including apoE analog peptides. By increasing CNS penetration, the PTD-apoE analog conjugated compounds described herein can increase the efficacy of the apoE analogs and extend the therapeutic window, i.e., length of time between brain injury and efficacious administration of the apoE analogs, including COG133. Preliminary data indicate that COG133 was neuroprotective when administered up to 30 minutes post TBI, whereas a PTD-COG133 conjugate was equally effective when administered up to 150 minutes following TBI. This represents a substantial increase in the therapeutic window that could dramatically expand the number of patients that can be helped by this novel therapeutic compound. Furthermore, enhancing the BBB penetrability of the apoE analogs, including COG133, can render these compounds useful for the treatment, prevention or amelioration of numerous inflammation-based neurodegenerative diseases, regardless of whether the BBB is compromised.

The PTD conjugates of the invention also provide the added benefit of lowering the amount of drug (COG133) needed to be administered because of specific targeting to the brain. This provides a better therapeutic index for the conjugated compounds, which is the maximum tolerated dose of compound when no death is seen, divided by the minimum effective dose of compound needed to be given to see the desired protective effect. The greater the index, the safer a compound should be because the side effect profile should be decreased at the concentration needed to see the desired protective effect. Different PTD's could be made to preferentially target other specific tissues and/or organs depending on the disorder to be treated.

In one embodiment, the present invention provides compounds for the methods described below. In one aspect, the invention provides compounds that are ApoE analogs. In one aspect, the invention provides compounds that are α-helical peptides. In preferred embodiments, the compounds are analogs and derivatives of COG133, a peptide of the sequence LRVRLASHLRKLRKRLL (SEQ. ID. NO. 1). In more preferred embodiments, the present invention provides peptide compounds containing a sequence selected from the group consisting of:

```
                                           (SEQ. ID. NO. 2)
LRVRLASH-(NMe)-L-RKLRKRLL-NH2

(SEQ. ID. NO. 3)
Ac-ASH-Aib-RKLRKRLL-NH2

(SEQ. ID. NO. 4)
Ac-AS-Aib-LRKLRKRLL-NH2

(SEQ. ID. NO. 5)
Ac-DS-Aib-LRKLRKRLL-NH2

(SEQ. ID. NO. 6)
Ac-ASHLRKL-Aib-KRLL-NH2

(SEQ. ID. NO. 7)
Ac-AS-Aib-LRKL-Aib-KRLL-NH2

(SEQ. ID. NO. 8)
Ac-DR-Aib-ASHLRKLRKR-Aib-L-NH2

(SEQ. ID. NO. 9)
Ac-DS-Aib-LRKLRKR-Aib-L-NH2

(SEQ. ID. NO. 10)
Ac-DR-Aib-ASHLRKL-Aib-KRLL-NH2

(SEQ. ID. NO. 11)
Ac-DS-Aib-LRKL-Aib-KRLL-NH2

(SEQ. ID. NO. 12)
Ac-DR-Aib-AS-Aib-LRKLRKRLL-NH2

(SEQ. ID. NO. 13)
Ac-DR-Aib-ASHLRKLRKRLL-NH2

(SEQ. ID. NO. 14)
Ac-CAS-Aib-LRKL-Aib-KRLL-NH2

(SEQ. ID. NO. 15)
Ac-DS-Aib-LRKL-Aib-KRLL-NH2

(SEQ. ID. NO. 16)
Ac-AS-Aib-LRKL-Aib-KRLV-NH2

(SEQ. ID. NO. 17)
Ac-AS-Aib-LRKL-Aib-KRLM-NH2

(SEQ. ID. NO. 18)
Ac-AS-Aib-LRKL-Aib-KRLI-NH2

(SEQ. ID. NO. 19)
Ac-AS-Aib-LRKL-Aib-KRLA-NH2

(SEQ. ID. NO. 20)
Ac-AS-Aib-LRKL-Aib-KALL-NH2

(SEQ. ID. NO. 21)
Ac-AS-Aib-LRKL-Aib-K(orn)LL-NH2

(SEQ. ID. NO. 22)
Ac-AS-Aib-LRKL-Aib-K(narg)LL-NH2

(SEQ. ID. NO. 23)
Ac-AS-Aib-LRKL-Aib-K(harg)LL-NH2

(SEQ. ID. NO. 24)
Ac-AS-Aib-LRKL-Aib-K(dmarg)LL-NH2

(SEQ. ID. NO. 25)
Ac-AS-Aib-LRKL-Aib-ARLL-NH2

(SEQ. ID. NO. 26)
Ac-AS-Aib-LRKL-Aib-(aclys)RLL-NH2

(SEQ. ID. NO. 27)
Ac-AS-Aib-LRKL-Aib-(azlys)RLL-NH2

(SEQ. ID. NO. 28)
Ac-ASH-Aib-RKL-Aib-KRLL-NH2

(SEQ. ID. NO. 29)
Ac-AS-Aib-LRKL-Aib-KRL-(NLe)-NH2

(SEQ. ID. NO. 30)
Ac-AS-Aib-LRKL-Aib-KR-(NLe)-L-NH2

(SEQ. ID. NO. 31)
Ac-AS-Aib-LRKL-Aib-KR-(NLe)-(Nle)-NH2

(SEQ. ID. NO. 32)
Ac-AS-Aib-LRKL-Aib-K(orn)L-(NLe)-NH2

(SEQ. ID. NO. 33)
Ac-AS-Aib-LRKL-Aib-K(orn)-(NLe)-L-NH2

(SEQ. ID. NO. 34)
Ac-AS-Aib-LRKL-Aib-K(orn)-(NLe)-(Nle)-NH2

(SEQ. ID. NO. 35)
Ac-AS-Aib-LRKL-Aib-K(harg)L-(NLe)-NH2

(SEQ. ID. NO. 36)
Ac-AS-Aib-LRKL-Aib-K(harg)-(NLe)-L-NH2

(SEQ. ID. NO. 37)
Ac-AS-Aib-LRKL-Aib-K(harg)-(NLe)-(Nle)-NH2

(SEQ. ID. NO. 38)
Ac-AS-Aib-L(orn)KL-Aib-KRLL-NH2

(SEQ. ID. NO. 39)
Ac-AS-Aib-L(orn)KL-Aib-K(orn)LL-NH2

(SEQ. ID. NO. 40)
Ac-AS-Aib-L(orn)KL-Aib-KRL-(NLe)-NH2

(SEQ. ID. NO. 41)
Ac-AS-Aib-L(orn)KL-Aib-KRL-(NLe)-(NLe)-NH2

(SEQ. ID. NO. 42)
Ac-AS-Aib-L(orn)KL-Aib-K(orn)L-(Nle)-NH2

(SEQ. ID. NO. 43)
Ac-AS-Aib-L(orn)KL-Aib-K(orn)-(NLe)-(Nle)-NH2

(SEQ. ID. NO. 44)
Ac-ASHLRKLRKRLL-NH2 (apoe138-149)

(SEQ. ID. NO. 45)
Ac-ASHCRKLCKRLL-NH2

(SEQ. ID. NO. 46)
Ac-ASCLRKLCKRLL-NH2

(SEQ. ID. NO. 47)
Ac-CSHLRKLCKRLL-NH2

(SEQ. ID. NO. 48)
Ac-ASHLRKCRKRCL-NH2

(SEQ. ID. NO. 49)
Ac-ASHCRKLRKRCL-NH2
``` wherein (NMe)-L is an N-methylated Leucine, Aib is amino iso-butyric acid, (orn) is ornithine, (narg) is nitroarginine, (NLe) is neurleucine, (harg) is homoarginine, (dmarg) is dimethyl arginine, (aclys) is acetyl lysine, (azlys) is azalysine and Ac is an acetylated amino terminus. The one letter abbreviation for the amino acid residues are well known to those skilled in the art.

The present invention provides protein transduction domains (PTD) conjugated to an apoE analog. PTDs are heterogeneous in size and lack sequence homology, although most share a positive charge and are amphipathic. The PTDs of the present invention are those that facilitate CNS penetration or facilitate intracellular transport. In certain embodiments, PTDs can be antimicrobial peptides such as protegrin 1, Bactenecin 7, Buforin, and Maginin; a host of arginine-rich RNA- and DNA-binding peptides (e.g., HIV-1 transactivating protein (TAT) and *Drosophila* homeodomain transcription factor Antennapedia (a.k.a. Penetratin); chimeric PTDs such as Transportan; lysine- and arginine-rich peptides derived from phage-display libraries; polyarginine; and most recently, β-homolysine oligomers (See, Fisher et al., 2001; Lindsay, 2002; Tung et al., 2003; Leifert et al., 2003; Bogoyevitch et al., 2002; Garcia-Echeverria 2003, incorporated herein by reference in their entireties). In certain embodiments, the PTDs are addition, reverso-, retro-inverso, and enantio-forms of many of the PTDs described herein.

In a preferred embodiment, the present invention provides PTD conjugates selected from the group consisting of:

| | |
|---|---|
| GRKKRRQRRRPPQ | (SEQ. ID. NO. 50) |
| RQIKIWFQNRRMKWKK | (SEQ. ID. NO. 51) |
| RRMKWKK | (SEQ. ID. NO. 52) |
| RGGRLSYSRRRFSTSTGR | (SEQ. ID. NO. 53) |
| RRLSYSRRRF | (SEQ. ID. NO. 54) |
| RGGRLAYLRRRWAVLGR | (SEQ. ID. NO. 55) |
| RRRRRRRR | (SEQ. ID. NO. 56) |

In certain embodiments, the PTD conjugate is RGGRLAYLRRRWAVLGR (SEQ. ID. NO. 55), referred to as SynB5, or RRLSYSRRRF (SEQ ID NO. 54) referred to as SynB3. PTD-apoE conjugate compounds of the invention include, for instance, SynB5-COG133, SynB3-COG133, or SynB5 and SynB3 conjugates of any of the COG133 analogs described herein. Accordingly, PTD transport was initially characterized as receptor- and energy-independent, nonendocytic, and lacking in cell specificity. However, these data were collected through analysis of cellular uptake via fluorescence microscopy on fixed cells or flow cytometry. Several groups have recently demonstrated that data collected in this manner was subject to an artifact of cell fixation (Futaki, 2002; Vives et al., 2003; Suzuki, 2001; Richard et al., 2003; Lundberg et al., 2002; Thoren, et al., 2003, incorporated herein by reference in their entireties). It is becoming clear that a number of these PTDs, e.g., penetratin TAT, poly-arginine; are taken up via endocytosis (Drin et al., 2003; Thoren et al., 2003, incorporated herein by reference in their entireties). The same methodology was also used for analysis of structure-activity relationships of PTDs. The validity of the results of these studies, as well as studies of cell specificity, which were also derived from fixed cells, is therefore called into question. For example, the uptake of penetratin in living cells was recently demonstrated to be endocytic. Furthermore, substitution of two tryptophan residues, previously identified as critical for transcytosis, did not modify the uptake of penetratin (Thoren et al., 2003, incorporated herein by reference in its entirety). Questions regarding mechanism of transport aside, there are numerous reports of the biological effects of cargo carried by PTDs, including peptides, proteins, peptide nucleic acids, oligonucleotides, liposomes, and magnetic nanoparticles, substantiating their capability for translocation (Schwarze et al., 2000; Bogoyevitch et al., 2002; Tung et al., 2003; Vivés et al., 2003, incorporated herein by reference in their entireties). It is becoming clear that our knowledge regarding PTDs needs to be re-evaluated, and that transport mechanisms likely vary among the PTDs, perhaps as their primary structures also vary.

Comparative studies indicated that PTDs are not interchangeable; they differ in uptake rate, concentration required for translocation, toxicity, and cellular context (Thoren et al., 2003; Suzuki et al., 2002; Mai, et al., 2002, incorporated herein by reference in their entireties). Studies using live cells have reported that a PTD can have multiple modes of transport which can differ according to cellular context (Drin et al., 2003; Futaki, 2002; Leifert et al., 2003, incorporated herein by reference in their entireties). Recent data indicate that PTDs exhibit cell specificity, the source of which can be preferential interaction of PTDs with specific cell surface glycosaminoglycans (Mai et al., 2002; Console et al., 2003; Koppelhus et al., 2002, incorporated herein by reference in their entireties). Evidence to this effect comes from studies that show dextran sulfate inhibited uptake of TAT, but not penetratin complexes, and heparin inhibited internalization of TAT and penetratin complexes to different degrees (Console et al., 2003, incorporated herein by reference in their entireties). These data suggest selectively targeting tissues may be possible by optimizing the PTD to target specific cell surface-expressed glycosaminoglycans. Clearly, there is no PTD that is optimal for cargo delivery across the board. PTD, cargo, and target organ all must be taken into account.

In one aspect, the compounds are analogs or peptide mimetics of an apoE protein. In yet another preferred embodiment, the peptide is AcASHLRKLAibKRLL (SEQ. ID. NO. 6) (COG432). In another preferred embodiment, the peptide is Ac-AS-Aib-LRKL-Aib-KRLL-$NH_2$ (SEQ. ID. NO. 7) (COG1410). COG1410 in particular exhibits a 4-fold gain in therapeutic window and a 7.4 fold gain in Therapeutic Index as compared to COG133. In certain embodiments, the present invention provides peptide mimetics that mimic the functionality of the active peptide and methods of making the same, as described in detail hereinbelow.

Compound Preparation

Peptides of the present invention can be produced by standard techniques as are known in the art. Modification of the peptides disclosed herein to enhance the functional activities associated with these peptides could be readily accomplished by those of skill in the art. For instance, the peptides used in the methods of the present invention can be chemically modified or conjugated to other molecules in order to enhance parameters like solubility, serum stability, etc, while retaining functional activity. In particular, the peptides of the invention may be acetylated at the N-terminus and/or amidated at the C-terminus, or conjugated, complexed or fused to molecules that enhance serum stability, including but not limited to albumin, immunoglobulins and fragments thereof, transferrin, lipoproteins, liposomes, α-2-macroglobulin and α-1-glycoprotein, PEG and dextran. Such molecules are described in detail in U.S. Pat. No. 6,762,169, which is herein incorporated by reference in its entirety.

Small molecules that target the conjugate to specific cells or tissues may also be used. It is known that presence of a biotin-avidin complex increases uptake of such modified peptides across endothelial cells. Linkage of peptides to carbohydrate moieties, for example to a β-glycoside through a serine residue on the peptide to form a β-O linked glycoside, enhances transport of the glycoside derivative via glucose transporters (PoIt, R. et al. Proc. Natl. Acad. Sci. USA 91:7144-7118 (1994); Oh et al. Drug Transport and targeting, In Membrane Transporters as Drug Targets, Amidon, G. L. and Sadee, W. eds., pg 59-88, Plenum Press, New York, 1999).

The peptides may have attached various label moieties such as radioactive labels and fluorescent labels for detection and tracing. Fluorescent labels include, but are not limited to, fluorescein, eosin, Alexa Fluor, Oregon Green, rhodamine Green, tetramethylrhodamine, rhodamine Red, Texas Red, coumarin and NBD fluorophores, the QSY 7, dabcyl and dabsyl chromophores, BODIPY, Cy.sup.5, etc.

In another aspect, other naturally occurring or synthetic peptides and proteins may be used to provide a carrier immunogen for generating antibodies to the subject peptides, where the antibodies serve as reagents for detecting the immunomodulatory peptides or for identifying other peptides having a comparable conformation. Suitable carriers for generating antibodies include, among others, hemocyanins (e.g., Keyhole Limpet hemocyanin—KLH); albumins (e.g., bovine serum albumin, ovalbumin, human serum albumin, etc.); immunoglobulins; thyroglobulins (e.g., bovine thyroglobulin); toxins (e.g., diptheria toxoid, tetanus toxoid); and polypeptides such as polylysine or polyalanine-lysine. Although proteins are preferred carriers, other carriers, preferably high molecular weight compounds, may be used, including carbohydrates, polysaccharides, lipopolysaccharides, nucleic acids, and the like of sufficient size and immunogenicity. In addition, the resulting antibodies may be used to prepare anti-idiotypic antibodies which may compete with the subject peptides for binding to a target site. These anti-idiotypic antibodies are useful for identifying proteins to which the subject peptides bind.

Another variation of the therapeutic peptides of the present invention is the linking of from one to fifteen amino acids or analogs to the N-terminal or C-terminal amino acid of the therapeutic peptide. Analogs of the peptides of the present invention can also be prepared by adding from one to fifteen additional amino acids to the N-terminal, C-terminal, or both N- and C-terminals, of an active peptide, where such amino acid additions do not adversely affect the ability of the peptide to bind to receptors at the site bound by a peptides of the invention.

The peptides of the present invention further include conservative variants of the peptides herein described. As used herein, a conservative variant refers to alterations in the amino acid sequence that do not adversely affect the biological functions of the peptide. A substitution, insertion or deletion is said to adversely affect the peptide when the altered sequence prevents or disrupts a biological function associated with the peptide. For example, the overall charge, structure or hydrophobic/hydrophilic properties of the peptide may be altered without adversely affecting a biological activity. Accordingly, the amino acid sequence can be altered, for example to render the peptide more hydrophobic or hydrophilic, without adversely affecting the biological activities of the peptide.

Ordinarily, the conservative substitution variants, analogs, and derivatives of the peptides, will have an amino acid sequence identity to the disclosed sequences SEQ ID NOs: 1-56 of at least about 55%, at least about 65%, at least about 75%, at least about 80%, at least about 85%, at least about 90%, at least about 95%, or at least about 96% to 99%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the peptides of the present invention include molecules having the amino acid sequence disclosed in SEQ ID Nos. 1-56; fragments thereof having a consecutive sequence of at least about 3, 4, 5, 6, 10, 15, or more amino acid residues of the therapeutic peptide; amino acid sequence variants of such peptides wherein an amino acid residue has been inserted N- or C-terminal to, or within, the disclosed sequence; and amino acid sequence variants of the disclosed sequence, or their fragments as defined above, that have been substituted by another residue. Peptide compounds comprising the peptide sequences of the invention may be 15, 20, 25, 30, 35, 40, 45, 50 or more amino acids. Contemplated variants further include those containing predetermined mutations by, e.g., homologous recombination, site-directed or PCR mutagenesis, and the corresponding peptides of other animal species, including but not limited to rabbit, rat, porcine, bovine, ovine, equine and non-human primate species, and derivatives wherein the peptide has been covalently modified by substitution, chemical, enzymatic, or other appropriate means with a moiety other than a naturally occurring amino acid (for example a detectable moiety such as an enzyme or radioisotope).

Therapeutic peptides of the present invention can be in free form or the form of a salt, where the salt is pharmaceutically acceptable. These include inorganic salts of sodium, potassium, lithium, ammonium, calcium, magnesium, iron, zinc, copper, manganese, and the like. Various organic salts of the peptide may also be made with, including, but not limited to, acetic acid, propionic acid, pyruvic acid, maleic acid, succinic acid, tartaric acid, citric acid, benozic acid, cinnamic acid, salicylic acid, etc.

Methods

It was previously found that COG133 peptide significantly suppresses neuronal cell death and calcium influx associated with N-methyl-D-aspartate exposure. U.S. application Ser. No. 10/252,120, herein incorporated by reference in its entirety. Thus, the peptides of the present invention provide the basis for improved therapeutic compositions for treating diseases associated with NMDA excitotoxicity. For instance, NMDA excitotoxicity has been associated with HIV dementia and encephalopy (Perez et al., 2001; Haughey et al., 2001; Doble, 1999).

NMDA excitotoxicity has also been associated with neurolathyrism, amyotrophic lateral sclerosis (ALS) (Doble, 1999; Nguimfack, 2002), schizophrenia, Huntington's chorea, Parkinson's (Nguimfack, 2002; Mytilineou et al., 1997; Klopman and Sedykh, 2002; Le and Lipton, 2001), bipolar disorder (Farber et al. 2002), multiple sclerosis in humans and experimental autoimmune encephalitis (EAE) in animals (Paul and Bolton, 2002), depression, stroke (Le and Lipton, 2001), epilepsy and the inherited neurometabolic disease d-2-hydroxyglutaric aciduria (Kolker et al., 2002), in addition to Alzheimer's Disease (Bi et al., 2002; Bi and Sze, 2002) and traumatic brain injury (Rao et al., 2001; Regner e et al., 2001; Xu and Luo, 2001). NMDA antagonists are also used in clinical anesthesia (Farber et al., 2002), and have been shown to inhibit chronic pain (McKenna and Melzack, 2001; Le and Lipton, 2001), drug tolerance (Cady, 2001) and alcohol dependency in an animal model (Kotlinska, 2001).

Thus, the present invention includes the use of the disclosed peptides and peptide mimetics in methods and pharmaceutical formulations for the treatment of any of the above diseases or disorders, and in combined therapeutic compositions containing other known compounds useful for treating the various disorders. For instance, the peptides and other compounds of the invention can be combined with any known HIV drug, including HIV reverse transcriptase and protease inhibitors, in a combined therapeutic regimen geared toward inhibiting viral replication and preventing or treating HIV dementia, or can be administered alone or with other NMDA antagonists in a supplementary formulation. One author recently commented that, even though antiretroviral therapy of the CNS is essential for improvement in function and prognosis in patients demonstrating AIDS dementia complex, it may also be necessary in the long term to provide additional neuroprotection, blocking secondary mechanisms of neurotoxicity, since a significant portion of toxicity seems to be mediated by indirect mechanisms that continue even during antiretroviral therapy (Clifford, 2002).

In one embodiment, the peptides can be combined with an anti-atherosclerotic drug, including HMG-CoA reductase inhibitors, also termed statins. Suitable statins for use in the methods of the invention include, for example, lovastatin (MEVACOR®, Merck), simvastatin (ZOCOR®, Merck), pravastatin (PRAVACHOL®, Bristol Myers Squibb), rosuvastatin (CRESTOR®, AstraZeneca), fluvastatin (LESCOL®, Novartis) and atorvastatin (LIPITOR®, Warner-Lambert).

Riluzole (RILUTEK®, Rhone-Poulenc) is a substance with glutamate antagonistic properties that is used for neuroprotective treatment in amyotrophic lateral sclerosis and which is currently being tested in clinical trials for treatment of Huntington's disease and Parkinson's disease (Schiefer et al., 2002; Doble, 1999). Schiefer and colleagues recently demonstrated that riluzole prolongs survival time and alters nuclear inclusion formation in a transgenic mouse model of Huntington's disease. Thus, given the NMDA antagonistic role of the peptides and compounds of the invention, these peptides and compounds could be used in pharmaceutical formulations for the treatment of ALS, Huntington's and Parkinson's, alone or in combination with other glutamate antagonists such as riluzole.

L-deprenyl is an inhibitor of monoamine oxidase (MAO)-B that delays the emergence of disability and the progression of signs and symptoms of Parkinson's disease, and is predicted to exert a protective effect from events occurring downstream from activation of glutamate receptors (Mytilineou et al., 1997). MAO-B inhibitors, dopamine receptor antagonists such as levodopa and NMDA receptor antagonists have all been shown to have an antiparkinson effect, and multidrug combinations have been shown to synergistically enhance the antiparkinson effects of the drugs (Klopman and Sedykh, 2002). Thus, given the NMDA antagonistic role of the peptides and compounds of the invention, these peptides and compounds could be used in pharmaceutical formulations for the treatment of Parkinson's, alone or in combination with other NMDA receptor antagonists, MAO-B inhibitors such as L-deprenyl and dopamine receptor antagonists such as levodopa.

The production of free radicals as a result of glutamate excitotoxicity has been implicated in the pathogenesis of schizophrenia (Nguimfack, 2002). Thus, researchers have begun to examine treatment of schizophrenia with antioxidizing substances used in other neurological diseases such as ALS, Parkinson's and Huntington's disease. Given that the NMDA receptor antagonistic peptides and compounds of the invention can be used to inhibit the production of free radicals as a result of glutamate excitotoxicity, these peptides and compounds can be used in pharmaceutical formulations for the treatment of schizophrenia, alone or in combination with other antioxidizing substances.

Anticonvulsant, antiepileptic agents that inhibit NMDA receptor hypofunction have found to be of clinical use in bipolar disorder (Farber et al., 2002). Such agents include phenyloin (DILANTIN®, Pfizer), carbamazepine (TEGRETOL®, Novartis), valproic acid (DEPAKOTE®, Abbott), lamotrigine (LAMICTAL®, GlaxoSmithKline), riluzole (RILUTEK®, Rhone-Poulenc), tetrodotoxin, felbamate (FELBATOL®, Wallace), gabapentin (NEURONTIN®, Pfizer) and ethosuximide (ZARONTIN®, Pfizer). Given that the peptides of the compounds of the present invention also inhibit NMDA receptor-associated neurotoxicity, the peptides and compounds of the present invention can be used alone or in combination with other NMDA receptor antagonists or inhibitors of NMDA receptor hypofunction in pharmaceuticals and methods of treating bipolar disorder or epilepsy.

Multiple sclerosis (MS) is an immunologically mediated disease, as determined by observation of the response to immunotherapy and the existence of an animal model, experimental autoimmune encephalitis (EAE). See, for example, Mix et al., 2004, *J. Neuroimmunol.* 151(1-2): 158-70, Anderson, et al., 2004, *Ann. Neurol.* 55(5):654-9 and Ni et al., 2004, *Mult. Scler.* 10(2): 158-64. Interferon (IFN) beta-1b, IFN beta-1a, and glatiramer acetate (COPAXONE®, Teva), current therapies used for relapsing or remitting MS, have mechanisms of action that address the immunologic pathophysiology of MS (Dhib-Jalbut, 2002). For instance, the interferons bind to cell surface-specific receptors, initiating a cascade of signaling pathways that end with the secretion of antiviral, antiproliferative, and immunomodulatory gene products. Glatiramer acetate, a synthetic molecule, inhibits the activation of myelin basic protein-reactive T cells and induces a T-cell repertoire characterized by anti-inflammatory effects. Several currently marketed treatments, including IV immunoglobulin (GAMAGARD®, Baxter), methotrexate (RHEUMATREX®, American Cyanamid), and azathioprine (IMURAN®, GlaxoSmithKline), are being evaluated as treatments for relapsing-remitting multiple sclerosis in combination with the approved therapies (Calabresi, 2002). Given that the NMDA receptor antagonist memantine (NAMENDA®, Merz) has been shown to prevent the breakdown of and restore the blood-brain barrier and reduce symptoms associated with pathogenesis of EAE in vivo (Paul and Bolton, 2002), the peptides and compounds of the present invention can be used alone or in combination with other NMDA receptor antagonists or in addition to interferons or glatiramer acetate for the treatment of MS in humans.

Using an animal model of persistent human pain, McKenna and Melzack recently showed that pain behavior was significantly reduced by treatment with the NMDA receptor antagonist AP5 (McKenna and Melzack, 2001). Similarly, Von Bergen and colleagues recently demonstrated that intrathecal administration of LY293558, a competitive non-N-methyl-D-aspartate excitatory amino acid receptor antagonist, blocked both sensory and motor responses in rats through 180 min. with complete recovery observed the following day. The effects of LY293558 were more pronounced and sustained than those of bupivacaine, leading the authors to conclude that drugs like LY293558 that block glutamate receptors can be an alternative to local anesthetics for spinal anesthesia in humans (Von Bergen et al., 2002). Thus, the peptides and compounds of the present invention can be used alone or in combination with other NMDA receptor antagonists or in addition to other anesthetic compounds as local anesthetics in humans and animals.

NMDA receptors are also believed to play a major role in the pathophysiology of substance use (Kotlinska, 2001; Soyka et al., 2000). For instance, Kotlinska showed that the NMDA receptor antagonist memantine given prior to ethanol administration prevented the development of ethanol dependence in rats. Jones and colleagues demonstrated that the intensity of morphine withdrawal syndrome was reduced in rat pups pre-treated with the NMDA receptor antagonist, LY235959. Withdrawal behaviors such as head moves, moving paws, rolling, and walking were decreased, and vocalizations were completely eliminated in pups pre-treated with LY2359559 (Jones et al., 2002). According to a recent review, strategies aimed at targeting the basic mechanisms of addiction rely on the premise that addiction is caused by adaptive changes in the central nervous system and that craving, which is the main cause of relapse, depends on dopaminergic mechanisms and requires high general excitability. Thus, pharmacological approaches have involved drugs that reduce neuronal adaptability by inhibiting the calcium entry to neurons both through voltage-gated channels (e.g. nimodipine) and NMDA receptors (e.g. memantine), as well as drugs that stimulate the inhibitory GABAergic system (gamma-vinyl-GABA, baclofen). Thus, the peptides and compounds of the present invention can be used alone or in combination with other NMDA receptor antagonists such as memantine or in addition to other neuronal adaptability compounds such as nimodipine, gamma-vinyl-GABA and baclofen in compositions and methods for the prevention and treatment of alcohol and drug addiction in humans.

Rao et al. reported neuroprotection by memantine after traumatic brain injury in rats (Rao et al., 2001). Other authors recently commented that excessive activation of NMDA receptors can be one of the most important factors to induce secondary cerebral impairments, and NMDA receptor antagonists such as AP5 can protect the brain from edema after brain injury. Thus, the peptides and compounds of the present invention can be used alone or in combination with other NMDA receptor antagonists in compositions and methods for the treatment of brain injury and associated secondary cerebral impairments in humans and animals.

Statins have been shown to be effective in treating patients with head trauma and in reducing inflammation associated with head trauma and Alzheimers Disease. For instance, as reported by McGirt et al., 2002, Stroke, December, 2002, simvastatin treatment was shown to reduce vasospasm and improve functional outcomes in a murine model of subarachnoid hemorrhage (SAH). Further studies have shown that pretreatment with atorvastatin has similar protective effects, suggesting a role for statins as a class of agents effective in improving outcomes in SAH and closed head injury. Thus, the peptides and compounds of the present invention can be used in combination with one or more statin agents in compositions and methods for the treatment of brain injury and associated secondary cerebral impairments in humans and animals, including simvastatin and/or atorvastatin.

New therapies for arthritis include peptides and proteins that bind with tumor necrosis factor. Etanercept (ENBREL®, Amgen) is a dimeric fusion protein consisting of the extracellular ligand binding portion of the human 75 kd tumor necrosis factor receptor linked to the Fc portion of human IgG1. Adalimumab (HUMIRA®, Abbott) is a recombinant human IgG1 monoclonal antibody. Tumor necrosis factor binding proteins have shown outstanding results in slowing the progression and lessening the symptoms of rheumatoid arthritis and other rheumatic diseases. Thus the peptides and compounds of the present invention can be used alone or in combination with other drug for the treatment of rheumatic diseases, including for example, rheumatoid arthritis, ankylosing spondylitis, polyarticular-course juvenile rheumatoid arthritis and psoriatic arthritis.

The present methods and compounds are useful in preventing, treating, or ameliorating neurological signs and symptoms associated with acute CNS injury. As used herein, acute CNS injury includes but is not limited to stroke (caused by thrombosis, embolism or vasoconstriction), closed head injury, global cerebral ischemia (e.g., ischemia due to systemic hypotension of any cause, including cardiac infarction, cardiac arrhythmia, hemorrhagic shock, and post coronary artery bypass graft brain injury), focal ischemia and intracranial hemorrhage. Ischemic damage to the central nervous system can result from either global or focal ischemic conditions. Global ischemia occurs where blood flow to the entire brain ceases for a period of time, such as during cardiac arrest. Focal ischemia occurs when a portion of the brain is deprived of normal blood flow, such as during thromboembolytic occlusion of a cerebral vessel, traumatic head injury, edema and brain tumors. Much of the CNS damage due to cerebral ischemia occurs during the hours or even days following the ischemic condition, and is secondary to the release of cytotoxic products by damaged tissue.

In certain embodiments, the methods of the present invention provide for use of the compounds, before, during or contemporaneously with coronary artery bypass graft (CABG) surgery. According to a study performed at Duke University, published in the New England Journal of Medicine in February, 2001, a substantial proportion of patients after coronary artery bypass surgery experience a measurable impairment in their mental capabilities called the "pump-head" phenomenon. According to this study, 42% of patients tested had at least a 20% drop in test scores after surgery. Further, the decrease in cognitive capacity persisted for 5 years.

The present methods and compounds are also useful in preventing, treating, or ameliorating neurological signs and symptoms associated with chronic neurological disease, including but not limited to Alzheimer's disease (AD) and HIV-associated encephalopathy. The finding by the present inventors that ApoE peptides can be used to suppress glial activation provides a role for the peptides and compounds of the invention in the treatment of any neurological disease involving microglial activation. For example, microglia express markers of activation in AD, suggesting that crucial inflammatory events in AD involve microglia. Such activated microglia cluster near amyloid plaques (Griffin et al., 1995). Microglia are also activated in epilepsy (Sheng et al., 1994).

It has been recently shown that uptake and pathogenic effects of amyloid beta peptide are blocked by NMDA receptor antagonists (Bi et al., 2002). Other studies indicate that anti-inflammatory drugs can delay the onset or progression of AD (Breitner et al., 1995; Rogers et al., 1993). Thus, the peptides and compounds of the present invention can be used alone or in combination with other NMDA receptor antagonists or other known pharmaceuticals and especially anti-inflammatory drugs used for the treatment of AD in compositions and methods for the treatment of AD in humans.

The present methods and compounds are also useful in preventing, treating, or ameliorating the neurological signs and symptoms associated with inflammatory conditions affecting the nervous system including the CNS, including but not limited to multiple sclerosis, vasculitis, acute disseminated encephalomyelitis and Guillain-Barre syndrome. In this regard, the ApoE peptides and other compounds of the invention can be used alone or in combination with other known anti-inflammatory drugs or cytokines to formulate pharmaceutical compositions for the treatment of CNS inflammatory conditions.

The present methods and compounds are useful in preventing, suppressing or reducing the activation of glia in the CNS that occurs as a part of acute or chronic CNS disease. The effect of the present methods and compounds can be assessed at the cellular or tissue level (e.g., histologically or morphometrically), or by assessing a subject's neurological status. The suppression or reduction of glial activation can be assessed by various methods as would be apparent to those in the art; one such method is to measure the production or presence of compounds that are known to be produced by activated glia, and compare such measurements to levels of the same compounds in control situations. Alternatively, the effects of the present methods and compounds in suppressing, reducing or preventing microglial activation can be assessed by comparing the signs and/or symptoms of CNS disease in treated and control subjects, where such signs and/or symptoms are associated with or secondary to activation of microglia.

ApoE receptor binding peptides have also been shown to protect against LPS-induced production of cytokines in the periphery in an in vivo animal model of sepsis. U.S. application Ser. No. 10/252,120, hereby incorporated by reference in its entirety. Thus, the peptides and compounds of the present invention can be used alone or in combination with other known anti-inflammatory cytokines and antibodies in compositions and methods for the treatment of sepsis.

As used herein, the terms "treating" and "ameliorating" are not necessarily meant to indicate a reversal or cessation of the disease process underlying the CNS or sepsis condition afflicting the subject being treated. Such terms indicate that the deleterious signs and/or symptoms associated with the condition being treated are lessened or reduced, or the rate of progression is reduced, compared to that which would occur in the absence of treatment. A change in a disease sign or symptom can be assessed at the level of the subject (e.g., the function or condition of the subject is assessed), or at a tissue or cellular level (e.g., the production of markers of glial or macrophage activation is lessened or reduced). Where the methods of the present invention are used to treat chronic CNS conditions (such as Alzheimer's disease), the methods can slow or delay the onset of symptoms such as dementia, while not necessarily affecting or reversing the underlying disease process.

It is known that the inflammatory process mediates an aspect of the atherosclerotic process. See, e.g., Hansson (1994); Berliner et al. (1995); Watanabe et al. (1997). ApoE is known to be secreted by macrophages locally at blood vessel walls (although the amount secreted by macrophages in an individual is trivial compared to the amount of ApoE produced by the liver). In the classic model of atherosclerosis, ApoE functions to remove cholesterol from the blood stream and deliver it to macrophages or to the liver. However, it has become apparent that ApoE secreted by macrophages at the blood vessel wall decreases atherosclerotic plaque formation, independent of any lipid metabolism effects. For instance, ApoE-deficient mice are accepted as a model of hypercholesteremia and atherosclerotic disease. Providing ApoE-secreting macrophages to such mice dramatically decreases atherosclerotic plaque formation. Linton et al. (1995). Conversely, replacing a wild-type mouse's macrophages with ApoE-deficient macrophages accelerates atherosclerotic changes, even though the animal continues to produce ApoE by the liver. Fazio et al. (1997).

In atherosclerosis it is hypothesized that ApoE, via a receptor-mediated event, downregulates macrophage activation in the vicinity of blood vessel walls. Such down-regulation of macrophage activation interrupts or interferes with the cascade of events associated with atherosclerotic plaque formation, to thereby reduce or slow the formation of atherosclerotic lesions. The cascade of events known to be associated with atherosclerosis includes smooth muscle cell and endothelial cell proliferation, and foam cell formation. Evidence exists that ApoE downregulates each of these processes. ApoE thus affects the presence and progression of atherosclerosis in vivo, independent of its effects on lipids. The progression of atherosclerosis can be assessed by measuring the amount or size of atherosclerotic plaques, or the percentage of the blood vessel blocked by an atherosclerotic lesion, or the rate of growth of such plaques.

It has been shown that ApoE transduces a calcium-mediated signal ($Ca^{2+}$/inositol triphosphate signal transduction) in macrophage, indicating that ApoE modifies macrophage function by downregulating macrophage activation and, therefore, subsequent inflammation. Peptides, compounds, methods and pharmaceutical formulations as described herein in relation to microglia and CNS disease are accordingly useful in methods of suppressing the activation of macrophages to suppress, prevent, or slow atherosclerosis.

Atherosclerosis refers to the thickening of the arterial intima and accumulation of lipid in artherosclerotic plaques. Administration of compounds of the present invention to treat or prevent atherosclerosis can be by any means discussed herein as well as other suitable methods that are known in the art. When using the present compounds to prevent, slow or treat atherosclerotic changes, it is apparent that they need not be formulated to pass through the blood brain barrier. Conditions that can be treated by the present method include atherosclerosis of the coronary arteries; arteries supplying the Central Nervous System, such as carotid arteries; arteries of the peripheral circulation or the splanchnic circulation; and renal artery disease. Administration, such as parenteral administration, can be site-specific or into the general blood stream.

The present methods and compounds are also useful in protecting subjects from the damaging effects of radiation. Findings of increased brain inflammation following irradiation suggested to the present inventors that anti-inflammatory treatment strategies may protect normal brain tissue from damage following irradiation. It has been reported that apoE-deficient animals have an increased systemic inflammatory response and higher mortality following LPS injection, and that the administration of exogenous apoE improves mortality by downregulating/suppressing the inflammatory cascade (Van Oosten et al., 1991). Accordingly, the present invention encompasses the administration of ApoE and particularly ApoE mimetic peptides to protect subjects from the damaging effects of radiation.

In particular, the present invention encompasses methods for protecting a subject in need thereof against at least one effect of radiation, comprising administering to said subject a protective dose of ApoE or at least one ApoE mimetic peptide. Preferred ApoE mimetic peptides include COG133, a peptide of the sequence LRVRLASHLRKLRKRLL (SEQ. ID. NO. 1), and derivatives of COG133 as described herein.

Types of radiation exposure that may be addressed by the methods of the present invention include total body irradiation (TBI), for instance wherein said subject has undergone a transplantation procedure or more specifically a blood or bone marrow transplantation, radiation therapy, for instance of one or more specific organs during the treatment of cancer, and environmental radiation exposure, i.e., either accidental or intentional for instance as encountered in nuclear facilities or nuclear waste sites, warfare, acts of terrorism and laboratory or other work involving exposure to radiation. The methods of the invention may be performed before, after or concurrently with the radiation exposure.

Where the radiation exposure is radiotherapy of cancer, such cancers include any cancer susceptible to radiotherapy, including but not limited to brain tumors, head and neck cancers, lung cancer, breast cancer, prostate cancer, skin cancer, rectal cancer, cervix and uterine cancers, lymphoma, and sarcoma. Radiotherapy may be given by external beam irradiation or brachytherapy. The methods of the invention may be performed before, after or concurrently with the radiotherapy.

For example, in general, the methods of the invention may be performed within minutes to hours after radiation exposure, or within about 1 day, about 2 days, about 3 days, about 4 days, about 5 days, about 6 days, about 7 days, about 10 days or about two to three weeks to one month after radiation exposure. In general, ApoE and the peptides should be administered as soon after radiation exposure as possible for best results. Where the methods are performed so as to prevent or mitigate the effects of radiation exposure in a subject about to be exposed to—or at risk of exposure to—radiation, the compounds of the invention can be administered at about 10 days, about 7 days, about 6 days, about 5 days, about 4 days, about 3 days, about 2 days, or about 1 day prior to exposure, or immediately prior to exposure (e.g., within hours to minutes before exposure). Administration can then be continued after exposure as above.

As noted above, the methods of the present invention protect a subject in need thereof against at least one effect of radiation. When given after the symptoms or effects of radiation exposure have developed, the methods of the present invention may be used to treat or decrease at least one effect of radiation. As used herein, the terms "protect," "treat" and "decrease" are not necessarily meant to indicate a reversal or cessation of the disease process accompanying or caused by the radiation exposure. Such terms indicate that the deleterious signs and/or symptoms associated with the radiation exposure are lessened or reduced, or the rate of progression is reduced, compared to that which would occur in the absence of treatment. A change in a disease sign or symptom may be assessed at the level of the subject (e.g., the function or condition of the subject is assessed), or at a tissue or cellular level (e.g., the production of markers of glial or macrophage activation is lessened or reduced). Where the methods of the present invention are used to treat radiation exposure, the methods of the invention can slow or delay the onset of symptoms of radiation toxicity, while not necessarily affecting or reversing the underlying disease process.

The effects of radiation exposure or TBI or radiotherapy according to the present invention include, but are not limited to the radiation-induced production of at least one cytokine. Such cytokines include, among others, cytokines selected from the group consisting of tumor necrosis factor alpha (TNFα), transforming growth factor beta (TGF-β), interleukin-1 alpha (IL1α), interleukin-1 beta (IL1β), interleukin-6 (IL6) and interleukin-12 (IL12). Changes in enzyme markers of leukocyte activation (e.g., myeloperoxidase, COX-2 expression, iNOS expression, etc.) and cellular apoptosis (e.g., DNA fragmentation, caspase activation, etc.) are also included. Radiation-induced effects also include, but are not limited to behavioral effects, xerostomia, including acute and late xerostomia, radiation-induced neurotoxicity, late delayed radiation-induced brain necrosis, radiation-induced soft tissue or vascular injuries, including, among others, injuries selected from the group consisting of skin atrophy, radiation cystitis (inflammation of the bladder), proctitis (inflammation of the rectum and anus) and injury to the larynx, leucopenia, purpura, hemorrhage, hair loss, diarrhea, fever, electrolyte disturbance, convulsions, ataxia, tremors and lethargy. Radiation-induced skin damage collectively termed radiation cutaneous syndrome may include acute skin reactions involving swelling, desquamation, ulceration, and late cutaneous fibrosis including fistualla formation.

The present invention further provides a method of treating inflammatory bowel disease (IBD); Crohn's disease or ulcerative colitis, comprising administering to a subject in need thereof. ApoE protein or one or more ApoE mimetic peptides in an amount that reduces symptoms of IBD, Crohn's disease or ulcerative colitis as compared to that which would occur in the absence of the protein. In practicing the methods of this invention, the therapeutic peptides and/or derivatives thereof may be used alone or in combination with other active ingredients. If desired, one or more agents typically used to treat inflammatory bowel disease may be used as a substitute for or in addition to the therapeutic peptides in the methods and compositions of the invention. Such agents include biologics (e.g., inflixamab, adelimumab, and CDP-870), small molecule immunomodulators (e.g., VX 702, SCIO 469, doramapimod, RO 30201 195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate and azathioprine) and alosetron. Thus, in one embodiment, the invention features the combination of a peptide compound comprising a sequence of SEQ ID NO: 1-56 and any of the foregoing agents, and methods of treating inflammatory bowel disease therewith.

Suitable subjects benefiting from the methods of the present invention include male and female mammalian subjects, including humans, non-human primates, and non-primate mammals. Subjects include veterinary (companion animal) subjects, as well as livestock and exotic species.

Compositions

Compounds and therapeutic peptides of the present invention can be in free form or the form of a salt, where the salt is pharmaceutically acceptable.

As used herein, the term "administering to the brain of a subject" refers to the use of routes of administration, as are known in the art, that provide the compound to the central nervous system tissues, and in particular the brain, of a subject being treated.

Preferably, the compounds of the present invention are used in combination with a pharmaceutically acceptable carrier. The present invention thus also provides pharmaceutical compositions suitable for administration to a subject. Such compositions comprise an effective amount of the compound of the present invention in combination with a pharmaceutically acceptable carrier. The carrier can be a liquid, so that the composition is adapted for parenteral administration, or can be solid, i.e., a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. Active compounds can alternatively be formulated encapsulated in liposomes, using known methods. Additionally, the intranasal administration of peptides to treat CNS conditions is known in the art (see, e.g., U.S. Pat. No. 5,567,682, incorporated herein by reference to Pert, regarding intranasal administration of peptide T to treat AD). Preparation of a compound of the present invention for intranasal administration can be carried out using techniques as are known in the art.

The immunomodulatory peptides may be used alone or in combination with other therapeutic agents, such as, e.g., oxygen radical scavenging agents such as superoxide dismutase or anti-inflammatory agents such as corticosteroids, hydrocortisone, prednisone and the like; anti-diarrheal agents such as loperamide and the like, antibacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, gancyclovir, ribavirin, interferons and the like; analgesic agents such as salicylic acid, acetaminophen, ibuprofen, flurbiprofen, morphine and the like; local anesthetics such as lidocaine, bupivacaine, benzocaine and the like; growth factors such as colony stimulating factor, granulocyte-macrophage colony stimulating factor, and the like; antihistamines such as diphenhydramine, chlorphencramine and the like; anti-nausea medications, nutritional additives such as leukovorin, and other like substances. Nutritional supplements for the treatment of subjects having undergone radiation exposure are described in US application 20030105027, which is herein incorporated by reference in its entirety.

The present invention may also be used in combination with anti-inflammatory cytokines, growth factors, or leukocyte migration inhibitory compounds. Useful cytokines include, but are not limited to, IL-4, IL-10, IL-11, and IL-13, particularly IL-4 and IL-10, which are known to suppress production of inflammatory cytokines and to be involved in restoring the immune system. Growth factors include GM-CSF among others. These cytokines and growth factors may be administered as purified proteins—obtained naturally or from recombinant sources—or administered in the form of nucleic acids that express these peptides, particularly as fusion proteins.

Pharmaceutical preparations of the compounds of the present invention can optionally include a pharmaceutically acceptable diluent or excipient.

An effective amount of the compound of the present invention is that amount that decreases microglial activation compared to that which would occur in the absence of the compound; in other words, an amount that decreases the production of neurotoxic and neuromodulatory compounds by the microglia, compared to that which would occur in the absence of the compound. Neuromodulatory refers to a nonlethal alteration in neuron function. The effective amount (and the manner of administration) will be determined on an individual basis and will be based on the specific therapeutic molecule being used and a consideration of the subject (size, age, general health), the condition being treated (AD, acute head injury, cerebral inflammation, etc.), the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the compounds described herein can be determined using in vitro tests, animal models or other dose-response studies, as are known in the art.

The compounds of the present invention can be administered acutely (i.e., during the onset or shortly after events leading to cerebral inflammation or ischemia), or can be administered prophylactically (e.g., before scheduled surgery, or before the appearance of neurologic signs or symptoms), or administered during the course of a degenerative disease to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

The typical daily regime can be from about 0.01 μg/kg body weight per day, from about 1 mg/kg body weight per day, from about 10 mg/kg body weight per day, from about 100 mg/kg body weight per day, from about 1,000 mg/kg body weight per day. Preferred dosages are between about 0.01 μg/kg and about 10 mg/kg body weight per day, depending on the compound, and more preferably between about 1 mg/kg and about 10 mg/kg body weight per day.

The blood-brain barrier presents a barrier to the passive diffusion of substances from the bloodstream into various regions of the CNS. However, active transport of certain agents is known to occur in either direction across the blood-brain barrier. Substances that can have limited access to the brain from the bloodstream can be injected directly into the cerebrospinal fluid. Cerebral ischemia and inflammation are also known to modify the blood-brain barrier and result in increased access to substances in the bloodstream.

Administration of a compound directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical compound into the cerebrospinal fluid ("spinal injection") is known in the art, and is suited for administration of the present compounds. Use of PTD domains as described herein and other peptides and non-peptide moieties known in the art may also be used to facilitate transport across the blood-brain barrier.

Pharmacologic-based procedures are also known in the art for circumventing the blood brain barrier, including the conversion of hydrophilic compounds into lipid-soluble drugs. The active agent can be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with compounds to be delivered to the interstitial fluid compartment of the brain, to cause an increase in the permeability of the blood-brain barrier and effect increased delivery of the compounds to the brain.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. Examples of suitable carriers include pyridinium, fatty acids, inositol, cholesterol, and glucose derivatives also add vitamin C. The carrier can be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 to Pardridge et al. These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198 to Poduslo et al. Specific carrier molecules disclosed include hemoglobin, lysozyme, cytochrome c, ceruloplasmin, calmodulin, ubiquitin and substance P. See also U.S. Pat. No. 5,017,566 to Bodor.

An alternative method of administering peptides of the present invention is carried out by administering to the subject a vector carrying a nucleic acid sequence encoding the peptide, where the vector is capable of entering brain cells so that the peptide is expressed and secreted, and is thus available to microglial cells. Suitable vectors are typically viral vectors, including DNA viruses, RNA viruses, and retroviruses. Techniques for utilizing vector deliver systems and carrying out gene therapy are known in the art. Herpesvirus vectors are a particular type of vector that can be employed in administering compounds of the present invention.

The examples which follow are set forth to illustrate the present invention, and are not to be construed as limiting thereof.

7. EXAMPLES

Example 1

Design and Characterization of Improved Peptide Analogs

Retro Inverso Peptide

Peptide analogs comprising substitutions of L-amino acids with D-amino acids were made to investigate the stereospecific nature of apoE 130-150 activity. Applicants compared all L-amino acid to all D-amino acid peptides to test whether a retro-inverso analog of apoE 130-150 was active. The retro-inverso analog was the reverse sequence (i.e. apoE 150-130) made with only D-amino acids (all-D apoE 150-130). Contrary to the experience reported by Pescarolo et al. (2001), Applicants found that the retro-inverso peptide was incredibly toxic at any concentration above 0.01 uM. Thus, the dramatic reduction observed in BV-2 microglial cell production of nitric oxide was artifact because the cells in the assay had been killed with the application of this retro-inverso peptide. In addition, all-D amino acid analogs of apoE 130-150 were without activity in suppressing nitric oxide (NO) release from lipopolysaccharide (LPS) treated BV2 microglial cells. The potential use of this compound would be for cases where one would want to kill off the macrophages, and perhaps other cells that would be killed by retro inverso apoE 133-149 as potential for immunosupression therapy as a precursor to bone marrow transplant in cancer treatments. The activity of all-L amino acid apoE 130-150 peptide to suppress both NO and TNFα release from LPS treated BV2 cells and the lack of activity of all D-amino acid analog of apoE 130-150 are consistent with a stereospecific binding of the all-L amino acid peptides to the appropriate cellular receptor. Based on this data, further pursuit of the retro-inverso approach will need to be extended in future studies to immunosuppression paradigms.

Site Directed Substitutions

Applicants then systematically replaced each amino acid in apoE 133-149 (COG133) with an alanine and then measured the activity of each apoE peptide analog. The shorthand nomenclature used for these replacements is known to those of skill in the art, for example, L 149 A which means that the leucine (L) at position 149 of the apoE 133-149 peptide (133-LRVRLASHLRKLRKRLL-149) (SEQ. ID. NO. 1) has been replaced with an alanine (A) to give the L149A analog (133-LRVRLASHLRKLRKRLA-149) (SEQ. ID. NO. 14).

As shown in Table 1, alanine scanning substitutions revealed decreases in potency with respect to binding and/or suppression of inflammatory activity when alanine was present at positions 139, 143, 144, 146, 147 and 149. Similar to the decrease found in L144A, the L144M replacement revealed decreased potency when compared to apoE 133-149 receptor binding and suppression of inflammatory activity. This is an interesting finding because leucine is a hydrophobic residue with a short branched carbon side chain and methionine is also hydrophobic, but with a slightly longer side chain having a sulfur atom. This opens the possibility that side chain size matters because the decreased activity was due to an increased side chain size either because of the longer side chain or the increased size of sulfur atom versus a carbon atom or both.

Decreased activity was also observed in the R142E replacement in which a basic arginine was replaced with an acidic glutamate residue suggesting that charge is important at this position. Decreased activity was also observed in the L148N replacement where a hydrophobic leucine was replaced with asparagine whose side chain displays a similar carbon backbone structure, but places an oxygen and an amino group at the end of that similar carbon backbone, suggesting that size and/or reactivity play an important role at this position. The remainder of the replacements tested failed to show any significant change in activity compared to the apoE 130-150 parent peptide or COG133 (apoE 133-149 peptide).

TABLE 1

Structure activity in the COG133 peptide from single amino acid replacements wherein the superscript (⁻) designates reduced activity of the peptide (EC50 higher than 3.5 uM).

| Sequence | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|
| COG133 SEQ. ID. NO. 1 | L | R | V | R | L | A | S | H | L | R | K | L | R | K | R | L | L |
| Reduced Activity SEQ ID NO. 67 | | | | | | | A⁻ | | | | A⁻ | A⁻ | | A⁻ | A⁻ | | A⁻ |
| SEQ ID NO. 68 | | | | | | | | | | E⁻ | | M⁻ | | | | N⁻ | |
| Neutral SEQ ID NO. 69 | | | | | | | | A | A | A | | | A | | | A | |
| SEQ ID NO. 70 | | | | | | | | | | | | | | E⁻ | E⁻ | E⁻ | M N |

Based on the proposed crystal structure of the entire 299 amino acid apoE protein (holo-apoE), the region from 130-150 forms an alpha helix that contains the region necessary for binding to the receptor for apoE protein ligands. Applicants have also published that the apoE 130-150 peptide displays an alpha helical conformation in solution as measured by circular dichroism spectra (Laskowitz et al. 2001). A typical alpha helix contains 3.6 amino acid residues per one complete turn of 360 degrees or 36 residues per 10 complete turns. Using this information together with a helical wheel representation of the peptide, it appears that there is one side/surface of this helical structure associated with activity of the peptide in our assays (FIG. 1, helical wheel). This information is valuable as it provides an initial map for those residues that are important for the activity of the apoE 130-150.

To arrive at the results in Table 1, multiple studies were performed on each peptide analog. For suppression of inflammation profiling, each peptide analog was tested at a final concentration of 0.1, 0.5, 1, 3, 5, 10 and 25 µM in an LPS induced BV2 microglial cell release of NO and/or TNFα. Reduced activity at a particular residue position is shown with a superscript—sign and refers to EC50's whose concentrations were higher than the 3.5 µM EC50 of COG133 (defined as the concentration where a 50% reduction of NO or TNFα release was observed on at least 2 different testing days). Receptor binding was obtained through a modified published procedure (Misra et al. 2001) and virtually identical results were obtained with the published procedure. The modification was a biotin label on the apoE peptide (biotin-LRVR-LASHLRKLRKRLL-amide, SEQ. ID. NO. 1) which allows detection with $^{125}$I-streptavidin (ISA, Amersham). In addition, Applicants employed binding to 250,000 cells per well in 6 well dishes (Nunc) at 4° C. which helped to provide more consistent and larger numbers of counts of specific binding of peptide. As an example of this approach, Applicants determined that unlabeled apoE 133-149 inhibited 50% of the binding of biotinylated apoE 133-149 at 4 µM (IC50=4 µM), a number that is in good agreement with the 3.5 µM EC50 of apoE 133-149 for suppression of inflammation activity. In general, the values for EC50's and IC50's for different peptide analogs were consistent between the binding assay and the biological activity assay.

Truncated Derivatives

In an effort to minimize the size of apoE 130-150 while preserving maximal activity, the peptide was progressively truncated from the amino-terminal and from the carboxy-terminal ends. Starting with the carboxy-terminus, apoE 130-149 maintained the activity of the apoE 130-150 parent peptide. In contrast, apoE 130-148 and apoE 130-147 failed to show activity at 25 µM. Starting from the amino-terminus, apoE 133-149 maintained the activity of the apoE 130-150 parent peptide. ApoE 139-149 failed to show activity even at 25 µM. Of the remaining intervening peptides, apoE 134-149 was the most active, but was 2.5 fold less potent than apoE 130-150. ApoE 135-149 and apoE 136-149 were 5 and 8 fold less potent than apoE 130-150, while apoE 137-149 and apoE 138-149 failed to show activity even at 25 µM. From these activity measurements, apoE 133-149 (COG133) was the shortest apoE peptide that maintains the complete activity of the apoE 130-150 parent peptide. Applicants have based the new peptide analogs on apoE 133-149 (COG133) to further refine the structure activity relationships of the residues that are critical to the pharmacological activity of the apoE peptide.

Characterization of Structure-Activity Relationships

The field of peptide mimetics comprises the transformation of selected peptide compounds into small molecules with drug-like pharmaceutical properties (Olson et al. 1993, 1995; Smith et al. 1997, 1998, 2000; Hirschmann et al. 1996, Liu e et al. 2000). Peptide mimetics encompasses a range of technologies, from peptide analogs (with unnatural amino acids in the backbone), peptide surrogates (replacing a peptide amide bond with an olefin or other isostere), and small molecule mimetics, in which the peptide is replaced in a rational way by a designed small molecule using non-peptide templates. New characteristics are incorporated into mimetics that extend their utility to many potential receptor targets, and vastly increase diversity by creating novel building blocks, structural templates, and pathways of assembly that are not possible through natural processes or via genetic engineering. These peptide mimetics incorporate unique, proprietary scaffolds that couple potent biological activity with enhanced bioavailability, and constitute novel, patentable new chemical entities. See, FIGS. 2-5, for example. Templates suitable for enzyme inhibition have been designed based on a pyrrolinone chemical class (Provid Pharmaceuticals, Piscataway, N.J.). Other systems are based on carbohydrates as privileged templates for non-peptide mimetics of peptides, an area that has led to inhibitors of protein-protein interactions and of G-protein coupled receptors. Non-peptide mimetics such as HIV-protease inhibitors and RGD-based blockers of integrin receptors are clinically and commercially successful examples of the technology. Examples include saquinavir (INVIRASE®, Roche), indinavir (CRIXIVAN®, Merck), ritonavir (NORVIR®, Abbott), nelfinavir (VIRACEPT®, Agouron/Pfizer), amprenavir (AGENERASE®, Vertex/Glaxo), commercially successful drugs (sales exceeding $1 billion as a group) that are medically responsible for transforming HIV/AIDS into a treatable, chronic disease.

As an example, Provid's efforts in non-peptido mimetic chemistry have led to the identification of lead compounds for clinical development in autoimmune disease based on the inhibition of antigen presentation by MHC class II, specifically HLA-DR2 molecules, which are associated with the disease. Related studies on HLA-DR1 and HLA-DR4 inhibitors performed by the Provid senior staff when they were affiliated with Hoffmann-LaRoche have also been published by these investigators (Bolin et al. 2000).

One example of the approach to convert peptides to non-peptide compounds is illustrated in the design of inhibitors that block the interaction between vascular cell adhesion molecule (VCAM-1) on activated endothelial cells and the integrin very late antigen-4 (VLA-4) receptor found on circulating lymphocytes. In this example, the starting point was a peptide antagonist that was molecularly modeled and converted, using a similar strategy as proposed below, to potent non-peptide molecules (Fotouhi et al. 2000, Chen et al. 2002). This approach is exemplified by conversion of a cyclic peptide to a small molecule, but the methodology applies to organic compounds as well as to peptides.

Helix mimetics are particular areas of application of non-peptide mimetics technology (Olson et al. 1993). In cases where a helical peptide is involved in a receptor interaction, the backbone amide groups of the peptide are all intramolecularly hydrogen bonded to form the structural scaffold of the helix (Ernst et al. 2002, Orner et al. 2001). In this case, the side chain functional groups are the dominant pharmacophore, and the helix can be viewed as a replaceable template. Applicants' preliminary studies on COG133 support the proposition that the receptor's recognition of a helical structure is important for biological activity and that the helical dipole structure in receptor binding is also important for biological activity such as, for example, to suppress inflammatory responses.

To further elucidate the role structure activity relationship of the apoE analogs, Applicants set out to synthesize new analogs of COG133 as follows: (a) analogs incorporating helix breakers or alpha helix stabilizers to substantiate the need for alpha helical character, (b) analogs incorporating new amino acids at sites adjacent to residues that are critical to activity to determine the relative size and composition of critical sites, and, (c) analogs in which the amino acid backbone is replaced with organic templates.

The COG133 17 mer peptide represents a prototypic active sequence that has been explored utilizing single amino acid replacement and truncation studies; the structure activity data from which is summarized in Table 1 (above). Analysis of the data identified key residues S139, R142, K143, L144, K146, R147 and L149 that affect biological activity. In the apoE protein, this segment is part of one of the helices in a four helix bundle, and the residues cluster, or border, on one face of the helix, and would present a similar epitope if COG133 exerts its observed biological effect as a helical peptide (FIG. 1). The 20 residue apoE (130-149) peptide, and two truncated 17-mer peptides [(130-146) and (133-149)] have been examined by circular dichroism spectrometry and all are qualitatively consistent with a mixture of helical and random coil structure (Laskowitz et al., 2001).

To test the hypothesis that the apoE 133-149 peptide must assume a helical conformation to be biologically active, Applicants tested analogs that incorporated amino acid residues that are well known to inhibit folding into a helical structure such as D-proline (Balaram et al., 1994; Mitchell et al. 2003). Applicants synthesized two analogs of COG133 that contain the helix breaking amino acid residue, D-proline (p), at positions L141 and R145. Neither the L141p nor the R145*p* analogs of COG133 showed any activity at 25 μM in an assay for the suppression of inflammatory cytokine (TNFa) release or in an assay for the suppression of free radical release (nitric oxide). Thus, this supports Applicants' hypothesis that COG133 and active analogs of COG1 33 are likely to assume a helical conformation when displaying biological activity, such as in suppression of inflammation assays.

natural and unnatural amino acid building blocks will be incorporated into the COG133 sequence (using standard FMOC solid phase synthesis protocols), both as single and as multiple replacements to develop a pharmacophore model for this peptide. This will lead to a greater understanding of which functional groups are required for biological activity and the nature of their spatial presentation/relationship. The importance of positively charged side chains, as well as their relative position and conformational mobility will be investigated. Table 3 illustrates the scope of modifications that may be synthesized, with combinations selected on the basis of potential neighboring group interactions which either enhance or destabilize structural properties (Karle, 2001; Vijayalakshmi et al., 2000; Karle et al., 1990).

TABLE 3

Initial analog synthesis for pharmacophore model development wherein hydrophobic residues are underlined, positively charged amino acids are designated by the symbol (+), negatively charged amino acids are designated by the symbol (−), polar/non-charged amino acids are designated with (*) and Orn is ornithine.

| 133 | 134 | 135 | 136 | 137 | 138 | 139 | 140 | 141 | 142 | 143 | 144 | 145 | 146 | 147 | 148 | 149 | SEQ ID NO. |
|---|---|---|---|---|---|---|---|---|---|---|---|---|---|---|---|---|---|
| L | R | V | R | L | A | S | H | L | R | K | L | R | K | R | L | L | 1 |
| <u>V</u> | <u>V</u> | $K^+$ | <u>V</u> | <u>V</u> | <u>I</u> | <u>V</u> | $K^+$ | <u>V</u> | <u>V</u> | $R^+$ | <u>V</u> | <u>V</u> | $R^+$ | <u>V</u> | <u>V</u> | <u>I</u> | 73 |
| <u>F</u> | $K^+$ | $E^-$ | $K^+$ | <u>F</u> | $K^+$ | N* | $E^-$ | <u>F</u> | $K^+$ | $Orn^+$ | <u>F</u> | <u>F</u> | $Orn^+$ | $K^+$ | <u>F</u> | <u>F</u> | |
| $K^+$ | $Orn^+$ | | $Orn^+$ | $K^+$ | $E^-$ | $K^+$ | N* | $K^+$ | $Orn^+$ | $E^-$ | $K^+$ | $K^+$ | N* | $Orn^+$ | $K^+$ | $R^+$ | |
| $E^-$ | $E^-$ | | $E^-$ | $E^-$ | | $E^-$ | | $E^-$ | | <u>L</u> | | $Orn^+$ | <u>L</u> | | | $K^+$ | |
| | | | | | | | | | | | | | | | | E | |

ApoE3 and apoE4 holo-proteins reduce inflammatory responses. Thus, the hypothesis that COG133 forms a helical conformation to exert its biological activity to reduce release of inflammatory mediators is reasonable (FIG. 1 and Lynch et al. 2003). In general small peptides such as COG133 (17 mer) would be expected to have little helical content when free in solution (CD spectra consistent with majority of random coil structure with some small helical content), however, they may be induced to fold into such structural units in the presence of a receptor. Especially in light of new preliminary data with helix breakers (Table 2, above), stabilizing the helical form of such a peptide would be expected to favor, and enhance affinity to receptor binding by virtue of pre-organization. Also the intramolecular hydrogen bonding associated with helix formation reduces exposure of the polar amide backbone, and results in improved membrane permeation and stability against proteolytic digestion.

Based on these ideas, Applicants propose to test the helicity of COG133 by initially incorporating both helix-stabilizing and helix-destabilizing amino acids (see Table 4). Residues

TABLE 2

Preliminary data on structure activity of analogs of COG133 peptide containing the helix breakers, D-proline

| SEQ ID NO. | 133 | 134 | 135 | 136 | 137 | 138 | 139 | 140 | 141 | 142 | 143 | 144 | 145 | 146 | 147 | 148 | 149 | helicity | Biologic Activity |
|---|---|---|---|---|---|---|---|---|---|---|---|---|---|---|---|---|---|---|---|
| 1 | L | R | V | R | L | A | S | H | L | R | K | L | R | K | R | L | L | yes | yes |
| 71 | L | R | V | R | L | A | S | H | D pro | R | K | L | R | K | R | L | L | disrupt | no |
| 72 | L | R | V | R | L | A | S | H | L | R | K | | D pro | K | R | L | L | disrupt | no |
| 7 | | | | | | A | S | Aib | L | R | K | L | Aib | K | R | L | L | enhance | >5x COG133 |

The initial peptide analog design and synthesis probes both structural requirements and pharmacophore elements (side chain functionality) required for biological activity. Both such as D-proline (Balaram et al., 1994, Mitchell et al. 2003) have been shown to be effective helix destabilizers. In contrast alpha disubstituted glycines such as Aib (dimethyl glycine-like) have been shown to greatly enhance helical propensities in peptides sequences as short as seven residues (Karle, 2001, Vijayalakshmi et al., 2000, Karle et al., 1990). Other approaches to enhancing helicity include amino and carboxy terminal capping (Doig et al., 2002, 1994, 1993), and formation of intramolecular side-chain to side-chain covalent bonds that restrict the conformation of the peptide. Such covalent linkages shown to be useful in this context are disulfides; lactam bridges and carbon-carbon linkages derived from olefin metathesis chemistry (Grubbs et al. 2001, Verdine et al. 2000).

out incorporating the required functionalities (as determined by the pharmacophore modeling proposed above) at positions X, Y and Z of the scaffolds. Compounds may then be evaluated for biological activity in cell-based and animal-based models. For instance, the activity of each analog may be tested in cell based assays of reduction of inflammation, in receptor binding assays and in longitudinal behavioral measures of performance in a TBI mouse model.

In Vitro Inflammation Suppression Assay

For the inflammation suppression assay, a published, cell-based model of suppression of inflammation may be used

TABLE 4

Modulation of helix propensity

| SEQ ID NO. | 133 | 134 | 135 | 136 | 137 | 138 | 139 | 140 | 141 | 142 | 143 | 144 | 145 | 146 | 147 | 148 | 149 | helicity |
|---|---|---|---|---|---|---|---|---|---|---|---|---|---|---|---|---|---|---|
| 1 | L | R | V | R | L | A | S | H | L | R | K | L | R | K | R | L | L | |
| 71 | L | R | V | R | L | A | S | H | Dpro | R | K | L | R | K | R | L | L | disrupt |
| 72 | L | R | V | R | L | A | S | H | L | R | K | L | Dpro | K | R | L | L | disrupt |
| 2 | L | R | V | R | L | A | S | H | NmeL | R | K | L | R | K | R | L | L | disrupt |
| 74 | L | R | V | R | Aib | A | S | H | L | R | K | L | R | K | R | L | L | enhance |
| 13 | | Ac | D | R | Aib | A | S | H | L | R | K | L | R | K | R | L | L | enhance |
| 4 | | | | | Ac | A | S | Aib | L | R | K | L | R | K | R | L | L | enhance |
| 3 | | | | | Ac | A | S | H | Aib | R | K | L | R | K | R | L | L | enhance |
| 6 | | | | | Ac | A | S | H | L | R | K | L | Aib | K | R | L | L | enhance |
| 7 | | | | | Ac | A | S | Aib | L | R | K | L | Aib | K | R | L | L | enhance |
| 5 | | | | | Ac | D | S | Aib | L | R | K | L | R | K | R | L | L | enhance |
| 5 | | | | | Ac | D | S | Aib | L | R | K | L | R | K | R | L | L | enhance |
| 75 | | | | | Ac | D | S | H | X | R | K | L | X | K | R | L | L | enhance |
| 76 | | | | | Ac | D | S | H | L | R | K | X | R | K | R | X | L | enhance |
| 77 | | | | | Ac | D | S | H | L | R | K | L | X | K | R | X | L | enhance |

Once a minimal length of sequence which retains the correct spatial array of required molecular functionality for biological activity is obtained, the unrequired peptide character (amide NH's/linkages) can be removed and the required functionality presented on non-peptidic scaffolds or templates that intrinsically possess many of the superior properties (such as stability, etc.) desired in pharmaceutical agents.

The structure-activity relationship data may be used to guide synthesis of new generations of analogs, to select appropriate mimetics and to select appropriate scaffolds/templates to replace peptidic segments not required for activity. The properties of these building blocks will be selected to be consistent with the molecular features determined to be important for bioavailability as recently reported by a group at GlaxoSmithKline (Veber et al., 2002).

In the case of helix mimetics, non-peptidic scaffolds have been reported that successfully mimic 2-4 turns of an alpha helix (about 7 to 14 amino acid residues). Mimetics in this class are low molecular weight organic compounds such as the terphenyls, which have been shown to compete with protein-protein interactions involving helix recognition (Hamilton et al., 2003; 2002; 2001).

Specific side chain functionality identified from the SAR studies and/or pharmacophore model can be presented on the template/scaffold (e.g. terphenyl framework as illustrated in FIG. 2) to mimic the functionality provided by the desired peptide (FIG. 3 shows tricyclic scaffolds as helix mimetics). Modeling studies have identified additional molecular frameworks which can serve as scaffolds to present required functionality, and flexible synthetic routes have been developed for two classes of tricyclic scaffolds; the carbazoles and phenothiazines. Synthesis of a series of functionalized analogs of the terphenyls, carbazoles and phenothiazines may be carried employing the BV-2 mouse microglial cell line stimulated with lipopolysaccharide (LPS) in the absence or presence of increasing amounts of COG133 or analogs of COG133 (Laskowitz et al. 2001). In overview, BV-2 cells are plated in 96 well plates in complete media and then the media is replaced the next day with serum free media or reduced serum (1%) media. Cells are stimulated by the addition of LPS or by the addition of LPS plus various concentrations of COG133 as a positive control. LPS plus various concentrations of analogs of COG133 are also added to separate wells. Various concentrations of analogs of COG133 are also added to separate wells to control for activities of the peptides alone (in the absence of LPS). Each concentration of peptide (standard initial concentrations are 0.1, 0.5, 1, 3, and 25 μM) is added to at least 6 wells of cells (e.g. 6 wells get 0.1 μM peptide, 6 wells get 0.5 μM peptide, etc.) and data are averaged from all 6 wells. After 24 hours of incubation, TNFα and nitrite levels in conditioned media are measured with ELISA and Griess assay as described in Laskowitz et al. (2001). Cell viability is also measured with an MTT assay (Laskowitz et al. 2001). The EC50 of each test peptide may be compared to the EC50 of COG133 for biological activity with the help of t-tests and/or ANOVA where $p<0.05$ is considered significant.

Receptor Binding Assay

Receptor binding may be tested as a modification of published procedure (Misra et al. 2001). Applicants' modification is to use a biotin label on the apoE peptide by synthesizing biotin-LRVRLASHLRKLRKRLL-amide (SEQ. ID. NO. 1) which can be detected with $^{125}$I-streptavidin (ISA, Amersham). In addition, Applicants employ binding to 250,000 cells per well in 6 well dishes (Nuns) at 4° C., which helps to provide more consistent and larger numbers of counts of specific binding of peptide. $^{125}$I-streptavidin may be replaced with a streptavidin-horseradish peroxidase conjugate, or with a streptavidin-alkaline phosphatase conjugate using CDPStar (Roche Applied Science) as the detection reagent.

Toxicity Testing

Candidate compounds are then be screened in our closed head injury model of traumatic brain injury by intravenous dosing at 30 minutes post injury. Novel compounds are initially tested at one half their maximum tolerated dose (0.5× MTD). The maximum tolerated dose (MTD) is the dose of peptide given in a tail vein injection that results in no death of mice. Death is defined as a complete lack of breathing and complete unresponsiveness to external stimuli such as tail pinch and/or toe pinch for a period of 10 or more minutes. Animals are given an initial dose of 1 mg/kg of peptide analog or non-peptide mimetic and observed continuously for 15 minutes and then at 15 minute intervals for 2 hours and then at 1 hour intervals for 4 hours more. Animals are also observed at 24 hours post injection.

The maximum tolerated dose is the maximum dose at which no animals die at any of these observation times. As an example of this procedure, the MTD is determined empirically by initially dosing groups of 3 mice at 1 mg/kg. If this dose is tolerated, then another group of 3 mice is dosed at 3 mg/kg. If this dose is tolerated, then another group of 3 mice is dosed at 9 mg/kg, etc. If, for example, 9 mg/kg is not tolerated because 1 or more animal died, then doses in-between 3 mg/kg and 9 mg/kg are investigated until the MTD is found. Once the MTD is empirically determined, it is confirmed in another group of 7 mice for a total of 10 mice being tested at the MTD and all of which must not die to confirm that this is the MID. While somewhat arbitrary, this has proved to be a rapid and robust method to profile toxicity of new compounds in whole animals.

In Vivo Traumatic Brain Injury Model

Experimental models of TBI play an important role in the process of evaluating and understanding the complex physiologic, behavioral and histopathologic changes associated with TBI. To further clarify this interacting network, the existing preclinical models of TBI have been designed to mimic closely the clinical sequelae of human TBI. One of the most widely used experimental technique to produce TBI employs a rigid impactor to generate the mechanical energy to impact the intact skull of the animal which is usually kept restrained during the delivery of the impact. Currently, the most popular method to produce this type of injury utilizes pressurized air as the source of the mechanical energy that drives a steel tip impactor into the skull and is referred to as traumatic brain injury, as described below. Adapted for use in several species including the mouse (Smith et al. 1995), the ability to control deformation parameters with pneumatically driven devices (time, velocity and depth of impact) and the absence of risk for rebound injury (Lighthall 1988) make the traumatic brain injury (TBI) model superior to devices which are driven by gravity of a free falling, guided weight (Feeney et al., 1981; Dail et al., 1981).

Several different preclinical paradigms have been developed to model closed head injury. Traditionally, many of these head injury models were performed in rodents in which a craniotomy was performed, and a reproducible injury such as fluid-percussion or controlled cortical impact was applied directly to the brain parenchyma (Rinder, 1969). This type of model has the advantage of creating a reproducible and well-defined area of tissue injury. However, the injury produced by this model may not be clinically relevant, as human closed head injury caused by rapid acceleration-deceleration forces (such as occurs during a motor vehicle accident) produces a much more heterogenous insult, often with elements of torsional forces (diffuse axonal injury), cortical contusion and hemorrhage, subdural and epidural hematoma. To address these limitations, weight-drop models were developed to apply a more physiological impact against the closed skull. This produced a more clinically relevant injury that created short term neurological and longer term cognitive deficits (Zohar et al., 2003). However, one shortcoming of these early models was the lack of experimental control and reproducibility caused by incomplete physiological monitoring and variability of the mechanical injury caused by the weight drop. To address these limitations and take advantage of currently available transgenic murine technology, this model was adapted for the mouse by utilizing a calibrated pneumatic impact against the intact skull of ventilated mice in which relevant physiological parameters (core and pericranial temperatures, mean arterial pressure, blood glucose, blood gas, etc.) are monitored (FIG. 5).

Mechanics of Closed Head Injury Paradigm

C57B1/6J male mice (The Jackson Laboratory, ME), 12-16 weeks of age and weighing 24-32 g, are used for all experiments. Anesthesia is first induced with isoflurane in 30% $O_2$/balance $N_2$. The trachea is intubated and the lungs mechanically ventilated with 1.6% isoflurane in 30% $O_2$/balance $N_2$. Temperature is monitored with a rectal probe and maintained at 36.5° C. with a heat lamp. The right internal jugular vein is cannulated with silicone catheter. This injury model was adapted from a previously described model of closed cranial trauma for the rat (Marmarou et al., 1994), as previously described (Lynch et al., 2002). Intubated animals are then placed prone on a molded acrylic cast (FIG. 6A). Placing animals on an acrylic mold helps stabilize the animals and prevent movements during the impact procedure, creating a more homogeneous insult. The scalp is incised and the skull exposed. A concave 3 mm metallic disc is secured to the skull surface (with the concave surface in juxtaposition to the skull) by an adhesive. During model development, it was found that the placement of this disk helped to reduce the incidence of skull fracture, and created a more diffuse brain injury. The disc is placed directly midline just caudal to bregma (FIG. 6B). Again, this midline injury was determined to be a more clinically relevant model of diffuse axonal injury. This insult results in relatively mild bilateral hippocampal injury as measured by FluoroJade (HistoChem, Inc.) staining, as compared to a unilateral insult with comparable functional deficit. The mice are positioned in a stereotactic frame. Although the stereotactactic frame helps to stabilize the animal and exactly calibrate the vertical displacement on impact (3 mm), ear bars are not used due to a much higher rate of skull fracture (or brainstem injury if the head rotates around the axis of the ear bars during impact). The piston is discharged at 6.8±0.2 m/s so as to impact the skull in the acrylic mold to move a maximum of approximately 3 mm (FIG. 6C). Inspired isoflurane is decreased to 0.7% immediately after impact. The scalp was infiltrated with lidocaine and closed with suture. Ophthalmic ointment was applied to the eyes for protection. The incidence of skull fracture is low (approximately 10%), as the metal disk helps to diffuse the impact, and the absence of ear bar fixation allows for displacement of the entire head. Mice were excluded if a depressed skull fracture was observed (incidence of approximately 10%). The animals are allowed to recover spontaneous ventilation then extubated. The use of a surrogate physiologic control group is necessary in the experiments involving long term outcomes. Placement of an arterial catheter is necessary for measuring physiological parameters; other placement can damage the femoral nerve plexus and creates a motor deficit. Other placement makes behavioral testing involving motor skills (including swimming in the Morris water maze) uninterpretable. In these mice, arterial blood pressure, blood gas and glucose measurement at baseline, immediately after injury, and 15 minutes after injury are monitored during the recovery period.

Histological Outcomes

This midline closed head injury results in reproducible pathology in CA3 region of hippocampus visualized by FluoroJade staining. However, unlike unilateral fluid percussion models, this paradigm results in a more diffuse injury and there is proportionately less hippocampal neuronal injury relative to behavioral deficit. Applicants have also demonstrated that this midline injury results in radiographic cerebral edema and upregulation of inflammatory cytokines. This supports the contention that this is a clinically relevant model of diffuse axonal injury.

Behavioral Outcomes

This paradigm was designed as a survival model of mild-moderate closed head injury. Mice will initially have motor and cerebellar deficits, assessed by Rotorod and neurological severity score on days 1-5 post-injury, as described below. To model the more subtle long-term neurological deficits common in survivors of head injury, memory is assessed with the Morris Water maze on days 21-25 post-injury. Specifically, this tests the animal's ability to find a 7.5 cm diameter hidden platform in a 105 cm diameter pool within a 90 second interval.

Rotorod Testing

Traumatic brain injury (TBI), intravenous administration of peptides and behavioral performance will be performed as described above and as published (Lynch et al. 2002 and Lynch et al. submitted). Briefly, baseline performance on rotorod is established before the mice are intubated, the skin over the scalp reflected and a controlled cortical impact from a pneumatic impactor given on the midline. The skin is closed with surgical clips and the animals are constantly monitored until awake from anesthesia and then hourly for the next 4 hours. At 30 minutes post-impaction, saline vehicle or test article (COG133, analogs of COG133 or non-peptide analogs of COG133) are administered via tail vein injection. Performance on rotorod is tested at 24 hours post impaction and then every day for 5 days and data is presented as described. Groups of 12 mice are used for each compound at 0.5×MTD. The negative control group receives only saline vehicle and the positive control group receives 4 mg/kg of COG 133 in 100 ul volume of saline by tail vein injection. Novel peptides and non-peptide analogs are also given by tail vein injection.

As a control for activity of the peptide alone, sham animals may be prepared and dosed with test article as detailed above, except that no cortical impact will be given. Behavioral performance on rotorod will be measured as described above and compared to the performance of sham animals given COG133 at 4 mg/kg via tail vein injection (total of 12 groups× 12 animals per group=144 animals). The Prism and/or Instat computer programs will be used to assist in the determination of significance between COG133 and novel compounds by repeated measures ANOVA.

Daily Rotarod (RR) testing was used to assess short term motor and cerebellar deficit following head injury (Hamm et al., 1994). Mice were held by their tails and placed on the RR facing the wall by using gentle swinging motion while running in a constant speed mode. Once all mice are in place, the RR is switched to accelerating mode and the latency time to either falling from the rod or turning twice (720 degrees) was recorded. The mean latency time for the three trials was reported for each day.

Post Injury In Vivo Model

Analogs may be further tested in our mouse TBI model at 60, 90 and 180 minutes following the traumatic brain injury. In this more stringent delay test, the efficacy of novel compounds may be compared to COG133 administered by tail vein injections at 60 minutes after a standard closed head injury that gives a reproducible traumatic brain injury (TBI) as described above. If a compound proves to be significantly better than COG 133 at a 60 minute post TBI delay as determined by rotorod performance that is analyzed with repeated measures ANOVA, then it is tested at a 90 minute post TBI delay. If a compound proves to be significantly better than COG133 at a 90 minute post TBI delay as determined by rotorod performance that is analyzed with repeated measures ANOVA, then it is tested at a 180 minute post TBI delay.

Behavioral Testing of Motor Deficits and Long-term Memory Testing

Cognitive and learning abnormalities are common long-term sequelae of TBI in the clinical population. To maximize the sensitivity and clinical relevance of our model, learning, retention and behavioral deficits in neurological function may be assessed. For this purpose, changes in performance in the Morris Water Maze task may be studied (Morris, 1984). This task takes advantage of rodents being natural swimmers and measures the ability of the animal to incorporate visuospatial cues into working and reference memory. Performance on this task may be a correlate of the neuropsychiatric deficit seen in a human clinical population. In theory, the mice could escape from the task by swimming randomly, or in non-systematic paths throughout the pool; however, if working memory is intact, they will use distal cues from fixed objects in the testing chamber to learn the relative position of the platform. Thus, the time latency to find the platform should decrease as a function of practice, and may be used as an index of learning ability.

Proteolytic Cleavage Assays

Some peptides could be cleaved by trypsin-like proteases. The cleavage of peptides may be measured using trypsin and brain homogenates in a Liquid Chromatography—Electrospray Ionization Mass Spectrometry (LC/MS) method. Briefly, trypsin linked to beaded agarose (Pierce) is washed twice with 0.1 M ammonium bicarbonate, pH 8.0 followed by two washes with calcium, magnesium free phosphate buffered saline, pH 8.0 (PBS-8). Resin is resuspended in PBS-8 containing 20 ug/ml of peptide substrate and digested at 37 C for 0, 0.1, 1, 5, and 20 hours. Triplicate samples are evaluated at each time point. Samples are briefly centrifuged, resin free supernatants were extracted with ATI (acetonitrile, TFA, internal standard), processed and submitted for LC/MS quantitation under the following conditions:

LC Conditions:
Column: Agilent Zorbax 300 SBC$_{18}$ 2.1×75 mm×Sum particles 300 A pore size
Gradient: 5% B to 65% B in 4.5 minutes
A=5% acetonitrile/95% water (0.025% TFA)
B=95% acetonitrile/5% water (0.025% TFA)
Flowrate: 0.5 mL/min
Injection volume: 10 uL
Analysis time: 4.5 min with a 3.5 min equilibration time
MS Conditions:
Mode of operation: Positive ion electrospray on Agilent 1100 MSD system
Scan range: SIM, detecting the $[M+3H]^{+3}$ ion for COG133 at m/z 724.1 and for IS-11 at m/z 695.7
Dwell time: 49 ms per ion
Capillary exit voltage: 200V
Drying gas: 9.5 L/min at 350 C Nebulization pressure: 50 psi Similarly, whole mouse brain homogenates can be used as a source of intracellular and extracellular proteases that may degrade peptides. In this case, fresh mouse brains may be homogenized at 100 mg wet weight per ml PBS (pH 7.4). Peptide substrates at 40 ug/ml in PBS (pH 7.4) are mixed with an equal volume of brain homogenate and incubated at 37 C for 0, 0.1, 1, 5, and 20 hours before extraction with ATI, processing and submission for quantitation of degradation products against our internal standard peptide by LC/MS as described above. Triplicate samples are evaluated at each time point. In each experiment, the moles of intact, non-degraded peptide and the moles of major metabolites (fragments that are at least 20% of the molar amount of intact, non-degraded peptide) are measured at each time point. Homogenized brains may also be used to measure peptide uptake into the brain using the LC/MS procedure.

Plasma half-life of peptides may also be measured using the LC/MS procedure by exposing each peptide derivative to mouse blood plasma and measuring recovery over time as compared to a standard control.

Example 2

Characterization of COG432

Figure 4:
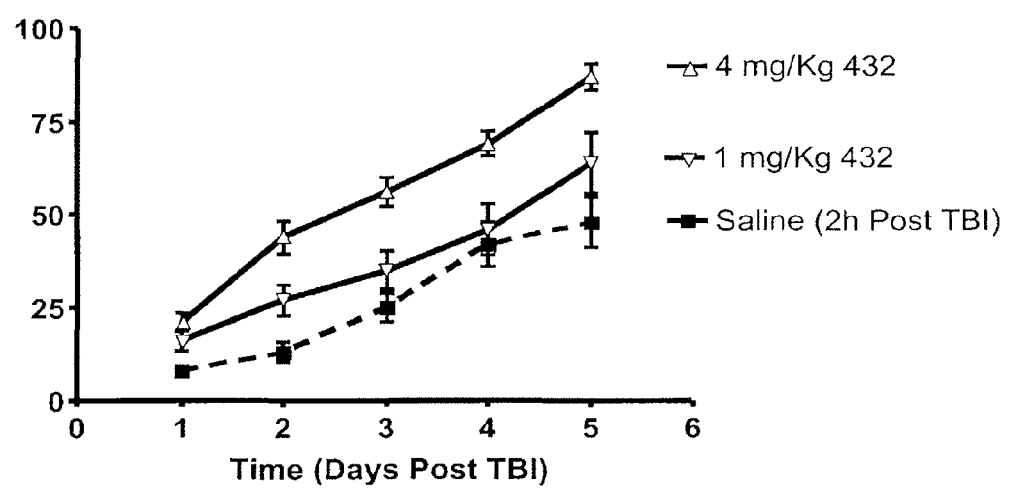

FIG. 4 provides the results of rotorod testing following post TBI with 4 mg/kg or 1 mg/kg of COG432, (COG432: Ac-ASHLRKLAibKRLL (SEQ. ID. NO. 6)) or control (saline). The vertical axis provides the rotorod performance (100% is rotorod performance prior to TBI). Treatment with COG432, 4 mg/kg or with saline was started at 2 hours post traumatic brain injury and the animals were tested beginning on day 1 post TBI and every day for the next 5 days. By day 5 post TBI, animals treated with 4 mg/kg of COG432 peptide had recovered to about 80% functioning as measured by the rotorod test. Control mice treated with saline vehicle alone recovered less than 50% of function.

Example 3

Characterization of COG1410

We synthesized COG1410, an analog containing two aminoisobutyric acid (Aib) substitutions, at positions L140 and R145. Aib is a non-natural amino acid which has been shown to form helical conformations regardless of the amino acid types present in the peptide (Marshall et al. 1990). In addition, Aib improves binding affinity because it exhibits a reduction in conformational entropy loss upon binding, relative to other amino acids (Ratnaparkhi et al. 2000).

Cell-Based Assay

As depicted in FIG. 7, COG1410 was significantly more potent than COG133 in our cell based assay of suppression of nitric oxide (9A) and TNFa (9B) release. In addition, preliminary screening in vivo indicated that COG1410 was neuroprotective when administered at 120 minutes following TBI, unlike COG133 which was devoid of neuroprotective activity at this time point (FIG. 8).

Dose Response Studies

Preliminary dose response studies indicated that the minimum effective dose (MED; the lowest dose which exhibits a statistically significant improvement in performance compared to vehicle treated controls) of COG1410 was about the same as that of COG133, 0.3 mg/Kg vs. 0.4 mg/Kg, respectively. However, the maximum tolerated dose (MTD; the highest dose that results the death of no mice in 24 hours) of COG1410 was 8 mg/Kg versus an MTD of 1.4 mg/Kg for COG 133. The Therapeutic Index (TI; the ratio of the MTD to the MED) of COG1410 is 26 and is significantly better than the TI of 3.5 for COG 133. The higher the TI, the more safe the drug is considered to be. This high TI of COG1410 indicates that it would take a much higher dose to invoke a toxic response than it does to cause a beneficial and desired protective effect.

Analysis of Pharmacokinetic Parameters

Of the many pharmacokinetic parameters to consider, plasma half-life and resistance to proteolytic degradation are two characteristics of peptides that can be precisely measured with Liquid Chromatography—Electrospray Ionization Mass Spectrometry (LC/MS) methodology. With the help of LCMS-LLC, we have developed an LC/MS method to measure peptide amounts and peptide fragments in blood plasma and in mouse brain extracts.

Briefly, a calibration curve was constructed by adding 0, 0.005, 0.025, 0.1, 1.0, 5, 10, or 25 ug/ml of COG133 to mouse blood plasma. These same concentrations of COG 133 were also added to PBS (phosphate buffered saline, pH 7.4). Plasma or PBS containing COG1 33 was extracted by addition of 1 volume of PBS and 1 volume of ATI (ATI=0.6% trifluoroacetic acid and 3 ug/ml of an internal standard peptide [LAVLLASHLRKLRKRLL, SEQ. ID. NO. 58] in acetonitrile), vortexing, centrifuging at 15,000×g for 10 minutes, and collecting the top organic phase layer as extracted samples. Extracted samples were submitted for LC/MS quantitation under the conditions described above (Example 1) and gave a linear concentration/signal curve (data not shown, $R^2=0.9984$) indicating that increases in signal were linearly proportional to increased amounts of COG133 in a sample.

Compared to our internal standard peptide (LAVLLASHL-RKLRKRLL, SEQ. ID. NO. 58), we consistently recovered >80% of COG133 in each plasma sample to give the Analytical Results shown in the following table.

TABLE 5

| Analytical Results: | | | |
|---|---|---|---|
| Precision: % Deviation | Accuracy: % Deviation | Linearity: $R^2$ | LOQ µg/ml |
| <10% | <15% | 0.9984 | 0.05 µg/ml |

Figure 9:
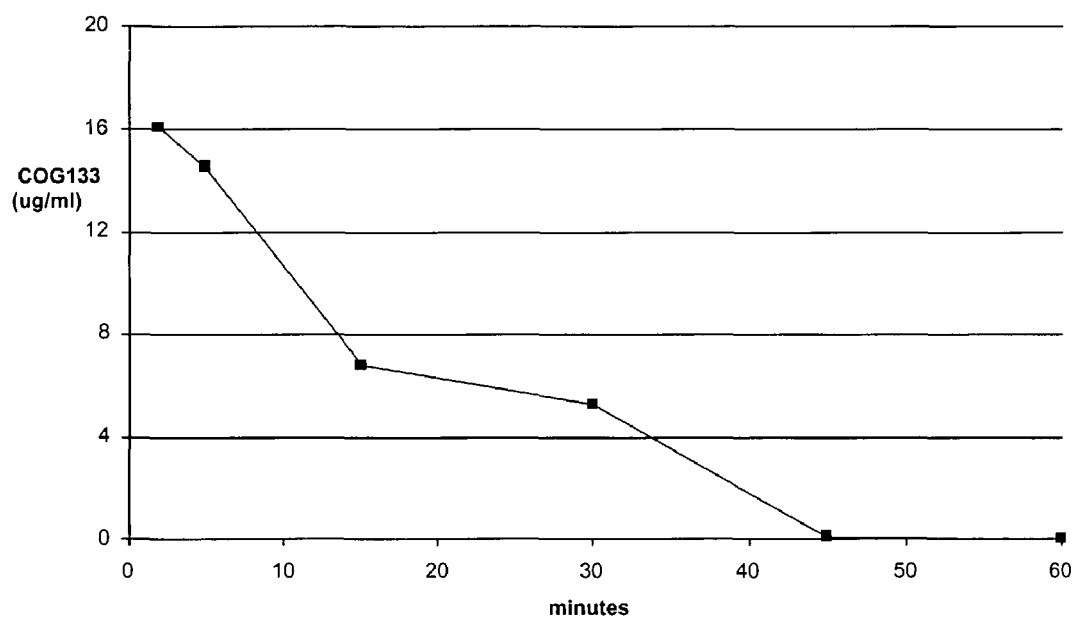

For our half-life experiment, COG133 (0.4 mg/Kg) was injected into the tail vein of male C57B1/6 mice, 1 ml of blood collected by cardiac puncture at the indicated times, and blood plasma processed as described above. The plasma concentration-time graph gives COG133 an 8 minute half-life in mouse blood plasma (FIG. 9). Using this same procedure with internal standards, we calculate a 2 minute half-life for intact, non-degraded COG1410 in mouse blood plasma (data not shown).

We have employed a similar LC/MS procedure to measure the amount of intact, non-degraded COG1410 in brain. Briefly, we administered 4 mg/Kg of COG1410 via tail vein injection at time 0, perfused mice at 5 minutes post injection with isotonic saline via cardiac puncture to remove blood from the cerebrovasculature, and removed the perfused brains at 10 minutes post-injection. Brains were homogenized in 1 ml of PBS containing a protease inhibitor cocktail (Roche Diagnostics, 10 mg/ml) per 0.1 g wet weight of brain material. Homogenates were mixed with an equal volume of ATI, vortexed, centrifuged and samples submitted for LC/MS as described above. Using this method, we find a peak at 4.90 minutes in the "3d COG1410" and in the "2d COG1410"

brains with the proper m/z ratio of 705 for the [M+2H]+2 ion of COG1410. This preliminary experiment indicates that a measurable amount of COG1410 enters the brain within the 5 minute entry phase and stays in the brain during the next 5 minute perfusion phase of this experiment. This is consistent with our pharmacological data showing significant COG1410-mediated improvements in behavioral tests of performance after TBI (data not shown).

We have employed a similar LC/MS procedure to identify fragments of COG1410 that may arise by degradation processes. Briefly, using plasma from mice receiving COG1410, several smaller peptide fragments were identified with this LC/MS method that are not found in plasma from untreated mice (data not shown). Using the MS/MS option on the mass spectrometer to obtain partial sequence of these fragments, it appears that at least one of the major metabolites is likely to be acetyl-AS-Aib-LRKL-Aib-KR (SEQ. ID. NO. 59), a fragment which could result from digestion of intact COG1410 by trypsin-like proteases or carboxypeptidase activities. The presence of this fragment suggests that the one explanation for the shorter half-life of COG1410 could be its susceptibility to trypsin-like proteases and/or carboxypeptidase activities.

Conclusions

These data with COG1410 indicate the feasibility of developing compounds with increased stability, enhanced potency and BBB permeability, decreased toxicity, increased therapeutic index, and expanded therapeutic window for the treatment of TBI. Additional analogs with even better pharmaceutical properties, such as increased resistance to degradation, are achievable by synthesis of limited numbers of derivatives using the guidelines provided above.

Example 4

Further Optimization of COG1410

COG1410 is a significant improvement over COG133 by a number of criteria. Our preliminary data showed that alpha helical structure is very important and enhancement of this helical structure resulted in COG1 410. Our initial strategy to include amino acids like Aib that encourage helix conformations will be extended to two new positions which are potentially allowable from the alanine scanning work (see Example 1). Further enhancements to the helical nature of COG1410 may be achieved by derivatization of the side chains of the amino acids on the face of the helix that does not appear to directly confer bioactivity of the peptide. The overall nature of these derivatives would be to include an olefin bridge between selected amino acids that would constrain its flexibility and increase the propensity to remain in a helical structure.

Our preliminary data also showed that proteolysis of COG1410 may contribute to its lack of stability. In addition, our alanine scanning data showed the carboxy-terminal leucine was critical for activity, suggesting that proteolytic removal of this residue would result in lack of bio-activity. More precise definition of proteolytic fragments followed by substitution of selected amino acids and/or derivatization of selected amino acids should increase resistance to proteolysis while maintaining bio-activity.

Thus, COG1410 may be further derivatized to increase helicity in 3 ways: 1) enhance helicity by incorporation of Aib residues at selected positions; 2) enhance helicity by amino terminal capping (Doig et al., 2002, 1994, 1993); and 3) enhance helicity by forming intramolecular side-chain to side-chain covalent bonds that restrict the conformation of the peptide. Covalent linkages that have shown to be useful in this context derive from olefin metathesis chemistry, and would span the i to i+4 or i to i+7 positions with alkene containing bridges (Grubbs et al. 2001, Schafineister et al. 2000).

Sidechain Crosslinks

Using a ring closing metathesis (RCM) strategy, olefin sidechains may be incorporated to covalently link side-chain to side-chain on selected residues in the sequence: ASHLRKLRKRLL (SEQ. ID. NO. 44). COG1410 appears to form an amphipathic alpha helix with all of the charged residues on one face of the helix and all of the hydrophobic residues on the opposite face of the helix. Since alanine substitutions of most charged residues significantly reduced anti-inflammatory activity (Table 1), charged residues are not candidates for side-chain linking procedures (with the exception of R145 where Aib substitution enhanced bioactivity). This leaves most of the hydrophobic residues available for modification by side-chain linking procedures. Thus, the following cross-linked molecules may be synthesized where amino acids, denoted as X and Z, can be any amino acid which contains a side chain that will be linked to the cross-linking olefin bridge: ASHXRKLZKRLL (SEQ. ID. NO. 60), XSHLRKLZKRLL (SEQ. ID. NO. 61), ASXLRKLRKZLL (SEQ. ID. NO. 62) and ASHXRKLRKRZL (SEQ. ID. NO. 63).

Briefly, X and Z are alpha-methyl, alpha-alkenyl di-substituted amino acids (both butenyl for i: i+4 crosslinks; one butenyl and one pentenyl for i: i+7 crosslinks) incorporated into the peptide chain during conventional solid phase synthesis. While still on the solid support and in the capped state, the peptide is reacted with the Grubbs catalyst (Bis(tricyclohexylphosphine)benzylidine ruthenium (IV) dichloride) in 1,2 dichloroethane. Catalyst is removed by washing the resin and metathesized peptide is cleaved from the resin with trifluoroacetic acid, purified on a C18 reverse phase HPLC column and confirmed by electrospray mass spectrometry. In addition to the potential for enhancing the helical structure, the presence of the bridge may also increase resistance to proteolysis by the olefin side chain physically blocking binding of the peptide to proteases (Verdine et al. 2000).

Enhancing Resistance at Protease Sensitive Sites

Our preliminary data with LC/MS has identified acetyl-AS-Aib-LRKL-Aib-KR (SEQ. ID. NO. 59) as a potentially important metabolite of COG1410. This fragment could be generated by endoproteolytic cleavage by trypsin-like proteases and/or exoproteo lytic cleavage by carboxypeptidases. To address the endoprotease possibility, derivatives of COG1410 may be synthesized which substitute ornithine, nitroarginine, homoarginine or dimethyl-arginine for arginine at position 147 via standard Fmoc chemistry on an automated peptide synthesizer. To address the exoprotease possibility, derivatives of COG1410 may be synthesized which substitute valine, methionine or isoleucine for leucine at position 149.

Example 5

Protective Effect of ApoE Mimetic Peptides in the Murine Model of Experimental Autoimmune Encephalomyelitis As one of the reliable animal models of multiple sclerosis (MS), experimental autoimmune encephalomyelitis (EAE) is an inflammatory disease causing severe demyelination in the central nervous system (CNS) (Pender & Wolfe 2002). EAE and MS share common histological features including microglia activation and prominent infiltration into the CNS of iinflammatory cells that consist mainly of T lymphocytes and macrophages (Heber-Katz 1993) (Hemmer, Archelos, et al. 2002). These activated effector cells release a cascade of proinflammatory cytokines, such as TNFα, IL-1β, IFNγ, and lymphotoxins. These factors, in turn, encourage further accumulation of infiltrating cells, which are associated with inflammation, and tissue damage (Eng, Ghirnikar, et al. 1996) (Benveniste 1997) (Wiemann, Van, et al. 1998).

On screening the chromosomal localization of the multiple sclerosis genes, a MS gene is linked to markers located in the 19q13.3 region, where apolipoprotein E (ApoE) gene locates (Lucotte 2002). This finding, together with the reports that patients having APOE Δ4 are more likely to be affected with severe MS (Chapman, Vinokurov, et al. 2001) (Fazekas, Strasser-Fuchs, et al. 2001) (Schmidt, Barcellos, et al. 2002) (Materman, Zhang, et al. 2002), suggests that APOE may participate in the development of multiple sclerosis (Weatherby, Mann, et al. 2000) (Weatherby, Mann, et al. 2000).

Materials and Methods

Mice

Female C57BL/6J mice (12 weeks old) were purchased from Jackson Laboratories and housed in the Duke University Experimental Animal Facility. Animal care and experimental procedures conformed to the regulations approved by the Duke University Animal Care and Use Committee.

Reagents

Myelin oligodendrocyte glycoprotein (MOG) peptide is derived from residues 35-55 of the mouse MOG protein (MOG 35-55, MEVGWYRSPFSRVVHLYRNGK, SEQ. ID. NO. 64), and apoE mimetic peptide (COG133) is derived from residues 133 to 149 of human apolipoprotein-E with the sequence of acetyl-LRVRLASHLRKLRKRLL-amide (SEQ. ID. NO. 1). ApoE reverse peptide (designated as COG-149) is treated as scrambled control of COG133 here. Antennapedia-linked peptide (designated as COG 134, aka COG4502) combines antennapedia prefix peptide with COG133. All the peptides were synthesized by the Peptide Synthesis Facility at UNC using FMOC reagents with Merrifield solid-phase chemistry and purified through RP-HPLC. The following reagents were purchased from Sigma: pertussis toxin, LPS and IFN-γ. Quantitative ELISA kits for TNFα and IL-6 were obtained from Biosource.

Induction of EAE with MOG Peptide

EAE was induced in mice following the method of Feinstein et al. (Feinstein, Galea, et al. 2002) 1) two s.c. injections, one on each flank of the hind legs with 300 μg MOG35-55 peptide in 0.1 ml PBS emulsified in an equal volume of CFA containing 5 mg/ml of *Mycobacterium tuberculosis* H37RA (Difco, St. Louis, Mo.) were given on Day 0.2) Pertussis toxin (200 ng per mouse in 0.1 ml PBS) was given i.p. immediately and 48 h after first MOG injection. 3) a booster immunization with an identical emulsion, route of administration and location was given on Day 7.

Treatment with ApoE Peptide

After the first MOG injection (Day 0), mice were randomly separated into three groups of 15 mice per group to serve as: control group, apoE 133-149 (COG133, SEQ. ID. NO. 1) treated group and apoE reverse peptide treated group. COG133 in saline, reverse peptide in saline or normal saline was intravenously injected at a dose of 1 mg/kg in 100 μl volume on Day 6, 7, 8, 10, 12, 14, 16, 18, 20 and 22 to give a total of 10 doses for each treatment group.

Clinical Evaluation of EAE

Following the encephalitogenic challenge, mice were monitored daily and neurological impairment was evaluated by clinical score (C.S.) as follows: 0, no clinical signs of EAE; 1, limp tail; 2, flaccid tail and abnormal gait (ataxia and/or paresis of hind limbs); 3, severe hind limb paresis; 4, complete paralysis with hind body; and 5, moribund or death.

Peritoneal Macrophage Preparation, Culture and Treatment

For this purpose, three mice with clinical scores of 0 and three with clinical scores of 4 at 30 dpi (day post-immunization) were used for preparation of peritoneal macrophage cultures. Macrophages were collected after peritoneal lavage with 3 ml heparin (10 U/ml)-containing PBS and then seeded to 96-well microplates at a density of $1 \times 10^5$ cells/well in Dulbecco's MEM containing 10% fetal bovine serum, 2 mM L-glutamine serum, 1% HEPES and 100 U/ml penicillin and 100 μg/ml streptomycin, 37° C. in a humidified incubator with 5% $CO_2$. 24 h later, the serum-containing medium was removed and cells were washed once with serum-free medium. To examine the differentiated response of macrophage to immune stimulators, macrophages obtained from mice with clinical scores of 0 or 4 were exposed to serial concentrations of IFN-γ/LPS or MOG35-55 peptide. To investigate the effect of COG133 or COG134 peptide on IFN-γ/LPS or MOG-induced cytokine production, designated concentrations of these peptides were applied 30 min prior to IFN-γ/LPS or MOG treatment. Media were collected at 45 h or 72 h, and analyzed by ELISA for TNF-γ and IL-6 or for nitric oxide (NO) as detailed below.

Measurement of Nitrite and Total Protein

As the stable end product of nitric oxide release, nitrite levels in conditioned media were determined by injecting 50 μl media sample into a Sievers 280 NOA analyzer (Boulder, Colo., USA). Total protein (μg/well) was measured using the BCA method (Pierce, Rockford, Ill., USA) according to manufacturer's instructions with BSA as standard. BCA values were measured using a Molecular Devices Thermomax Microplate Reader (Menlo Park, Calif., USA) at OD562. Nitric oxide levels ere expressed as μM $NO_2$—/mg protein.

Measurement of TNF-γ and IL-6 by ELISA

For cytokine assays, supernatants were collected 45 h after tNF-γ/LPS or MOG treatments and quantitative ELISAs using selected pairs of monoclonal antibodies (as recommended by the manufacturer Biosource) were performed to quantify the cytokines, TNF-α and IL-6. For TNF-α ELISA, 96-well ELISA plates were pre-coated with rabbit anti-mouse polyclonal to TNF-α as capture antibodies for 18 h at 2-8° C. and then blocked for 2 h at room temperature. The wells were incubated with samples or mouse TNF-α standards. Following incubation for 2 h at room temperature, the wells were washed, after which hamster anti-mouse TNF-α biotinylated secondary antibody and horseradish peroxidase conjugate were added. Tetramethylbenzidine (TMB) solution was then added, and peroxidase-catalyzed color change was stopped by acidification with 2 $NH_2SO_4$. The plates were scanned at wavelength 450 nm and the absorbance were measured. The results are expressed as the mean concentration (pg/ml) ±SEM.

For IL-6 ELISA, rat anti-mouse monoclonal to IL-6 was used as capture antibody, and biotinylated rat anti-mouse monoclonal to IL-6 as detection antibody. The rest of procedure is identical to that of TNF-α ELISA.

Routine Histology

Mice were anesthetized, bled, and perfused with 25 ml PBS and 25 ml 4% paraformaldehyde in buffered PBS. Brains and spinal cords were dissected out from 3 mice with a clinical score of 0 and another 3 mice with a clinical score of 4 on day 30 post-immunization. Tissues were post-fixed in 4% paraformaldehyde for another 24 h and then stored in 1×PBS with 0.1% sodium azide. Fixed tissues were embedded in paraffin and 5 μm thick sections were cut from brain, the brain stem and three different levels of spinal cord (cervical, thoracic and lumbar). Sections were stained with hematoxylin/eosin for evidence of inflammation and Luxol fast blue (for demyelination). The severity of inflammation was evaluated using the following criteria: 0, no inflammation; 1, cellular infiltrates only in the perivascular areas and meninges; 2, mild cellular infiltrates only in parenchyma (1-10/section); 3, moderate cellular infiltrates in parenchyma (11-100/section); 4, marked cellular infiltrates in parenchyma (>100 section).

Statistical Analysis

Rotarod data, cytokines and nitrite concentrations were analyzed by ANOVA followed by Dunnet's comparison. Disease scores were analyzed by Mann-Whitney test.

Results

COG133 Attenuates Development of Active EAE

Figure 10:
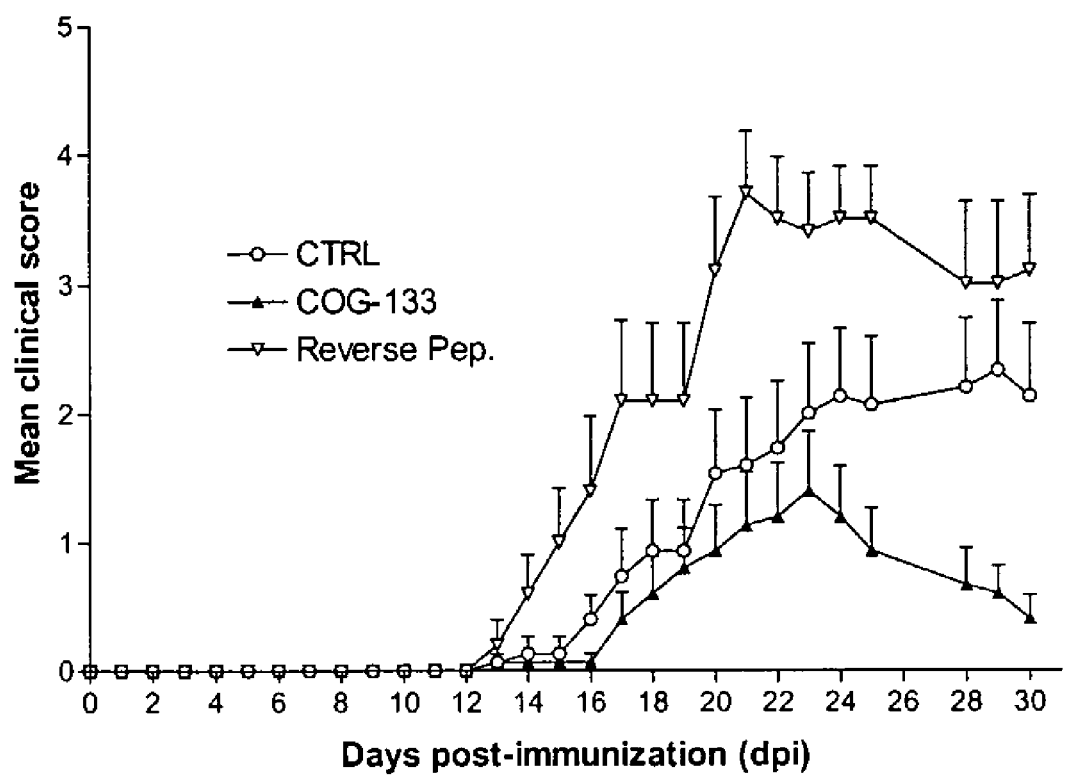

To examine the putative protective effect of COG133, intravenous administration of ten doses of 1 mg/kg COG133, or reverse peptide, or normal saline were given by tail vein injection beginning on Day 6 and ending on Day 22. Clinical signs were examined daily and behaviors on RotaRod by every other day. The mean maximum clinical scores of COG133-treated group were significantly lower than that of saline or scramble peptide-treated group (P<0.05) (FIG. 10). This result matched our general observation that animals treated with COG133 appeared to display less severe clinical signs of disease.

Using death which generates a clinical score of 5 as an endpoint, 4 mice died of disease in saline treated group of 15, whereas no animals died in the COG133 treated group of 15 and the treated group's highest clinical score was 3 (see Table 6). The mean time to disease onset of the COG133 treated group seemed to be a little delayed in comparison with control groups, although there was no statistically significant difference. Furthermore, COG133 treatment robustly facilitated the recovery from the disease by the data showing that the mean clinical score of COG133 group was much lower than control groups at Day 30.

Performance on RotaRod of each mouse was tested at a every two day regimen. Values were expressed as a percentage versus that of d0. RotaRod data didn't show significance at the developing phase of disease, whereas the value of COG133 treated group was much higher than that of control groups at the recovery phage (P<0.05) (data not shown).

TABLE 6

COG133 ameliorates EAE

| | Treatments | | |
| --- | --- | --- | --- |
| | CTRL | COG133 | Reverse Pep. |
| Day of onset | 18.5 ± 1.06 | 18.8 ± 1.24 | 17.3 ± 1.12 |
| Incidence | 11/15 | 8/15 | 10/10 |
| Mean maximum score | 2.53 ± 0.6 | 1.6 ± 0.45 | 3.9 ± 0.31 |
| Mortality | 4/15 | 0/15 | 3/10 |

Data expressed as mean ± SEM

Figure 11:
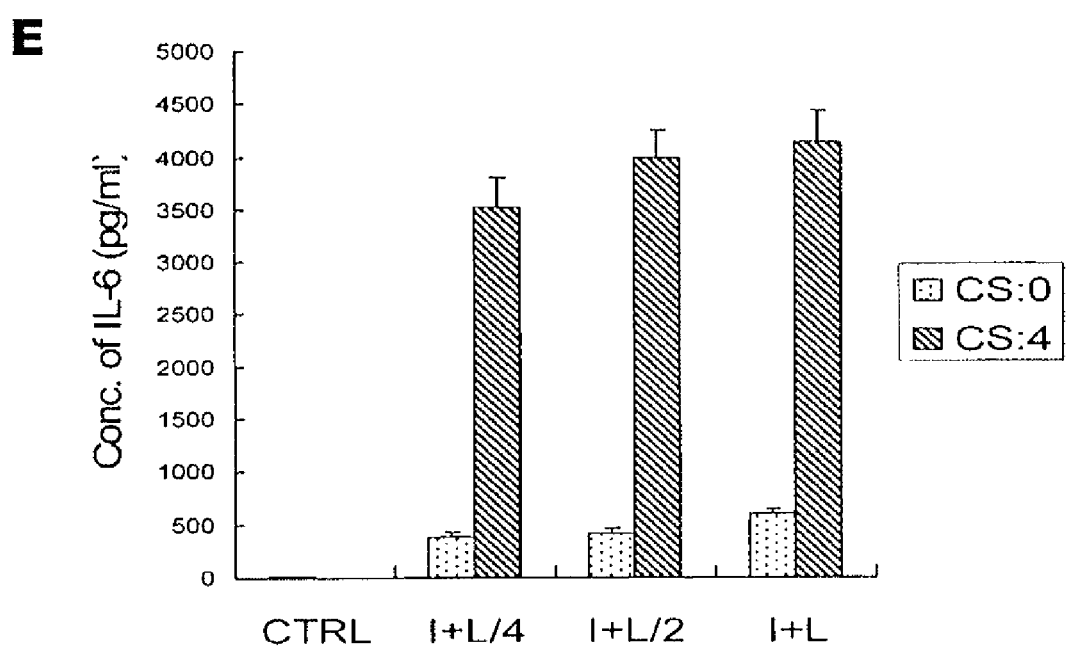

MOG or LPS/IFN-γ-treatments Induce Macrophage Production of NO, TNF-α and IL-6 in a Clinical Score-dependent Manner To examine the roles of cytokines such as TNF-α and IL-6 and the free radical, nitric oxide or NO, in the pathogenesis of EAE, macrophages were collected from mice with different clinical severity (C.S. 0 and 4) and then challenged with various immune stimulators, i.e. LPS and IFN-γ or MOG peptide. Although MOG peptide is a relatively mild immune stimulator compared with LPS+IFN-γ, a robust production of NO was still observed in macrophages from EAE mice in a concentration-dependent fashion (FIG. 11A). High concentrations of MOG (20 μg/ml, equivalent to 7.75 μM) treated macrophages from severely impaired mice with a C.S. of 4 mice elicited much higher release of nitric oxide than from MOG treated macrophages from non-impaired mice with a C.S. of 0, suggesting that production of NO may significantly contribute to the development of deleterious disease.

MOG-treatment induced TNFα secretion which showed a pattern that differs from the NO release pattern. The baseline of TNF-α at C.S. 0 is much higher than that of C.S. 4 (FIG. 11B), suggesting a role for TNF-α in initiating of the disease. In addition, MOG-induced IL-6 secretion was undetectable in the present study.

In macrophages from C.S. 4 mice, LPS+IFN-γ stimulated significantly higher production of NO, TNF-γ and IL-6 than in LPS+IFN-γ stimulated macrophages from C.S. 0 mice (FIGS. 11C, D, E).

COG133 Inhibited MOG-Induced Production of NO and TNFα

To explore the mechanism of beneficial effect of COG133 on the development of EAE, levels of NO and TNFα in the media of macrophages from C.S. 4 mice were measured 72 h after exposure to MOG (20 μg/ml, 7.75 μM). COG133 inhibited production of NO and TNFα in a concentration dependent manner (FIGS. 12A and B, respectively), whereas reverse peptide did not display such an inhibitory effect.

COG133 Inhibited LPS/IFN-γ-Induced Production of NO, TNFα and IL-6.

Figure 13:
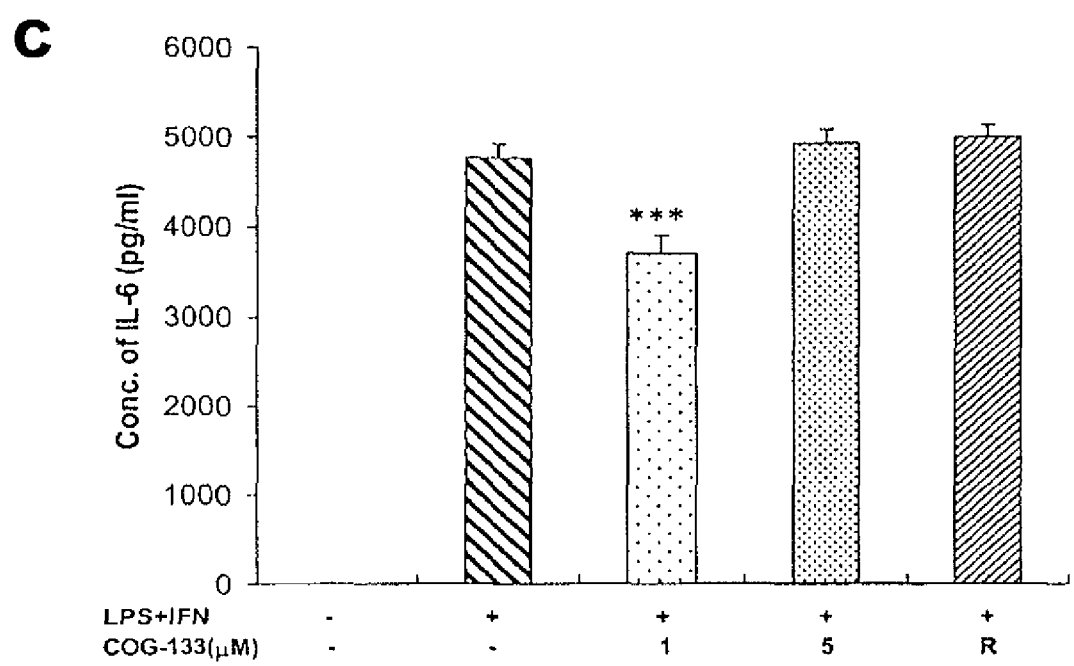

Robust production of NO, TNFα and IL-6 was induced by LPS and IFNγ treatments of macrophages (FIG. 13). At lower concentration (1 μM), rather than at higher concentration (5 μM), COG133 significantly inhibited production of NO (A), TNFα (B) and IL-6 (C) (P<0.05). Reverse peptide again failed to inhibit this production.

COG 134 (Antennapedia-COG133 Chimera, Aka COG4502) Potently Suppressed the Production of Cytokines Induced by MOG or by LPS/IFN-γ Treatments.

Compared with COG133, the chimeric peptide composed of antennapedia followed by apoE 133-149 (aka COG134 or COG4502) is significantly more powerful in inhibiting cytokine production induced by either MOG or by LPS/IFN-γ treatments (FIG. 14). COG134 (COG4502) at 5 μM inhibited the production of NO, TNFα and IL-6 completely, showing that the levels of all cytokines were turned back to basal level. COG134 also displays a dose-dependent ability to inhibit cytokine and free radical release. As a control for COG134, the portion of antennapedia that serves as a prefix to COG133 was synthesized and also tested in this system. This antennapedia prefix peptide showed no activity in our system.

COG133 Inhibits Cytokine Release in Cellular and In Vivo Systems

Figure 15:
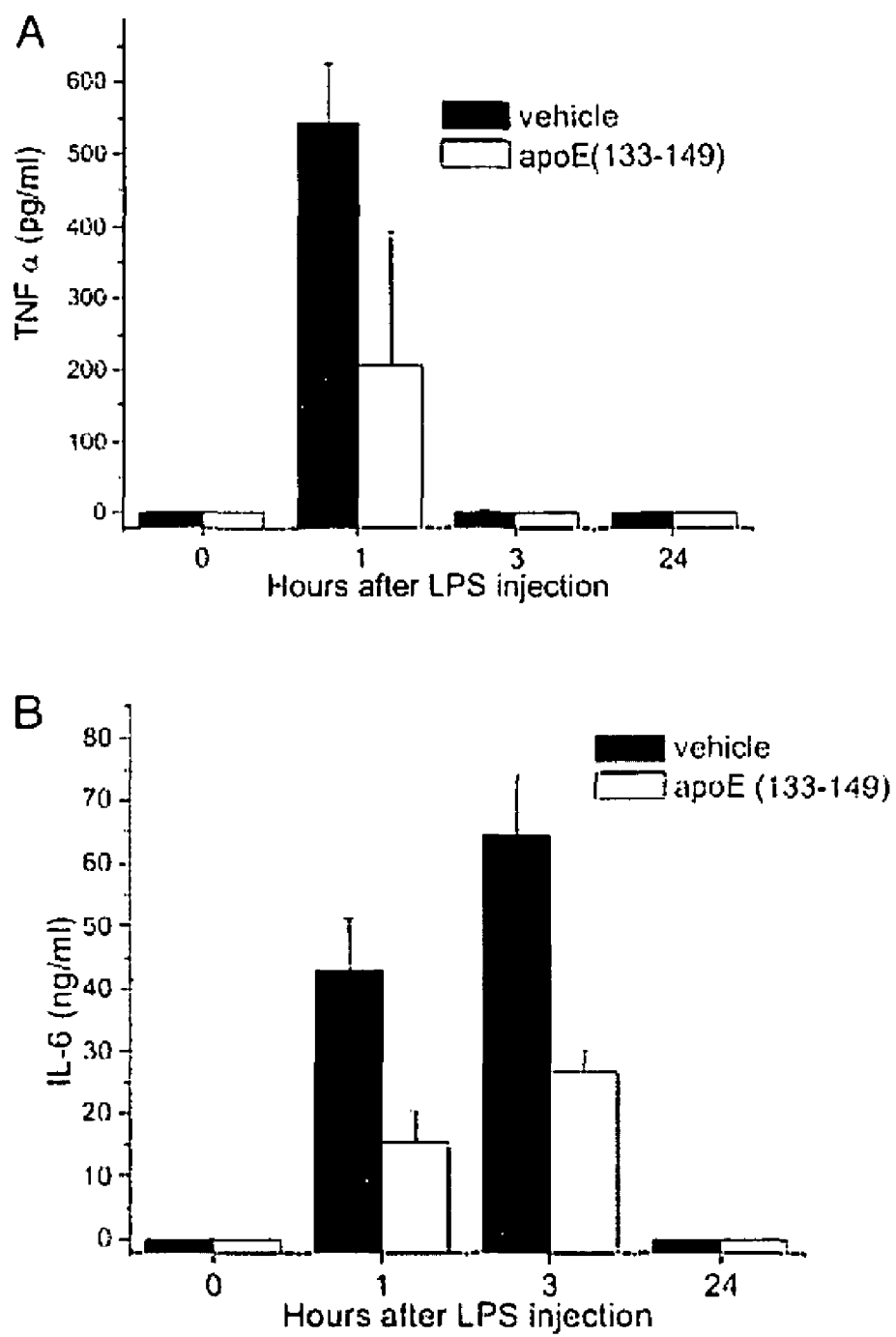

We have previously shown that COG133 retains the bioactivity of the intact apoE holoprotein in its ability to suppress microglia (the brain's macrophage) activation (Laskowitz et al. 2001) and initiate an intracellular signaling cascade in cultured cells (Misra et al. 2001). To investigate the mechanism by which apoE exerts its immunomodulatory effects, we examined the ability of COG133 to suppress systemic inflammatory responses in vivo in C57BL6 mice. The inflammatory response to LPS was monitored by measuring the temporal secretion and expression profiles of two well-described pro-inflammatory cytokines, Tumor Necrosis Factor alpha (TNFa) and interleukin-6 (IL-6), in the peripheral circulation and in the brain. Mice were injected with LPS via the tail vein and serum samples were obtained at indicated times and levels of TNFa and IL-6 were measured with ELISA. When co-administered with LPS, COG133 significantly reduced serum TNFa levels at one hour, and reduced serum IL-6 levels at one and three hours (FIG. 15). There was no measurable TNFa or IL-6 protein at 24 hours post-injection in either group. These results indicate that COG133 can suppress LPS-induced inflammation in a whole animal model and appears to be particularly effective at suppressing TNFa and IL6 release (Lynch et al., 2003).

In addition to suppression of cytokine release in the periphery, we also examined the ability of COG133 to suppress CNS inflammatory responses induced following tail vein administration of LPS. To prevent the contamination of brain samples with blood and other cells, mice in these studies were perfused with saline, i.e., the blood is flushed out of the microvasculature, and thus, only cytokines inside the brain compartment are present in the sample. Animals treated with COG133 exhibited TNFa levels in the brain that were significantly reduced at 1 and 3 hours post injection of LPS compared to animals receiving vehicle ($p<0.05$; FIG. 16A). Similarly, animals treated with COG133 exhibited IL6 levels in the brain that were significantly reduced at 3 hours post injection of LPS, compared to animals receiving vehicle ($p<0.05$; FIG. 16B). There was no measurable TNFa or IL-6 at 24 hours post-injection in either group. These results clearly show that IV administration of COG133 significantly suppressed LPS-induced inflammation in brain parenchyma (Lynch et al., 2003). The reduction in levels in the brain can not be the result of cytokines synthesized in the periphery and crossing the blood brain barrier since the mice were perfused prior to sacrifice. In addition, Lynch et al. (2003) reported the brain mRNA levels for these cytokines are reduced in LPS plus COG133 treated animals compared to those treated with LPS alone. These results demonstrate that, in an intact whole animal, COG133 administered via tail vein is able to control inflammation in the parenchyma of the brain, a compartment separated from the blood by the blood brain barrier (BBB).

Discussion

In this study, we demonstrate that COG133, an apoE mimetic peptide, shows significant ability to ameliorate the behavioral consequences of an experimentally induced allergic encephalomyelitis (EAE), which mimics most of the features of multiple sclerosis in humans. MS is a chronic inflammatory disease of the central nervous system characterized by widespread inflammation, focal demyelination, and a variable degree of axonal loss (Kornek, Storch, et al. 2000). Massive infiltration of macrophages and T-lymphocytes could be observed as a significant sign of inflammation throughout the whole brain, especially in spinal cord (Raine 1994). Release of Pro-inflammatory cytokines by infiltrated and activated macrophage and T-lymphocytes are key mediators of CNS pathology in EAE. Indeed, large amounts of TNF-α, IFN-α, and IL-1β are present in demyelinating plaques (Brosnan, Cannella, et al. 1995). In addition, infiltrated immune-reactive cells directly, or indirectly by releasing toxic cytokines, activate astroglia and microglia, which are thought of as macrophage in CNS, and therefore lead to a secondary cascade of inflammatory response (Prineas, Kwon, et al. 2001). Inflammation in spinal cord then becomes prominent during exacerbations and leads to significant impairment of movement and in some case, death of the mouse subject. Hence, anti-inflammatory intervention has extracted considerable interest as a promising strategy to prevent the deleterious process of the disease (Rieckmann & Maurer 2002).

The beneficial effects of apoE mimetic peptides as seen in this study include delaying the onset of symptoms of EAE, attenuating the severity of disease and facilitating recovery. Using a standard protocol of immunization with MOG peptide or treatment with LPS/IFN gamma, a robust debilitating disease was observed. Animals treated with this immunization protocol and with subsequent tail-vein injections of saline vehicle or with the reverse peptide (i.e. apoE 149-133), display significantly worse signs of clinical disease than those animals injected with COG133. Thus, the present study indicates a possible utility for COG133 in the therapeutic intervention of MS, and suggests that improved peptide derivatives such as COG432 and COG1410, which exhibit a wider therapeutic window and a higher therapeutic index, will also be useful for therapeutic intervention. Interestingly, previous works of our laboratory showed that COG133 exerted an anti-inflammatory effect (Lynch, Tang, et al. 2003). COG133 significantly inhibited LPS-induced production of NO and TNF-α in both primary glial cultures and BV2 cell, a murine microglial cell line (Laskowitz, Thekdi, et al. 2001). Now, the present study that COG133 significantly improves the symptom of EAE provides novel evidence to support the notion that apoE peptide exerts anti-inflammatory effect in vivo.

Example 6

Anti-Inflammatory Activity of ApoE Mimetic Peptides in a Collagen-Induced Model of Rheumatoid Arthritis in Mice Separate in vivo studies of apoE deficiency in the autoimmunity models, EAE and EAN, have indicated that apoE protects mice from greater disease severity and death by inhibiting: 1) the magnitude of the inflammatory response and 2) the amount of tissue destruction that is sustained in a chronic, Th 1 mediated, autoimmune response. Thus, ApoE mimetic peptides may be tested for efficacy in a collagen-induced model of rheumatoid arthritis.

The protocol written by Moore (2003) will be followed to produce collagen-induced arthritis in DBA/1 mice. This protocol is analogous the procedure Chondrex Inc recommends for generating CIA in mice using type II collagen. A disease incidence of 80-100% is routinely achieved using this method. We will begin treating mice on the first day that disease appears and for a further 14 days, putting mice at approximately 40 days post sensitization.

Mice will be sensitized to type II collagen by the following protocol. A solution of 0.01 M acetic acid will be added to chicken type II collagen to create a concentration of 4 mg/ml (Chondrex Inc., Redmond Wash.). Collagen will be dissolved overnight and the suspension will be mixed on a roller-mixer at 4° C. Dissolved collagen will be emulsified by adding an equal volume of ice-cold Freund's complete adjuvant. Freund's complete adjuvant will consist of Freund's incomplete adjuvant combined with heat-killed *Mycobacterium tuberculosis* (strain H37Ra) at a final concentration of 4 mg/ml (Difco Laboratories, Detroit Mich.). Each mouse will receive a 100 ul intradermal injection at the base of the tail. A 100 ul booster injection that contains 1 mg/ml bovine type II collagen in 0.01 acetic acid will be given i.p. on day 21 post sensitization. Using this protocol, symptoms routinely develop starting about 25 days after sensitization. However mice will not begin the 14 day treatment until the first day symptoms of arthritis appear. The mean time after sensitization that we expect animals to be sacrificed is Day 40. The sham arthritis group will not receive injections of antigen when other groups are sensitized and boosted. A total of 270 male DBA/mice (Jackson Laboratory, Bar Harbour, Me.) ranging from 10-12 weeks in age will be used in 3 separate experiments as well as two preliminary experiments to validate the disease model.

Mice will be randomly assigned to treatment groups. Each group will contain 15 mice. A negative control consisting of vehicle alone (PBS), a reverse peptide control (2.7 mg/kg), a positive control consisting of dexamethasone (1.0 mg/kg) and three doses of COG133 or other ApoE peptide diluted in sterile saline will be tested: 0.3, 0.9 and 2.7 mg/kg. Dosages are based on data obtained in vitro and in vivo experiments presented in the preliminary results section. ApoE peptide, vehicle or dexamethasone will be given by intraperitoneal injection each day, according to the following schedule: Day 0, sensitization; Day 21, booster; about Days 21-25, treatment for 14 days of active disease; about Day 40, sacrifice after 14 days of disease. Mice will be analyzed daily for disease severity and paw swelling throughout the experiment until mice are sacrificed. On day 14 of disease, mice will be sacrificed by asphyxiation with $CO_2$, weighed, assessed for inflammation and disease severity. Each patella will be dissected out, dried and weighed.

The effect of COG133 therapy on inflammation and bone loss in healthy mice will also be assessed. A group of sham mice will not be sensitized and boosted at the time other mice are given collagen-induced arthritis. These mice will receive the high dose COG133 therapy (2.7 mg/kg) or COG1410 (0.6 mg/Kg) for 14 days. Prior to initiation of the study, we will validate the CIA model in a group of untreated mice by histological and biochemical means. Ten DBA/1 male mice will be sensitized and boosted as outlined above but not treated, rather parameters of inflammation will be monitored by means of paw volume and after 14 days of disease, mice will be sacrificed, weighed and blood will be collected to test for anti-type II collagen IgG. Five mice will have bone joints removed for histological analysis to confirm the presence and uniformity of CIA, the other five mice will have each patella removed, dried and weighed to confirm measurable and reproducible bone loss. A further five healthy age-matched controls will be sacrificed to obtain baseline values for histology and patellar bone mass. This experiment will be repeated a second time to confirm that our disease severity is consistent and reproducible. At the time of sacrifice, peripheral blood will be collected; plasma will be separated and then assayed in an ELISA for the amount of anti-collagen antibody present. A commercial assay kit, arthrogen-CIA® Mouse IgG Anti-Type II Collagen ELISA kit will be used to confirm the uniformity of the collagen type II sensitization and boost (Chondrex).

Validation of CIA by Means of Histology:

Ankle and wrist joints will be excised and fixed in 10% buffered formalin and then decalcified for three days in a solution of 10% formic acid (Kawabuta et al., 2003). Tissues will be sent to the Department of Pathology at Duke University Medical Center or an acceptable commercial vendor to be embedded in paraffin, cut into 6 um sections and mounted on glass slides. Slides will be stained by three different means to enable the following markers of disease to be evaluated: changes in the amount of collagen present in the bone joint (masson's trichrome), reductions in cartilage (safranin O) and formation of pannus tissue, narrowing of joint spaces as well as inflammatory cell infiltrate (hematoxylin and eosin). Tissue sections will be evaluated using a semi-quantitative means (van Meurs et al. 1999; Beehler et al., 2003; Kawabata et al. 2004).

Quantification of the Inflammatory Response by Paw Volume:

The disease severity/clinical score will be assessed as outlined by Moore (2003). Each digit that shows signs of involvement is scored as 1, any inflammation in the hind or fore limbs is scored as 1/limb, swelling in the foot pad, ankle, or wrist, each adds a score of 1 to the clinical score. The total number of inflamed limbs/mouse will also be noted. A digital plethysmometer (paw volume meter, Stoelting Co. Wood Dale, Ill.) will be used to measure changes in paw swelling over time and expressed as the mean+/−standard error of the mean (SEM)/experimental group. To ensure consistency in measuring paw volume changes, mice will be tattooed 2 weeks before the experiments begin with a line at the elbow and the knee joints prior to sensitization so that a consistent amount of the paw of each mouse is measured. Total paw swelling will be determined by calculating the area under the curve for each animal during the study. Data from each experimental group will be expressed as the mean total paw swelling±S.E.M.

Quantification of Bone Loss:

At the time mice are sacrificed, each patella will be dissected out. Each patella will be dried overnight at 70° C. and weighed again. Patella weights are expressed as a percentage compared to healthy mice of similar age and weight. Likewise, the dry weight of patellas will be expressed as mean±S.E.M. for the experimental group.

Statistics:

Differences between experimental groups will be determined by an analysis of variance (ANOVA) while differences between pairs of groups will be determined by the Mann-Whitney U-test. A p value of <0.05 will be considered significant.

We expect that COG133, COG1410 and other ApoE mimetic peptides at the doses and length of treatment proposed above will be well tolerated in normal mice. Preliminary data using COG133 in mice with EAE has shown the peptide was well tolerated. Furthermore, it is expected that this treatment will elicit a dose-dependent inhibition in the severity of CIA as well as measures of inflammation and bone loss after 14 days of disease. We do not expect COG133 to act exclusively on the inflammatory process or bone loss, but attenuate both arms of the disease process equally.

Example 7

Anti-Inflammatory Activity of ApoE Mimetic Peptides in Stimulated Rabbit Synovial Fibroblasts Pannus tissue is comprised of synovial cells that have undergone hyperproliferation within the bone joints of patients with rheumatoid arthritis and mice with CIA. This tissue is a major contributor to the destruction of cartilage and bone because of it's production of cytokines, MMPs and nitric oxide (Pillinger et al. 2000). Testing a candidate therapy for RA using cells that are physiologically relevant to the disease process will aid in determining the potential benefit the treatment will have in vivo.

HIG-82 cells (American Type Culture Collection, Manassas, Va.) are cultured in Ham's F-12 medium supplemented with 10% by volume fetal bovine serum, 50 ug/ml penicillin-streptomycin and 1 mM L-glutamine (InVitrogen). Cells are grown in 150 mm vented-flasks (Nunc) and maintained in a humidified atmosphere, 37° C. with 5% $CO_2$. HIG-82 cells are detached from the bottom of the flask by first washing twice with 10 ml $Ca^{+2}/Mg^{+2}$-free D-PBS followed by the addition of 5 ml of a 1/5000 dilution stock of versene (InVitrogen). The versene-treated cells are washed by centrifugation (200×g, 7 minutes) and gently resuspended in media.

The experimental protocol for measuring MMP's and NO in supernatants from HIG-82 cells cultures is based on procedures published by Panagakos et al. (2000) as well as Kolomyikin et al. (2002). Briefly, $2.0 \times 10^5$ cells in 2 ml of media will be added to each well of a 12-well plate (Nunc) and grown to confluency. When cells are confluent, media will be aspirated out of the wells and 1 ml of serum-free media is added. Twenty-four hours later the synovial fibroblasts will be treated with inflammatory mediators in the presence or absence of increasing concentrations of COG133. After an additional 24 hr, the supernatants will be harvested and assayed for nitric oxide, TNF-alpha, as well as MMP's-1, 3-9 and 13.

In order to test if COG133 or COG1410 will inhibit TNF-alpha production from synovial fibroblasts, HIG-82 cells will be activated with LPS (0.001, 0.01 and 0.1 ug/ml) in the presence or absence of COG133 or COG1410 (0.1, 0.5, 1, 3, 10 and 25 uM). Supernatants will be collected and analyzed with a commercially available rabbit TNF-alpha ELISA kit (BD Biosciences). As with the MMP and NO experiments, time-course studies will be conducted to determine the peak time of TNF-alpha production prior to testing COG133 or COG1410.

It is our goal to test vehicle, reverse peptide, COG1410 or COG133 (or other ApoE mimetic peptide)-treated synovial fibroblasts for TNF-alpha, MMP and NO production after stimulation with multiple doses of each proinflammatory mediator at a concentrations and incubation times that are optimal for each assay. Preliminary experiments will establish the optimal concentrations and incubation times for activating HIG-82 cells with: LPS (*E. coli* 055:B5, Sigma), IL-1Beta (R&D Systems) or TNF-alpha (R&D Systems) as well as co-treatment of cultures with IL-1 Beta and TNF-alpha.

Pillinger et al. (2000) used recombinant human IL-1Beta or TNF-alpha at 20 ng/ml to activate the HIG-82 cells in assays for MMP's (MMP-1 and 13) and NO. Optimal times for MMP production by HIG-82 cells is reported to range from 14-48 hours. The concentration of human IL-1B used to stimulate peak MMP production also varied (0.001-20 ng/ml) (Panagakos et al. 2000; Kolomytkin et al. 2002; Pillinger et al. 2004). Once optimal conditions for production of TNF-alpha, NO and MMP's 1, 3, 9 and 13 have been established, a minimum of 3 independent experiments will be performed in replicates of 4 as summarized in Table 3. A sub-optimal, optimal and high dose of each mediator will be tested. Statistical significance will be determined using ANOVA followed by Dunnetts' t-test.

Assay for Matrix Metalloprotease (MMP) Activity:

We propose to measure MMP's, 1, 3, 9 and 13 using a method developed at Cognosci: multiple-enzyme/multiple reagent assays system (MEMRAS; Rasmussen et al. 2004). MEMRAS enables the measurement of the activity of multiple MMP's in a single sample. Data will be expressed as the mean concentration±S. E. M. of each MMP detected in each experimental group.

Assay for NO:

Supernatants from cell culture experiments will be assayed using the Greiss reagent system (Promega, Madison Wis.) to measure a stable, nonvolatile degradation product of nitric oxide, nitrite ($NO_2^-$). Data will be expressed as the mean percentage±S.E.M. of the positive control (cells plus LPS or cytokine).

Assay for Rabbit TNF-Alpha:

Antibody pairs for capture and detection of rabbit TNF-alpha, as well as rabbit TNF-alpha (standard) are commercially available (BD Biosciences) and will be used according to the manufacturers' instructions to quantify the amount of TNF-alpha that HIG-82 cells produce. Data will be expressed the mean percentage±S.E.M. of the positive control (cells plus LPS or cytokine).

To ensure that any reductions in the amounts MMP's, NO or TNF-alpha we observe are not due to cell death, viability assays will be performed on HIG-82 cells under all the experimental conditions proposed, using the MTT assay (Promega, Madison Wis.).

Example 8

Penetratin-COG133 Conjugate

ApoE Mimetic is Neuroprotective in a Murine Model of TBI

Thirty minutes following TBI, mice were treated with 406 µg/kg COG133 or saline vehicle. At 24 hours post injury, the saline injected animals exhibited a profound deficit in motor coordination and balance as measured by the rotorod test (FIG. 15A). This motor deficit was associated with weight loss (data not shown). Mice treated with COG133 performed significantly better on each day than their saline-treated counterparts, p<0.01 (Lynch et al., 2001). This recovery of function was correlated with decreased neuronal death in the hippocampus of COG133 treated mice compared to saline treated mice, p<0.05; data not shown. These results strongly suggest that intravenous administration of COG133 improved performance on rotorod and prevented the neuronal death associated with head trauma.

In addition to gross testing of acute recovery of neurological function with rotorod, Applicants also measured chronic recovery at 20 days after TBI by studying changes in performance in the Morris Water Maze task (Morris, 1984). This task measures the ability of the animal to incorporate visual-spatial cues into working and reference memory. Performance on this task is a correlate of the neuropsychiatric deficit seen in a human clinical population for head injury (Skelton et al., 2000). As depicted in FIG. 15B, head injured mice treated intravenously with COG133 performed significantly better on days 23 and 24 than injured animals receiving intravenous saline vehicle as a control, p<0.01 (Lynch et al., 2001). This series of experiments has demonstrated proof of principle that intravenously administered COG133 is neuroprotective when administered 30 minutes following TBI in mice. This protection extended to neuromotor, neurocognitive, and neuropathological endpoints.

Penetratin-COG133 Activity In BV-2 Cells

Figure 16:
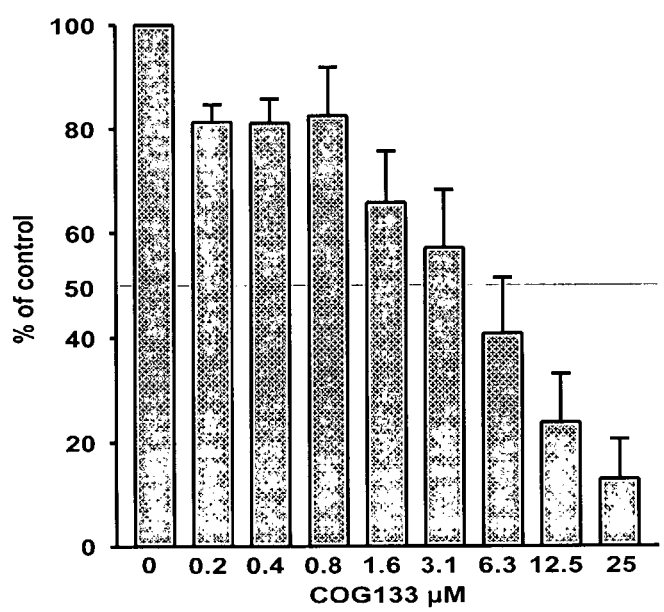
Figure 17:
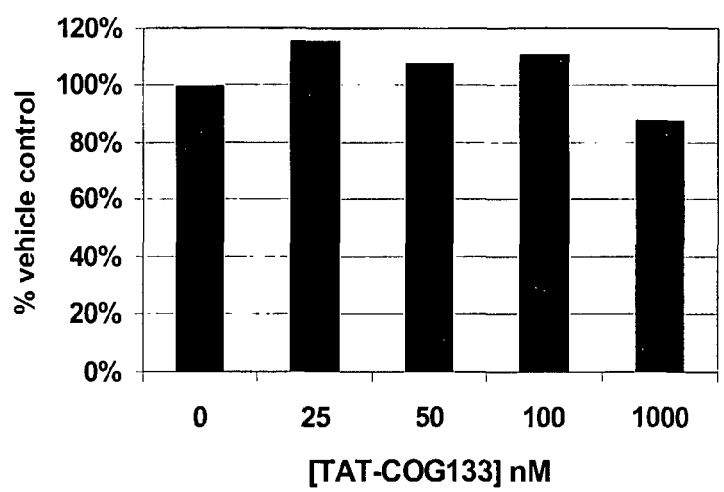
Figure 18:
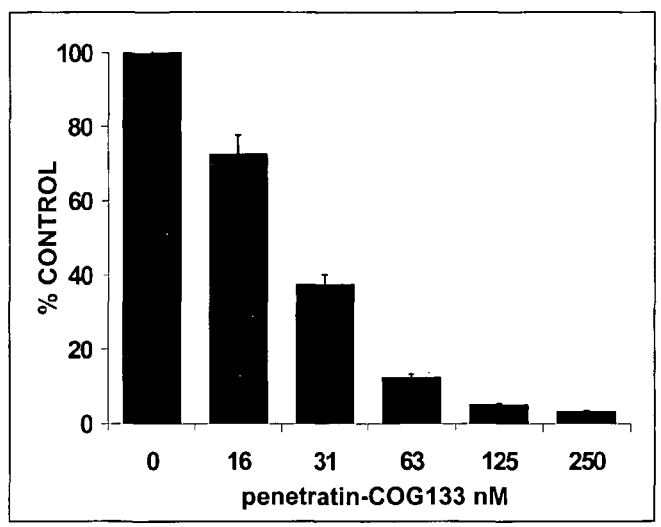

In previous work Applicants demonstrated that COG133 exhibited a dose dependent suppression of LPS-stimulated nitrite secretion in BV2 murine microglial cells. As depicted in FIG. 16, 50% suppression was achieved at a dose of approximately 3 µM COG133. For Applicants preliminary work, the two most common PTDs, TAT and penetratin, were used. As depicted in FIG. 17, the TAT-COG133 conjugate was not effective in the range of 25-1000 nM. Doses greater than 1000 nM resulted in death of greater than 90% of cells (data not shown). FIG. 18 illustrates that the penetratin-COG133 conjugate was significantly more potent than COG133. Fifty percent suppression by penetratin-COG133 (COG4502) occurred at approximately 30 nM, whereas COG133 alone did not achieve 50% suppression within the dose range utilized in this experiment. Comparison of the data in FIG. 18 with that in FIG. 16, in which 50% suppression was achieved at 3 µM, indicate that the efficacy of COG133 was increased about 100 fold when conjugated to penetratin (COG4502).

These preliminary data indicate that TAT-COG133 was cytotoxic, whereas penetratin-COG133 (COG4502) significantly increased the efficacy of COG133 in BV2 microglial cells.

Figure 19:
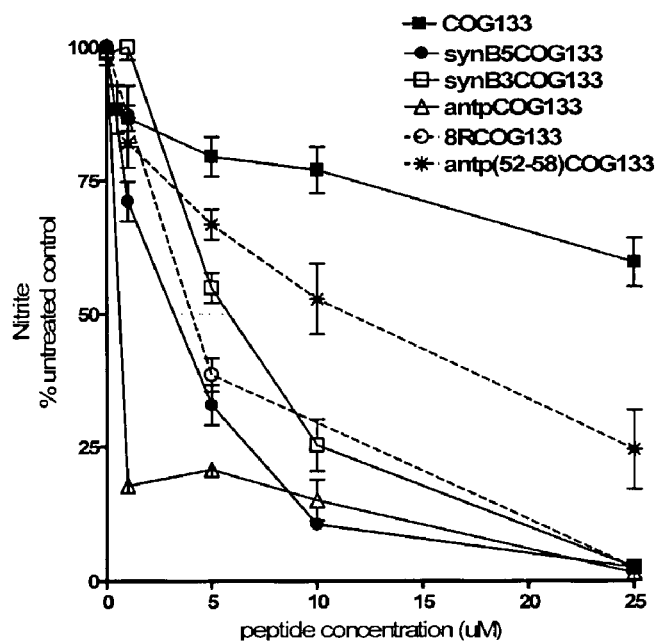

To further determine the efficacy of PTD conjugated COG133s, BV2 cells were treated with various concentrations of the PTD-COG133s (see Table 7 for PTD and COG133 sequences) and NO production was quantified and normalized based on cell viability. As depicted in FIG. 19, conjugation of COG133 to all of the PTDs tested enhanced the efficacy of COG133 to varying degrees. The IC50, i.e., the concentration of a PTD-COG133 conjugate that resulted in 50% suppression of NO production relative to untreated controls, was determined for each compound. As depicted in FIG. 19 and detailed in Table 7, COG133 was barely able to reduce NO production to 50% of untreated controls at the highest concentration tested, i.e., 25 µM, whereas antpCOG133 did so at a dose of 0.7 µM, and achieved 100% suppression at 25 µM. Interestingly, the truncated antp PTD, i.e., antp(52-58), which was reportedly as effective as full length antp in other in vitro studies (Fisher et al. 2000), exhibited significantly reduced efficacy with an IC50 of 11 µM. SynB3, SynB5, and 8R enhanced the activity of COG133 to similar degrees with IC50s of 5.9 µM, 3.2 µM, and 4 µM, respectively. AntpCOG133 was the most effective conjugate, resulting in a 40-fold increase in potency relative to COG133.

data are consistent with the results obtained screening the activity of COG conjugates in BV2 cells, thereby establishing the validity of the BV2 cells as a primary screen for COG activity.

Applicants have demonstrated in vitro and in vivo that COG133 exhibits anti-inflammatory and neuroprotective properties. Though the mechanism of transport is likely through one or more of the known apoE receptors, it is clear that PTDs such as penetratin possess the capability to transport cargo across cell membranes, and, in some cases, across the BBB. Preliminary data in BV2 cells and in vivo form the solid base upon which Applicants propose to test the hypothesis that conjugation of COG133 to various PTDs can increase the efficacy and therapeutic window of COG133. Currently, there are no definitive neuroprotective agents available to treat TBI. This is a first step in a strategy for the development of a novel PTD as a platform delivery vehicle. The enhanced delivery through the BBB afforded by a novel PTD analog will expand the range neurological disorders that can be treated with COG133 to include those that lack the overt BBB breach seen in TBI. In addition, the ability of COG133 to transcytose will enhance its activity systemically, potentially enabling COG133 to enjoy broad application as an anti-inflammatory therapeutic agent.

TABLE 7

PTDCOG133 characteristics

| PTD | Sequence | In vitro | | | In vivo Therapeutic window |
|---|---|---|---|---|---|
| | | IC50 NO | IC50 TNFα | LD50 | time expanded? |
| Antp | RQIKIWFQNRRMKWKK (SEQ ID NO. 51) | 0.7 | 1.1 | 7.0 | Yes; tested at 4 X |
| antp (52-58) | RRMKWKK (SEQ ID NO. 52) | 11 | not determined | 20 | not determined |
| SynB3 | RRLSYSRRRF (SEQ ID NO. 54) | 5.9 | 5.1 | 9.5 | Yes; tested at 4 X |
| SynB5 | RGGRLAYLRRRWAVLGR (SEQ ID NO. 55) | 3.2 | 4.2 | 7.7 | No; Tested at 6 X |
| polyArg (8R) | RRRRRRRR (SEQ ID NO. 56) | 4.0 | 4.2 | 5.3 | not determined |
| COG133 | LRVRLASHLRKLRKRLL (SEQ ID NO. 1) | 25 | 15 | 20 | |

To determine if a similar outcome would occur in vivo, Applicants administered TAT-COG133 and penetratin-COG133 (COG4502) conjugates to mice at varying times following TBI.

Penetratin-COG133 (COG4502) Activity In Vivo

Figure 20:
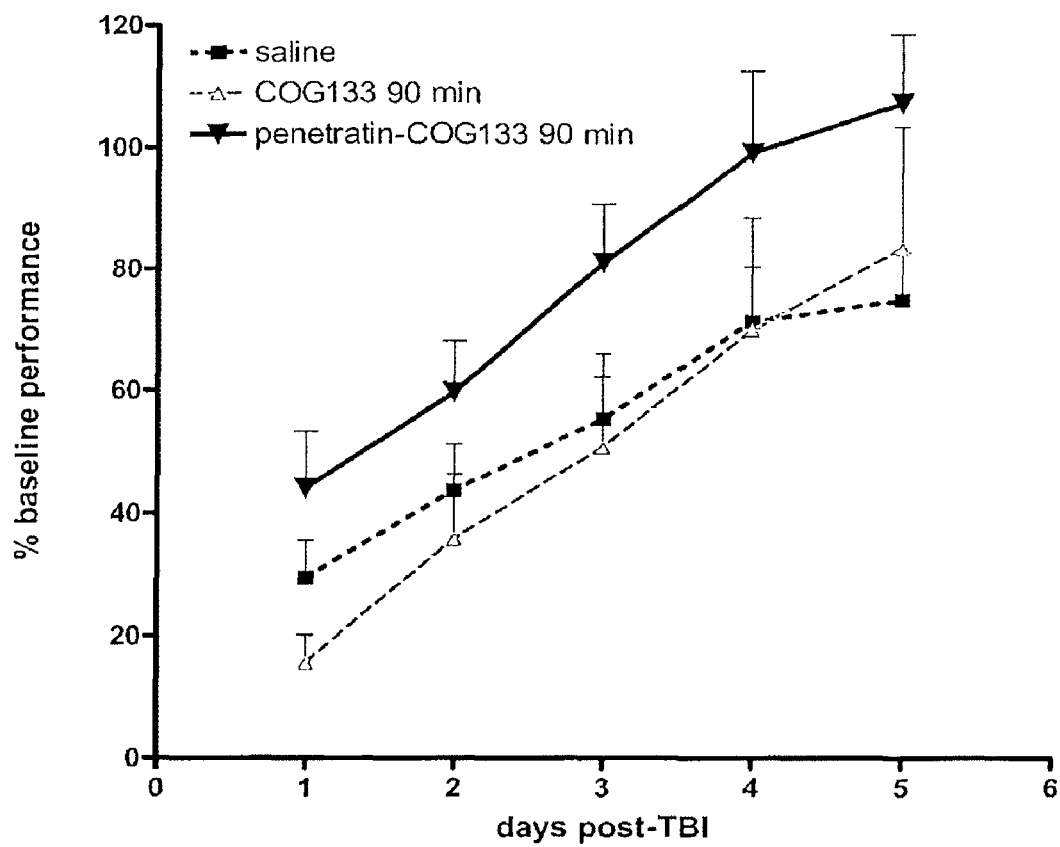
Figure 21:
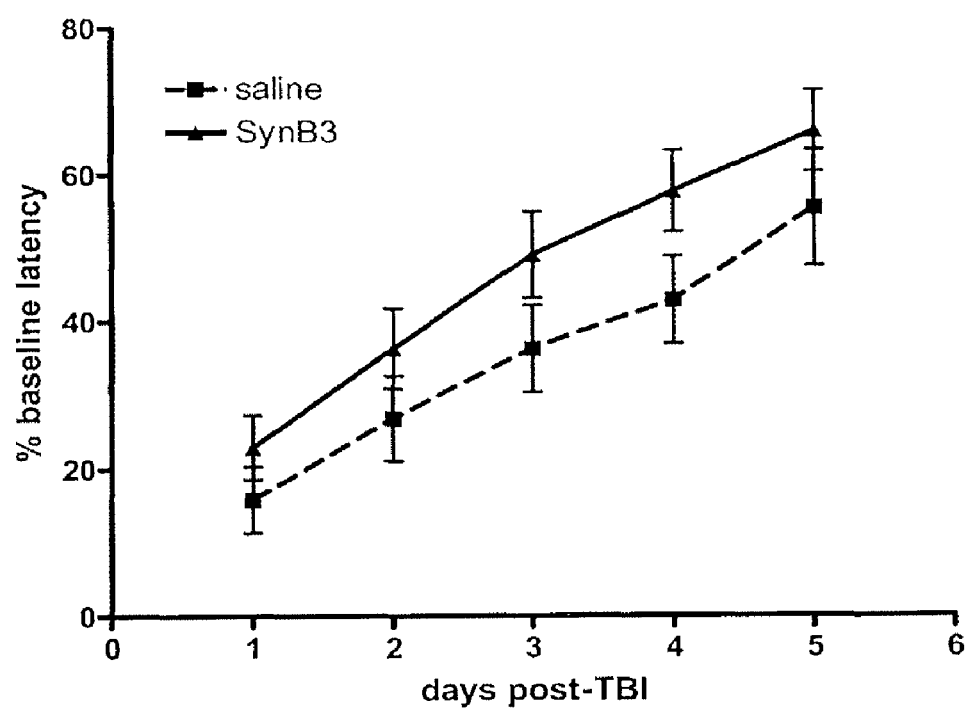

Mice were administered COG133, TAT-COG133, or penetratin-COG133 (COG4502) at varying times following TBI and the effects were analyzed by performance on the rotorod task. The results depicted in FIG. 20 suggest that conjugation of COG133 to penetratin can increase the therapeutic window of COG133, whereas treatment with TAT-COG 133 was not effective and was similar to saline (data not shown). These Example 9

Identification of PTDs that Promote the Intracellular Delivery and Function of the COG133 in BV2 (Murine Microglial) Cells Experimental Design:

A randomized design is used where the independent variable is the PTD and the dependent variable will be levels of nitric oxide present in the culture media.

Synthesis of PTD-COG133 Conjugates:

Peptides are synthesized by New England

Peptides or other suitable vendor to a purity of 95% and reconstituted in sterile isotonic PBS. Each PTD is appended to the N terminus of COG133, whose sequence is LRVR-LASHLRKLRKRLL (SEQ ID NO. 1). Note that COG133 possesses 5 arginines. The presence of arginines, which are reportedly crucial for transcytosis of PTDs, suggest that COG133 can itself possess characteristics of PTDs and/or can facilitate PTD transport.

| PTD Sequences | |
|---|---|
| TAT (48-60) | GRKKRRQRRRPPQ (SEQ ID NO. 50) |
| Penetratin (aka Antp 43-58) | RQIKIWFQNRRMKWKK (SEQ ID NO. 51) |
| Antp (52-58) | RRMKWKK (SEQ ID NO. 52) |
| SynB1 | RGGRLSYSRRRFSTSTGR (SEQ ID NO. 53) |
| SynB3 | RRLSYSRRRF (SEQ ID NO. 54) |
| SynB5 | RGGRLAYLRRRWAVLGR (SEQ ID NO. 55) |
| polyArg (8) | RRRRRRRR (SEQ ID NO. 56) |

Cell Culture:

BV-2, a well-characterized murine microglial cell line (Bochinni, 1992), is cultured in high glucose content DMEM supplemented with 1% penicillin/streptomycin, 10% fetal calf serum, 1% nonessential amino acids, and 1% sodium pyruvate. Cells are grown to confluency; trypsinized; spun down; resuspended in serum-free OptiMEM containing 1% N2 supplement, 1% penicillin/streptomycin, 1% nonessential amino acids, and 1% sodium pyruvate; and plated at a concentration of 20,000 cells/well to remove any nonadherent cells and serum.

LPS Stimulation of Cells and Treatment with PTD-COG133s:

BV2 cells are washed with OptiMEM to assure the removal of serum, covered with 200 μl of fresh OptiMEM, and then treated with a range of concentrations of PTD-COG 133 (or appropriately diluted ammonium bicarbonate vehicle control solution) and 100 ng/ml LPS from *E. coli* (Catalog No. L8274, Sigma). Supernatant is collected 24 and/or 48 h after LPS stimulation and assayed for nitrite.

Quantification of Nitric Oxide (NO):

Accumulation of nitrite (stable end product of NO production) in the medium is measured by colometric Griess reagent system (Promega); the absorbance is determined at 540 nm.

Cell Viability Assay:

Cell viability is measured using a nonradioactive cell viability assay (cell titer 96 AQ, Promega). The assay measures the bioreduction of MTS (3-(4,5-dimethylthiazole-2-)-5-(3-carboxymethoxyphenyl)-2-(4-sulfophenyl)-2H-tetrazolium by viable cells into formazan. The absorbance of the colorimetric assay is measured at λ 490 nm. Viability is assessed and used to normalize the nitrite data.

Data Collection and Statistical Analysis:

Experiments are carried out on a minimum of six wells analyzed per experimental condition for a minimum of three different culture groups. Values may be expressed as mean±SEM. Significance will be determined using the unpaired Student's t test or ANOVA.

Example 10

Assess the Ability of Candidate PTD-COG133 Conjugates to Enhance the Efficacy of and/or Expand the Therapeutic Window of COG133 Using an Established Recovery Model of Traumatic Brain Injury in the Mouse Experimental Design:

A randomized design is used with two independent variables, a) time elapsed between injury and treatment (i.e., 30, 60, 90, and 180 minutes) and b) the top three PTD-COG133 conjugates based performance in BV-2 cells. The dependent variables will be rotorod score and weight.

Head Injury Model with Controlled Pneumatic Impact Device:

Mice are anesthetized with 4.3% isoflurane in oxygen at a FiO2 of 50% in an anesthesia induction box for 90 seconds. The trachea are intubated and the lungs mechanically ventilated and anesthetized with 1.4% isoflurane in 50% $O_2$ and 50% $N_2$. Body temperature is maintained at 37° C. using surface heating/cooling. Each mouse is positioned in a stereotactic device. The top of the skull is exposed to identify anatomical landmarks. Animals are subjected to controlled skull impact with a pneumatic impactor (Air-Power, High Point, N.C.) using a 2.0 mm steel tip impounder at a controlled velocity (6.0±0.2 m/sec) and vertical displacement (3.0 mm). The animals will be allowed to recover spontaneous ventilation prior to extubation. Following recovery, mice will be allowed free access to food and water (Lynch, et al., 2001a, b).

Drug Administration:

At 30, 60, 90, or 180 minutes following TBI, mice are intravenously injected with 100 ul of sterile phosphate buffered saline vehicle, COG133 at a dose of 1 mg/kg, or various PTD-COG133 conjugates at a dose of 1 mg/kg. Based on previous experience, 20 animals per experimental treatment group will be employed to obtain enough data to be able to make significant statistical comparisons.

Rotorod Test:

The Rotorod Test is given about 2 hours before experimentally applied TBI. Briefly, each mouse is lifted by the tail and gently placed on the rotating rod that is revolving at a slow and constant speed. After 5 to 10 seconds, the rotating rod is switched to acceleration mode and a timer is started. The timer is stopped when the mouse falls off of the rotating rod or when the mouse has held onto the rod and rotated twice around (720 degrees of rotation). After a 5 minute rest period, a second trial ise performed by placing the same mouse on the rotating rod again, and the "latency" or time spent on the rotating rod is measured again. After another 5 minute rest period, a third trial is performed and the latency time will be measured for each mouse again. On the day following TBI (approximately 20 to 24 hours post-impaction) and then every day for the next five days, each mouse is tested by 3 trials on the rotorod test as described below, thereby enabling each mouse to serve as his own control. For data analysis, the 3 latency times for each mouse in a group of mice are averaged together and standard deviations calculated. This testing paradigm was selected based on our previous research on TBI which demonstrated that it possesses the sensitivity to detect the presence of post traumatic dysfunction, and subsequent recovery (Lynch et al., 2001a, b). All tests are conducted by an investigator blinded to group assignment.

Data Collection and Statistical Analysis:

Values may be expressed as mean±SEM. Significance is determined using the unpaired Student's t test or ANOVA.

Results for SynB3-COG133

Figure 23:
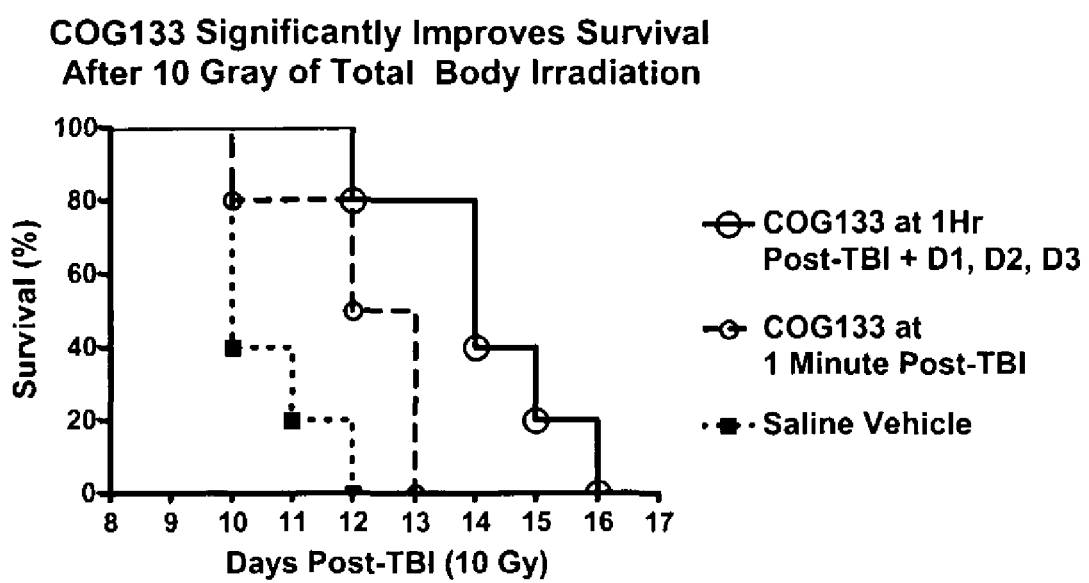

Data depicted in FIG. 23 indicate that SynB3-COG133 conjugate significantly improves outcome from head trauma in mice when administered by a single tail vein injection at 2 hours post traumatic brain injury (as measured by rotorod latency).

Example 11

Anti-Inflammatory Properties of COG133

To test whether a peptide derived from ApoE holo-protein could confer the same anti-inflammatory activities as holo-ApoE protein, we initially showed that addition of COG133 (aka. ApoE 133-149) or ApoE 130-149 resulted in a dose dependent inhibition of TNFα release from a BV2 microglial cell line stimulated with lipopolysaccharide (LPS) (Laskowitz et al. 2001). In contrast, cells treated with a scrambled peptide failed to inhibit TNFα release. Similarly, COG133 and Apoe 130-149 significantly reduced nitric oxide release from LPS-treated BV2 cells while scrambled peptide treatments failed to inhibit nitric oxide release. These data demonstrated that the release of a cytokine (TNFα) and of a free radical (NO) following LPS-induced stimulation of macrophagic cells is significantly reduced in the presence of COG133 indicating that COG133 may function as an anti-inflammatory agent. See U.S. application Ser. No. 10/252,120, which is herein incorporated by reference in its entirety.

We next investigated whether COG133 (apoE 133-149) would suppress inflammatory responses in whole animals (Lynch et al. 2003) in the same fashion as in cell-based models (Laskowitz et al. 2001). When co-administered with LPS, the COG133 apoE-mimetic peptide significantly reduced serum TNFα and serum IL-6 levels. In addition to suppression of cytokine release in the periphery, we also investigated the effects of tail vein injection of LPS plus COG133 on cytokine mRNA levels in the brains of wild-type mice (Lynch et al. 2003). Compared to LPS plus saline, TNFα and IL6 mRNA levels were significantly reduced in animals at 3 hours post injection of LPS plus COG133, showing that administration of COG133, an apoE mimetic peptide, can significantly suppress LPS-induced inflammation in a whole animal model.

Example 12

Radioprotective Role of Endogenous ApoE Protein

Figure 22:
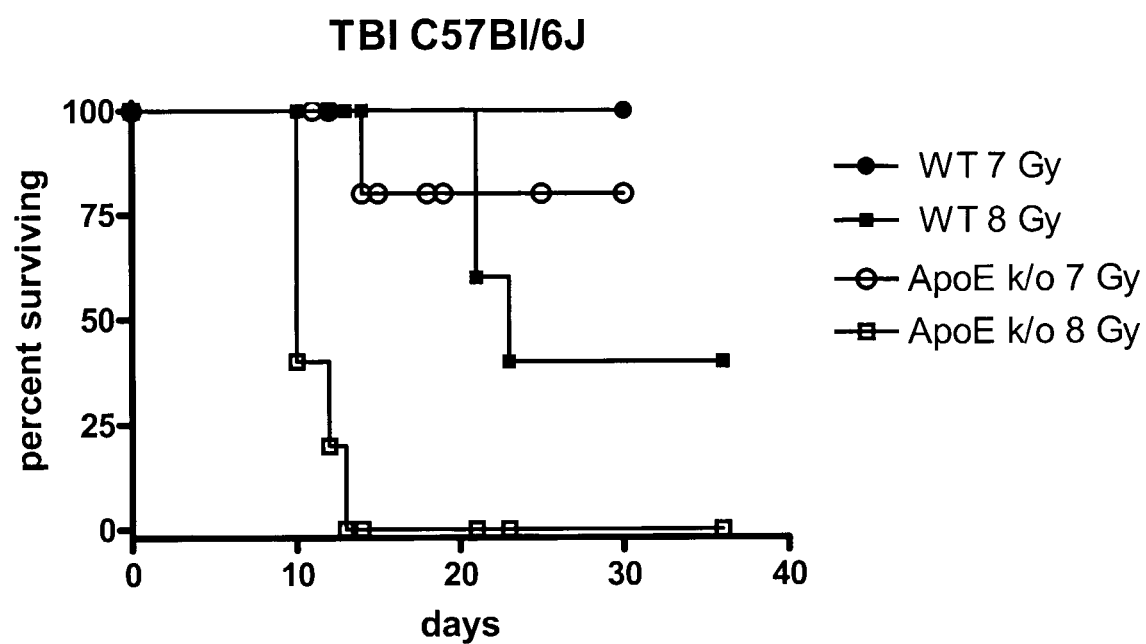

In order to confirm that the anti-inflammatory effects of ApoE would be useful for the protection of subjects undergoing TBI and radiotherapy, we compared the effects of 7 Gy and 8 Gy of TBI in wild-type C57Bl/6 mice that express mouse ApoE protein to the effects of 7 Gy and 8 Gy of TBI in ApoE knockout mice (Jackson Labs, Bar Harbor, Me.). Groups of 10 mice were irradiated at time 0 and their survival followed over the next 36 days. As shown in FIG. 22, none of the wild-type mice exposed to 7 Gy died during the 30 day time course while 2 of the apoE knockout mice died (20% mortality/80% survival) on Day 13 post irradiation with no further deaths during the 30 day time course. When a group of 10 wild-type mice were exposed to 8 Gy of TBI, 4 died on Day 21 post irradiation, and 2 more died on Day 23 with no more deaths out to Day 36. When a group of 10 apoE knockout mice were exposed to 8 Gy of TBI, 6 died on Day 10 post irradiation, 2 more died on Day 11 and the last 2 died on Day 12.

There are several ways to summarize this 8 Gy TBI data: A maximum of 100% of apoE knockout mice die by Day 12 post irradiation compared to a maximum of 60% of wild type mice die by Day 23 post irradiation. Alternatively, 60% of apoE knockout mice die by Day 10 post irradiation compared to 60% of wild-type mice die by Day 23 post irradiation. From either representation of the data, it is clear that the absence of apoE protein in APOE knockout mice is associated with death at an earlier time and a greater percentage of APOE knockout animals die at a given dose of TBI compared to their wild-type, apoE containing counterparts. This finding suggested to the present inventors that ApoE protein confers a protective effect that enhances survival of whole animals following TBI, and is consistent with previous experiments suggesting that ApoE deficiency may exacerbate the behavioral toxicity of high charge, high energy (HZE) particle exposure (Higuchi et al. 2002).

Total Body Irradiation is associated with a significant increase in whole body inflammation. We and others have found a significant increase in the levels of cytokines in the blood of mice exposed to TBI (Budagov 2004 and unpublished). A recent report by Budagov and Ul'ianova (2004) found that administration of an anti-IL6 monoclonal antibody to mice receiving 7.5 Gy of TBI plus a 10% body surface full-thickness burn resulted in significantly improved survival to the 60% level at 30 days post-injury compared to 100% lethality in mice exposed to the same injury and not receiving anti-IL6 monoclonals. An excellent report from Van der Meeren et al. (2002) showed that mice receiving 8 Gy of TBI, followed by a 2 hour delay, and then receiving rIL11 every day for 5 days, were significantly protected from death. Specifically, at 30 days post-TBI, the rIL11 treated group enjoyed a 74% survival rate while placebo treated controls only reached an 11% survival fraction (p<0.001). These studies strongly support the idea that modulation of the body's immune response may play a significantly positive role in survival of the individual exposed to total body irradiation.

Based on the role that apoE plays in inflammation, we have created COG133, which is a small peptide possessing the tissue-protective activity of holo-apoE (FIG. 22) (Laskowitz et al. 2001, Lynch et al. 2003, Lynch et al. 2005). Using lipopolysaccharide (LPS) induced inflammation in a wild-type mouse, treatment with COG133 significantly reduced tumor necrosis factor alpha (TNFa) and interleukin-6 (IL6) release in the blood and in the brain when compared to their wild-type counterparts treated with LPS and saline vehicle. In another wild-type mouse model where inflammation is induced following experimentally applied traumatic brain injury, we reported that COG133 was effective in significantly preventing death and restoring behavioral function when given 30 minutes AFTER the traumatic brain injury (Lynch et al. 2005). In more recent studies, we have found that COG133 administered by an intraperitoneal route is also effective at reducing the inflammation see after LPS injection in mice (data not shown). Our results indicate that COG133 can effectively reduce inflammation in the presence of endogenous levels of naturally-occurring apoE protein and can do so even though COG133 is administered AFTER the inflammatory stimulus.

Example 13

Survival of Mice Undergoing TBI in the Presence and Absence of COG133

Combining the information that TBI stimulates inflammation and that cog133, an apoe mimetic, can modulate inflammation in a whole animal, we tested the ability of cog133 to improve survival in wild-type mice exposed to total body irradiation.

From independent studies that we have performed, the maximum tolerated dose of COG133 is 14 mg/Kg (data not shown). This maximum tolerated dose is the dose at which no animal dies within 24 hours of tail vein injection of the COG133. We have also reported that LPS-mediated TNFa and IL6 levels were significantly reduced by co-administration of COG133 (Lynch et al. 2003). Thus, we will administer amounts (doses) of COG133 which range between zero and one half the maximum tolerated dose (0 to 0.5×MTD) to mice receiving 0 to 12 grey of total body irradiation (TBI). In this way, the effects of TBI alone, the effects of COG133 alone, and the effects of TBI plus COG133 can be compared.

The range of radiation doses to be initially tested (0 to 12 Gy) will cover both intermediate and low dose irradiation (Hall, 2000). At intermediate doses of radiation (5 to 12 Gy), death is expected to occur in a matter of days and is associated with diarrhea and destruction of the gastrointestinal mucosa (termed gastrointestinal syndrome). At low doses of radiation (approximately 2.5 to 5 Gy), death occurs several weeks after exposure and is caused by effects on the blood-forming organs (termed bone-marrow death or hematopoietic syndrome). Thus, one would expect earlier gastrointestinal syndrome in the higher dose groups and delayed hematopoietic syndrome in the lower dose groups.

As shown in FIG. 23, wild-type mice that express apoE protein suffer an $LD_{100/12}$ when exposed to 10 Gy of TBI (ie. 100% of the mice exposed to 10 Gy of TBI die at 12 days post-irradiation). In contrast, mice receiving a single, intraperitoneal injection of COG1 33 (4 mg/Kg in saline) at 1 minute post-TBI (10 Gy) display better survival with an $LD_{100/13}$ which is better than their saline treated counterparts. If we administer 10 Gy of TBI to the mice, followed by a 1 hour delay, and then an initial administration of COG133 (4 mg/Kg) followed by additional administrations of COG133 on day 1, day 2 and day 3 post-TBI, survival was further enhanced with an $LD_{100/16}$ which is significantly better than their saline treated counterparts (p<0.01). These pilot experiments, and literature reports of immune modifiers in TBI (see above), propel us to further test the ability of COG133 to meet the radiobiological standard of significantly increasing survival at 30 days post-TBI.

These data show that exposure of C57B16 mice to TBI followed by administration of COG133 resulted in an extension of life span compared to mice that received radiation and saline vehicle lacking COG133. Although none of these animals lived to 30 days, we employed a higher dose of 10 Gy which gave 100% lethality in saline treated mice at 12 days post-irradiation ($LD_{100/12}$). Even though all animals receiving 10 Gy followed by treatment with COG133 also died, they died by day 14 and by day 16, survival times which apparently related to the paradigm by which COG133 was administered. Animals receiving 4 doses of COG133 survived a significantly longer time following irradiation then the saline vehicle treated control group when analyzed by ANOVA (p<0.05). Presented in another way, the LD50's for each group exposed to 10 Gy were saline controls, LD50/10; COG133 at 1 minute post irradiation, LD50/12 and COG133 at 1 hour post irradiation plus days 1, 2 and 3 post irradiation (total of 4 doses of COG 133 at 1 mg/Kg), LD50/14. Although we would like to present this data as a dose reduction factor or DRF, this is not possible to do with this limited data set obtained with a single dose of radiation. Varying doses of radiation would need to given in an experiment to empirically measure the LD50/30 in the presence and in the absence of COG133, which would then permit a DRF calculation. At a given level of lethality, the dose reduction factor equals the dose of radiation in the presence of COG133 divided by the dose of radiation in the absence of COG133. Using this calculation method, Hall (2000) reports a dose reduction factor of 2.7 for amifostene at 30 days post-irradiation in mice when amifostene is given immediately before the irradiation event. While the maximum dose reduction factor is calculated to be between 2.5 and 3 (Hall 2000), we are focused on the ability of COG133 treatment, when given AFTER the TBI event, to extend survival times in mice. Thus, our goal is to show that COG133 can protect tissues and thereby extend survival time of an animal receiving TBI and subsequently receiving COG133 post-TBI.

We will also perform these experiments in wild-type, C57B1/6 mice that express mouse apoE protein. We will be testing whether the addition of COG133 to these wild-type, apoE-containing mice, will improve their survival. We feel this is important because a radioprotection therapy such as COG133 would potentially be given to humans who already have apoE protein. We considered doing experiments in APOE knockout mice with COG133, but felt that this was a lower bar and would not meet the long-term criteria of a therapy that could be given to humans that already expressed their own endogenous, apoE protein.

Peptide Synthesis: Peptides are synthesized by Multiple Peptide Systems (San Diego) to a purity of 95% as confirmed by mass spectrometry and are reconstituted from a trifluoracetic acid salt. COG133 has the sequence: LRVRLASHL-RKLRKRLL (SEQ ID No. 1) and Reverse-COG133 has the sequence: LLRKRLKRLHSALRVRL (SEQ ID No. 57).

Treatment Conditions: In general, each treatment group will consist of 12 male, C57BL/6 mice at 12 to 16 weeks of age. We will administer doses of COG133 corresponding to 0×MTD (ie. saline vehicle), 0.1×MTD, 0.2×MTD, and 0.5× MTD (0, 2.6, 5.2, and 13 mg/Kg, total of 50 mg for this expt.) (Table 8). The initial intraperitoneal administration of COG133 will be 1 hour AFTER total body irradiation (ie. 1 hour post-TBI) and will be followed by daily injections for a total of 30 days or until the animal dies. Based on values from the literature and our own preliminary data with TBI, we will employ 0, 4, 5, 6, 7, 8, 9, and 10 Gy of total body ionizing irradiation with each of the different doses of COG133 listed above. Thus, 4 amounts of COG133 times 8 different amounts of radiation gives 32 different conditions. 32 different conditions times 12 mice per condition will total 384 mice. To receive total body irradiation (TBI), mice are placed in a calibrated irradiator and exposed for a length time to generate the desired dose of ionizing radiation as was done in the Preliminary Results section above. Saline alone and all compounds will be administered in sterile physiological saline vehicle via intraperitoneal injection at 60 minutes post-TBI and then each day for 30 days (QD dosing of COG133).

TABLE 8

Overview of Mice to be used in this study

| Radiation Dose | Saline Control | 0.1 × MTD COG133 | 0.2 × MTD COG133 | 0.5 × MTD COG133 |
|---|---|---|---|---|
| 0 Gy | 12 | 12 | 12 | 12 |
| 4 Gy | 12 | 12 | 12 | 12 |
| 5 Gy | 12 | 12 | 12 | 12 |
| 6 Gy | 12 | 12 | 12 | 12 |
| 7 Gy | 12 | 12 | 12 | 12 |

TABLE 8-continued

Overview of Mice to be used in this study

| Radiation Dose | Saline Control | 0.1 × MTD COG133 | 0.2 × MTD COG133 | 0.5 × MTD COG133 |
|---|---|---|---|---|
| 8 Gy | 12 | 12 | 12 | 12 |
| 9 Gy | 12 | 12 | 12 | 12 |
| 10 Gy | 12 | 12 | 12 | 12 |
| Total Mice | 96 | 96 | 96 | 96 |

Animal Assessment:

Survival of animals will be measured in a variety of ways. Death is the lack of survival which we define as a complete lack of breathing and complete unresponsiveness to external stimuli such as tail pinch and/or toe pinch for a period of 10 or more minutes. Survival will be assessed in each animal on a daily basis for each of the 30 days following TBI exposure. Animals will be weighed on an electronic scale each day for three days preceding TBI and on each day for the 30 days following TBI.

Clinical signs are observations related to CNS activity of the animal (motor activity, ataxia, righting reflex, and convulsions) and are early indicators of toxicity or morbidity. These observations can be used to assess ability of animals to perform following TBI and whether this performance is improved with COG133. We will use the Modified Neuro-Severity Scoring system to give a Summary Neuro-Severity Score (NSS) as described by Dr. Laskowitz, our collaborator (Sheng et al. 1999). Each animal will be assessed on each of the three days before TBI and on each of the 30 days following TBI. A trained observer who is blinded as to group assignment performs these assessments. A score of 0 points means normal neurological exam and a score of 10 points means the most severe neurological deficit. Values are summarized as "Summary NSS Scores" as follows: 1=normal (0 points); 2=moderate deficit (1-6 points); 3=severe deficit (7-10 points); 4=dead. Between assessments, animals will then be returned to their cages and allowed free access to food and water. Neuro-severity scores will be compared by use of the Mann Whitney U statistic.

Animals that appear to be exhibiting signs of undue distress they will be immediately euthanized as per the guidelines of the IACUC for human use and care of animals. Measurements of non-lethal morbidity will be addressed in Example 4. Mortality data were analyzed by comparing the survival curves of treated and untreated animals using the log rank test and/or Fisher's exact test (two sided). Statistical analysis of survival data will be compared between all groups with the Prism computer program. Significance will be determined using the unpaired Student's t test or ANOVA with statistical significance assumed when $p<0.05$.

Dose Reduction Factor:

Hall (2000) defines DRF as the ratio of radiation dose in the presence of an agent (such as COG133) to the radiation dose in the absence of an agent (such as COG133) for the same level of effect (such as $LD_{50/30}$). Thus, DRF=dose of radiation in presence of COG133 divided by the dose of radiation in the absence of COG133 to produce a 50% level of lethality (=50% survival). Using the data collected from the above study, we will plot survival versus exposure curves from which the dose of total body irradiation that gives 50% survival at 30 days post-TBI can be interpolated (Henschke and Morton 1957). Using the $LD_{50/30}$ from saline control animals, and the $LD_{50/30}$ for 0.1×MTD of COG133, 0.2×MTD of COG133 and 0.5×MTD of COG133, we will calculate the DRF for each amount of COG133. If the DRF is greater than 1, this result would suggest that treatment of animals with COG133 post-TBI has a protective effect on animal survival following exposure to TBI. If the DRF is 1, then no protection is afforded by COG133 treatment. If the DRF is less than 1, then COG133 may be acting as an agent that sensitizes animals to TBI. Based on our preliminary studies in FIG. 3, we predict that COG133 will act as a radio-protector that significantly increases the survival of mice exposed to TBI and will generate a DRF of greater than 1.

Mice are the animals of choice for this proof-of-principle experiment because they respond consistently to TBI, are small enough to conveniently fit into an irradiator machine and they their small size conserves on the use of COG133 in this testing paradigm. In order to accurately determine the effect of COG133 in subsequent tasks, we must generate a complete radiation dosage versus survival fraction curve for each treatment condition. With respect to mice, TBI exposures of less than 4 Gy typically have no measurable effect on survival and thus, we have not chosen to expend precious animal resources on those low dose experiments in this proposal. However, different outcomes from low dose irradiation studies could be the subject of future proposals. On the other end, TBI exposures of more than 10 Gy typically result in less than 10% survival (greater than 90% death). Although responses of animals to greater than 10 Gy is important for both military and civilian reasons, we have chosen to focus on the range of exposures which are also significantly associated with animal death. If our treatment interventions can significantly improve survival at these low to intermediate doses of TBI, then future proposals will focus on the potential for protection of survival following higher does of TBI, such as those above 10 Gy of TBI.

Schedule of Experiments:

One group of 48 animals will be tested approximately every 6 weeks for the one year duration of the project. Thus, the following schedule is proposed

| Weeks 0-6 | Weeks 7-12 | Weeks 13-18 | Weeks 19-24 | Weeks 25-30 | Weeks 31-36 | Weeks 37-42 | Weeks 43-48 |
|---|---|---|---|---|---|---|---|
| 0 Gy | | | | | | | |
| | 4 Gy | | | | | | |
| | | 5 Gy | | | | | |
| | | | 6 Gy | | | | |
| | | | | 7 Gy | | | |
| | | | | | 8 Gy | | |
| | | | | | | 9 Gy | |
| | | | | | | | 10 Gy |

Example 14

Behavioral Performance on Wirehang/Rotorod of TBI Animals Treated with and without COG133

In overview, mice will be tested on the wire hang test to show that they have strength in their limbs. If they do have strength, then they will then be tested on rotorod which is an integrated test of behavioral performance of motor strength and coordination. Animals which fail to pass these tests before any stress is applied will not be used in our subsequent studies. If animals receiving TBI plus COG133 perform significantly better than those receiving TBI alone, then this will indicate that COG133 may not only improve mortality, but may improve morbidity as well.

Wire Hang Testing:

To assess the prehensile reflex and general motor strength, the wire hang test will be used. In our version of this test, mice are picked up by the tail and placed on the wire lid of a standard shoe box cage (this consists of parallel stainless steel wires of approximately 2 mm diameter placed about 1 cm apart that covers the entire top of the 20 cm×30 cm shoe box). The mouse typically grasps the wires on the lid and the entire lid with the mouse holding on is inverted at about 20 to 30 cm above the top of a foam rubber pad sitting on top of the bench. The mouse is allowed to remain grasping the lid for 30 seconds. If the mouse fails to grasp the lid and falls off before 30 seconds, the time from inversion to falling off is recorded as the latency time. If the mouse does not fall off, then it is given a 30 second latency time. Three trials are performed for each mouse on each day for the three days before TBI. Each trial is separated by at least 5 minutes as a rest period. The average latency time and standard deviation are calculated for each group on each day. Wire hang is also performed in the same way on each day following TBI. If animals are unable to successfully perform wire hang and to hold onto the wire lid for the entire 30 seconds on each trial on each of the three days preceding TBI, they will be excluded from TBI and further studies. Our experience has been that all healthy wild-type, C57B1/6 mice easily pass this test.

Rotorod Testing:

Daily Rotorod (RR) testing will be used to assess short-term motor and cerebellar deficit following total body irradiation (Hamm et al. 1994). The Rotorod Test will be given each day for 3 days before TBI and each day for 30 days following TBI. Briefly, each mouse will be lifted by the tail and gently placed on the rotating rod that is revolving at a slow and constant speed. After 5 to 10 seconds, the rotating rod will be switched to acceleration mode and a timer will be started. The timer will be stopped when the mouse falls off of the rotating rod or when the mouse has held onto the rod and rotated twice around (720 degrees of rotation). After a 5 minute rest period, a second trial will be performed by placing the same mouse on the rotating rod again, and the "latency" or time spent on the rotating rod will be measured again. After another 5 minute rest period, a third trial was performed and the latency time will be measured for each mouse again.

On each day, each mouse will be tested by 3 trials per day on the rotorod test as described above, thereby enabling each mouse to serve as his own control. For data analysis, the 3 latency times for each mouse in a group of mice will be averaged together and standard deviations calculated. This testing paradigm was selected based on our previous experience with behavioral performance which demonstrated that rotorod possesses the sensitivity to detect the presence of post traumatic dysfunction and subsequent recovery. An investigator blinded to group assignment will conduct all tests. We will employ repeated measures ANOVA with the Prism statistical analysis program to calculate the significance of the differences between groups of mice receiving an experimental compound and those receiving saline controls where $p<0.05$ will be considered to be significant. If animals are unable to successfully perform on the rotorod, which is typically a latency time of about 200 seconds for healthy mice of this age on each trial on each of the three days preceding TBI, they will be excluded from TBI and further studies.

Statistical Analysis:

Statistical analysis of behavioral outcome is performed with repeated measures analysis of variance with Dunnet's post-hoc method for correcting for multiple comparisons against the control group. Significance is assumed when $p<0.05$. All values are expressed as mean±standard deviation.

Example 15

COG133: an apoE Mimetic Peptide with Anti-Inflammatory Properties

Based on the anti-inflammatory properties of apoE protein, we developed COG133 which is a peptide derived from amino acid residues (133-149) located in the receptor-binding region of the 299 amino acid, apoE holoprotein (Laskowitz D T et al., 2001). We demonstrated that COG133 retains the anti-inflammatory properties of the apoE holoprotein using cultured macrophages (Laskowitz D T et al., 2001) and C57B1/6 mice (Lynch J. R. et al., 2003). Inflammation was elicited in naïve mice by LPS injection±COG133 and serum harvested at 0, 1, 3 and 24 hours after injection (FIGS. 24A and B). Using cytokine ELISA kits (Pierce), COG133 treated animals had significantly less serum TNF-α and significantly less serum IL-6, compared to saline controls (Lynch J. R. et al., 2003). We also reported in Lynch et al. that brain levels of TNF-α and IL-6 were significantly less in COG133 treated animals compared to saline controls by measurement of either protein levels or of mRNA levels by quantitative RT-PCR. LPS stimulation of fresh human blood±COG 133 also showed that COG133 significantly reduced nitric oxide and TNF-α levels compared to saline treated controls (data not shown). These data show that COG133 reduces inflammation in vitro, in vivo and ex vivo; which supports our idea that COG133 may effectively reduce inflammation in human disease.

Example 16

COG133 Reduces Disease Severity in Mice with EAE

MOG-induced Experimental Allergic Encephalomyelitis (EAE) in mice is one of the most frequently used murine models of the inflammation associated with Multiple Sclerosis (MS) because the clinical and histopathological features of MS and EAE are regarded as similar in many essential respects. These include clinical manifestations, the occurrence of multifocal lesion throughout the CNS, demyelinating plaques, perivascular inflammation and involvement of invading inflammatory cells that release inflammogens like TNF-α, IL-6, and NO (Ransohoff R. M., 1999). Thus, this model was chosen to test our hypothesis that COG133 may ameliorate the impairment of MS through its anti-inflammatory property.

Briefly, C57BL/6 female mice were first immunized with MOG peptide (pMOG$_{35-55}$, MEVGWYRSPFSRV VHLYRNGK (SEQ. ID. NO. 64)) and starting from day 6 to day 24 after immunization, 1 mg/kg of COG133 or reverse COG133, or same volume of normal saline was administered by tail vein bolus injection every other day. In total, 10 doses of peptides were given. We found that COG133 significantly ameliorates the severity of EAE by showing that the mean maximum clinical score in COG133 treated animals is significantly lower than in saline control animals (FIG. 10). COG133 treatment also significantly reduced the mortality from 4 of 15 in saline group and 5 of 15 in reverse peptide group, to 0 of 15 in COG133 treated group (p<0.05). The pattern of disease progression revealed that the mice started to recover from day 23 after immunization in the COG133-treated group, while the control animals still remained at a high level of severity (FIG. 2). Reverse COG133 lacked bioactivity in vitro on a BV2 cell line and did not improve the behavioral symptoms of EAE (FIG. 10). There is no statistically significant difference between reverse peptide group and normal saline group (p>0.05), but there is a statistically significant improvement in the COG133 group when compared to either control group (p<0.05). Although not shown, a highly similar result was obtained using an intraperitoneal route of administration (i.p. instead of i.v.) with COG133 treated animals showing significant improvement compared to saline controls (p<0.05). These results suggest that COG133 may significantly reduce the inflammation associated with EAE and facilitate the recovery from disease.

Figure 25:
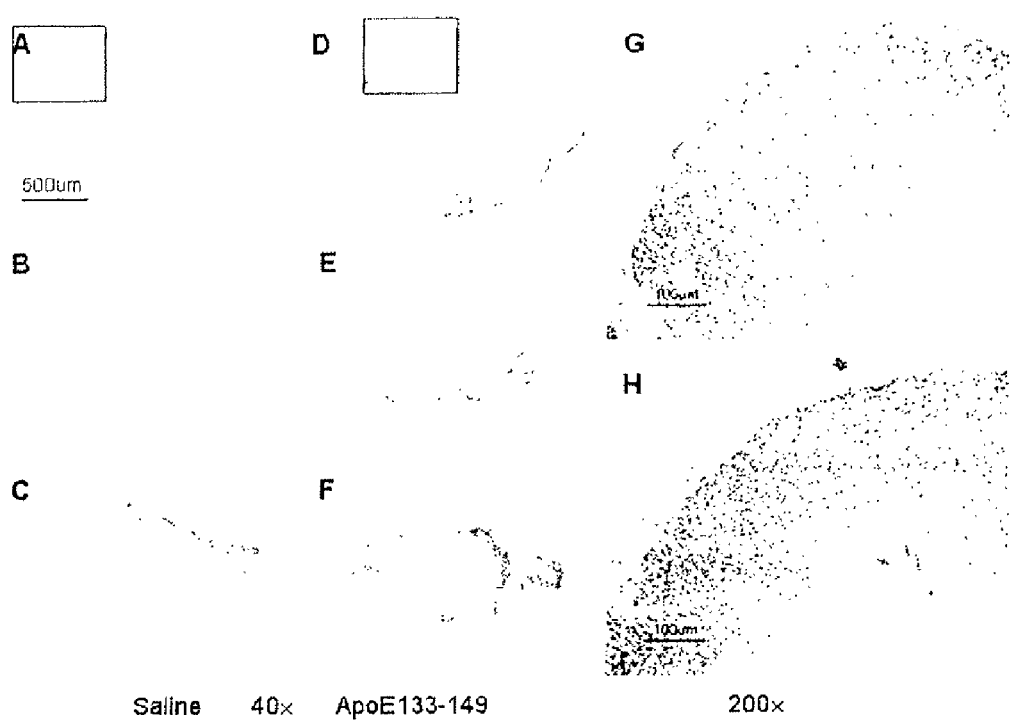

To show pathological changes including invading inflammatory cells, the animals were sacrificed on day 30, whole spinal cords were dissected out and 5 µm-thick sections were made from cervical, thoracic and lumbar segments of spinal cords of COG133-treated animals and saline-treated controls. These sections were stained with Luxol fast blue (for myelin, stained in blue) and then counterstained with eosin (showing peripheral infiltrates, in red-purple). As shown in FIGS. 25-A, B, and C, massive demyelination (loss of blue staining) and enhanced infiltrates (shown in red-purple particles) can be observed in white matter throughout spinal cord in control animals. Consistent with behavioral changes, COG133 reduced demyelination and reduced inflammatory infiltrates in MOG-treated animals (FIGS. 25-D, E, F, H).

Example 16

Analogs of COG133 also Possess Anti-Inflammatory Activities

Figure 26:
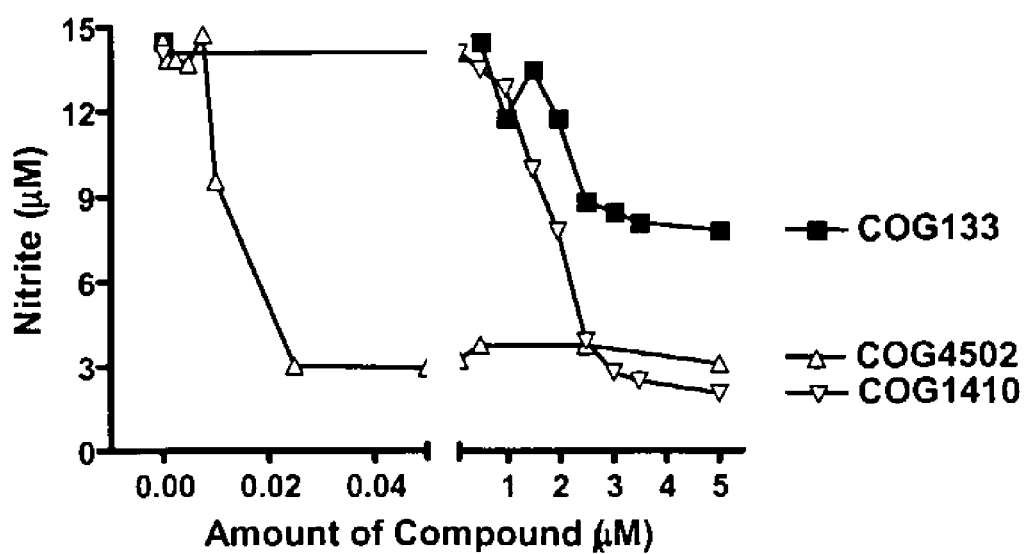

Using COG133 as a template, we continue to generate new analogs with enhanced and desirable pharmaceutical properties. As shown in FIG. 26, COG1410 is a analog that contains non-natural amino acids and is able to suppress NO release in LPS-stimulated, BV2 microglia cells better than the COG133 parent compound. Similarly, COG4502 is another analog that contains a prefix of extra amino acids followed by the COG133 sequence and is able to suppress NO release in this system much better than the COG133 parent. To further validate the utility of COG4502 in a more physiological system, we isolated mouse peritoneal macrophages and stimulated them with LPS in the presence or absence of COG4502. As shown in FIG. 27, COG4502 produces a dose dependent inhibition of TNFa release and a dose dependent inhibition of IL6 release. These results strongly indicate that COG compounds are potent anti-inflammatory molecules on cell lines, on peritoneal macrophages and in whole animals (as detailed above).

Example 17

Mouse Models of Colitis: Protective Role of Arginase and ODC and Deleterious Effects of iNOS Inflammation underlies the progression and symptoms of Crohn's Disease and ulcerative colitis; in some cases this can progress to complications of stricture formation, fistulas, obstruction, and perforation. Part of this inflammatory response in IBD is the stimulation of NO release which has been generally linked to worsening of disease activity. NO is generated by NO synthases (NOS) from arginine as a substrate, and the inducible form of this enzyme (iNOS) is the major player implicated in IBD. Arginine, however, can also be used by an alternative pathway to generate polyamines. This sets up a competition between the two pathways for a limiting arginine substrate.

The Wilson Lab has been focusing on the competing activities of the iNOS and the arginase/ODC pathways in mucosal immunology (Cross R K et al., 2003; Gobert A P et al., 2004; Chaturvedi R. et al., 2004; Xu H. et al., 2004, Bussiere F I et al., 2005, Gobert A P et al., 2001, 2002, Cheng Y. et al., 2005). Mouse models of colitis have been used to discover that the alternative arginase-ornithine decarboxylase (ODC) pathway leads to the formation of polyamines in the colon, which play an important role in the amelioration of colitis (Gobert et al. 2004). It has been shown that either iNOS-deficient mice (lacking the enzyme to make high levels of NO) or wild-type mice administered supplemental arginine (to increase the amount of arginine entering the alternative pathway), demonstrate improved colitis induced by *Citrobacter rodentium* or dextran sulfate sodium (DSS). Furthermore, treatment of iNOS-deficient mice with arginine resulted in dramatic improvement of disease and reversal of pro-inflammatory cytokine production. In contrast, treatment of mice with inhibitors of arginase or ODC causes a dramatic worsening of colitis. These data suggest that there is a competition for arginine at the site of disease where arginine metabolism to NO makes matters worse, while arginine metabolism to polyamines ameliorates the disease. Based on this indication, therapeutic strategies aimed at reducing NO production and/or increasing polyamine synthesis, should be effective treatments for Inflammatory Bowel Diseases.

*C. rodentium* colitis:

Of the two existing mouse models (Gobert A P et al., 2004; Cheng Y. et al., 2003), the *C. rodentium* model was selected because it produces a Th1-predominant mucosal inflammation that has histologic changes similar to human IBD (Higgins L M et al., 1999). In this model, mice are infected by oral gavage with *C. rodentium* (Gobert A P et al., 2004), a gram negative pathogenic bacterium that is the rodent equivalent of enteropathogenic *E. coli* that causes diarrhea in humans.

Induction of Arginase I and iNOS.

Figure 28:
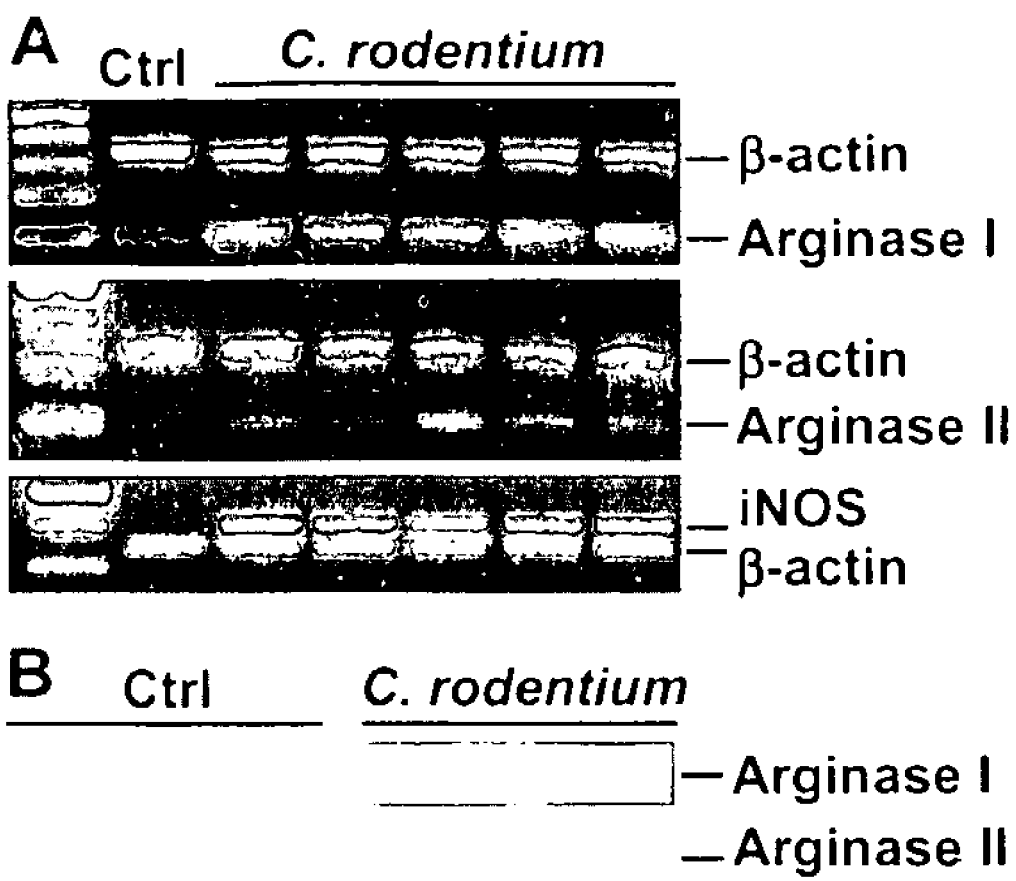
Figure 29:
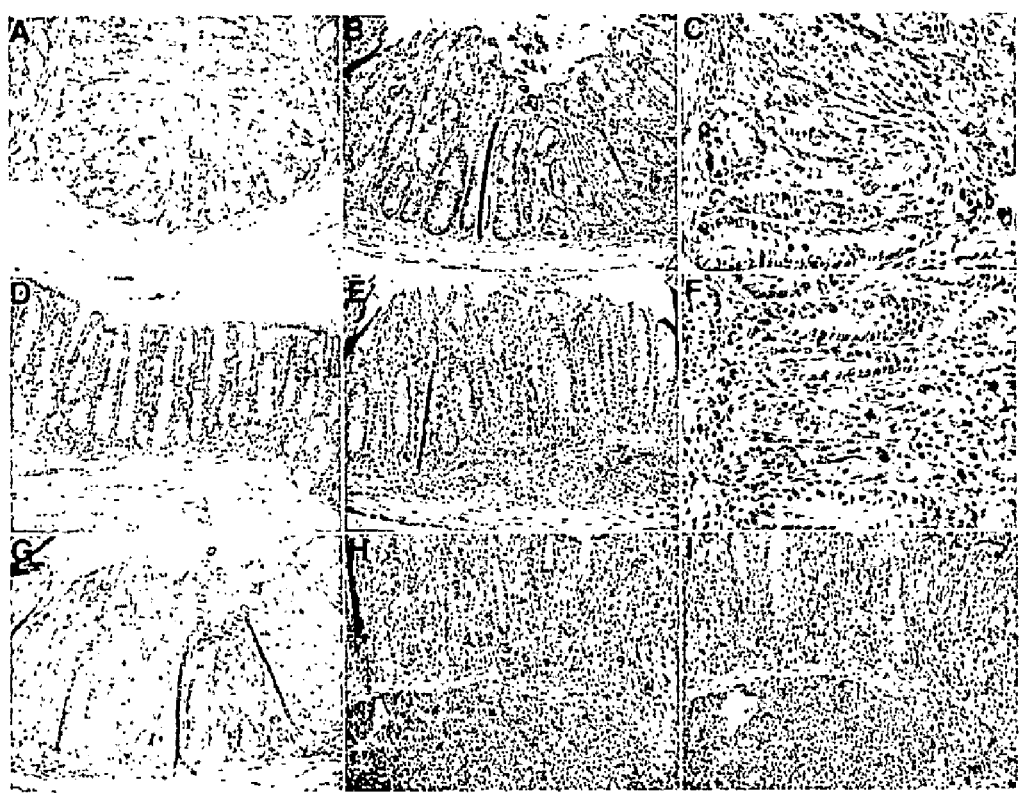

When we studied the expression of the arginase and iNOS enzymes in colitis tissues we found that arginase I mRNA and protein expression were significantly increased while arginase II was not induced (FIGS. 28A and B). These data were confirmed by real-time PCR, where we found a 9.7±2.5-fold increase for arginase I, but no increase for arginase II. iNOS mRNA was also consistently increased by RT-PCR (FIG. 28A) and this was confirmed by real-time PCR as well. By immunohistochemistry, we found focally intense staining for arginase I in colonic tissues of infected mice as shown in FIGS. 29B-C, and 29H. Staining was present in epithelial cells (FIGS. 29B and C), but was also found throughout the mucosa in severe colitis (FIG. 29I), with staining of infiltrating inflammatory cells. In serial sections from the same tissues, iNOS localized to the epithelium, and the lamina propria and submucosal inflammatory cells (FIGS. 29E-F, and 29I). Staining was absent in uninfected tissues with Ab to arginase I (FIG. 29A) or iNOS (FIG. 29D) or in infected tissues incubated with an isotype Ig control (FIG. 29G). iNOS staining was completely absent in tissues from iNOS$^{-/-}$ mice (data not shown).

Figure 30:
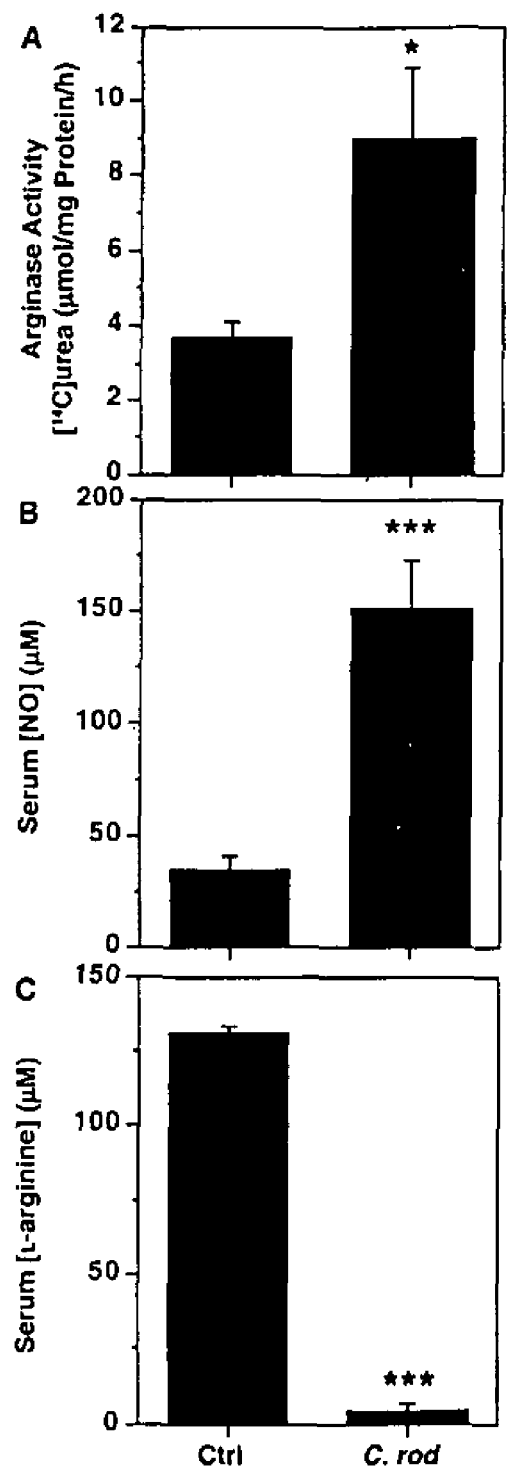

We were able to confirm that arginase activity was increased by 2.4-fold in infected vs. control mice (FIG. 30A). A significant increase in NO concentration was observed in the serum of infected mice compared to control mice (FIG. 30B). A concomitant marked decrease of L-Arg concentration was observed in the serum of infected mice (FIG. 30C). These data indicate that under conditions of significant intestinal inflammation, as in the *C. rodentium* model, there was a near complete depletion of systemic arginine.

Figure 31:
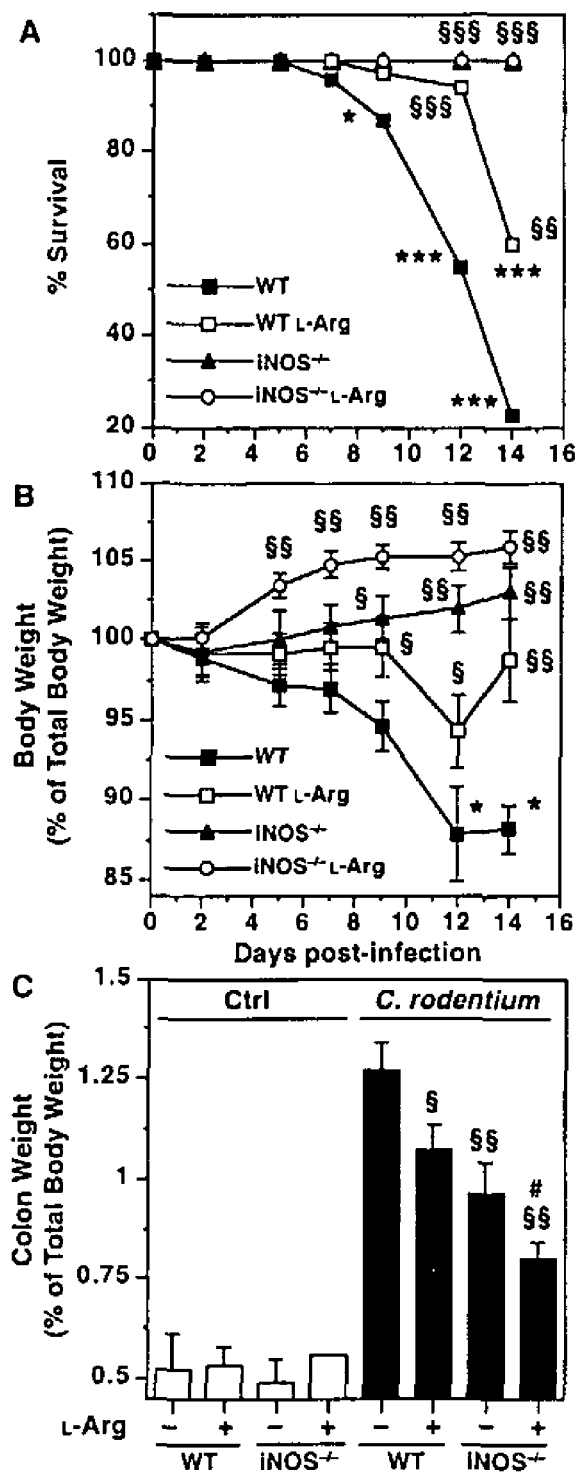
Figure 32:
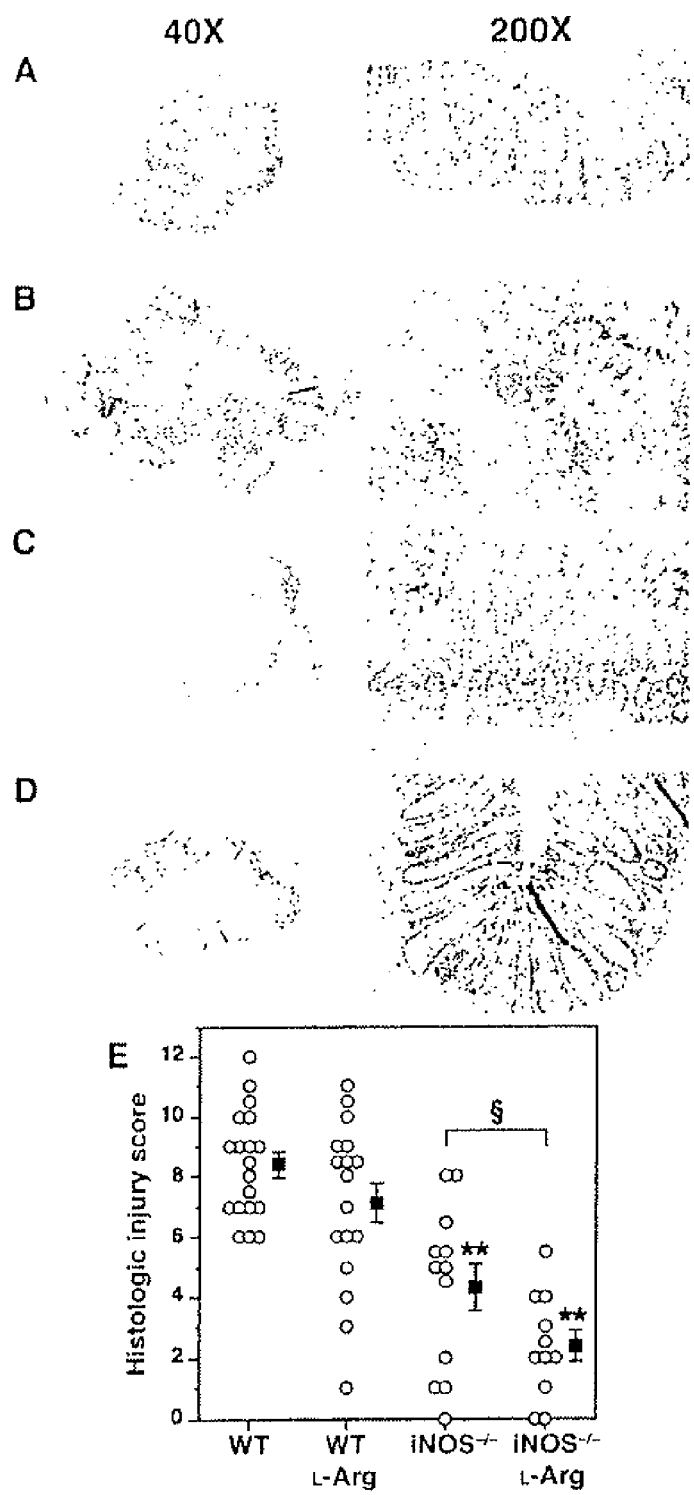

Contrasting Role of iNOS and Arginase: Amelioration of Clinical Parameters by L-Arg Supplementation and iNOS Deletion Since arginase I and iNOS were both abundantly expressed in the colitis tissues and L-Arg was completely metabolized, we investigated the effect of administration of 1% L-Arg in the drinking water. In wild type (WT) mice, *C. rodentium* colitis induced a high level of mortality that began on day 9 post-infection (FIG. 31A). In WT animals treated with L-Arg, mortality was inhibited by 42% and 62% compared to mice receiving water alone, after 12 and 14 days of infection, respectively (FIG. 31A). By Cox regression analysis, WT mice treated with L-Arg had only a 31% hazard of death compared with mice receiving water alone (p<0.0009). In iNOS$^{-/-}$ mice, no deaths were observed, with or without L-Arg (FIG. 31A). In WT mice, L-Arg treatment reduced weight loss, and iNOS-deficient mice given L-Arg had further improvement, actually gaining weight in the presence of infection (FIG. 31B). Note that the weight loss of WT mice is underestimated, since only the weights of animals still alive could be included. Colon weight was significantly increased by more than 2-fold in *C. rodentium*-infected WT mice (FIG. 31C), and decreased by 28%, and 38% in the WT-L-Arg and iNOS$^{-/-}$ mice, respectively. There was an additive effect of iNOS deletion and L-Arg administration, with a 68% decrease in colon weight. Neither iNOS deletion nor L-Arg treatment affected colon weight in uninfected control mice. Importantly, these changes were closely paralleled by changes in colon histology (FIG. 32).

Induction of Pro-Inflammatory Cytokines in Colitis Tissues is Attenuated by L-Arg Treatment or iNOS Deletion.

Figure 33:
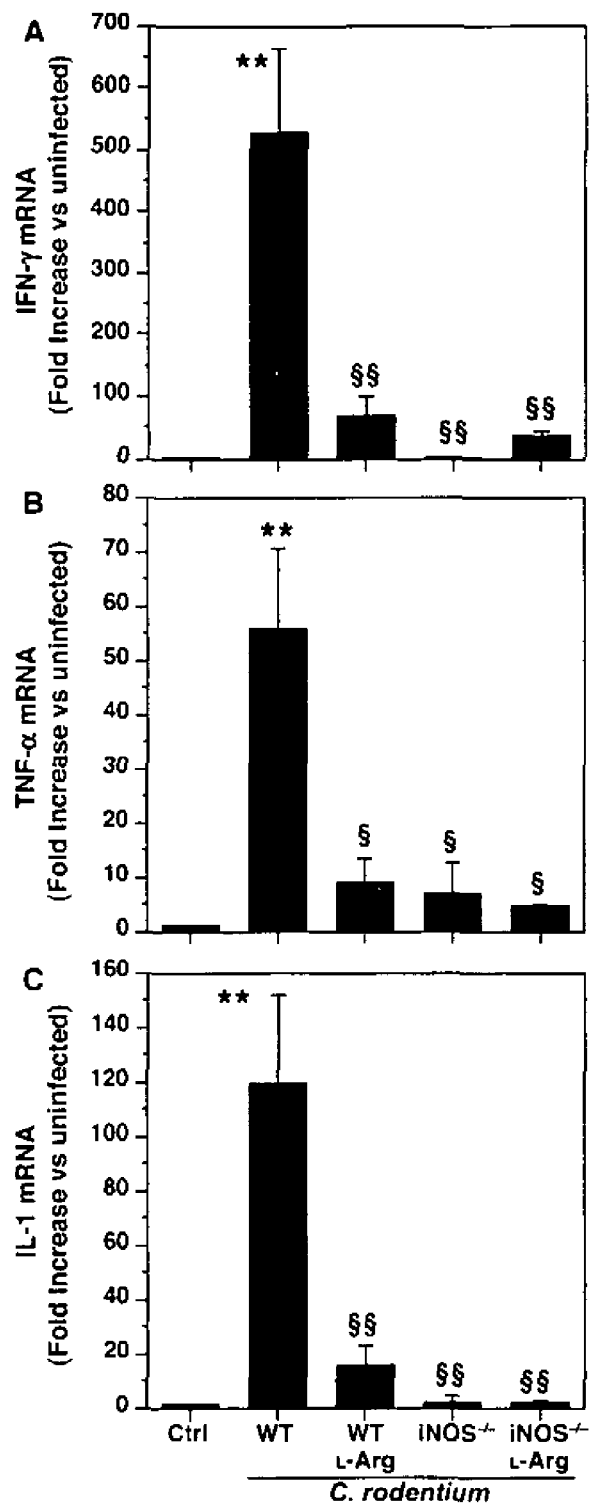

Because *C. rodentium* colitis has been strongly associated with activation of the Th1 cytokine IFN-γ, and the associated pro-inflammatory cytokines TNF-α, and IL-1 (30, 46), we sought to determine the relationship between the clinical and histologic effects we observed with these immunologic parameters. Real-time PCR analysis demonstrated a marked increase in IFN-γ (FIG. 33A), TNF-α (FIG. 33B), and IL-1 (FIG. 33C) in *C. rodentium* colitis tissues compared to normal tissues, and a significant attenuation of these increases with either iNOS deletion or L-Arg treatment.

ODC Activity is Induced in the Colon of *C. rodentium*-Infected Mice.

Figure 34:
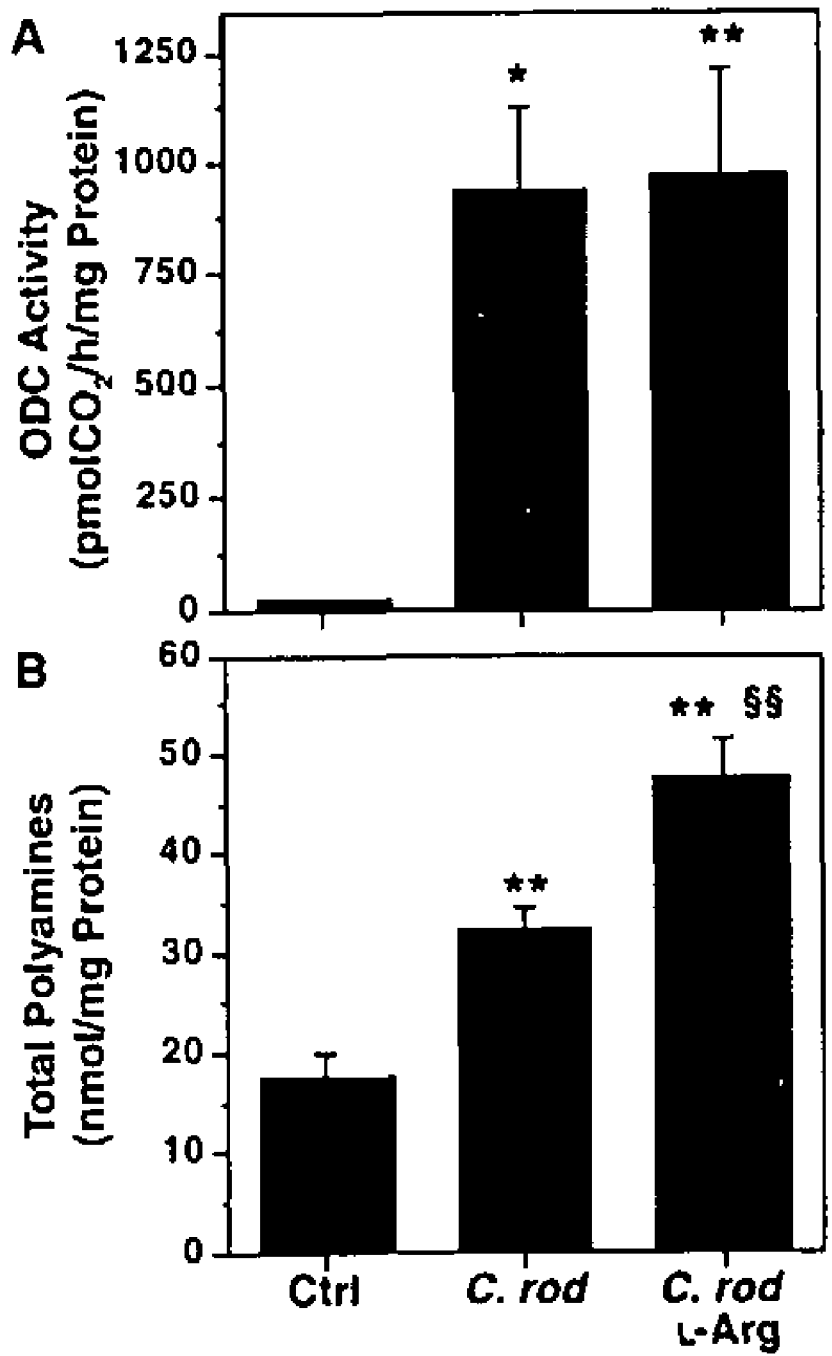

Since ornithine, the product of arginase, is metabolized by ODC to form polyamines, we investigated ODC expression in the colon of *C. rodentium*-infected WT mice. By real time PCR we found a 2.5±0.5-fold increase of mRNA level in infected (n=13) compared to control mice (n=4; not shown). However, a 40-fold increase in ODC activity was measured in the colon of either infected WT or infected WT mice treated with L-Arg (FIG. 34A). This increase was not likely to be due to ODC activity from *C. rodentium* itself, since we measured bacterial ODC activity and determined that it represented no more than 1% of the total ODC activity in the tissue. There was a 1.8±0.1-fold increase in colonic polyamines in *C. rodentium*-infected WT mice, and a significant, further increase of 2.7±0.2-fold with L-Arg treatment (FIG. 34B), indicating that arginase activity was an important determinant of polyamine synthesis. The modest increase in polyamines vs. the larger increase in ODC activity most likely reflects the fact that polyamines are rapidly acetylated, leading to efflux out of cells and excretion (31).

Exacerbation of *C. rodentium* Colitis by Arginase or ODC Inhibition.

To further demonstrate the beneficial effect of arginase and polyamine formation, mice were given S-(2-boronoethyl)-L-cysteine (BEC) or -difluoromethylornithine (DFMO), inhibitors of arginase and ODC, respectively, in the drinking water. In uninfected control mice, BEC or DFMO had no effect (Table I). However, there was significant loss of survival in *C. rodentium*-infected mice treated with BEC or DFMO (Table 9). In fact, experiments had to be terminated early at 10 days post-infection, because of deaths and severe disease at this point. Colons of *C. rodentium*-BEC and *C. rodentium*-DFMO groups had a greater increase in weight and histologic injury than those of the *C. rodentium*-water group (Table 9).

When compared with the infected WT mice treated with water alone, the colons of both the BEC- and DFMO-treated mice showed marked transmural inflammation and mucin depletion (Gobert AP et al., 2004). The BEC-treated mice had substantial submucosal abscess formation and the DFMO-treated mice exhibited mucosal and submucosal hemorrhage, both indicative of severe acute inflammation. When BEC was given to iNOS$^{-/-}$ *C. rodentium*-infected mice, colitis increased; compared to iNOS$^{-/-}$

TABLE 9

Effect of 0.1% BEC or 2.5% DFMO on WT mice 10 days after inoculation with *C. rodentium* or PBS

| Body wt (% Total Body wt) | Colon wt (% Total Body wt) | Histology Score |
|---|---|---|
| 102.6 ± 1.6 | 0.51 ± 0.04 | 0.43 ± 0.05 |
| 110.1 ± 2.2 | 0.42 ± 0.04 | 0.67 ± 0.17 |
| 101.3 ± 2.6 | 0.61 ± 0.07 | 0.75 ± 0.25 |
| 98.7 ± 2.7 | 0.83 ± 0.08$^a$ | 3.82 ± 1.01$^b$ |
| 82.4 ± 5.2$^{a,c}$ | 1.25 ± 0.07$^{b,d}$ | 9.25 ± 0.69$^{b,d}$ |
| 78.6 ± 0.4$^{b,c}$ | 1.35 ± 0.12$^{b,d}$ | 9.54 ± 0.68$^{b,d}$ |

$^a$p < 0.05,
$^b$p < 0.01 vs control; and
$^c$p < 0.05,
$^d$p < 0.01 vs *C. rodentium*. wt, weight.

alone, BEC caused a significant worsening of colon histologic injury scores (iNOS$^{-/-}$: 2.42±0.46, n=12; vs. iNOS$^{-/-}$+BEC: 6.44±0.98, n=8, p<0.01) and colon weight (iNOS$^{-/-}$: 0.36±0.01% of total body weight, vs. iNOS$^{-/-}$+BEC: 0.92±0.20%, p<0.05). These data provide further evidence that it is not prevention of NO production alone that protects the iNOS$^{-/-}$ mice, but rather shunting of L-Arg to the arginase pathway.

Example 18

Dextran Sulfate Sodium (DSS) Colitis Model

This model was selected because it has become commonly accepted as a mouse model of colitis and is quite practical to employ, since it simply involves adding DSS to the drinking water (Moteau O. et al., 2000, Williams K L et al. 2001, Andres P G et al., 2000, Mahler M. et al., 1998, Tesser T G et al., 1998). In initial experiments, we tested a variety of doses in the reported range from the literature of 2.5% to 5% (Moteau O. et al., 2000, Williams K L et al. 2001, Andres P G et al., 2000, Mahler M. et al., 1998, Tesser T G et al., 1998) and found that we obtained the most reliable response with 4% DSS. Additionally, we found that including DSS in the water for 6 days and then removing it provided us with sufficient surviving mice; when the DSS was left in the water for longer consecutive days, rates of mortality were too high to have enough mice surviving the procedure that one could reliably analyze the survivors.

Induction of Arginase I iNOS, and ODC in DSS Colitis.

Figure 35:
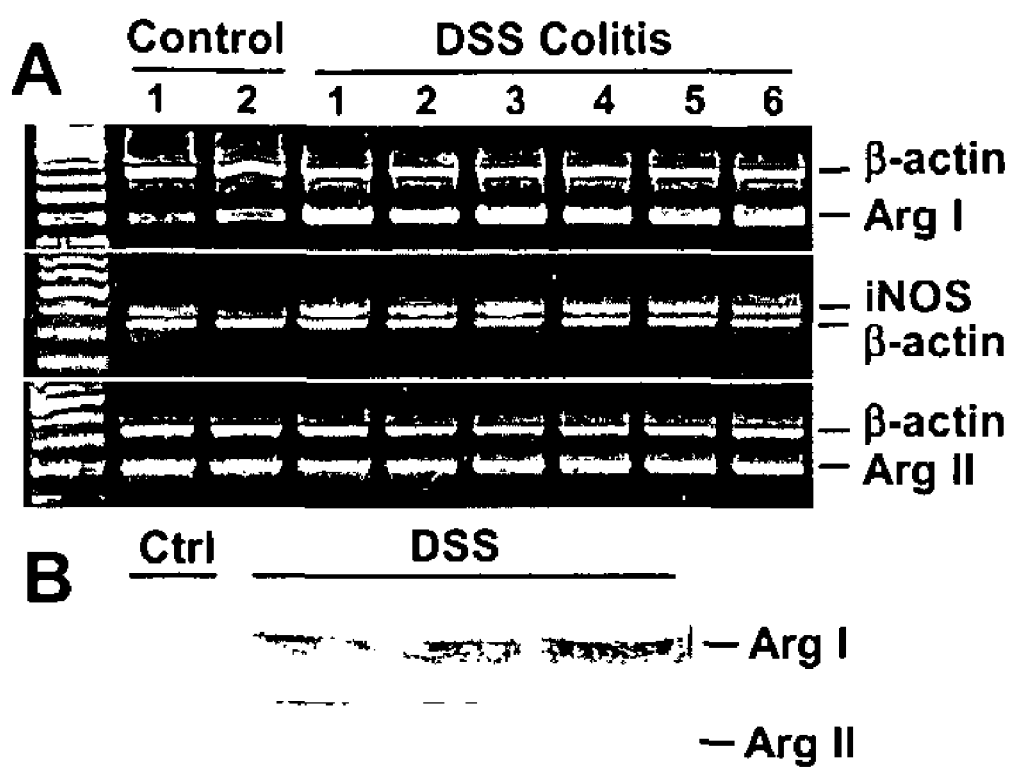
Figure 36:
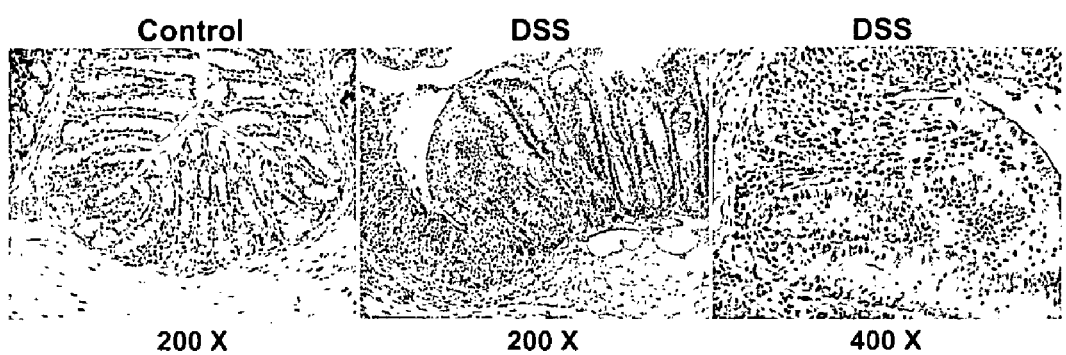

Once established, we assessed arginase and iNOS expression in mice at day 10 in this model. As shown in FIG. 35A, as in the *C. rodentium* model, there was up-regulation of arginase I but not arginase II mRNA expression, and increased iNOS levels. We confirmed that arginase I expression at the protein level by Western blotting (FIG. 35B) and by immunohistochemistry (FIG. 36).

Consistent with these data we detected a parallel increase in arginase I mRNA by real-time PCR and of arginase enzymatic activity in the colitis tissues (data not shown). Similarly there was an increase in ODC mRNA and enzyme activity (data not shown).

Improvement in DSS Colitis with Arginine Supplementation or iNOS Deletion.

Figure 37:
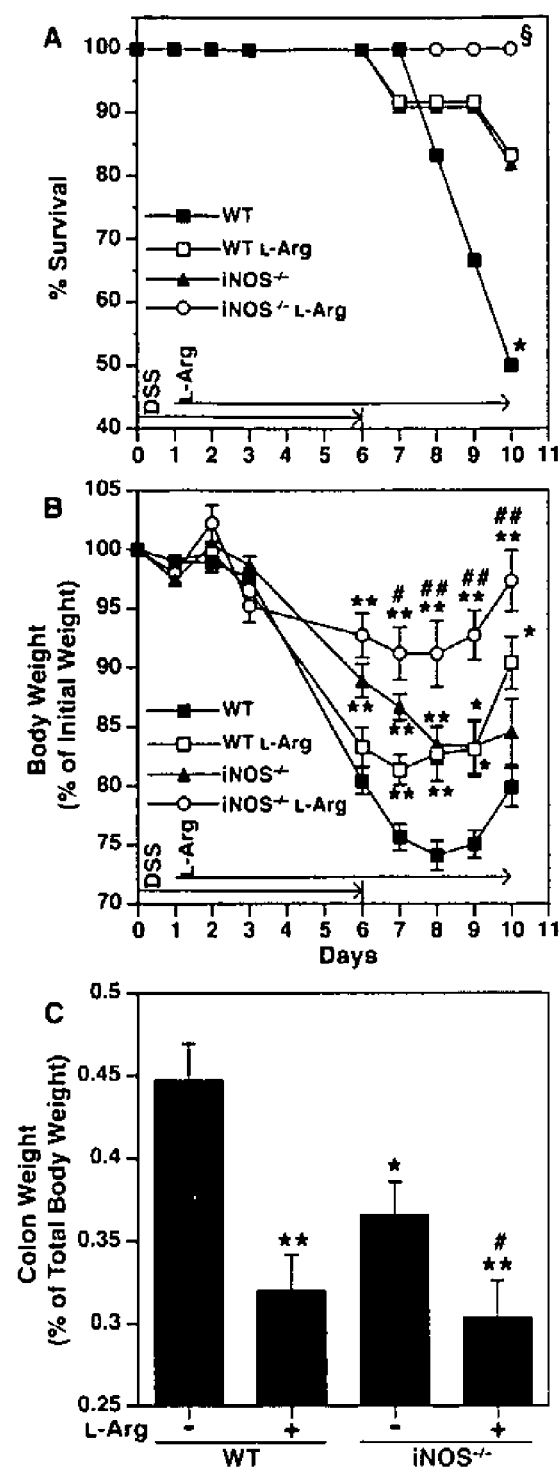
Figure 38:
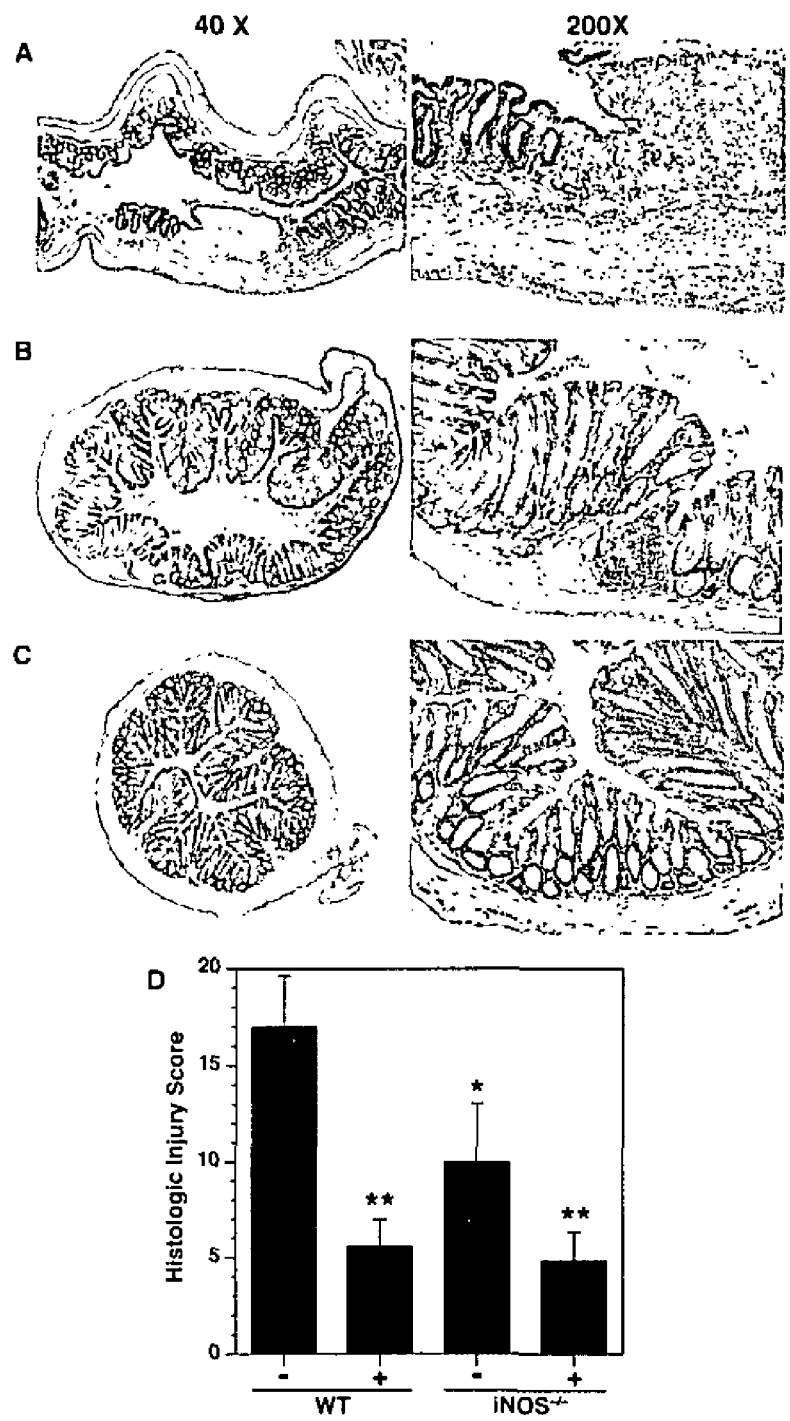

Consistent with the results above in our *C. rodentium* model, there was again a reduction in clinical parameters of colitis in the DSS model with either iNOS deletion or L-Arg administration, and when L-Arg was given to the iNOS$^{-/-}$ mice, there was a further improvement in survival, body weight and colon weight (FIG. 37). These data were paralleled by an amelioration of colon histopathology (FIG. 38).

Figure 39:
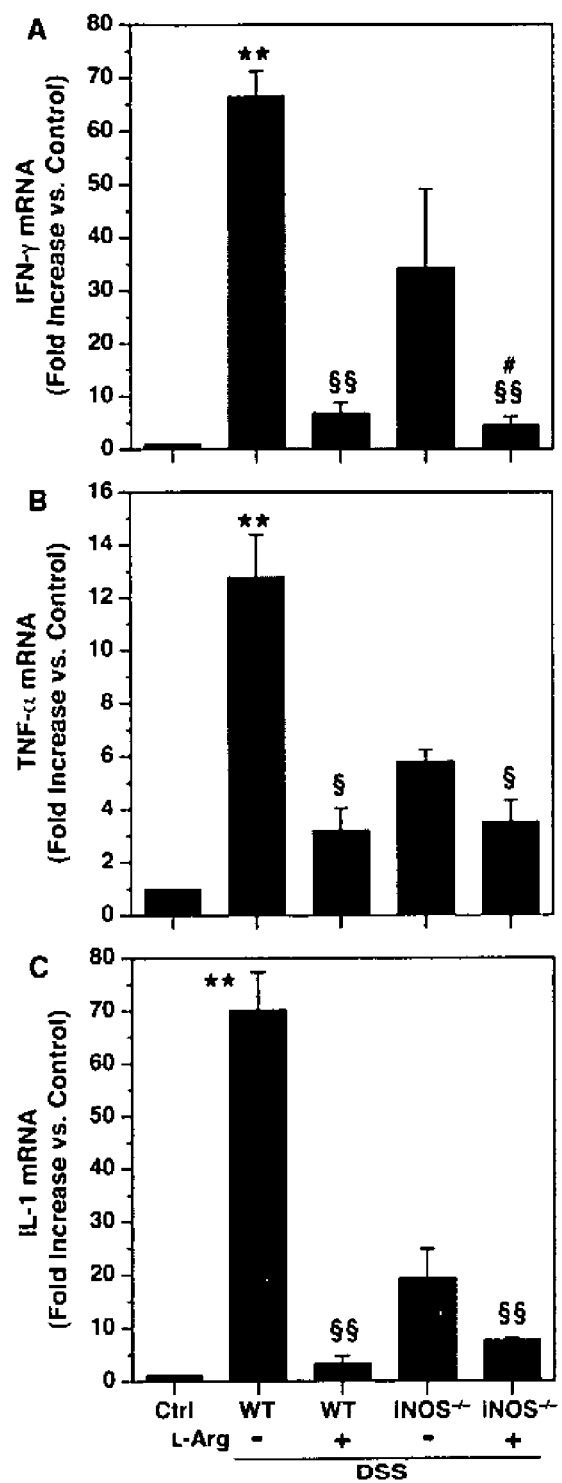

Levels of the pro-inflammatory cytokines IFN-$\gamma$, TNF-$\alpha$, and IL-1 were also induced in DSS colitis tissues (FIG. 39), and similar to our findings in the *C. rodentium* model, levels were decreased in the mice with reduction of colitis, indicating that they are useful markers of disease severity. It is notable that the levels in the iNOS$^{-/-}$ mice were not as reduced as in the L-Arg treated mice, which parallels the findings of day 10 body weight, colon weight and histology in FIGS. 37 and 38. Taken together, these findings suggest that in the DSS model, arginine supplementation acting through the arginase pathway is beneficial.

Polyamine Levels are Increased by L-Arg and iNOS Deletion

Figure 40:
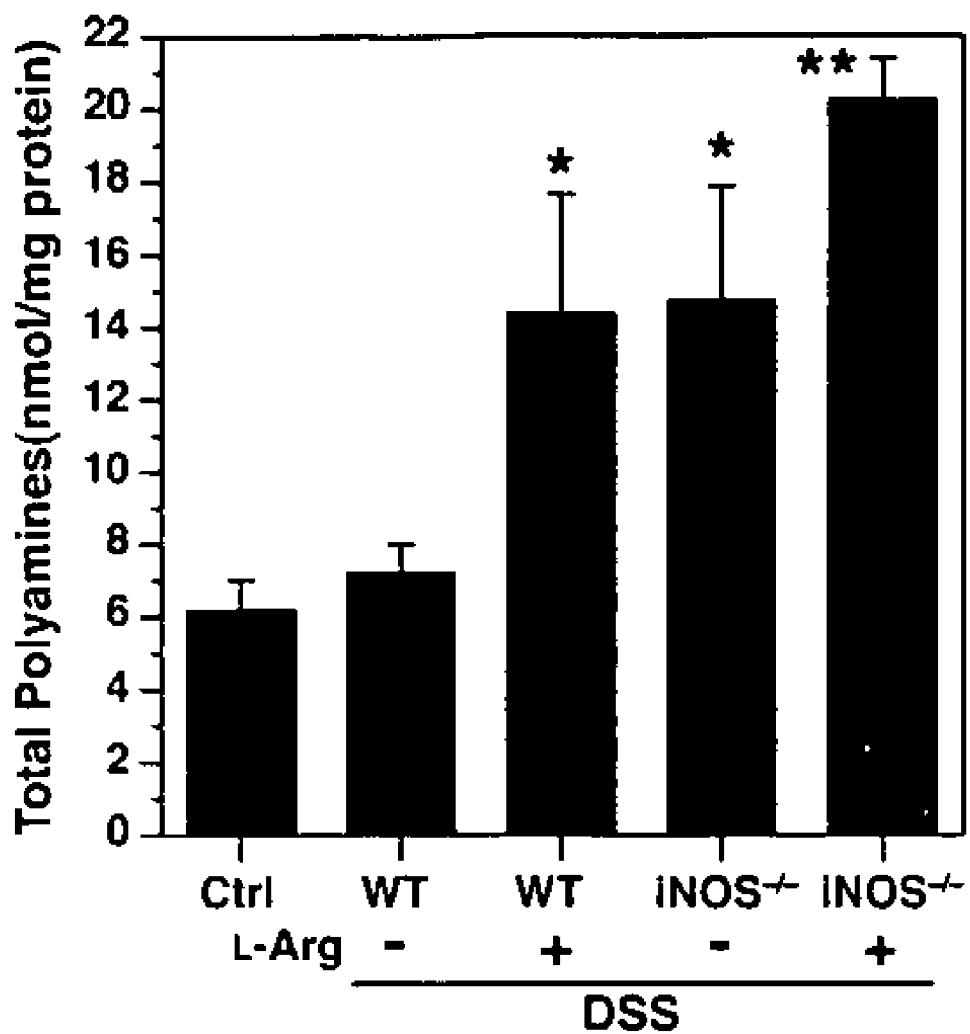
FIG. 40 is a graph showing colonic polyamine levels in DSS colitis. *p<0.01, **p<0.01 vs. control mice.

Intriguingly, when polyamine levels were assessed, there was a consistent increase in those groups with clinical improvement (FIG. 40). As in the *C. rodentium* model, addition of L-Arg enhanced polyamine levels. However, in contrast to *C. rodentium*, there was not an increase in polyamines in the WT mice without L-Arg; we speculate that this is due to the induction of the polyamine metabolizing enzymes spermine oxidase and spermidine/spermine N$^1$-acetyltransferase (SSAT) that we have observed in these tissues (data not shown).

Additional Data Supporting the Importance of the Arginase-ODC Pathway in Colitis.

Figure 41:
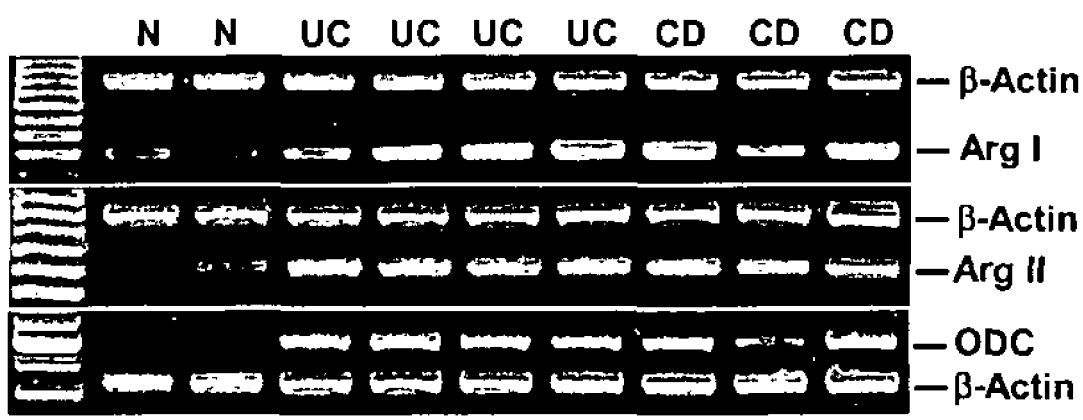
FIG. 41 shows increased mRNA levels of arginase I, II, and ODC in human IBD tissues by RT-PCR.

Consistent with the protective role of arginase in the DSS model, when the arginase inhibitor BEC was administered, we observed an exacerbation of clinical and histologic parameters of colitis in both WT and iNOS$^{-/-}$ mice (data not shown). Finally, in human IBD tissues from both ulcerative colitis and Crohn's disease, we have observed an increase in arginase I and ODC mRNA levels (FIG. 41). Unlike the mice, there was also an increase in arginase II, suggesting that the mitochondrial enzyme is also induced in these tissues.

Example 19

Apo-E Mimetic Peptides Inhibit iNOS in *C. rodentium*-stimulated Macrophages

To initiate studies to verify the likely relevance of the apo-E mimetic COG peptides to models of IBD, we have tested them in murine RAW 264.7 macrophages activated with *C. rodentium*. We used bacterial lysates to more closely mimic the bacterial products to which lamina propria macrophages are likely to be exposed. In fact, we have observed bacterial aggregates in the subepithelial mucosa in infected mice with regularity (see FIG. 32, high power view).

Excitingly, we have found that with both peptides tested, namely COG1410, and COG4502, the antennapedia-linked form of COG133, there was inhibition of NO production as measured by nitrite (NO2$^-$) levels in macrophage supernatants (FIG. 42). For COG1410, cell toxicity was noted at concentrations of 5 $\mu$M and above, so only data at 2 $\mu$M is shown; for COG4502, toxicity was noted at 10 $\mu$M by the XTT cell viability assay, so data in the 0.1-5 $\mu$M range is shown, where toxicity did not occur. Additionally, when mRNA levels were assessed with the COG4502 treatment, there was a significant, concentration-dependent inhibition of iNOS mRNA expression.

7. LITERATURE CITED

All references and patents cited herein are herein incorporated by reference in their entireties, including, but not limited to, the following:

Alberts, et al., 1995, ApoE genotype and survival from intracerebral haemorrhage, *Lancet* 346: 575.

Alberts, et al., 1996, *Stroke* 27:183 (abstract).

Amador, et al., 1963, Serum lactate dehydrogenase activity: an analytical assessment of current assays, *Clin. Chem.* 9: 391-4.

Aono M., Lee Y., Grant, E. R., Zivin, R. A., Pearlstein, R. D., Warner, D. S., Bennett, E. R., and Laskowitz, D. T. (2002). Apolipoprotein E protects against NMDA excitotoxicity. *Neurobiol. Dis.* 11:214-20.

Aono, M., Bennett, E. R., Kim, K. S., Lynch, J. R., Myers, J., Pearlstein, R. D., Warner, D. S., and Laskowitz, D. T. (2003). Protective effect of apolipoprotein E-mimetic peptides on N-methyl-D-aspartate excitotoxicity in primary rat neuronal-glial cell cultures. *Neuroscience*, 116: 431-45.

Asoh, S., Ohsawa, I., Mori, T., Katsura, K., Hiraide, T., Katayama, Y., Kimura, M., Ozaki, D., Yamagata, K., and Ohta, S (2002) Protection against ischemic brain injury by protein therapeutics. *PNAS* 99: 17107-17112.

Avila, et al., 1982, *J. Biol. Chem.* 257:5900.

Bacq, Z. M. 1965. Chemical protection against ionizing radiation, Charles C Thomas, Springfield, Ill.

Balaram and Gurunath., 1994, Incorporation of a potentially helix breaking D-Phe-Pro sequence into the center of a right handed 16 residue peptide helix, *Biochem. Biophys. Res. Commun.*, 202(1), 241.

Baraboi, V. A., Beloshiskii, P. V., Krasiuk, A. N. and Korkach, V. I. 1994. Oxygen dependent processes in the irradiated organisms. Fiziol. Zh. 40: 116-128.

Bart, et al., 1998, Regional cerebral blood flow in apolipoprotein E deficient mice and wildtype mice during focal cerebral ischemia, *NeuroReport.* 9: 2615-2620.

Bellosta, et al., 1995, Stable expression and secretion of apolipoproteins E3 and E4 in mouse neuroblastoma cells produces differential effects on neurite outgrowth, *J. Biol. Chem.* 270: 27063-27071.

Ben-Nathan D, Padgett D A, Loria R M. 1999. Androstenediol and dehydroepiandrosterone protect mice against lethal bacterial infections and lipopolysaccharide toxicity. J Med. Microbiol. 1999 May; 48(5):425-31.

Benveniste E N, 1997, Role of macrophages/microglia in multiple sclerosis and experimental allergic encephalomyelitis, J MoI Med. 75(3): 165-73.

Bolin, et al, 2000, Peptide and peptide mimetic inhibitors of antigen presentation by HLA-DR class II MHC molecules. Design, structure-activity relationships, and X-ray crystal structures, *J. Med. Chem.* 43, 2135-48.

Bacskai, et al, 2000, The endocytic receptor protein LRP also mediates neuronal calcium signaling via N-methyl-D-aspartate receptors. *Proc. Natl. Acad. Sci.* 97: 11551-11556.

Barger and Harmon, 1997, *Nature* 388:878.

Bart, et al., 1998, Regional cerebral blood flow in apolipoprotein E deficient vs wildtype mice undergoing middle cerebral artery occlusion. *Neuroreport* 11:2615-2620.

Bell, et al., 1994, Upregulation of the macrophage scavenger receptor in response to different forms of injury in the CNS, *J. Neurocytol.* 23(10):605-13.

Berliner, et al., 1995, *Circulation* 91:2488.

Bi, et al., 2002, Uptake and pathogenic effects of amyloid beta peptide 1-42 are enhanced by integrin antagonists and blocked by NMDA receptor antagonists, *Neuroscience* 112(4):827-40.

Bi, et al., 2002, N-methyl-D-aspartate receptor subunit NR2A and NR2B messenger RNA levels are altered in the hippocampus and entorhinal cortex in Alzheimer's disease, *J. Neurol. Sci.* 200(1-2):1 1-8.

Biakov, V. M. and Stepanov, S. V. 1997. Mechanism of primary radiobiologic action. Radiat. Biol. Radioecol. 37: 469-474.

Bocchini, V. R., Mazzolla, R., Barluzzi, E., Blasi, P., Sick, and H. Kettenmann (1992) An immortalized cell line expresses properties of activated microglial cells. *J. Neurosci. Res.* 31: 616-621.

Bogoyevitch, M. A., Kendrick, T. S., Ng, D. C. H. and Barr, R. K. (2002) Taking the cell by stealth or storm? Protein transduction domains (PTDs) as versatile vectors for delivery. *DNA and Cell Biology* 21: 879-894

Bolton, S J., Jones, D. N. C., Darker, J. G., Eggleston, D. S., Hunter, J., and Walsh, F. S. (2000) Cellular uptake and spread of the cell-permeable peptide penetratin in adult rat brain. *European Journal of Neuroscience* 12: 2847-2855.

Brain Injury Association of America (2002) Brain Injury Fact Sheet. http://www.biausa.org/word.files.to.pdf/good.pdfs/2002FactSheetBrainInjury.pdf Breitner, et al., 1995, *Neurobiol. Aging* 16:523.

Broderick, et al., 2001, Apolipoprotein E phenotype and the efficacy of intravenous tissue plasminogen activator in acute ischemic stroke, *Ann. Neurol.* 49:736-744.

Centers for Disease Control and Prevention. Traumatic brain injury in the United States. Unpublished data from the National Center for Injury Prevention and Control, May 1998.

Cao, G., W. Pei, H., Ge, Q., Liang, Y., Luo, F. R., Sharp, A., Lu, R., Ran, S. H., Graham, and Chen, J. (2002) In vivo delivery of a Bcl-xL fusion protein containing the TAT protein transduction domain protects against Ischemic Brain Injury and Neuronal Apoptosis. *Society of Neuroscience* 22: 5423-5431.

Cady, 2001, Understanding opioid tolerance in cancer pain, *Oncol. Nurs. Forum* 28(10): 1561-8.

Calabresi, 2002, Considerations in the treatment of relapsing-remitting multiple sclerosis, *Neurology* 58(8 Suppl 4): S10-22.

Centers for Disease Control and Prevention. Report to Congress on Mild Traumatic Brain Injury in the United States: Steps to Prevent a Serious Public Health Problem, September 2003.

Chapman, et al., 1999, Preliminary observations on APOE epsilon 4 allele and progression of disability in multiple sclerosis, *Arch. Neurol.* 56: 1484-1487.

Chapman J, Vinokurov S, Achiron A, Karussis D M, Mitosek-Szewczyk K, Birnbaum M, Michaelson D M, Korczyn A D, 2001, APOE genotype is a major predictor of long-term progression of disability in MS, Neurology. 56(3):312-6.

Chen, et al., 1997, Motor and cognitive deficits in apolipoprotein-E deficient mice after closed head injury, Neuroscience 80: 1255-1262.

Chen, et al., 2002, N-acyl-L-phenylalanine derivatives as potent VLA-4 antagonists that mimic a cyclic peptide conformation, *Bioorg. Med. Chem. Lett.* 12, 137-40.

Chesnut, et al., Rehabilitation for traumatic brain injury. Evidence report no. 2 (Contract 290-97-0018 to Oregon Health Sciences University). Rockville, Md.: Agency for Health Care Policy and Research. February 1999.

Chensue et al., 1991, *Am. J. Pathol.* 138:395-402.

Chiang C S, Hong J H, Stalder A, Sun J R, Withers H R, McBride W H. 1997. Delayed molecular responses to brain irradiation. Int J Radiat Biol. 1997 July; 72(1):45-53.

Coleman N, Bump E, Kramer R: Chemical modifiers of cancer treatment. 1988. J Clin Oncol 6:709-733.

Clifford, 2002, AIDS dementia, *Med. Clin. North Am.* 86(3): 537-50, vi.

Cohen, et al., 1992, Interaction of lactoferrin and lipopolysaccharide (LPS): effects on the antioxidant property of lactoferrin and the ability of LPS to prime human neutrophils for enhanced superoxide formation, *J. Infect. Dis.* 166: 1375-1378.

Connolly, et al., 1996, *Stroke* 27: 174 (abstract).

Clodi, and Younes, 1997, Reed-Sternberg cells and the TNF family of receptors/ligands, Leuk. Lymphoma 27: 195-205.

Colton, C. A., Brown, C M., Cook, D., Needham, L. K., Xu, Q., Czapiga, M., Saunders, A. M., Schmechel, D. E., Rasheed, K., and Vitek, M. P. (2002). APOE and the regulation of microglial nitric oxide production: a link between genetic risk and oxidative stress. *Neurobiology of Aging* 23:177-85.

Console, S., Marty, C, Garcia-Echeverria, C, Schwendener, R. and Ballmer-Hofer, R. (2003) Antennapedia and HIV TAT 'protein transduction domains' promote endocytosis of high Mr cargo upon binding to cell surface glycosaminoglycans. *J Biol Chem*, in press.

Corder, et al., 1993, Gene doses of apolipoprotein E type 4 allele and the risk of Alzheimer's disease in late onset families, Science 261:921-923.

Crawford F C, Vanderploeg R D, Freeman M J, Singh S, Waisman M, Michaels L, Abdullah L, Warden D, Lipsky R, Salazar A, Mullan M J, 2002, APOE genotype influences acquisition and recall following traumatic brain injury. Neurology 58(7): 1115-8.

Crawley, 2000, What's wrong with my mouse: Behavioral phenotyping of transgneic and knockout mice. (John Wiley and Sons, New York).

Dail, et al., 1981, Responses to cortical injury: II. Widespread depression of the activity of an enzyme in cortex remote from a focal injury, *Brain Res.* 211:79-89.

Denicourt, C, and Dowdy, S. F. (2003). Protein transduction technology offers novel therapeutic approach for brain ischemia. *Trends in Pharmacological Sciences* 24: 216-218.

Dietz, G. P. H, Kilic, E., and Bahr, M. (2002) Inhibition of neuronal apoptosis in vitro and in vivo Using TAT-mediated protein transduction. *Molecular and Cellular Neuroscience* 21: 29-37.

de Bont N, Netea M G, Demacker P N, Verschueren I, Kullberg B J, van Dijk K W, van der Meer J W, Stalenhoef A F. 1999. Apolipoprotein E knock-out mice are highly susceptible to endotoxemia and *Klebsiella pneumoniae* infection. J Lipid Res. 1999 April; 40(4):680-5.

DiScala, et al., 1997, Children hospitalized for traumatic brain injury: transition to postacute care, *J. Head Trauma Rehabil.* 12(2):1-10.

Doig, 2002, Recent Advances in helix-coil theory, *Biophys. Chem.,* 101-102, 281.

Doig, et al., 1994, Determination of free energies of N-capping in alpha helices by modification of the Lifson-Roig helix-coil theory to include N- and C-capping, *Biochemistry* 33(11), 3396.

Doig and Baldwin, 1993, N- and C-capping preferences for all 20 amino acids in alpha-helical peptides, *Protein Sci.,* 4(7), 1325.

Dhib-Jalbut, 2002, Mechanisms of action of interferons and glatiramer acetate in multiple sclerosis, *Neurology* 58(8 Suppl 4):S3-9.

Doble, 1999, The role of excitotoxicity in neurodegenerative disease: implications for therapy, *Pharmacol. Ther.* 81 (3): 163-221.

Drin, G. S., Cottin, E. Blanc, A. R., Rees, and Temsamani. J. (2003) Studies on the internalization mechanism of cationic cell-penetrating peptides. *The Journal of Biological Chemistry.* In press.

Dragaric, I. G. and Dragaric, Z. D. 1971. The radiation chemistry of water, pp. 256, Academic Press, New York.

Dunlop, et al., 1997, HIV dementia and apolipoprotein E, *Acta Neurol. Scand.* 95(5):315-8.

Dyer, et al., 1991, *J. Biol. Chem.* 266: 15009.

Ernst, et al., 2002, Design of a protein surface antagonist based on alpha-helix mimicry: inhibition of gp41 assembly and viral fusion, *Angew Chem. Int. Ed. Engl.* 41, 278-81.

Edgington and Curtiss, 1981, *Cancer Res.* 41:3786.

Eng L F, Ghirnikar R S, Lee Y L, 1996, Inflammation in EAE: role of chemokine/cytokine expression by resident and infiltrating cells, Neurochem Res. 21(4):511-25.

Fazekas F, Strasser-Fuchs S, Kollegger H, Berger T, Kristoferitsch W, Schmidt H, Enzinger C, Schiefermeier M, Schwarz C, Kornek B, Reindl M, Huber K, Grass R, Wimmer G, Vass K, Pfeiffer K H, Hartung H P, Schmidt R, 2001, Apolipoprotein E epsilon 4 is associated with rapid progression of multiple sclerosis, Neurology, 57(5):853-7.

Feinstein D L, Galea E, Gavrilyuk V, Brosnan C F, Whitacre C C, Dumitrescu-Ozimek L, Landreth G E, Pershadsingh H A, Weinberg G, Heneka M T, 2002, Peroxisome proliferator-activated receptor-gamma agonists prevent experimental autoimmune encephalomyelitis, Ann Neurol. 51(6):694-702.

Feeney, et al., 1981, Responses to cortical injury: I. Methodology and local effects of contusions in the rat, *Brain Res.* 211:67-77.

Fisher, P. M., E. Krausz., D. P. Lane. 2001. Cellular delivery of impermeable effector molecules in the form of conjugates with peptides capable of mediating membrane translocation. Bioconjugate Chemistry 12: 825-841.

Fike J R, Cann C E, Turowski K, Higgins R J, Chan A S, Phillips T L, Davis R L. 1988. Radiation dose response of normal brain. Int J Radiat Oncol Biol Phys. 1988 January; 14(1):63-70.

Flegel W A, Baumstark M W, Weinstock C, Berg A, Northoff H. 1993. Prevention of endotoxin-induced monokine release by human low- and high-density lipoproteins and by apolipoprotein A-I. Infect Immun. 1993 December; 61(12):5140-6.

Fleming, et al., 1996, Differential binding of apolipoprotein E isoforms to tau and other cytoskeletal proteins, *Exp. Neurol.* 138: 252-260.

Friedman, et al., 1999, Apolipoprotein E-epsilon 4 genotype predicts a poor outcome in survivors of traumatic brain injury, *Neurology* 52: 244-248.

Fotouhi, et al., 2000, The design and synthesis of potent cyclic peptide VCAM-VLA-4 antagonists incorporating an achiral Asp-Pro mimetic, *Bioorg. Med. Chem. Lett.* 10, 1171-3.

Futaki, S. (2002) Arginine-rich peptides: potential for intracellular delivery of macromolecules and the mystery of the translocation mechanisms. *International Journal of Pharmaceutics* 245: 1-7.

Farber, et al., 2002, Antiepileptic drugs and agents that inhibit voltage-gated sodium channels prevent NMDA antagonist neurotoxicity, *Mol. Psychiatry.* 7(7): 726-33.

Fazio, et al., 1997, *Proc. Natl. Acad. Sci.* 94:4647.

Flaherty, et al., 1999, Regulation of tau phosphorylation in microtubule fractions by apolipoprotein E, *J. Neurosci. Res.* 56(3):271-4.

Garcia-Echeverria, C, Jiang, L., Ramsey, T. M., Sharma, S. K., and Chen, Y.-N. P. (2001) A new Antennapedia-derived vector for intracellular delivery of exogenous compounds. *Bioorganic & Medicinal Chemistry Letters* 11: 1363-1366.

Garcia-Echeverria, C, and Ruetz, S. (2003) β-Homolysine oligomers: a new class of Trojan carriers. *Bioorganic & Medicinal Chemistry Letters* 13: 247-251.

Gaffin S L, Wells M, Jordan J P. 1985. Anti-lipopolysaccharide toxin therapy for whole body X-irradiation overdose. Br J. Radiol. 1985 September; 58(693):881-4.

Girinsky T A, M Pallardy, E Comoy, T Benassi, R Roger, G Ganem, J M Cosset, G Socie, and H Magdelenat. 1994. Peripheral blood corticotropin-releasing factor, adrenocorticotropic hormone and cytokine (interleukin beta, interleukin 6, tumor necrosis factor alpha) levels after high- and low-dose total-body irradiation in humans. Radiat Res. 139:360-363.

Gallo, et al., 1994, Potential role of apolipoprotein-E in fibrillogenesis. *Am. J. Pathol.* 145: 526-530.

Gotschall, et al., 1995, Comparison of three measures of injury severity in children with traumatic brain injury, *J. Neurotrauma* 12, 611-619.

Grubbs, et al., 2001, Ring-closing metathesis of olefinic peptides: Design, Synthesis, and Structural characterization of macrocyclic helical peptides, *J. Org. Chem.,* 66, 5291.

Gutman, et al., 1997, Apolipoprotein E binds to and potentiates the biological activity of ciliary neurotrophic factor. *J. Neurosci.* 17: 6114-6121.

Gehrmenn, et al., 1995, Microglia: intrinsic immuneffector cell of the brain, *Brain Res. Brain Res. Rev.* 20(3):269-87.

Giulian, et al., 1996, *J. Neuroscience,* 16:3139.

Griffin, et al., 1995, *J. Neuropath. Exp. Neurol.* 54:276.

Grubbs R. H., Blackwell H. E., Sadowsky J. D., Howard R. J., Sampson J. N., Chao J. A., Steinmetz W. E., and O'Leary D J., 2001, "Ring-closing metathesis of olefinic peptides:

Design, Synthesis, and Structural characterization of macrocyclic helical peptides", J. Org. Chem., 66, 5291.

Hall, E J. 2000. Radiobiology for the Radiologist. Lippincott Williams and Wilkins, 5th edition, p. 138.

Hamm, et al., 1994, The Rotarod Test: An Evaluation Of Its Effectiveness In Assessing Motor Deficits Following Traumatic Brain Injury, *J. Neurotrauma* 11, 187-196.

Hamilton, et al., 2003, Design and application of an alpha helix mimetic scaffold based on an Oligoamide-foldamer strategy: Antagonism of the Bak BH3/Bcl-xL complex, *Angew. Chem. Int. Ed.,* 42(5), 535.

Hamilton, et al., 2002, Design of a protein surface antagonist based on alpha-helix mimicry: Inhibition of gp41 assembly and viral fusion, *Angew. Chem. Int. Ed.,* 41(2), 278.

Hamilton, et al., 2001, Towards proteomimetics: terphenyl derivatives as structural and functional mimics of extended regions of an alpha helix, *J. Amer. Chem. Soc.,* 123, 5382.

Hayek, 1994, Increased plasma and lipoprotein lipid peroxidation in apo E-deficient mice, *Biochem. Biophys. Res. Commun.* 201:1567-1574.

Heber-Katz E, 1993, The ups and downs of EAE, Int Rev Immunol. 9(4):277-85.

Hemmer B, Archelos J J, Hartung H P, 2002, New concepts in the immunopathogenesis of multiple sclerosis, Nat Rev Neurosci. 3(4):291-301.

Hill G R, Crawford J M, Cooke K R, Brinson Y S, Pan L, Ferrara J L. 1997. Total body irradiation and acute graft-versus-host disease: the role of gastrointestinal damage and inflammatory cytokines. Blood. 1997 Oct. 15; 90(8): 3204-13.

Hill R P, H-P Rodemann, J H Hendry, S A Roberts, and M. S. Anscher. 2001. 'Normal tissue radiobiology: From the laboratory to the clinic. Int. J. Radiation Oncology Biol. Phys., 49:353-365.

Hong J H, Chiang C S, Campbell I L, Sun J R, Withers H R, McBride W H. 1995. Induction of acute phase gene expression by brain irradiation. Int J Radiat Oncol Biol Phys. 1995 Oct. 15; 33(3):619-26.

Hirschmann, et al., 1996, Synthesis of Potent Cyclic Hexapeptide NK-I Antagonists. Use of a Minilibrary in Transforming a Peptidal Somatostatin Receptor Ligand into an NK-I Receptor Ligand via a Polyvalent Peptidomimetic, *J. Med. Chem.,* 39, 2441-2448.

Holtzman, et al., 1995, Low density lipoprotein receptor-related protein mediates apolipoprotein E-dependent neurite outgrowth in a central nervous system-derived neuronal cell line, *Proc. Natl. Acad. ScL U.S.A.* 92: 9480-9484.

Horsburgh, et al., 1999, Increased neuronal damage in apolipoprotein E-deficient mice following global ischaemia, *Neuroreport* 10: 837-841.

Horsburgh, et al., 2000, Intraventricular infusion of apolipoprotein E ameliorates acute neuronal damage after global cerebral ischemia in mice, *J. Cerebral Blood Flow Metab.* 20:458-462.

Horsburgh, et al., 1999, Increased neuronal damage in apolipoprotein E-deficient mice following global ischaemia, *Neuroreport* 10: 837-841.

Hansson, 1994, *Basic Res. Cardiol.,* 89(1):41.

Harris, et al., 1998, *Hepatol.* 27: 1341-48.

Harris, et al., 1993, *J. Clin. Invest.* 91:1028-34.

Harris H W, Grunfeld C, Feingold K R, Rapp J H. 1990. Human very low density lipoproteins and chylomicrons can protect against endotoxin-induced death in mice. J Clin Invest. 1990 September; 86(3):696-702.

Haughey, et al., 2001, HIV-1 Tat through phosphorylation of NMDA receptors potentiates glutamate excitotoxicity, *J. Neurochem.* 78(3):457-67.

Henderson, et al., 1996, Microbiol. Rev. 60:316-34. Holtzman et ah, Low density lipoprotein receptor-related protein mediates apolipoprotein E-dependent neurite outgrowth in a central nervous system-derived neuronal cell line. *Proc. Natl. Acad. Sci.* 92:9480-9484 (1995).

Hensley, M L., L M Schuchter, C Lindley, N L Meropol, G I Cohen, G Broder, W J Gradishar, D M Green, R J Langdon, R B Mitchell, R Negrin, T P Szatrowski, J T Thigpen, D Von Hoff, T H Wasserman, E P Winer, D G Pfister for the American Society of Clinical Oncology. 1999. American Society of Clinical Oncology Clinical Practice Guidelines for the Use of Chemotherapy and Radiotherapy Protectants., J. Clin. Oncol. 17: 3333-3355.

Higuchi, Y, G A Nelson, M Vazquez, D T Laskowitz, J M Slater, and R D Pearlstein. 2002. Apolipoprotein E expression and behavioral toxicity of high charge, high energy (HZE) particle radiation. J. Radiat. Res. 43:S219-S224/

Huang, et al., 2001, Apolipoprotein E fragments present in Alzheimer's Disease brains induce neurofibrillary tangle-like intracellular inclusions in neurons, *Proc. Natl. Acad. Sci. USA* 91:11183-11186.

Huettinger, et al., 1988, Characteristics of chylomicron remnant uptake into rat liver, *Clin. Biochem.* 21(2):87-92.

Innerarity, et al., 1979, *J. Biol. Chem.* 254:4186-4190.

Innerarity, et al., 1983, The receptor-binding domain of human apolipoprotein E: binding of apolipoprotein E fragments, *J. Biol. Chem.* 258: 12341-47.

Jordan, et al., 1997, Apolipoprotein E epsilon-4 associated with chronic traumatic brain injury in boxing, *J. Am. Med. Assoc.* 278: 136-140.

Jones, et al., 2002, Attenuation of acute morphine withdrawal in the neonatal rat by the competitive NMDA receptor antagonist LY2359592002, *Neuropsychopharmacology* 26(3): 301-10.

Jordan et al., 1998, Isoform-specific effect of apolipoprotein E on cell survival and beta-amyloid-induced toxicity in rat hippocampal pyramidal neuronal cultures, *J. Neurosci.* 18: 195-204.

Joseph, J A, S Erat, and B M Rabin. 1998. CNS effects of heavy particle irradiation in space: behavioral implications. Adv. Space Res. 22: 209-216.

Karle, 2001, Controls exerted by the Aib residue: Helix formation and Helix reversal, *Biopolymers,* 60(5), 351.

Karle and Balaram, 1990, Structural characteristics of alpha helical peptide molecules containing Aib residues, *Biochemistry,* 29(29), 6747.

Kilic, U., Kilic, E., Dietz, G. P. H., and Bahr, M. (2003) Intravenous TAT-GDNF is protective after focal cerebral ischemia in mice. *Stroke* 34: 1304-1310.

Knouff, et al., 1999, ApoE structure determines VLDL clearance and atherosclerosis risk in mice, *J. Clin. Invest.* 103: 1579-86.

Kraus, et al., 1990, Brain injuries among infants, children, adolescents and young adults, *AJDC* 144, 684-691.

Kim, et al., 1996, Human apolipoprotein E receptor 2, *J. Biol. Chem.* 271, 8373-8380.

Klopman and Sedykh, 2002, An MCASE approach to the search of a cure for Parkinson's Disease, *BMC Pharmacol.* 2(1):8.

Kolker, et al., 2002, NMDA receptor activation and respiratory chain complex V inhibition contribute to neurodegeneration in d-2-hydroxyglutaric aciduria, *Eur. J. Neurosci.* 16(1):21-8.

Koppelhus, U., Awasthi, S. K., Zachar, V., Hoist H. U., Ebbsen, P., Nielson, P. E. (2002) Cell-dependent differential cellular uptake of PNA, peptides, and PNA-peptide conjugates. Antisense Nucleic Acid Drug Dev 12: 51-63.

Kotlinska, 2001, NMDA antagonists inhibit the development of ethanol dependence in rats, *Pol. J. Pharmacol.* 53(1): 47-50.

Krieger and Herz, 1994, Structures and functions of multiligand lipoprotein receptors: macrophage scavenger receptors and LDL receptor-related protein (LRP), *Ann. Rev. Biochem.* 63:601-37.

Kudo, et al., 2001, Absence of direct antioxidant effects from volatile anesthetics in mixed neuronal-glial culture, *Anesthesiology* 94:303-312.

Laskowitz, et al., 2000, Altered immune responses in apolipoprotein E deficient mice. J. Lipid Res. 41: 613-620.

Laskowitz, et al., 1998b, Apolipoprotein E and the CNS response to injury, *J. Cerebral Blood Flow Metab.* 18:465-471.

Laskowitz and Roses, 1998a, Apolipoprotein E: an expanding role in the neurobiology of disease, *Alzheimer's Reports* 1: 5-12.

Laskowitz, et al., 2001, Downregulation of microglia activation by apolipoprotein-E and apoE-mimetic peptides, *Expt. Neurol.* 167: 74-85.

Laskowitz, et al., 1997a, Apolipoprotein E deficient mice have increased susceptibility to focal cerebral ischemia, *J. Cereb. Blood Flow Metab.* 17: 753-758.

Laskowitz, et al., 1997c, Endogenous apolipoprotein E suppresses LPS-stimulated microglial nitric-oxide production, *Neuroreport* 9: 615-618.

Laskowitz, et al., 1997b, Apolipoprotein E suppresses glial cell secretion of TNFα. J. Neuroimmunology 76: 70-74.

Liefert, J. A., and Whitton, J. L. (2003) "Translocatory proteins" and "protein transduction domains": a critical analysis of their biological effects and the underlying mechanisms. *Molecular Therapy* 8: 13-19.

Lindsay, M. A. (2002). Peptide-mediated cell delivery: application in protein target validation. *Current Opinions in Pharmacology* 2: 587-594.

Lo, E. H., Singhal, A. B., Torchlin, V. P., and Abbott, N J. (2001) Drug delivery to damaged brain. *Brain Research Reviews* 38: 140-148.

Lomnitski, L., Chapman, S., Hochman, A., Kohen, R., Shohami, E., Chen, Y., Trembovler, V., and Michaelson, D. M. (1999). Antioxidant mechanisms in apolipoprotein E deficient mice prior to and following closed head injury. *Biochim Biophys Acta*, 1453: 359-68.

Lendon et al., No effect of apolipoprotein E on neuronal cell death due to excitotoxic and apoptotic agents in vitro and neonatal hypoxic ischaemia in vivo, *Euro. J. Neurosci.* 12:2235-2242 (2000).

Lighthall, 1988, Controlled cortical impact: a new experimental brain injury model. *J. Neurotrauma* 5: 1-15.

Linton et al., Phenotypes of apolipoprotein B and apolipoprotein E after liver transplantation, *J. Clin. Invest.* 270-81 (1991).

Linton et al., *Science*, 267: 1034 (1995).

Linton, et al., 1997, Phenotypes of apolipoprotein B and apolipoprotein E after liver transplantation. *J. Clin. Invest.*, 270-281.

Liu, et al., 2000, Synthesis of a Substance P Antagonist with a Somatostatin Scaffold: Factors Affecting Agonism/Antagonism at GPCRs and the Role of Pseudosymmetry, *J. Med. Chem.*, 43, 3827-3831.

Lucotte G L; French M S Consortium, 2002, Confirmation of a gene for multiple sclerosis (MS) to chromosome region 19q13.3, Genet Couns. 13(2): 133-8.

Lynch, et al., 2001a, Apolipoprotein E mimetic peptide is neuroprotective in a murine head injury model, *Soc. Neuroscience Abstracts*.

Lynch, et al., 2001b, Apolipoprotein E modulates glial activation and the endogenous central nervous system inflammatory response, *J. Neuroimmunology* 114: 107-113.

Lynch, et al., 2002, Apolipoprotein E affects the Central Nervous System Response to Injury and the Development of Cerebral Edema, *Ann. Neurol.* 51:113-7.

Lynch, Tang, et al., 2003, ApoE genotype and an apoE-mimetic peptide modify the systemic and CNS inflammatory response, *J. Biol. Chem.*, epub ahead of print.

Lalazar, et al., 1998, Site-specific mutagenesis of human apolipoprotein E. Receptor binding activity of variants with single amino acid substitutions, *J. Biol. Chem.* 263:3542-3545.

Le and Lipton, 2001, Potential and current use of N-methyl-D-aspartate (NMDA) receptor antagonists in diseases of aging, *Drugs Aging* 18(10):717-24.

Lendon, et al., 2000, No effect of apolipoprotein E on neuronal cell death due to excitotoxic and apoptotic agents in vitro and neonatal hypoxic ischaemia in vivo, *Euro. J. Neurosci.* 12:2235-2242.

Linton, et al., 1995, *Science*, 267:1034.

Lynn, W. A., and J. Cohen. 1995. Adjunctive therapy for septic shock: a review of experimental approaches. Clin. Infect. Dis. 20: 143-158.

Lovestone, et al., 2001, Apolipoprotein E gene and Alzheimer's disease: is tau the link? *Biochem. Soc. Symp.* (67): 111-20.

Lundberg, M and Johansson (2002). Positively charged DNA-binding proteins cause apparent cell membrane translocation. Biochem, Viophys Res Comm291; 367-371.

Mai, J. C., Shen, H., Watkins, S. C., Cheng, T., and Robbins, P. D. (2002). Efficiency of protein transduction is cell type-dependent and is enhanced by dextran sulfate. *The Journal of Biological Chemistry* 277: 30208-30218.

Mandell L R, Steinherz P, Fuks Z. 1990. Delayed central nervous system (CNS) radiation in childhood CNS acute lymphoblastic leukemia. Results of a pilot trial. Cancer. 1990 Aug. 1; 66(3):447-50.

Masterman T, Zhang Z, Hellgren D, Salter H, Anvret M, Lilius L, Lannfelt L, Hillert J, 2002, APOE genotypes and disease severity in multiple sclerosis, Mult Scler. 8(2):98-103.

Matthews and Beal, 1996, Increased 3-nitrotyrosine in brains of Apo E-deficient mice, *Brain Res.* 718: 181-184.

McArron, et al., 1998, The apolipoprotein E epsilon4 allele and outcome in cerebrovascular disease, *Stroke* 29, 1882-1887.

Misra, et al., 2001, Apolipoprotein E and mimetic peptide initiate a calcium-dependent signaling response in macrophages, *J. Leukocyte Biol.* 70: 677-683.

Mitchell and Smith, 2003, D-amino acid residues in peptide and proteins, *Proteins* 50(4), 563.

Miyata and Smith, 1996, Apolipoprotein E allele-specific antioxidant activity and effects on cytotoxicity by oxidative insults and beta-amyloid peptides, *Nat. Genet.* 14: 55-61.

Morris, 1984, Developments of a water maze procedure for studying spatial learning in the rat, *J. Neurosci. Methods* 11: 47-60.

Mossman K L. Frequent short-term oral complications of head and neck radiotherapy. 1994. Ear Nose Throat J. 73:316-320.

Muller, et al., 1998, Apolipoprotein E isoforms increase intracellular Ca2+ differentially through a omega-aga toxin IVa-sensitive Ca2+-channel, *Brain Pathology* 8: 641-653.

Matsubara, et al., 2002, Monoclonal antibodies against inflammatory mediators for the treatment of patients with sepsis, *Nippon Rinsho* 60(3):578-84.

Mayeux, et al., 1995, *Neurology* 45:555.

McArron et al., The apolipoprotein E epsilon4 allele and outcome in cerebrovascular disease. *Stroke* 29: 1882-1887 (1998).

McGeer, v, 1993, *Glia* 7:88.

McKenna and Melzack, 2001, Blocking NMDA receptors in the hippocampal dentate gyrus with AP5 produces analgesia in the formalin pain test, *Exp. Neurol.* 172(1):92-9.

Meldrum, et al., 1990, Excitatory amino acid neurotoxicity and neurodegenerative disease, *Trends Pharmacol. Sci.* 11:379-387.

Misra, et al. 1994, The relationship between low density lipoprotein-related protein/alpha 2-macroglobulin (alpha 2M) receptors and the newly described alpha 2M signaling receptor, *J. Biol. Chem.* 269(28): 18303-6.

Miyazawa, et al., 1991, Lactoferrin-lipopolysaccharide interactions. Effect of lactoferrin binding to monocyte/macrophage-differentiated HL-60 cells, *J. Immunol.* 146:723-729.

Moulder, et al. 1999, Analysis of a novel mechanism of neuronal toxicity produced by an apolipoprotein E-derived peptide. *J. Neurochem.* 72: 1069-1080.

Myers, et al., 1997, Helix propensities are identical in proteins and peptides. *Biochemistry* 36:10923-10929.

Mytilineou, et al., 1997, L-deprenyl protects mesencephalic dopamine neurons from glutamate receptor-mediated toxicity in vitro, *J. Neurochem.* 68(1):33-9.

Nair C K, D K Parida, and T J Nomura. 2001. Radioprotectors in radiotherapy. Radiat Res (Tokyo). 42(1):21-37.

Netea M G, de Bont N, Demacker P N, Kullberg B J, Jacobs L E, Verver-Jansen T J, Stalenhoef A F, Van der Meer J W. 1998. Lipoprotein(a) inhibits lipopolysaccharide-induced tumor necrosis factor alpha production by human mononuclear cells. Infect Immun. 1998 May; 66(5):2365-7.

NIAID Whte Paper, NIAID Expert Panel Review on Radiobiological Research, 26 Feb. 2003.

Nathan, et al., 1994, Differential effects of apolipoproteins E3 and E4 on neuronal growth in vitro, Science 264: 850-852.

NIH Consensus Statement: Rehabilitation of Persons with Traumatic Brain Injury, 1998. NIH (1999) Report of the Consensus Development Conference on the REHABILITATION OF PERSONS WITH TRAUMATIC BRAIN INJURY http://www.nichd.nih.gov/publications/pubs/traumatic/NIH_Consensus_Statement.htm Newman, et al., 1995, *Ann. Thomac. Surg.* 59: 1326.

Nguimfack, 2002, Do the glutamate excitotoxicity theory and potential free radicals implication in schizophrenia aetiopathogenesis provide a new enlightenment to links between: genome, environment and biology in the determinism of that disorder? *Encephale* 28(2): 147-53.

Nicoll, et al., 1995, *Nat. Med.* 1:135.

Novak, et al., 1996, A new low density lipoprotein receptor homologue with 8 binding ligand repeats in brain of chicken and mouse. *J. Biol. Chem.* 271: 11732-1 1736.

Olson, et al., 1993, Perspective: Concepts and Progress in the Development of Peptide Mimetics, *J. Med. Chem.* 36, 3039-3049.

Olson, et al., 1995, Peptide Mimetics of Thyrotropin Releasing Hormone Based on a Cyclohexane Framework Design, Synthesis, and Cognition-Enhancing Properties, *J. Med. Chem.*, 38, 2866-2879.

Orner, et al., 2001, Toward proteomimetics: terphenyl derivatives as structural and functional mimics of extended regions of an alpha-helix, *J. Am. Chem. Soc.* 123, 5382-3.

Paul and Bolton, 2002, Modulation of blood-brain barrier dysfunction and neurological deficits during acute experimental allergic encephalomyelitis by the N-methyl-D-aspartate receptor antagonist memantine, *J. Pharmacol. Exp. Ther.* 302(1):50-7.

Pearlstein, et al., 1998, Neuroprotective effects of NMDA receptor glycine recognition site antagonism: dependence on glycine concentration. *J. Neurochem.* 70:2012-2019.

Pender M P, Wolfe N P, 2002, Prevention of autoimmune attack and disease progression in multiple sclerosis: current therapies and future prospects, Intern Med J. 32(11): 554-63.

Perez, et al., 2001, Evaluation of HIV-I Tat induced neurotoxicity in rat cortical cell culture, *J. Neurovirol.* 7(1): 1-10.

Pescarolo, et al., 2001, A retro-inverso peptide homologous to helix 1 of c-Myc is a potent and specific inhibitor of proliferation in different cellular systems, *FASEB J.* 15:31-3.

Parker T S, Levine D M, Chang J C, Laxer J, Coffin C C, Rubin A L. 1995. Reconstituted high-density lipoprotein neutralizes gram-negative bacterial lipopolysaccharides in human whole blood. Infect Immun. 1995 January; 63(1): 253-8.

Poirier, J. 1994. Apolipoprotein E in animal models of CNS injury and Alzheimer's disease. Trends Neurosci. 17:525-530.

Pradhan, D. S., Nair, C. K. K. and Sreenivasan, A. 1973. Radiation injury repair and sensitization of microorganisms. Proc. Ind. Natl. Sci. Acad. 39B: 516-530.

Redlich C A, Gao X, Rockwell S, Kelley M, Elias J A. 1996. IL-11 enhances survival and decreases TNF production after radiation-induced thoracic injury. J. Immunol. 1996 Aug. 15; 157(4):1705-10.

Rao, et al., 2001, Neuroprotection by memantine, a noncompetitive NMDA receptor antagonist after traumatic brain injury in rats, *Brain Res.* 911(1):96-100.

Regner, et al., 2001, Neurochemical characterization of traumatic brain injury in humans, *J. Neurotrauma* 18(8):783-92.

Rensen, et al., 1997, Human recombinant apolipoprotein E redirects lipopolysaccharide from Kupffer cells to liver parenchymal cells in rats in vivo, *J. Clin. Invest.* 99(10): 2438-45.

Richard, J. P., Melikov, K., Vives, E., Ramos, C, Verbeure, B., Gait, M. J., Chemomordik, L. V. and Lebleu, B (2003). Cell-penetrating peptides. A reevaluation of the mechanism of cellular uptake. *The Journal of Biological Chemistry* 278: 585-590.

Rousselle, C, Clair, P., Lefauconnier, J., Kaczorek, M., Scherrmann, J., and Temsamani, J (2000) New advances in the transport of doxorubicin through the blood-brain barrier by a peptide vector-mediated strategy. *Molecular Pharmacology* 57: 679-686.

Rousselle, C, Smirnova, M., Clair, P., Lefauconnier, J., Chavanieu, A., Calas, B., Scherrmann, J., and Temsamani, J. (2001) Enhanced delivery of doxorubicin into the brain via a peptide-vector-mediated strategy: saturation kinetics and specificity. *The Journal of Pharmacology and Experimental Therapeutics* 296: 124-131.

Rousselle, C, Clair, P., Smirnova, M., Kolesnikov, Y., Pasternak, G. W., Gac-Breton, S., Rees, A. R., Scherrmann, J., and Temsamani, J. (2003) Improved brain uptake and pharmacological activity of dalargin using a peptide-vector-mediated-strategy. *The Journal of Pharmacology and Experimental Therapeutics* 36: 371-376.

Rogers, et al., 1993, *Neurology* 43: 1609.

Rothwell and Relton, 1993, *Cerebrovasc. Brain Metab. Rev.* 5:178.

Roselaar S E, Daugherty A. 1998. Apolipoprotein E-deficient mice have impaired innate immune responses to *Listeria monocytogenes* in vivo. J Lipid Res. 1998 September; 39(9): 1740-3.

Roses, A D and A M Saunders. 1998. ApoE, Alzheimer's disease, and recovery from brain stress. Ann. N.Y. Acad. Sci. 826: 200-212.

Schmidt S, Barcellos L F, DeSombre K, Rimmler J B, Lincoln R R, Bucher P, Saunders A M, Lai E, Martin E R, Vance J M, Oksenberg J R, Hauser S L, Pericak-Vance M A, Haines J L; Multiple Sclerosis Genetics Group, 2002, Association of polymorphisms in the apolipoprotein E region with susceptibility to and progression of multiple sclerosis, Am J Hum Genet. 70(3):708-17.

Sheng, et al., 1999a, Characterization of a recovery global ischemia model in the mouse, *J. Neurosci. Methods* 88:103-109.

Sheng, et al., 1999a, Characterization of a recovery global ischemia model in the mouse, J. Neurosci. Methods 88: 103-109.

Sheng, et al., 1998, Apolipoprotein E isoform-specific differences in outcome from focal ischemia in transgenic mice, *J. Cereb. Blood Flow Metab.* 18: 361-366.

Sheng, et al., 1999b, Apolipoprotein E deficiency worsens outcome from global cerebral ischemia in the mouse, *Stroke* 30: 1118-1124.

Scholes, G. 1983. Radiation effects on DNA: The Silvanus Thomson memorial lecture April 1982. Br. J. Radiol. 56: 221-231.

Schuchter L M, Glick J: The Current status of WR-2721 (Amifostine): A chemotherapy and radiation therapy protector. 1993. Biologic Ther Cancer 3:1-10.

Skelton, R. W., Bukach, C M., Laurance, H. E., Thomas, K. G., and Jacobs, J. W. (2000). Humans with traumatic brain injuries show place-learning deficits in computer-generated virtual space. *J Clin Exp Neuropsychol*, 22: 157-75.

Slooter, et al., 1997, Apolipoprotein E epsilon4 and the risk of dementia with stroke. A population-based investigation, J. Am. Med. Assoc. 277: 818-821.

Smith, et al., 1995, A model of parasagittal controlled cortical impact in the mouse: cognitive and histopathologic effects, *J. Neurotrauma* 12: 169-78.

Smith, et al., 1997, An Orally Bioavailable Pyrrolinone Inhibitor of HIV-1 Protease: Computational Analysis and X-Ray Structure of the Enzyme Complex, *J. Med. Chem.* 40, 2440-2444.

Smith, et al., 1998, Design, Synthesis, and Evaluation of a Pyrrolinone-peptide Hybrid Ligand for the Class II MHC Protein FILA-DR1, *J. Am. Chem. Soc.* 120, 12704-12705.

Smith, et al., 2000, Design, Synthesis and Evaluation of a Pyrrolinone-Based Matrix Metalloprotease Inhibitor, *Org. Lett.*, 2:3809-3812.

Strittmatter, et al., 1994, Isoform-specific interactions of apolipoprotein E with microtubule-associated protein tau: implications for Alzheimer disease, *Proc. Natl. Acad. U.S.A.* 91, 11183-11186.

Strittmatter, et al., 1993, Apolipoprotein E: high-avidity binding to beta-amyloid and increased frequency of type 4 allele in late-onset familial Alzheimer disease, *Proc. Natl. Acad. Sci. U.S.A.* 90:1977-1981.

Schiefer, et al., 2002, Riluzole prolongs survival time and alters nuclear inclusion formation in a transgenic mouse model of Huntington's disease, *Mov. Disord.* 17(4):748-57.

Schiefermeier, et al., 2000, Apolipoprotein E polymorphism. Survival and neurological outcome after cardiopulmonary resuscitation, *Stroke* 21:2068-2071.

Schwarze, S. R., Ho, A., Vocero-Akbani, A., and Dowdy, S. F. (1999) In vivo transduction: delivery of a biologically active protein into the mouse. *Science* 285: 1569-1572.

Schwarze, S. R., and Dowdy, S. F. (2000) In vivo protein transduction: intracellular delivery of biologically active proteins, compounds, and DNA. *Trends Pharmacol Sci* 21:45-48.

Seliger, et al., 1997, *Neurology* (Abstract) page A213.

Sheng, et al., 1994, *J. Neurochem.* 63:1872.

Sheng et al., 1999, Apolipoprotein E deficiency worsens outcome from global ischemia in the mouse, *Stroke* 30:1118-1123.

Sheng, H. D. T. Laskowitz, E. Bennett, D. E. Schmechel, R. D. Bart, A. M. Saunders, R. D. Pearlstein, A. D. Roses and D. S. Warner. 1998. Apolipoprotein E isoform-specific differences in outcome from focal ischemia in transgenic mice. J. Cereb. Blood Flow Metab. 18: 361-366.

Sheng H, D T Laskowitz, R D Pearlstein, and D S Warner. 1999a. Characterization of a recovery global ischemia model in the mouse. *J Neurosci Methods* 88: 103-109.

Sheng, H. D. T. Laskowitz, G. B. Mackensen, M. Kudo, R. D. Pearlstein, and D. S. Warner. 1999b. Apolipoprotein E deficiency worsens outcome from global cerebral ischemia in the mouse. *Stroke* 30: 1118-1124.

Shukitt-Hale, B, G Casadesus, J J McEwen, B M Rabin, and J A Joseph. 2000. Spatial learning and memory deficits induced by exposure to iron-56-particle radiation. *Radiat. Res.* 154: 28-33.

Sorbi, et al., 1996, *Neurology* 46:A307 (abstract).

Sorbi, et al., 1995, ApoE as a prognostic factor for post-traumatic coma. *Nat. Med.* 1:852.

Soyka, et al., 2000, NMDA receptor challenge with dextromethorphan—subjective response, neuroendocrinological findings and possible clinical implications, *J. Neural. Transm.* 107(6):701-14.

Stoll and Mueller, 1986, *Neurosci. Lett.* 72:233.

Stoll, et al., 1989, *Glia* 2:170.

Strittmatter, et al., 1993, Apolipoprotein-e-epsilon-4 allele distributions in late-onset α/zheimers disease and in other amyloid-forming diseases, *Proc. Natl. Acad. Sci. USA* 90:1977-81.

Suzuki. T., Futaki, S., Niwa, M., Tanaka, S., Uedo, K., and Sugiura, Y. (2002). Possible existence of common internalization mechanisms among Arginine-rich peptides. *The Journal of Biological Chemistry* 277: 2437-2443.

Takahashi, S, X-Z Sun, Y Kubota, N Takai, and K Nojima. 2002. Histological and elemental changes in rat brain after local irradiation with carbon ion beams. J. Radiat. Res. 43: 143-152.

Takeshima, K., Chikushi, A., Lee, K., Yonehara, S., and Matsuzaki, K. (2003) Translocation of Analogues of the antimicrobial peptides magainin and buforin across human cell membranes. *The Journal of Biological Chemistry* 278: 1310-1315.

Tardiff, et al., 1997, Preliminary report of a genetic basis for cognitive decline after cardiac operations. The Neurologic Outcome Research Group of the Duke Heart Center, *Ann. Thorac. Surg.* 64: 715-20.

Teasdale, et al., 1999, Challenges in translating the efficacy of neuroprotective agents in experimental models into knowledge of clinical benefits in head injured patients. *Acta Neurochir (Wien)* 73: Suppl:111-6.

Teasdale, et al., 1997, Association of apolipoprotein E polymorphism with outcome after head injury, *Lancet* 350: 1069-1071.

Tesseur, et al., 2000, Expression of human apolipoprotein E4 in neurons causes hyperphosphorylation of protein tau in the brains of transgenic mice, *Am. J. Pathol.* 156(3):951-64.

Thoren, P. E. G., Persson, D., Isakson, P., Goksor, M., Onfelt, A., and Norden, B (2003) Uptake of analogs of penetratin, Tat(48-60) and oligoarginine in live cells. *Biochemical and Biophysical Research Communications* 307: 100-107.

Tolar, et al., 1999, Truncated apolipoprotein E (ApoE) causes increased intracellular calcium and may mediate apoE neurotoxicity. *J. Neurosci.* 19:7100-71 10.

Tolar, et al., 1997, Neurotoxicity of the 22 kDa thrombin-cleavage fragment of apolipoprotein E and related synthetic peptides is receptor-mediated. *J. Neurosci.* 17:5678-5686.

Tung, C, and Weissleder, R. (2002) Arginine containing peptides as delivery vectors. *Advanced Drug Delivery Reviews* 55: 281-294.

Van Lenten B J, Fogelman A M, Haberland M E, Edwards P A. 1986. The role of lipoproteins and receptor-mediated endocytosis in the transport of bacterial lipopolysaccharide. Proc Natl Acad Sci USA. 1986 April; 83(8):2704-8.

Van Oosten M, Rensen P C, Van Amersfoort E S, Van Eck M, Van Dam A M, Breve J J, Vogel T, Panet A, Van Berkel T J, Kuiper J. 2001. Apolipoprotein E protects against bacterial lipopolysaccharide-induced lethality. A new therapeutic approach to treat gram-negative sepsis. J Biol. Chem. 2001 Mar. 23; 276(12):8820-4.

Veber, et al., 2002, Molecular properties that influence the oral bioavailability of drug candidates, *J. Med. Chem.* 45, 2615.

Verdine, et al., 2000, An all hydrocarbon cross-linking system for enhancing the helicity and metabolic stability of peptides, *J. Amer. Chem. Soc.,* 122, 5891.

Vijayalakshmi, et al., 2000, Comparison of Helix stabilizing effects of α,α-Dialkyl Glycines with Linear and Cycloalkyl Side Chains, *Biopolymers,* 53(1), 84.

Vives, E., Richard, J.-P., Rispal, C, and Lebleu, B. (2003) TAT peptide internalization: seeking the mechanism of entry. *Current Protein and Peptide Science* 4: 125-132.

Van Oosten, et al., 2001, Apolipoprotein E protects against bacterial lipopolysaccharide-induced lethality, *J. Biol. Chem.* 276(12):8820-24.

Veinbergs, et al., 2001, Role of apolipoprotein E receptors in regulating the differential in vivo neurotrophic effects of apolipoprotein E, *Exp. Neurol.* 170(1): 15-2.

Von Bergen, et al., 2002, Effect of intrathecal non-NMDA EAA receptor antagonist LY293558 in rats: a new class of drugs for spinal anesthesia, *Anesthesiology* 97(1):177-82.

Wellons, et al., 2000, A comparison of strain-related susceptibility in two murine recovery models of global cerebral ischemia, *Brain Res.* 868: 14-21.

Waage, et al., 1987, *J. Exp. Med.* 169:333-38.

Wang, et al., 1998, Apolipoprotein E (ApoE) peptide regulates tau phosphorylation via two different signaling pathways. *J. Neurosci. Res.* 51:658-665.

Wang, et al., 1997, Rapid elevation of neuronal cytoplasmic calcium by apolipoprotein E peptide. *J. Cell Physiol.* 173: 73-83.

Watanabe, et al., 1997, *Int. J. Cardiol.* 54:551.

Weisbarger et al., 1983, The receptor-binding domain of human apolipoprotein E: monoclonal antibody inhibition of binding, *J. Biol. Chem.* 258: 12348-54.

Weisgraber, et al., 1982, Abnormal lipoprotein receptor-binding activity of the human E apoprotein due to cysteine-arginine interchange at a single site. *J. Biol. Chem.* 257: 2518-2521.

Weisgraber, 1994, Apolipoprotein E: Structure-function relationships. *Adv. Protein Chem.* 45:249-302.

Wells M T, Gaffin S L, Jordaan J P. 1987. Radiation induced gram negative bacteremia and endotoxemia in rabbits: modification by anti-lipopolysaccharide hyperimmune equine plasma. Life Sci. 1987 Jun. 29; 40(26):2543-50.

Wells M T, Gaffin S L, Wessels B C, Brock-Utne J G, Jordaan J P, van den Ende J. 1990. Anti-LPS antibodies reduce endotoxemia in whole body 60Co irradiated primates: a preliminary report. Aviat Space Environ Med. 1990 September; 61(9):802-6.

Wender, P. A., Mitchell, D. J., Pattabiraman, K., Pelkey, E. T., Steinman, L., and Rothbard, J. B. (2000) The design, synthesis, and evaluation of molecules that enable or enhance cellular uptake: peptoid molecular transporters. *Proc. Nail. Acad. Sci.* 97: 13003-13008.

Wettereau, et al., 1988, Human apolipoprotein E3 is aqueaous solution. Evidence for two structural domains, *J. Biol. Chem.* 263:6240-48.

Wiemann B, Van G Y, Danilenko D M, Yan Q, Matheson C, Munyakazi L, Ogenstad S, Stames C O, 1998, Combined treatment of acute EAE in Lewis rats with TNF-binding protein and interleukin-1 receptor antagonist, Exp Neurol. 149(2):455-63.

Wisniewski, et al., 1992, Apolipoprotein E: a pathological chaperone in patients with cerebral and systemic amyloid. *Neurosci. Let.* 135:235-238.

Wright, L. R., Rothbard, J. B. and Wender, P. A. (2003) Guanidinium rich peptide transporters and drug delivery. Current Protein and Peptide Science 4: 105-124.

Xu and Luo, 2001, Relationship between changes of N-methyl-D-aspartate receptor activity and brain edema after brain injury in rats, *Chin. J. Traumatol.* 4(3): 135-8.

Ye, D., Xu, D., Singer, A. U., and Juliano, R. L. (2002) Evaluation of strategies for the intracellular delivery of proteins. *Pharmaceutical Research* 19:1302-1309.

Zanotti, et al., 2002, Cytokine modulation in sepsis and septic shock, *Expert Opin. Investig. Drugs* 11(8):1061-75.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

We claim:

1. A method of treating, preventing or ameliorating multiple sclerosis or Guillain-Barre syndrome in a subject in need thereof comprising administering to the subject a compound, said compound comprising a peptide consisting of less than about 50 amino acids comprising the sequence of peptide COG133 (SEQ ID NO: 1) or a peptide consisting of the sequence of peptide COG133 (SEQ ID NO: 1), wherein said peptide is conjugated to a protein transduction domain (PTD) derived from antennapedia.

2. The method of claim 1, wherein one to fifteen amino acids are linked to the amino or carboxy terminus of said sequence of peptide COG133.

3. The method of claim 1, wherein an amino acid has been inserted at the amino or carboxy terminus of said sequence of peptide COG133.

4. The method of claim 1, wherein said PTD derived from antennapedia is RQIKIWFQNRRMKWKK (SEQ. ID. NO: 51) or RRMKWKK (SEQ. ID. NO: 52).

5. The method of claim 4, wherein said PTD derived from antennapedia is conjugated to the amino terminus of the COG133 peptide.

6. The method of claim 5, wherein the peptide conjugate has a sequence of RQIKIWFQNRRMKWKK-LRVR-LASHLRKLRKRLL (SEQ ID NO: 66).

7. A method of treating, preventing, or ameliorating inflammatory bowel disease (IBD), Crohn's disease, or ulcerative colitis in a subject in need thereof comprising administering to the subject a peptide consisting of less than about 50 amino acids comprising the sequence of peptide COG133 (SEQ ID NO: 1) or a peptide consisting of the sequence of peptide COG133 (SEQ ID NO: 1), wherein said peptide is conjugated to a PTD derived from antennapedia.

8. The method of claim 7, wherein said PTD derived from antennapedia is RQIKIWFQNRRMKWKK (SEQ. ID. NO: 51) or RRMKWKK (SEQ. ID. NO: 52).

9. The method of claim 8, wherein said PTD derived from antennapedia is conjugated to the amino terminus of the COG133 peptide.

10. A method of treating, preventing, or ameliorating traumatic brain injury in a subject in need thereof comprising administering to the subject a peptide consisting of less than about 50 amino acids comprising the sequence of peptide COG133 (SEQ ID NO: 1) or a peptide consisting of the sequence of peptide COG133 (SEQ ID NO: 1), wherein said peptide is conjugated to a PTD derived from antennapedia.

11. The method of claim 10, wherein said PTD derived from antennapedia is RQIKIWFQNRRMKWKK (SEQ. ID. NO: 51) or RRMKWKK (SEQ. ID. NO: 52).

12. The method of claim 11, wherein said PTD derived from antennapedia is conjugated to the amino terminus of the COG133 peptide.

13. The method of claim 10, wherein the traumatic brain injury causes neurologic deficits in said subject.

14. The method of claim 10, wherein the treatment comprises neurological recovery.

15. The method of claim 10, wherein the treatment is improved cognitive function.

16. The method of claim 10, wherein the traumatic brain injury is CNS inflammation or CNS edema.

17. A method for protecting a subject in need thereof against at least one effect of radiation, comprising administering to said subject a compound, said compound comprising a peptide consisting of less than about 50 amino acids comprising the sequence of peptide COG133 (SEQ ID NO: 1) or a peptide consisting of the sequence of peptide COG133 (SEQ ID NO: 1), wherein said peptide is conjugated to a protein transduction domain (PTD) derived from antennapedia.

18. The method of claim 17, wherein said radiation is total body irradiation.

19. The method of claim 17, wherein said subject has undergone a transplantation procedure.

20. The method of claim 19, wherein said transplantation procedure is a blood or bone marrow transplantation.

21. The method of claim 17, wherein said radiation is radiation therapy.

22. The method of claim 21, wherein said radiation therapy is for the treatment of cancer.

23. The method of claim 22, wherein said cancer is selected from the group consisting of brain tumors, head and neck cancers, lung cancer, breast cancer, prostate cancer, skin cancer, rectal cancer, cervix and uterine cancers, lymphoma, and sarcoma.

24. The method of claim 23, wherein said administration blocks or reduces radiation-induced production of at least one cytokine.

25. The method of claim 24, wherein said at least one cytokine is selected from the group consisting of tumor necrosis factor alpha (TNFα), interleukin-1 alpha (IL1α), interleukin-1 beta (IL1β) and interleukin-6 (IL6).

26. The method of claim 17, wherein said administration blocks or reduces radiation-induced neurotoxicity, late delayed radiation-induced brain necrosis, radiation-induced soft tissue or vascular injury, or radiation-induced xerostomia.

* * * * *

UNITED STATES PATENT AND TRADEMARK OFFICE
CERTIFICATE OF CORRECTION

PATENT NO. : 8,288,335 B2
APPLICATION NO. : 13/096423
DATED : October 16, 2012
INVENTOR(S) : Michael P. Vitek and Suzanne E. McKenna It is certified that error appears in the above-identified patent and that said Letters Patent is hereby corrected as shown below:

ON THE FACE OF THE PATENT:

At field number [73], "Cognosei, Inc." should be changed to -- Cognosci, Inc. --.

Signed and Sealed this
Twenty-sixth Day of February, 2013

Teresa Stanek Rea
*Acting Director of the United States Patent and Trademark Office*

SEQUENCE LISTING

<160> NUMBER OF SEQ ID NOS: 77

<210> SEQ ID NO 1
<211> LENGTH: 17
<212> TYPE: PRT
<213> ORGANISM: Artificial Sequence

```
<220> FEATURE:
<223> OTHER INFORMATION: ApoE mimetic peptide COG133
<220> FEATURE:
<221> NAME/KEY: misc_feature
<222> LOCATION: (1)..(1)
<223> OTHER INFORMATION: Leucine may be biotinylated
<220> FEATURE:
<221> NAME/KEY: misc_feature
<222> LOCATION: (1)..(1)
<223> OTHER INFORMATION: Leucine may be acetylated
<220> FEATURE:
<221> NAME/KEY: misc_feature
<222> LOCATION: (17)..(17)
<223> OTHER INFORMATION: Leucine may be amidated

<400> SEQUENCE: 1

Leu Arg Val Arg Leu Ala Ser His Leu Arg Lys Leu Arg Lys Arg Leu
1               5                   10                  15

Leu

<210> SEQ ID NO 2
<211> LENGTH: 17
<212> TYPE: PRT
<213> ORGANISM: Artificial Sequence
<220> FEATURE:
<223> OTHER INFORMATION: Analog of COG133
<220> FEATURE:
<221> NAME/KEY: misc_feature
<222> LOCATION: (9)..(9)
<223> OTHER INFORMATION: Xaa is N-methylated leucine
<220> FEATURE:
<221> NAME/KEY: misc_feature
<222> LOCATION: (17)..(17)
<223> OTHER INFORMATION: Leucine may be amidated

<400> SEQUENCE: 2

Leu Arg Val Arg Leu Ala Ser His Xaa Arg Lys Leu Arg Lys Arg Leu
1               5                   10                  15

Leu

<210> SEQ ID NO 3
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (4)..(4)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 3

Ala Ser His Xaa Arg Lys Leu Arg Lys Arg Leu Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
```

-continued

```
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 4

Ala Ser Xaa Leu Arg Lys Leu Arg Lys Arg Leu Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 5

Asp Ser Xaa Leu Arg Lys Leu Arg Lys Arg Leu Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: COG432
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 6

Ala Ser His Leu Arg Lys Leu Xaa Lys Arg Leu Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: COG1410
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
```

-continued

<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 7

Ala Ser Xaa Leu Arg Lys Leu Xaa Lys Arg Leu Leu
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (14)..(14)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 8

Asp Arg Xaa Ala Ser His Leu Arg Lys Leu Arg Lys Arg Xaa Leu
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 9

Asp Ser Xaa Leu Arg Lys Leu Arg Lys Arg Xaa Leu
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Truncated analog of COG133
<220> FEATURE:

```
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 10

Asp Arg Xaa Ala Ser His Leu Arg Lys Leu Xaa Lys Arg Leu Leu
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 11

Asp Ser Xaa Leu Arg Lys Leu Xaa Lys Arg Leu Leu
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (6)..(6)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 12

Asp Arg Xaa Ala Ser Xaa Leu Arg Lys Leu Arg Lys Arg Leu Leu
1               5                   10                  15
```

```
<210> SEQ ID NO 13
<211> LENGTH: 15
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 13

Asp Arg Xaa Ala Ser His Leu Arg Lys Leu Arg Lys Arg Leu Leu
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Cysteine may be acetylated
<220> FEATURE:
<221> NAME/KEY: misc_feature
<222> LOCATION: (4)..(4)
<223> OTHER INFORMATION: Xaa is amino iso-butyric acid
<220> FEATURE:
<221> NAME/KEY: misc_feature
<222> LOCATION: (9)..(9)
<223> OTHER INFORMATION: Xaa is amino iso-butyric acid
<220> FEATURE:
<221> NAME/KEY: misc_feature
<222> LOCATION: (13)..(13)
<223> OTHER INFORMATION: Leucine may be amidated

<400> SEQUENCE: 14

Cys Ala Ser Xaa Leu Arg Lys Leu Xaa Lys Arg Leu Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 15

Asp Ser Xaa Leu Arg Lys Leu Xaa Lys Arg Leu Leu
```

```
1               5                    10

<210> SEQ ID NO 16
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Valine may be amidated

<400> SEQUENCE: 16

Ala Ser Xaa Leu Arg Lys Leu Xaa Lys Arg Leu Val
1               5                    10

<210> SEQ ID NO 17
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Methionine may be amidated

<400> SEQUENCE: 17

Ala Ser Xaa Leu Arg Lys Leu Xaa Lys Arg Leu Met
1               5                    10

<210> SEQ ID NO 18
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
```

```
<221> NAME/KEY: misc_feature
<222> LOCATION: (12)..(12)
<223> OTHER INFORMATION: Isoleucine may be amidated

<400> SEQUENCE: 18

Ala Ser Xaa Leu Arg Lys Leu Xaa Lys Arg Leu Ile
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Alanine may be amidated

<400> SEQUENCE: 19

Ala Ser Xaa Leu Arg Lys Leu Xaa Lys Arg Leu Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 20

Ala Ser Xaa Leu Arg Lys Leu Xaa Lys Ala Leu Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
```

```
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Leucine may be amidated

<400> SEQUENCE: 21

Ala Ser Xaa Leu Arg Lys Leu Xaa Lys Xaa Leu Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is nitroarginine
<220> FEATURE:
<221> NAME/KEY: misc_feature
<222> LOCATION: (12)..(12)
<223> OTHER INFORMATION: Leucine may be amidated

<400> SEQUENCE: 22

Ala Ser Xaa Leu Arg Lys Leu Xaa Lys Xaa Leu Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is homoarginine
<220> FEATURE:
<221> NAME/KEY: misc_feature
<222> LOCATION: (12)..(12)
<223> OTHER INFORMATION: Leucine may be amidated
```

```
<400> SEQUENCE: 23

Ala Ser Xaa Leu Arg Lys Leu Xaa Lys Xaa Leu Leu
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is dimethyl arginine
<220> FEATURE:
<221> NAME/KEY: misc_feature
<222> LOCATION: (12)..(12)
<223> OTHER INFORMATION: Leucine may be amidated

<400> SEQUENCE: 24

Ala Ser Xaa Leu Arg Lys Leu Xaa Lys Xaa Leu Leu
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 25

Ala Ser Xaa Leu Arg Lys Leu Xaa Ala Arg Leu Leu
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
```

```
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (9)..(9)
<223> OTHER INFORMATION: Xaa is acetyl lysine
<220> FEATURE:
<221> NAME/KEY: misc_feature
<222> LOCATION: (12)..(12)
<223> OTHER INFORMATION: Leucine may be amidated

<400> SEQUENCE: 26

Ala Ser Xaa Leu Arg Lys Leu Xaa Xaa Arg Leu Leu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric ac

```
Ala Ser His Xaa Arg Lys Leu Xaa Lys Arg Leu Leu
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated

<400> SEQUENCE: 29

```
Ala Ser Xaa Leu Arg Lys Leu Xaa Lys Arg Leu Xaa
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Leucine may be amidated

<400> SEQUENCE: 30

```
Ala Ser Xaa Leu Arg Lys Leu Xaa Lys Arg Xaa Leu
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated

```
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 31

Ala Ser Xaa Leu Arg Lys Leu Xaa Lys Arg Xaa Xaa
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 32

Ala Ser Xaa Leu Arg Lys Leu Xaa Lys Xaa Leu Xaa
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
```

```
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Leucine may be amidated

<400> SEQUENCE: 33

Ala Ser Xaa Leu Arg Lys Leu Xaa Lys Xaa Xaa Leu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 34

Ala Ser Xaa Leu Arg Lys Leu Xaa Lys Xaa Xaa Xaa
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino i

```
<220> FEATURE:
<221> NAME/KEY: misc_feature
<222> LOCATION: (10)..(10)
<223> OTHER INFORMATION: Xaa is homoarginine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 35

Ala Ser Xaa Leu Arg Lys Leu Xaa Lys Xaa Leu Xaa
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid -continued

```
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 37

Ala Ser Xaa Leu Arg Lys Leu Xaa Lys Xaa Xaa Xaa
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 38

Ala Ser Xaa Leu Xaa Lys Leu Xaa Lys Arg Leu Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Leucine may be amidated
```

```
<400> SEQUENCE: 39

Ala Ser Xaa Leu Xaa Lys Leu Xaa Lys Xaa Leu Leu
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated

<400> SEQUENCE: 40

Ala Ser Xaa Leu Xaa Lys Leu Xaa Lys Arg Leu Xaa
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Xaa is neurleucine
<220> FEATURE:
<221> NAME/KEY: misc_feature
<222> LOCATION: (13)..(13)
<223> OTHER INFORMATION: Neurleucine may be amidated
<220> FEATURE:
<221> NAME/KEY: misc_feature
<222> LOCATION: (13)..(13)
<223> OTHER INFORMATION: Xaa is neurleucine

<400> SEQUENCE: 41
```

```
Ala Ser Xaa Leu Xaa Lys Leu Xaa Lys Arg Leu Xaa Xaa
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 42

Ala Ser Xaa Leu Xaa Lys Leu Xaa Lys Xaa Leu Xaa
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated
```

```
<220> FEATURE:
<221> NAME/KEY: misc_feature
<222> LOCATION: (12)..(12)
<223> OTHER INFORMATION: Xaa is neurleucine

<400> SEQUENCE: 43

Ala Ser Xaa Leu Xaa Lys Leu Xaa Lys Xaa Xaa Xaa
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Truncation of COG133 peptide
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 44

Ala Ser His Leu Arg Lys Leu Arg Lys Arg Leu Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 45

Ala Ser His Cys Arg Lys Leu Cys Lys Arg Leu Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 46

Ala Ser Cys Leu Arg Lys Leu Cys Lys Arg Leu Leu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Truncated analog of COG133
```

```
<220> FEATURE:
<221> NAME/KEY: misc_feature
<222> LOCATION: (1)..(1)
<223> OTHER INFORMATION: Cysteine may be acetylated
<220> FEATURE:
<221> NAME/KEY: misc_feature
<222> LOCATION: (12)..(12)
<223> OTHER INFORMATION: Leucine may be amidated

<400> SEQUENCE: 47

Cys Ser His Leu Arg Lys Leu Cys Lys Arg Leu Leu
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 48

Ala Ser His Leu Arg Lys Cys Arg Lys Arg Cys Leu
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 49

Ala Ser His Cys Arg Lys Leu Arg Lys Arg Cys Leu
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Protein transduction domain conjugate Tat

<400> SEQUENCE: 50

Gly Arg Lys Lys Arg Arg Gln Arg Arg Arg Pro Pro Gln
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Protein transduction domain conjugate Antp

<400> SEQUENCE: 51

Arg Gln Ile Lys Ile Trp Phe Gln Asn Arg Arg Met Lys Trp Lys Lys
```

<210> SEQ ID NO 52
<211> LENGTH: 7
<212> TYPE: PRT
<213> ORGANISM: Artificial Sequence
<220> FEATURE:
<223> OTHER INFORMATION: Fragment of protein transduction domain
    conjugate Antp

<400> SEQUENCE: 52

Arg Arg Met Lys Trp Lys Lys
1               5

<210> SEQ ID NO 53
<211> LENGTH: 18
<212> TYPE: PRT
<213> ORGANISM: Artificial Sequence
<220> FEATURE:
<223> OTHER INFORMATION: Protein transduction domain conjugate

<400> SEQUENCE: 53

Arg Gly Gly Arg Leu Ser Tyr Ser Arg Arg Arg Phe Ser Thr Ser Thr
1               5                   10                  15

Gly Arg

<210> SEQ ID NO 54
<211> LENGTH: 10
<212> TYPE: PRT
<213> ORGANISM: Artificial Sequence
<220> FEATURE:
<223> OTHER INFORMATION: Protein transduction domain conjugate SynB3

<400> SEQUENCE: 54

Arg Arg Leu Ser Tyr Ser Arg Arg Arg Phe
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Protein transduction domain conjugate SynB5

<400> SEQUENCE: 55

Arg Gly Gly Arg Leu Ala Tyr Leu Arg Arg Arg Trp Ala Val Leu Gly
1               5                   10                  15

Arg

<210> SEQ ID NO 56
<211> LENGTH: 8
<212> TYPE: PRT
<213> ORGANISM: Artificial Sequence
<220> FEATURE:
<223> OTHER INFORMATION: PolyArg

<400> SEQUENCE: 56

Arg Arg Arg Arg Arg Arg Arg Arg
1               5

<210> SEQ ID NO 57
<211> LENGTH: 17
<212> TYPE: PRT
<213> ORGANISM: Artificial Sequence
<220> FEATURE:
<223> OTHER INFORMATION: Reverse of COG133

```
<400> SEQUENCE: 57

Leu Leu Arg Lys Arg Leu Lys Arg Leu His Ser Ala Leu Arg Val Arg
1               5                   10                  15

Leu

<210> SEQ ID NO 58
<211> LENGTH: 17
<212> TYPE: PRT
<213> ORGANISM: Artificial Sequence
<220> FEATURE:
<223> OTHER INFORMATION: Internal standard peptide

<400> SEQUENCE: 58

Leu Ala Val Leu Leu Ala Ser His Leu Arg Lys Leu Arg Lys Arg Leu
1               5                   10                  15

Leu

<210> SEQ ID NO 59
<211> LENGTH: 10
<212> TYPE: PRT
<213> ORGANISM: Artificial Sequence
<220> FEATURE:
<223> OTHER INFORMATION: COG1410 fragment
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid

<400> SEQUENCE: 59

Ala Ser Xaa Leu Arg Lys Leu Xaa Lys Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Peptide forming cross-linked olefin bridge
<220> FEATURE:
<221> NAME/KEY: misc_feature
<222> LOCATION: (4)..(4)
<223> OTHER INFORMATION: Xaa is any aa which contains side chain linked
      to the cross-linking olefin bridge
<220> FEATURE:
<221> NAME/KEY: misc_feature
<222> LOCATION: (8)..(8)
<223> OTHER INFORMATION: Xaa is any aa which contains side chain linked
      to the cross-linking olefin bridge

<400> SEQUENCE: 60

Ala Ser His Xaa Arg Lys Leu Xaa Lys Arg Leu Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Peptide forming cross-linked olefin bridge
<220> FEATURE:
<221> NAME/KEY: misc_feature
<222> LOCATION: (1)..(1)
```

```
<223> OTHER INFORMATION: Xaa is any aa which contains side chain linked
      to the cross-linking olefin bridge
<220> FEATURE:
<221> NAME/KEY: misc_feature
<222> LOCATION: (8)..(8)
<223> OTHER INFORMATION: Xaa is any aa which contains side chain linked
      to the cross-linking olefin bridge

<400> SEQUENCE: 61

Xaa Ser His Leu Arg Lys Leu Xaa Lys Arg Leu Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Peptide forming cross-linked olefin bridge
<220> FEATURE:
<221> NAME/KEY: misc_feature
<222> LOCATION: (3)..(3)
<223> OTHER INFORMATION: Xaa is any aa which contains side chain linked
      to the cross-linking olefin bridge
<220> FEATURE:
<221> NAME/KEY: misc_feature
<222> LOCATION: (10)..(10)
<223> OTHER INFORMATION: Xaa is any aa which contains side chain linked
      to the cross-linking olefin bridge

<400> SEQUENCE: 62

Ala Ser Xaa Leu Arg Lys Leu Arg Lys Xaa Leu Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Peptide forming cross-linked olefin bridge
<220> FEATURE:
<221> NAME/KEY: misc_feature
<222> LOCATION: (4)..(4)
<223> OTHER INFORMATION: Xaa is any aa which contains side chain linked
      to the cross-linking olefin bridge
<220> FEATURE:
<221> NAME/KEY: misc_feature
<222> LOCATION: (11)..(11)
<223> OTHER INFORMATION: Xaa is any aa which contains side chain linked
      to the cross-linking olefin bridge

<400> SEQUENCE: 63

Ala Ser His Xaa Arg Lys Leu Arg Lys Arg Xaa Leu
1               5                   10

<210> SEQ ID NO 64
<211> LENGTH: 21
<212> TYPE: PRT
<213> ORGANISM: Artificial Sequence
<220> FEATURE:
<223> OTHER INFORMATION: Myelin oligodendrocyte glycoprotein (MOG)
      peptide

<400> SEQUENCE: 64

Met Glu Val Gly Trp Tyr Arg Ser Pro Phe Ser Arg Val Val His Leu
1               5                   10                  15

Tyr Arg Asn Gly Lys
            20

<210> SEQ ID NO 65
<211> LENGTH: 17
<212> TYPE: PRT
```

```
<213> ORGANISM: Artificial Sequence
<220> FEATURE:
<223> OTHER INFORMATION: Analog of COG133

<400> SEQUENCE: 65

Leu Arg Val Arg Leu Ala Ser His Leu Arg Lys Leu Arg Lys Arg Leu
1               5                   10                  15

Ala

<223> OTHER INFORMATION: Xaa may be Arg or Glu
<220> FEATURE:
<221> NAME/KEY: misc_feature
<222> LOCATION: (12)..(12)
<223> OTHER INFORMATION: Xaa may be Leu or Met
<220> FEATURE:
<221> NAME/KEY: misc_feature
<222> LOCATION: (16)..(16)
<223> OTHER INFORMATION: Xaa may be Leu or Asn

<400> SEQUENCE: 68

Leu Arg Val Arg Leu Ala Ser His Leu Xaa Lys Xaa Arg Lys Arg Xaa
1 5 10 15

Leu

<210> SEQ ID NO 69
<211> LENGTH: 17
<212> TYPE: PRT
<213> ORGANISM: Artificial Sequence
<220> FEATURE:
<223> OTHER INFORMATION: COG133 neutral activity consensus peptide sequence
<220> FEATURE:
<221> NAME/KEY: misc_feature
<222> LOCATION: (8)..(8)
<223> OTHER INFORMATION: Xaa may be His or Ala
<220> FEATURE:
<221> NAME/KEY: misc_feature
<222> LOCATION: (9)..(9)
<223> OTHER INFORMATION: Xaa may be Leu or Ala
<220> FEATURE:
<221> NAME/KEY: misc_feature
<222> LOCATION: (10)..(10)
<223> OTHER INFORMATION: Xaa may be Arg or Ala
<220> FEATURE:
<221> NAME/KEY: misc_feature
<222> LOCATION: (13)..(13)
<223> OTHER INFORMATION: Xaa may be Arg or Ala
<220> FEATURE:
<221> NAME/KEY: misc_feature
<222> LOCATION: (16)..(16)
<223> OTHER INFORMATION: Xaa may be Leu or Ala

<400> SEQUENCE: 69

Leu Arg Val Arg Leu Ala Ser Xaa Xaa Xaa Lys Leu Xaa Lys Arg Xaa
1 5 10 15

Leu

<210> SEQ ID NO 70
<211> LENGTH: 17
<212> TYPE: PRT
<213> ORGANISM: Artificial Sequence
<220> FEATURE:
<223> OTHER INFORMATION: COG133 neutral activity consensus peptide sequence
<220> FEATURE:
<221> NAME/KEY: misc_feature
<222> LOCATION: (13)..(13)
<223> OTHER INFORMATION: Xaa may be Arg or Glu
<220> FEATURE:
<221> NAME/KEY: misc_feature
<222> LOCATION: (14)..(14)
<223> OTHER INFORMATION: Xaa may be Lys or Glu
<220> FEATURE:
<221> NAME/KEY: misc_feature
<222> LOCATION: (15)..(15)
<223> OTHER INFORMATION: Xaa may be Arg or Glu
<220> FEATURE:
<221> NAME/KEY: misc_feature
<222> LOCATION: (17)..(17)
<223> OTHER INFORMATION: Xaa may be Leu, Met or Asn

<400> SEQUENCE: 70

```
Leu Arg Val Arg Leu Ala Ser His Leu Arg Lys Leu Xaa Xaa Xaa Leu
1               5                   10                  15

Xaa

<210> SEQ ID NO 71
<211> LENGTH: 17
<212> TYPE: PRT
<213> ORGANISM: Artificial Sequence
<220> FEATURE:
<223> OTHER INFORMATION: COG133 analog
<220> FEATURE:
<221> NAME/KEY: misc_feature
<222> LOCATION: (9)..(9)
<223> OTHER INFORMATION: Xaa is D-proline

<400> SEQUENCE: 71

Leu Arg Val Arg Leu Ala Ser His Xaa Arg Lys Leu Arg Lys Arg Leu
1               5                   10                  15

Leu

<210> SEQ ID NO 72
<211> LENGTH: 17
<212> TYPE: PRT
<213> ORGANISM: Artificial Sequence
<220> FEATURE:
<223> OTHER INFORMATION: COG133 analog
<220> FEATURE:
<221> NAME/KEY: misc_feature
<222> LOCATION: (12)..(12)
<223> OTHER INFORMATION: Xaa may be Leu or absent
<220> FEATURE:
<221> NAME/KEY: misc_feature
<222> LOCATION: (13)..(13)
<223> OTHER INFORMATION: Xaa is D-proline

<400> SEQUENCE: 72

Leu Arg Val Arg Leu Ala Ser His Leu Arg Lys Xaa Xaa Lys Arg Leu
1               5                   10                  15

Leu

<210> SEQ ID NO 73
<211> LENGTH: 17
<212> TYPE: PRT
<213> ORGANISM: Artificial Sequence
<220> FEATURE:
<223> OTHER INFORMATION: COG133 potential modification consensus
      sequence
<220> FEATURE:
<221> NAME/KEY: misc_feature
<222> LOCATION: (1)..(1)
<223> OTHER INFORMATION: Xaa may be Leu, Val, Phe, Lys or Glu
<220> FEATURE:
<221> NAME/KEY: misc_feature
<222> LOCATION: (2)..(2)
<223> OTHER INFORMATION: X

```
<221> NAME/KEY: misc_feature
<222> LOCATION: (7)..(7)
<223> OTHER INFORMATION: Xaa may be Ser, Val, Asn, Lys or Glu
<220> FEATURE:
<221> NAME/KEY: misc_feature
<222> LOCATION: (8)..(8)
<223> OTHER INFORMATION: Xaa may be His, Lys, Glu or Asn
<220> FEATURE:
<221> NAME/KEY: misc_feature
<222> LOCATION: (9)..(9)
<223> OTHER INFORMATION: Xaa may be Leu, Val, Phe, Lys or Glu
<220> FEATURE:
<221> NAME/KEY: misc_feature
<222> LOCATION: (10)..(10)
<223> OTHER INFORMATION: Xaa may be Arg, Val, Lys or Orn
<220> FEATURE:
<221> NAME/KEY: misc_feature
<222> LOCATION: (11)..(11)
<223> OTHER INFORMATION: Xaa may be Lys, Arg, Orn, Glu or Leu
<220> FEATURE:
<221> NAME/KEY: misc_feature
<222> LOCATION: (12)..(12)
<223> OTHER INFORMATION: Xaa may be Leu, Val, Phe or Lys
<220> FEATURE:
<221> NAME/KEY: misc_feature
<222> LOCATION: (13)..(13)
<223> OTHER INFORMATION: Xaa may be Arg, Val, Phe, Lys or Orn
<220> FEATURE:
<221> NAME/KEY: misc_feature
<222> LOCATION: (14)..(14)
<223> OTHER INFORMATION: Xaa may be Lys, Orn, Asn or Leu
<220> FEATURE:
<221> NAME/KEY: misc_feature
<222> LOCATION: (15)..(15)
<223> OTHER INFORMATION: Xaa may be Arg, Val, Lys or Orn
<220> FEATURE:
<221> NAME/KEY: misc_feature
<222> LOCATION: (16)..(16)
<223> OTHER INFORMATION: Xaa may be Lys, Val, Phe or Lys
<220> FEATURE:
<221> NAME/KEY: misc_feature
<222> LOCATION: (17)..(17)
<223> OTHER INFORMATION: Xaa may be Leu, Ile, Phe, Arg, Lys or Glu

<400> SEQUENCE: 73

Xaa Xaa Xaa Xaa Xaa Xaa Xaa Xaa Xaa Xaa Xaa Xaa Xaa Xaa Xaa
1               5                   10                  15

Xaa

<210> SEQ ID NO 74
<211> LENGTH: 17
<212> TYPE: PRT
<213> ORGANISM: Artificial Sequence
<220> FEATURE:
<223> OTHER INFORMATION: COG133 helix modified analog
<220> FEATURE:
<221> NAME/KEY: misc_feature
<222> LOCATION: (5)..(5)
<223> OTHER INFORMATION: Xaa is amino iso-butyric acid

<400> SEQUENCE: 74

Leu Arg Val Arg Xaa Ala Ser His Leu Arg Lys Leu Arg Lys Arg Leu
1               5                   10                  15

Leu

<210> SEQ ID NO 75
<211> LENGTH: 12
<212> TYPE: PRT
<213> ORGANISM: Artificial Sequence
<220> FEATURE:
<223> OTHER INFORMATION: COG133 helix modified analog
<220> FEATURE:
<221> NAME/KEY: misc_feature
<222> LOCATION: (1)..(1)
```

```
<223> OTHER INFORMATION: Asp may be acetylated
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid

<400> SEQUENCE: 75

Asp Ser His Xaa Arg Lys Leu Xaa Lys Arg Leu Leu
1               5                   10

<210> SEQ ID NO 76
<211> LENGTH: 12
<212> TYPE: PRT
<213> ORGANISM: Artificial Sequence
<220> FEATURE:
<223> OTHER INFORMATION: COG133 helix modified analog
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid

<400> SEQUENCE: 76

Asp Ser His Leu Arg Lys Xaa Arg Lys Arg Xaa Leu
1               5                   10

<210> SEQ ID NO 77
<211> LENGTH: 12
<212> TYPE: PRT
<213> ORGANISM: Artificial Sequence
<220> FEATURE:
<223> OTHER INFORMATION: COG133 helix modified analog
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid

<400> SEQUENCE: 77

Asp Ser His Leu Arg Lys Leu Xaa Lys Arg Xaa Leu
1               5                   10
```